United States Patent
Lindsley et al.

(10) Patent No.: US 8,697,888 B2
(45) Date of Patent: Apr. 15, 2014

(54) SUBSTITUTED (1-(METHYLSULFONYL)AZETIDIN-3-YL)(HETEROCYCLOALKYL)METHANONE ANALOGS AS ANTAGONISTS OF MUSCARINIC ACETYLCHOLINE $M_1$ RECEPTORS

(71) Applicant: Vanderbilt University, Nashville, TN (US)

(72) Inventors: Craig W. Lindsley, Brentwood, TN (US); P. Jeffrey Conn, Brentwood, TN (US); Michael R. Wood, Brentwood, TN (US); Bruce J. Melancon, Nashville, TN (US); Yiu-Yin Cheung, Franklin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 13/692,969

(22) Filed: Dec. 3, 2012

(65) Prior Publication Data

US 2013/0178458 A1    Jul. 11, 2013

Related U.S. Application Data

(60) Provisional application No. 61/584,118, filed on Jan. 6, 2012.

(51) Int. Cl.
| | | |
|---|---|---|
| *C07D 205/00* | (2006.01) | |
| *A01N 43/00* | (2006.01) | |
| *C07D 403/00* | (2006.01) | |
| *C07D 401/00* | (2006.01) | |

(52) U.S. Cl.
USPC ...... 548/950; 514/210.18; 544/364; 544/363; 544/295

(58) Field of Classification Search
None
See application file for complete search history.

(56) References Cited

U.S. PATENT DOCUMENTS 7,439,264 B2 * 10/2008 Meltzer et al. ............ 514/431
2013/0178458 A1     7/2013 Lindsley et al.

FOREIGN PATENT DOCUMENTS

WO  WO-2009/146182 A1   12/2009
WO  WO-2010/086403 A1    8/2010

OTHER PUBLICATIONS

Almarasson O, et al. (2004) Crystal Engineering of the Composition of the Pharmaceutical Phases., Do Pharmaceutical Co-crystals Represent a New Path to Improved Medicines?, Journal of The Royal Society of Chemistry, *Chem. Commun.*, 18891896, 1889-1896.
Lindsley, Craig. (2012) Grant RO1MH082867, submitted on Jul. 2, 2012, pp. 1-14.
Conn, P. Jeffrey. (2009) Grant U01MH087965, submitted on Feb. 23, 2009, pp. 1-39.
Wess J, et al. (2007) Muscarinic acetylcholine receptors: mutant mice provide new insights for drug development, Nature Reviews, 6: 721-733.
Veeraragavan S, et al. (2011) Modulation of behavioral phenotypes by a muscarinic M1 antagonist in a mouse model of fragile; X syndrome. Psychopharmacology, 217(1): 143-151.

* cited by examiner

*Primary Examiner* — James O Wilson
*Assistant Examiner* — Oluwafemi Masha
(74) *Attorney, Agent, or Firm* — Ballard Spahr LLP

(57) ABSTRACT

In one aspect, the invention relates to substituted (1-(methylsulfonyl)azetidin-3-yl)(heterocycloalkyl)methanone analogs, derivatives thereof, and related compounds, which are useful as antagonists of the muscarinic acetylcholine receptor $M_1$ (mAChR $M_1$); synthesis methods for making the compounds; pharmaceutical compositions comprising the compounds; and methods of treating neurological and psychiatric disorders associated with muscarinic acetylcholine receptor dysfunction using the compounds and compositions. This abstract is intended as a scanning tool for purposes of searching in the particular art and is not intended to be limiting of the present invention.

8 Claims, No Drawings

SUBSTITUTED (1-(METHYLSULFONYL)AZETIDIN-3-YL)(HETEROCYCLOALKYL)METHANONE ANALOGS AS ANTAGONISTS OF MUSCARINIC ACETYLCHOLINE M₁ RECEPTORS

CROSS-REFERENCE TO RELATED APPLICATIONS

This application claims the benefit of U.S. Provisional Application No. 61/566,578, filed on Dec. 2, 2011, which is incorporated herein by reference in its entirety.

STATEMENT REGARDING FEDERALLY SPONSORED RESEARCH

This invention was made with U.S. Government support under grant numbers RO1MH082867 and U01 MH087965, awarded by the National Institute of Mental Health (NIMH). The U.S. government has certain rights in the invention.

BACKGROUND

Parkinson's disease (PD) is the second most common neurodegenerative disease with an increasing prevalence as a function of age. Although the precise cause and mechanistic dysfunctions associated with PD are not known, a progressive degeneration and loss of dopaminergic neurons in the substantia nigra is commonly observed, as are the hallmark motor deficits such as bradykinesia, tremor, rigidity, gait dysfunction and postural instability. Presently, levadopa is the standard of care for treating these symptoms; however this treatment is not curative. Prior to levadopa, compounds with anticholinergic activity represented the preferred mode of treatment for PD, however many of their undesirable side effects was believed to be a result of their non-selective antagonist activity across the spectrum of muscarinic acetylcholine receptors. Compounds possessing a more selective profile for the various muscarinic acetylcholine receptors may offer an advantage in restoring the balance between dopamine and acetylcholine in the CNS of PD patients. Along with PD, compounds modulating the muscarinic acetylcholine signaling pathways have been implicated in the treatment of diseases with similar motor symptoms such as, but not limited to, epilepsy, dystonia and fragile X syndrome.

Cholinergic neurotransmission involves the activation of nicotinic acetylcholine receptors (nAChRs) or the muscarinic acetylcholine receptors (mAChRs) by the binding of the endogenous orthosteric agonist acetylcholine (ACh). The historical use of naturally occurring anticholinergic belladonna alkaloids (atropine, scopolamine, etc.) were complicated by the presence of undesirable side effects believed to arise from their non-selective pharmacology across a variety of mAChRs. The mAChRs are widely expressed throughout the body. These mAChRs are members of the family A GPCRs and include five subtypes, designated $M_1$-$M_5$. $M_1$, $M_3$ and $M_5$ mainly couple to $G_q$ and activate phospholipase C whereas $M_2$ and $M_4$ mainly couple to $G_{i/o}$ and associated effector systems. These five distinct mAChR subtypes have been identified in the mammalian central nervous system where they are prevalent and differentially expressed. $M_1$-$M_5$ have varying roles in cognitive, sensory, motor and autonomic functions. The $M_1$ mAChR is found in both the central and peripheral nervous systems, particularly the cerebral cortex and sympathetic ganglia. Thus, without wishing to be bound by theory, it is believed that selective antagonists of various mAChR subtypes that regulate processes involved in neuronal motor function could prove superior to broad spectrum anticholinergics for the treatment of PD and related disorders. Based on the potential role of $M_1$ mAChR in seizure activity and motor control, it has been postulated that highly selective $M_1$ mAChR antagonists may have potential utility in the treatment of some epileptic disorders, as well as certain movement disorders, including PD, dystonia, and fragile X syndrome.

Evidence suggests that the most prominent adverse effects of anticholinergic agents are mediated by peripheral $M_2$ and $M_3$ mAChRs. Because of this, considerable effort has been focused on developing selective $M_1$ antagonists for treatment of PD. Unfortunately, these efforts have been largely unsuccessful because of the high similarity in the orthosteric acetylcholine binding site across the mAChRs. To fully understand the physiological roles of individual mAChR subtypes and to further explore the therapeutic utility of mAChR ligands in PD and other disorders, it is important to develop compounds that are highly selective antagonists of $M_1$ and other individual mAChR subtypes.

Despite advances in muscarinic receptor (mAChR) research, there is still a scarcity of compounds that are potent, efficacious and selective antagonists of the $M_1$ mAChR that are also effective in the treatment of neurological disorders associated with cholinergic activity and diseases in which the muscarinic $M_1$ receptor is involved. These needs and other needs are addressed by the present invention.

SUMMARY

In accordance with the purpose(s) of the invention, as embodied and broadly described herein, the invention, in one aspect, relates to substituted (1-(methylsulfonyl) azetidin-3-yl)(heterocycloalkyl)methanone analogs useful as antagonists of the muscarinic acetylcholine receptor $M_1$ (mAChR $M_1$), methods of making same, pharmaceutical compositions comprising same, and methods of treating neurological and psychiatric disorders associated with muscarinic acetylcholine receptor dysfunction using same.

Disclosed are compounds represented by a formula:

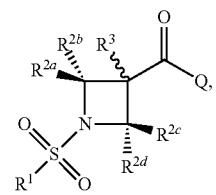

wherein Q is selected from a structure represented by a formula:

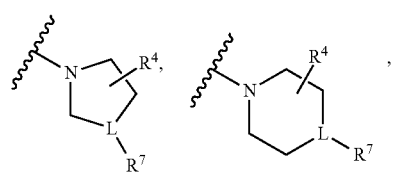

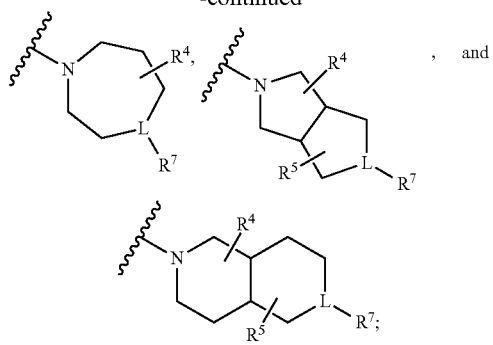

wherein L is N or $CR^6$; wherein $R^1$ is selected from C1-C8 alkyl, C1-C8 haloalkyl, C1-C8 polyhaloalkyl, C3-C8 cycloalkyl, C3-C9 heterocycloalkyl, aryl and heteroaryl; and wherein $R^1$ is substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; wherein each of $R^{2a}$, $R^{2b}$, $R^{2c}$, and $R^{2d}$ is independently selected from hydrogen, C1-C6 alkyl, C1-C6 haloalkyl, and C1-C6 polyhaloalkyl; wherein $R^3$ is selected from hydrogen, C1-C6 alkyl, C1-C6 haloalkyl, and C1-C6 polyhaloalkyl; wherein each occurrence of $R^4$ is independently selected from hydrogen, halogen, cyano, hydroxyl, $-NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein each occurrence of $R^5$ is independently selected from hydrogen, halogen, cyano, hydroxyl, $-NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein $R^6$, when present, is selected from hydrogen, halogen, C1-C6 alkyl, C1-C6 haloalkyl, and C1-C6 polyhaloalkyl; wherein $R^7$ is selected from $Ar^1$ and $Ar^2$; wherein $Ar^1$ is selected from phenyl, indenyl, and napthalenyl; and wherein $Ar^1$ is substituted with 0-3 groups selected from halo, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; wherein $Ar^2$ is a heteroaryl substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino; or a pharmaceutically acceptable salt, solvate, or polymorph thereof.

Also disclosed are pharmaceutical compositions comprising a therapeutically effective amount of one or more disclosed compounds, or pharmaceutically acceptable salt, solvate, or polymorph thereof, and a pharmaceutically acceptable carrier.

Also disclosed are methods for the treatment of a neurological and/or psychiatric disorder associated with muscarinic acetylcholine receptor dysfunction in a mammal comprising the step of administering to the mammal an effective amount of least one disclosed compound or pharmaceutically acceptable salt, solvate, or polymorph thereof.

Also disclosed are methods for inhibition of muscarinic acetylcholine receptor activity in a mammal comprising the step of administering to the mammal an effective amount of at least one disclosed compound or pharmaceutically acceptable salt, solvate, or polymorph thereof.

Also disclosed are methods for inhibition of muscarinic acetylcholine receptor activity in at least one cell, comprising the step of contacting the cell with an effective amount of least one disclosed compound or pharmaceutically acceptable salt, solvate, or polymorph thereof.

Also disclosed are kits comprising at least one disclosed compound, or a pharmaceutically acceptable salt, solvate, or polymorph thereof, and one or more of: (a) at least one agent known to increase mAChR $M_1$ activity; (b) at least one agent known to decrease mAChR $M_1$ activity; (c) at least one agent known to treat a disorder associated with cholinergic activity; (d) instructions for treating a disorder associated with cholinergic activity; (e) instructions for treating a disorder associated with mAChR $M_1$ receptor activity; or (f) instructions for administering the compound in connection with cognitive or behavioral therapy.

Also disclosed are methods for the manufacture of a medicament to inhibit mAChR $M_1$ activity in a mammal comprising combining at least one disclosed compound or at least one disclosed product with a pharmaceutically acceptable carrier or diluent.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthesis methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound If given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "allosteric site" refers to a ligand binding site that is topographically distinct from the orthosteric binding site.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor. For example, the orthosteric site in the mAChR $M_1$ receptor is the site that acetylcholine binds.

As used herein, the term "mAChR $M_1$ receptor antagonist" refers to any exogenously administered compound or agent that is capable of partially or completely inhibiting, or reversing, the effect of an agonist (e.g. acetylcholine) on the mAChR $M_1$ receptor. The term is inclusive of compounds or agents characterized or described as antagonists, partial antagonists, and negative allosteric modulators. For example, mAChR $M_1$ receptor antagonists can mediate their effects by binding to the orthosteric site or to allosteric sites on receptors, or they may interact at unique binding sites not normally involved in the biological regulation of the receptor's activity. Thus, a mAChR $M_1$ receptor antagonist directly or indirectly inhibits the activity of the mAChR $M_1$ receptor in the presence or in the absence of acetylcholine, or another agonist, in an animal, in particular a mammal, for example a human. It is understood that a mAChR $M_1$ receptor antagonist is a type of compound or agent that does not provoke a biological response itself upon binding to the mAChR $M_1$ receptor, but blocks or dampens agonist-mediated responses. Thus, mAChR $M_1$ receptor antagonists have affinity but no efficacy for their cognate receptors, and binding of a mAChR $M_1$ receptor antagonist will disrupt the interaction of the endogenous ligand, an agonist or inverse agonist with mAChR $M_1$ receptors, and thus, inhibit their response to such activators. In various aspects, a mAChR $M_1$ receptor antagonist decreases the activity of the mAChR $M_1$ receptor in a cell in the presence of extracellular acetylcholine. The cell can be Chinese hamster ovary (CHO-K1) cells transfected with human mAChR $M_1$. The cell can be Chinese hamster ovary (CHO-K1) cells transfected with rat mAChR $M_1$ receptor. The cell can be Chinese hamster ovary (CHO-K1) cells transfected with a mammalian mAChR $M_1$. The a compound that is a "mAChR $M_1$ receptor antagonist" includes a compound that is a "mAChR $M_1$ receptor competitive antagonist," a "mAChR $M_1$ receptor noncompetitive antagonist," a "mAChR $M_1$ receptor partial antagonist," and a "mAChR $M_1$ receptor negative allosteric modulator."

As used herein, the term "mAChR $M_1$ receptor competitive antagonist" refers to any exogenously administered compound or agent that is capable of binding to the orthosteric site of mAChR $M_1$ receptors without activating the receptor. Thus, a competitive antagonist can interact with a mAChR $M_1$ receptor and compete with the endogenous ligand, acetylcholine, for binding to the receptor and decrease the ability of the receptor to transduce an intracellular signal in response to endogenous ligand binding.

As used herein, the term "mAChR $M_1$ receptor non-competitive antagonist" refers to any exogenously administered compound or agent that binds to site that is not the orthosteric binding site of mAChR $M_1$ receptors, and is capable of partially or completely inhibiting, or reversing, the effect of an agonist (e.g. acetylcholine) on the mAChR $M_1$ receptor. Thus, a non-competitive antagonist can interact with a mAChR $M_1$ receptor and decrease the binding of the endogenous ligand, acetylcholine, to the receptor and/or decrease the ability of the receptor to transduce an intracellular signal in response to endogenous ligand binding.

As used herein, the term "mAChR $M_1$ partial antagonist" refers to any exogenously administered compound or agent that can bind to a orthosteric or an allosteric site, but the effect of binding is to only partially block effect of mAChR $M_1$ receptor response to an agonist, e.g. acetylcholine. Thus, a non-competitive antagonist can interact with a mAChR $M_1$ receptor and but is not capable of fully inhibiting the response of the mAChR $M_1$ receptor to an agonist, e.g. acetylcholine.

As used herein, the term "mAChR $M_1$ negative allosteric modulator" refers to any exogenously administered compound or agent that binds an allosteric site that directly or indirectly inhibits the activity of the mAChR $M_1$ receptor in the presence of acetylcholine, or another agonist, in an animal, in particular a mammal, for example a human. For example, while not intended to be limiting towards the present invention, a selective muscarinic $M_1$ negative allosteric modulator can preferentially bind to the muscarinic $M_1$ receptor and decrease muscarinic $M_1$ signaling by acting as a non-competitive antagonist. In one aspect, a mAChR $M_1$ receptor negative allosteric modulator decreases the activity of the mAChR $M_1$ receptor in a cell in the presence of extracellular acetylcholine. The cell can be Chinese hamster ovary (CHO-K1) cells transfected with human mAChR $M_1$. The cell can be Chinese hamster ovary (CHO-K1) cells transfected with rat mAChR $M_1$ receptor. The cell can be Chinese hamster ovary (CHO-K1) cells transfected with a mammalian mAChR $M_1$.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment of one or more neurological and/or psychiatric disorder associated with muscarinic acetylcholine receptor dysfunction prior to the administering step. In some aspects of the disclosed method, the subject has been diagnosed with a need for antagonism of muscarinic acetylcholine receptor activity prior to the administering step. In some aspects of the disclosed method, the subject has been diagnosed with a need for antagonism of muscarinic acetylcholine receptor activity prior to the administering step. In some aspects of the disclosed method, the subject has been diagnosed with a neurological and/or psychiatric disorder, e.g. schizophrenia, Parkinson's disease, a cognitive disorder, fragile X syndrome or pain prior to the administering step. In some aspects of the disclosed method, the subject has been identified with a disorder treatable by inhibition of the mAChR $M_1$ receptor and/or or a need for antagonism of mAChR $M_1$ activity prior to the administering step. In some aspects of the disclosed method, the subject has been identified with anxiety or a related disorder prior to the administering step. In one aspect, a subject can be treated prophylactically with a compound or composition disclosed herein, as discussed herein elsewhere.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein. For example, "diagnosed with a disorder treatable by inhibition of mAChR $M_1$" means having been subjected to a physical examination by a person of skill, for example, a physician, and found to have a condition that can be diagnosed or treated by a compound or composition that can diminish, abolish, or inhibit mAChR $M_1$ receptor activity. As a further example, "diagnosed with a need for inhibition of mAChR $M_1$" refers to having been subjected to a physical examination by a person of skill, for example, a physician, and found to have a condition characterized by mAChR $M_1$ activity. Such a diagnosis can be in reference to a disorder, such as a neurodegenerative disease, and the like, as discussed herein. For example, the term "diagnosed with a need for antagonism of muscarinic acetylcholine receptor activity" refers to having been subjected to a physical examination by a person of skill, for example, a physician, and found to have a condition that can be diagnosed or treated by antagonism of muscarinic acetylcholine receptor activity. For example, "diagnosed with a need for inhibition of muscarinic acetylcholine receptor activity" means having been subjected to a physical examination by a person of skill, for example, a physician, and found to have a condition that can be diagnosed or treated by inhibition of muscarinic acetylcholine receptor activity. For example, "diagnosed with a need for treatment of one or more neurological and/or psychiatric disorder associated with acetylcholine dysfunction" means having been subjected to a physical examination by a person of skill, for example, a physician, and found to have one or more neurological and/or psychiatric disorder associated with acetycholine dysfunction.

As used herein, the phrase "identified to be in need of treatment for a disorder," or the like, refers to selection of a subject based upon need for treatment of the disorder. For example, a subject can be identified as having a need for treatment of a disorder (e.g., a disorder related to mAChR $M_1$ activity) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor (e.g. a muscarinic acetylcholine receptor), or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index ($14^{th}$ edition), the Physicians' Desk Reference ($64^{th}$ edition), and The Pharmacological Basis of Therapeutics ($12^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process, including a protein, subunit, organelle, ribonucleoprotein, etc. For example, $EC_{50}$ can refer to the concentration of agonist that provokes a response halfway between the baseline and maximum response in an in vitro assay. Such in vitro assay systems frequently utilize a cell line that either expresses endogenously a target of interest, or has been transfected with a suitable expression vector that directs expression of a recombinant form of the target. For example, the $EC_{50}$ for mAChR $M_1$ can be determined using Chinese hamster ovary (CHO-K1) cells transfected with human mAChR $M_1$. Alternatively, the $EC_{50}$ for mAChR $M_1$ can be determined using Chinese hamster ovary (CHO-K1) cells transfected with rat mAChR $M_1$. In another example, the $EC_{50}$ for mAChR $M_1$ can be determined using Chinese hamster ovary (CHO-K1) cells transfected with a mammalian mAChR $M_1$.

As used herein, "$IC_{50}$," is intended to refer to the concentration of a substance (e.g., a compound or a drug) that is required for 50% inhibition of a biological process, or component of a process, including a protein, subunit, organelle, ribonucleoprotein, etc. For example, $IC_{50}$ refers to the half maximal (50%) inhibitory concentration (IC) of a substance as determined in a suitable assay. For example, an $IC_{50}$ for mAChR $M_1$ receptor can be determined in an in vitro assay system. Frequently, receptor assays, including suitable assays for mAChR $M_1$, make use of a suitable cell-line, e.g. a cell line that either expresses endogenously a target of interest, or has been transfected with a suitable expression vector that directs expression of a recombinant form of the target such as mAChR $M_1$. For example, the $IC_{50}$ for mAChR $M_1$ can be determined using Chinese hamster ovary (CHO-K1) cells transfected with human mAChR $M_1$. Alternatively, the $IC_{50}$ for mAChR $M_1$ can be determined using Chinese hamster ovary (CHO-K1) cells transfected with rat mAChR $M_1$. In another example, the $IC_{50}$ for mAChR $M_1$ can be determined using Chinese hamster ovary (CHO-K1) cells transfected with a mammalian mAChR $M_1$.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group", as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain $(4n+2)\pi$ electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein. The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C═O.

The terms "amine" or "amino" as used herein are represented by the formula $NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —NH2.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)$A^1$ or —C(O)O$A^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula -($A^1$O(O)C-$A^2$-C(O)O)$_a$— or -($A^1$O(O)C-$A^2$-OC(O))$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula -($A^1$O-$A^2$O)$_a$—, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo", "halogen" or "halide", as used herein can be used interchangeably and refer to F, Cl, Br, or I.

The terms "pseudohalide", "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl", as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, 1,2-oxazol-4-yl, 1,2-oxazol-5-yl, 1,3-oxazolyl, 1,2,4-oxadiazol-5-yl, 1,2,3-triazolyl, 1,3-thiazol-4-yl, pyridinyl, and pyrimidin-5-yl.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" as used herein is represented by the formula —$N_3$.

The term "nitro" as used herein is represented by the formula —$NO_2$.

The term "nitrile" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, —$S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R°$; —$(CH_2)_{0-4}OR°$; —$O(CH_2)_{0-4}R°$, —O—$(CH_2)_{0-4}C(O)OR°$; —$(CH_2)_{0-4}$—$CH(OR°)_2$; —$(CH_2)_{0-4}SR°$; —$(CH_2)_{0-4}Ph$, which may be substituted with $R°$; —$(CH_2)_{0-4}O(CH_2)_{0-1}Ph$ which may be substituted with $R°$; —CH=CHPh, which may be substituted with $R°$;

—(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —) N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched)alkylene)O—N(R°)$_2$; or —(C$_{1-4}$ straight or branched alkylene)C(O)O—N(R$^{602}$)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, —(haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$^\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet_2$, —NO$_2$, —SiR$^\bullet_3$, —OSiR$^\bullet_3$, —C(O)SR$^\bullet$, —(C$_{1-4}$ straight or branched alkylene)C(O)OR$^\bullet$, or —SSR$^\bullet$, wherein each R$^\bullet$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^\bullet$, -(haloR$^\bullet$), —OH, —OR$^\bullet$, —O(haloR$^\bullet$), —CN, —C(O)OH, —C(O)OR$^\bullet$, —NH$_2$, —NHR$^\bullet$, —NR$^\bullet_2$, or —NO$_2$, wherein each R$^\bullet$ is unsubstituted or where preceded by "halo" is substituted only with one or more halogens, and is independently C$_1$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^\dagger$, —NR$^\dagger_2$, —C(O)R$^\dagger$, —C(O)OR$^\dagger$, —C(O)C(O)R$^\dagger$, —C(O)CH$_2$C(O)R$^\dagger$, —S(O)$_2$R$^\dagger$, —S(O)$_2$NR$^\dagger_2$, —C(S)NR$^\dagger_2$, —C(NH)NR$^\dagger_2$, or —N(R$^\dagger$)S(O)$_2$R$^\dagger$; wherein each R$^\dagger$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^\dagger$ are independently halogen, —R$^\dagger$, -(haloR$^\dagger$), —OH, —OR$^\dagger$, —O(haloR$^\dagger$), —CN, —C(O)OH, —C(O)OR$^\dagger$, —NH$_2$, —NHR$^\dagger$, —NR$^\dagger_2$, or —NO$_2$, wherein each R$^\dagger$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

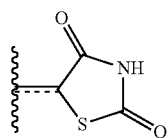

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthesis procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvate or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

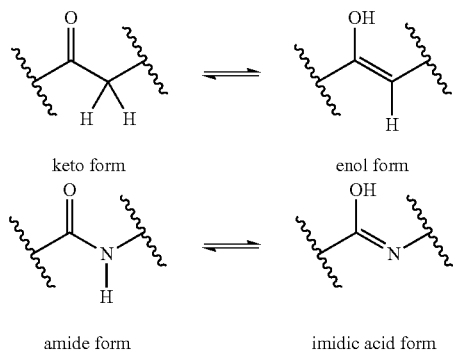

keto form      enol form amide form      imidic acid form

Likewise, amides with an N-hydrogen can exist in an equilibrium of the amide form and the imidic acid form. As another example, pyrazoles can exist in two tautomeric forms, $N^1$-unsubstituted, 3-$R^3$ and $N^1$-unsubstituted, 5-$R^3$ as shown below.

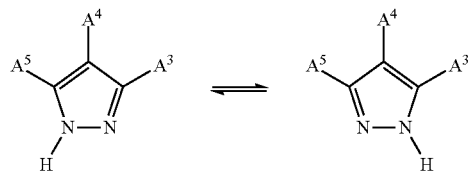

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

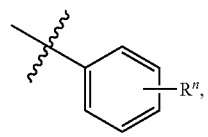

which is understood to be equivalent to a formula:

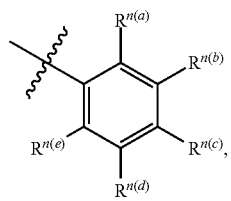

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as inhibitors of the muscarinic acetylcholine receptor $M_1$ (mAChR $M_1$). More specifically, in one aspect, the present invention relates to compounds that are antagonists of the mAChR $M_1$ receptor. The compounds can, in one aspect, exhibit subtype selectivity.

In one aspect, the disclosed compounds exhibit antagonism of mAChR $M_1$ response to acetylcholine as an decrease in response to acetylcholine in Chinese hamster ovary (CHO-K1) cells transfected with rat mAChR $M_1$ in the presence of the compound, compared to the response to acetylcholine in the absence of the compound. In further aspect, the Chinese hamster ovary (CHO-K1) cells are transfected with human mAChR $M_1$ instead of rat mAChR $M_1$. In yet a further aspect, Chinese hamster ovary (CHO-K1) cells are transfected with a mammalian mAChR $M_1$, e.g. a mouse mAChR $M_1$, instead of rat mAChR $M_1$.

In one aspect, the compounds of the invention are useful in the treatment of neurological and/or psychiatric disorders associated with muscarinic acetylcholine receptor dysfunction and other diseases in which muscarinic acetylcholine receptors are involved, as further described herein.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

In one aspect, the invention relates to a compound having a structure represented by a formula:

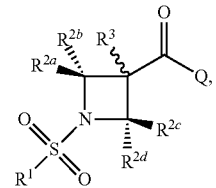

wherein Q is selected from a structure represented by a formula:

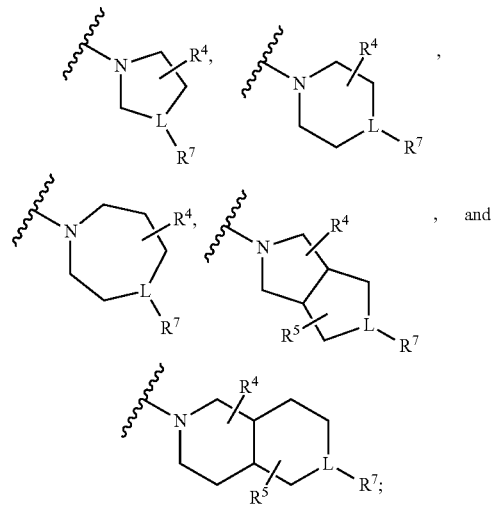

wherein L is N or $CR^6$; wherein $R^1$ is selected from C1-C8 alkyl, C1-C8 haloalkyl, C1-C8 polyhaloalkyl, C3-C8 cycloalkyl, C3-C9 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino; wherein each of $R^{2a}$, $R^{2b}$, $R^{2c}$, and $R^{2d}$ is independently selected from hydrogen, C1-C6 alkyl, C1-C6 haloalkyl, and C1-C6 polyhaloalkyl; wherein $R^3$ is selected from hydrogen, C1-C6 alkyl, C1-C6 haloalkyl, C1-C6 polyhaloalkyl; wherein each occurrence of $R^4$ is independently selected from hydrogen, halogen, cyano, hydroxyl, —NH$_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein each occurrence of R$^5$ is independently selected from hydrogen, halogen, cyano, hydroxyl, —NH$_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino; wherein R$^6$, when present, is selected from hydrogen, halogen, C1-C6 alkyl, C1-C6 haloalkyl, and C1-C6 polyhaloalkyl; wherein R$^7$ is selected from Ar$^1$ and Ar$^2$; wherein Ar$^1$ is selected from phenyl, indenyl, and napthalenyl; and wherein Ar$^1$ is substituted with 0-3 groups selected from halo, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; wherein Ar$^2$ is a heteroaryl substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; or a pharmaceutically acceptable salt, solvate, or polymorph thereof.

In a further aspect, a compound can have a structure listed herein. In a further aspect, the compounds can be selected from two or more of the structures listed herein.

In a further aspect, the invention relates to a compound having a structure represented by a formula:

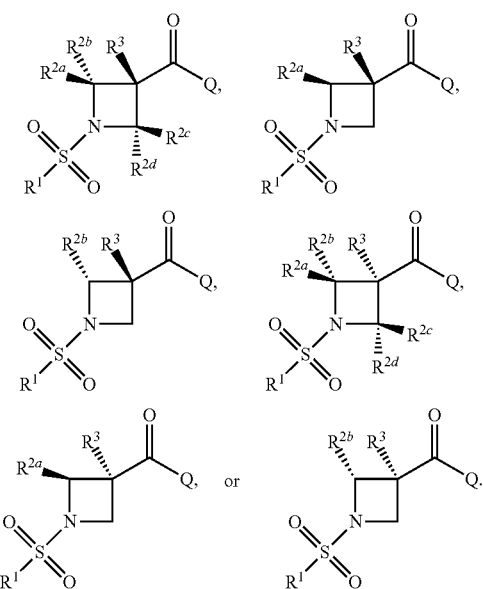

In a further aspect, the compound has a structure represented by a formula listed below:

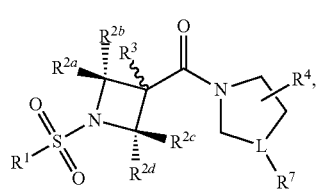

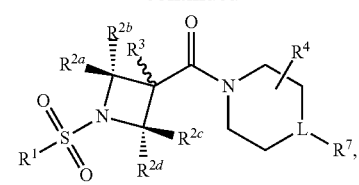

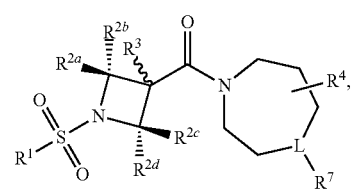

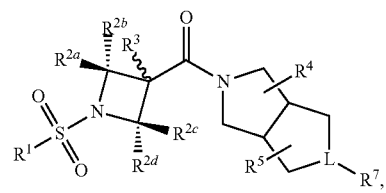

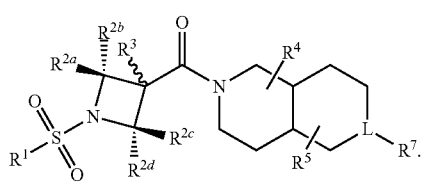

In a further aspect, the compound has a structure represented by a formula listed below:

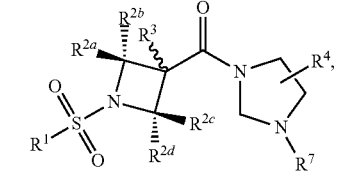

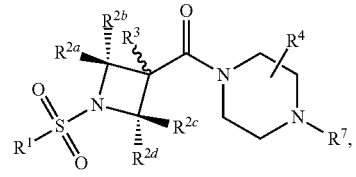

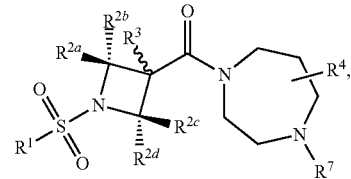

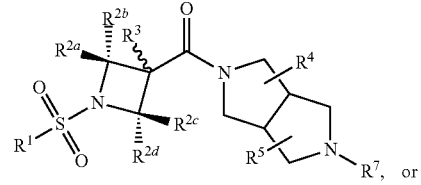

-continued

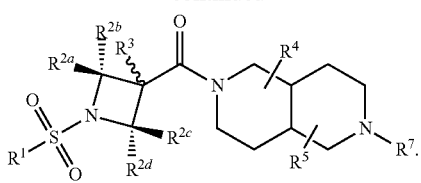

In a further aspect, the compound has a structure represented by a formula listed below:

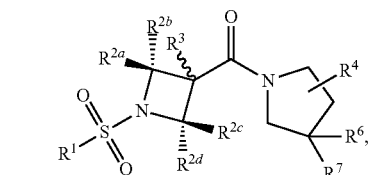

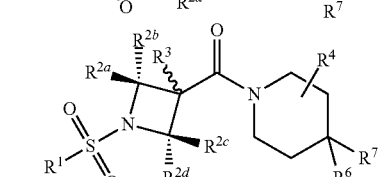

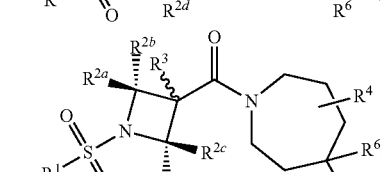

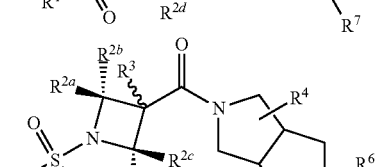

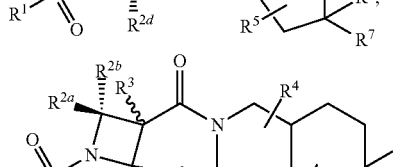

In a further aspect, the compound has a structure represented by a formula listed below:

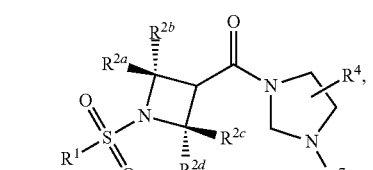

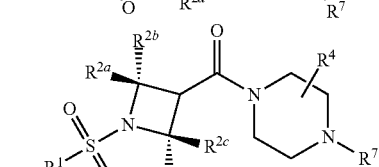

-continued

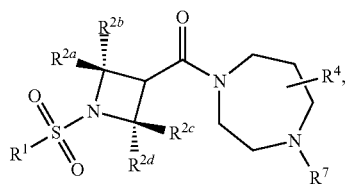

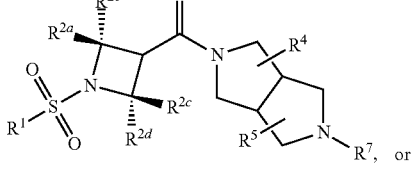

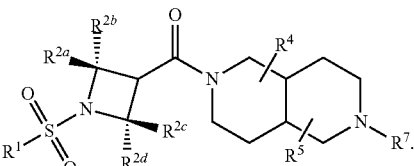

In a further aspect, the compound has a structure represented by a formula listed below:

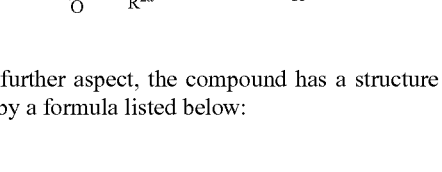

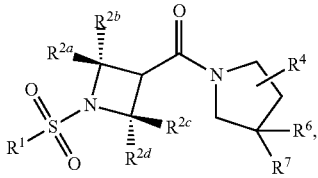

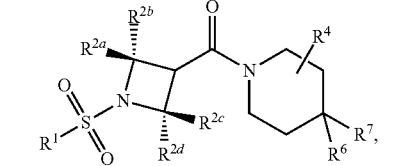

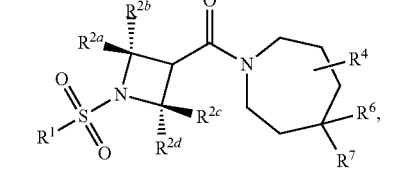

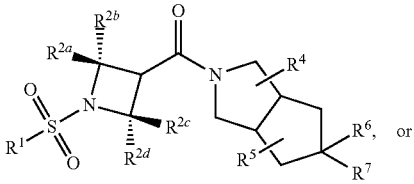

In a further aspect, the compound has a structure represented by a formula listed below:

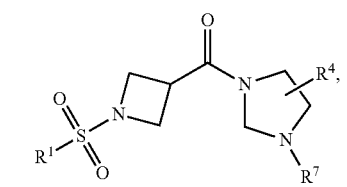
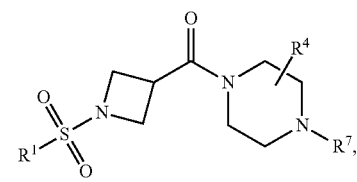
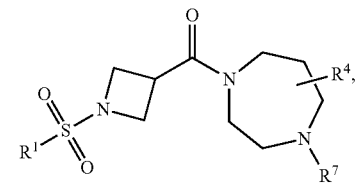
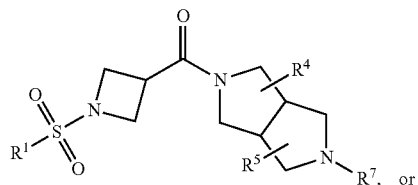
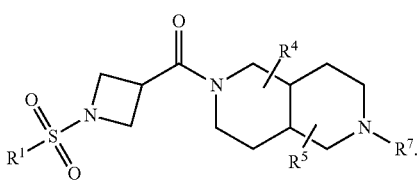
In a further aspect, the compound has a structure represented by a formula listed below:
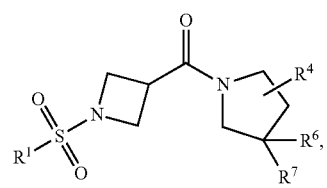
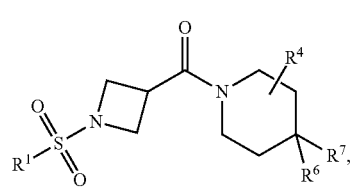
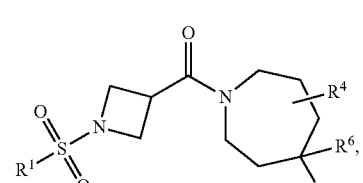
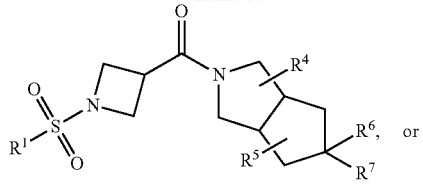
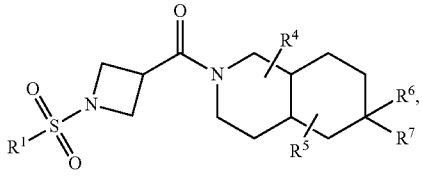
In a further aspect, the compound has a structure represented by a formula listed below:
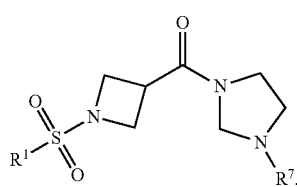
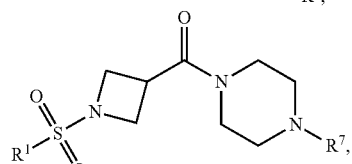
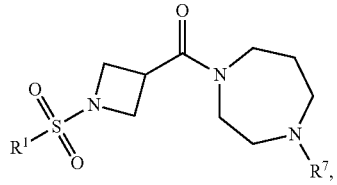
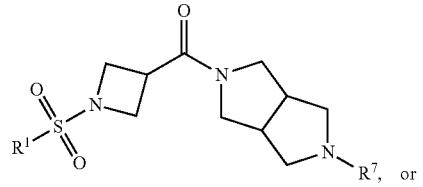
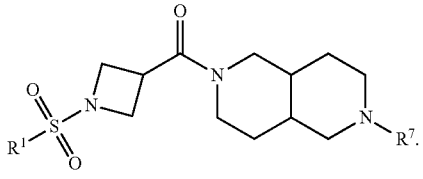
In a further aspect, the compound has a structure represented by a formula listed below:
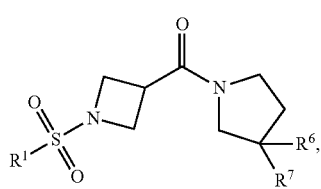

-continued

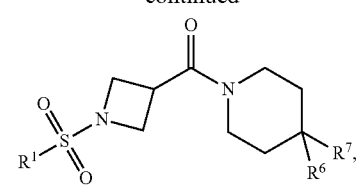

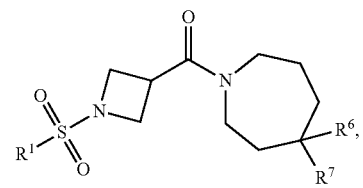

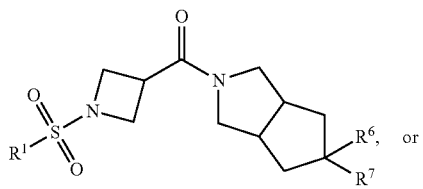

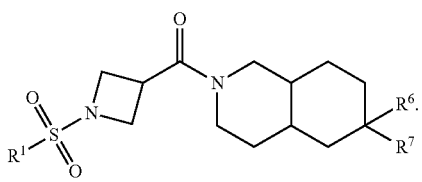

In a further aspect, the compound has a structure represented by a formula listed below:

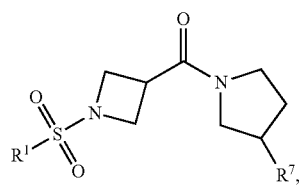

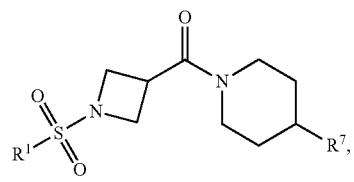

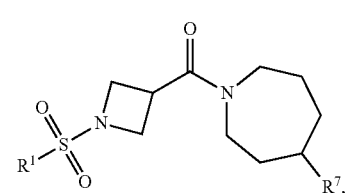

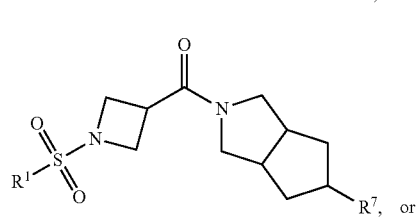

-continued

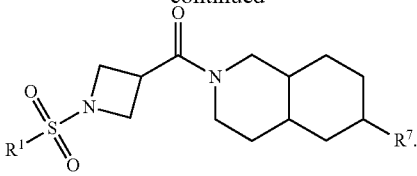

In a further aspect, the compound has a structure represented by a formula:

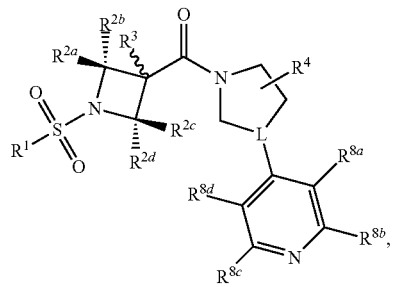

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

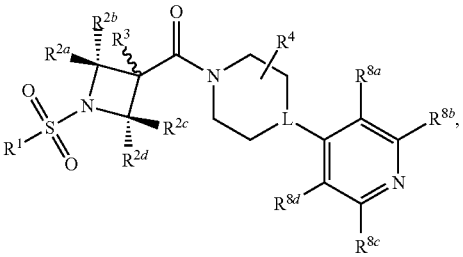

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

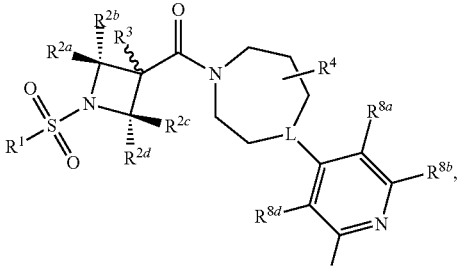

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

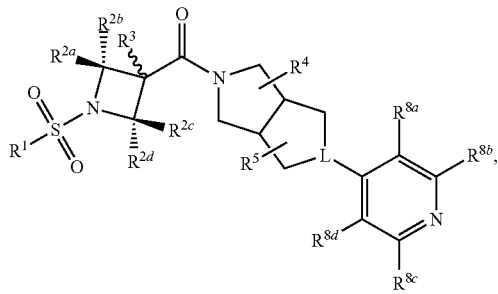

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

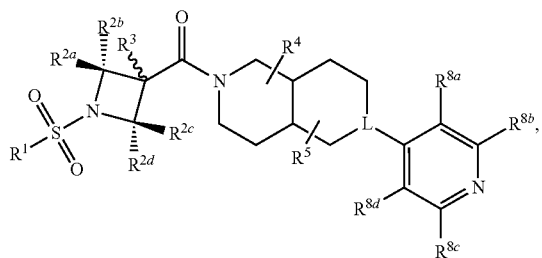

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

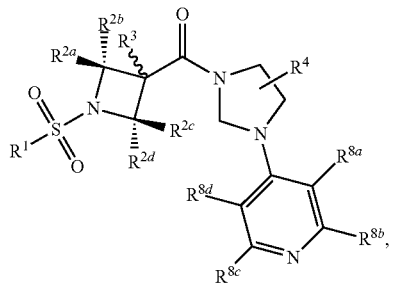

wherein each of $R^{8a}$, $R^{8b}$, $R^{8c}$ and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

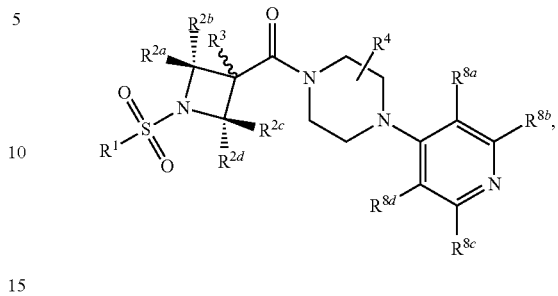

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

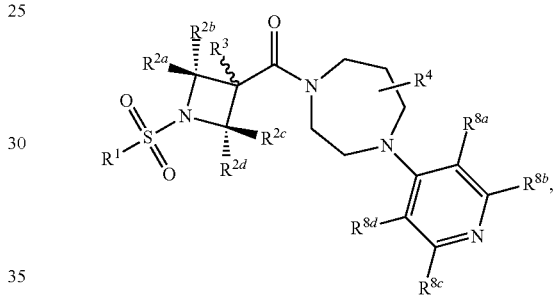

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

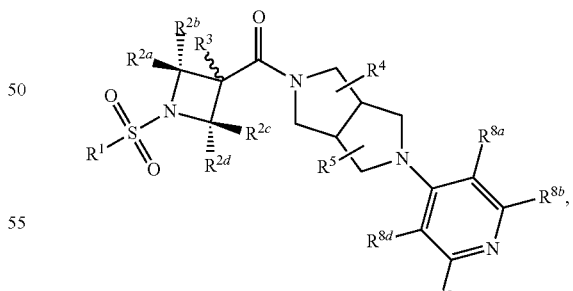

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

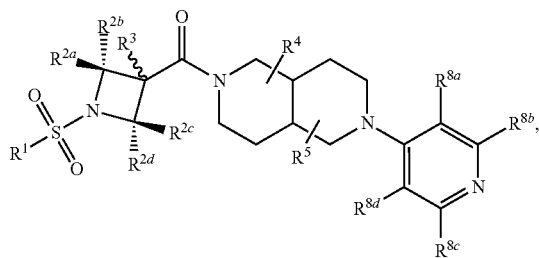

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

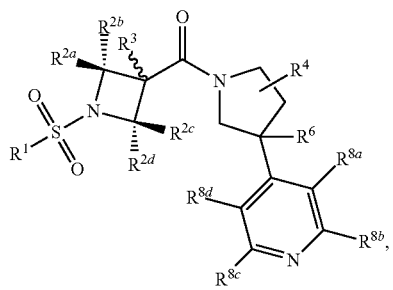

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

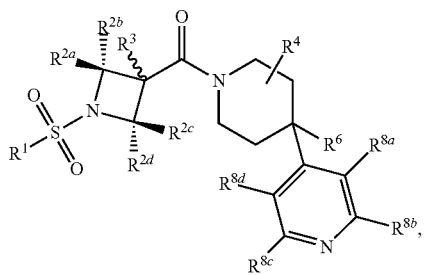

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

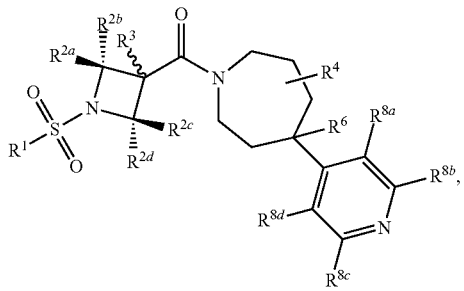

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

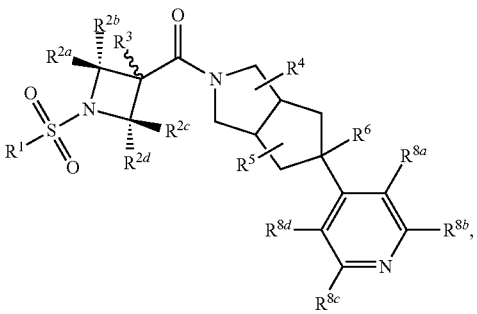

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

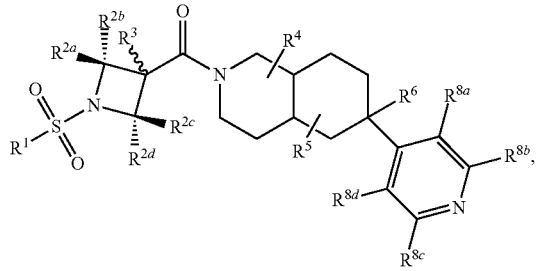

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

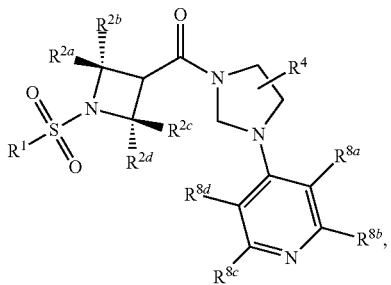

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

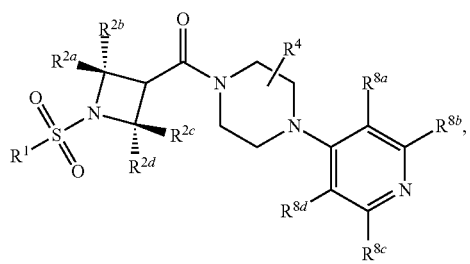

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

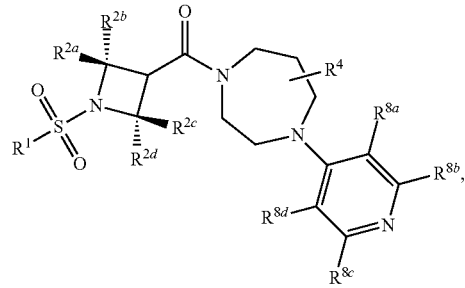

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

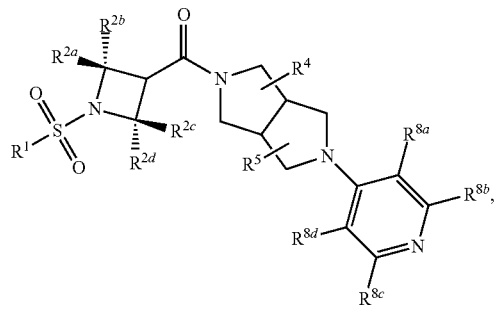

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

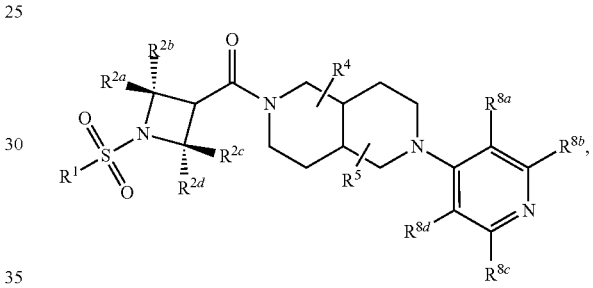

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

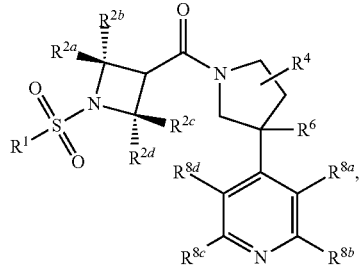

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

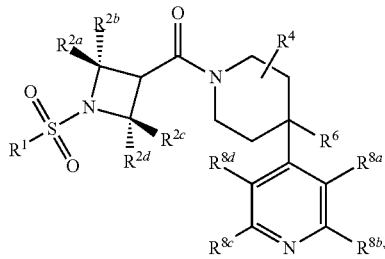

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

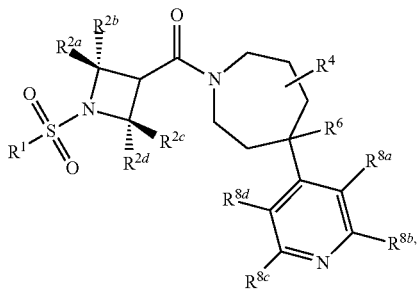

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

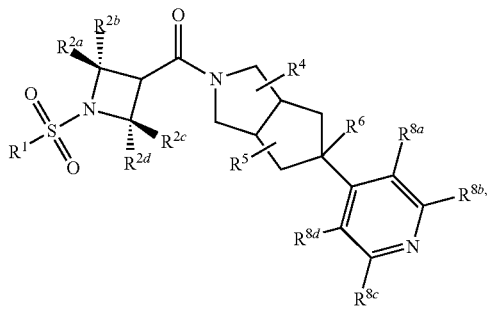

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

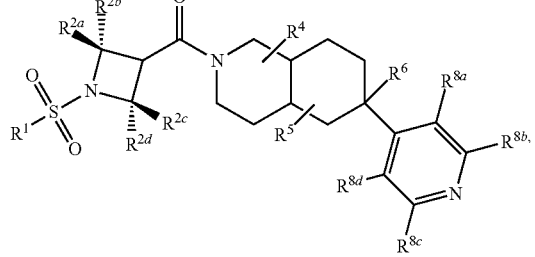

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

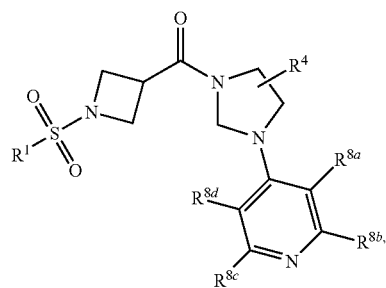

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

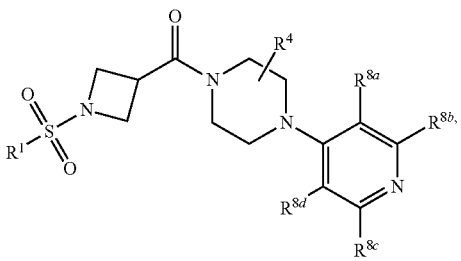

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

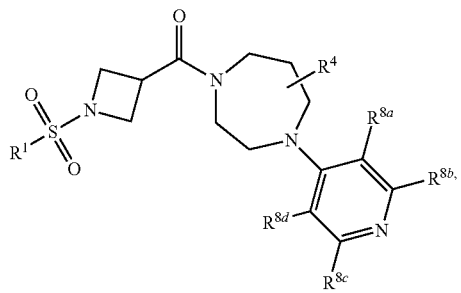

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

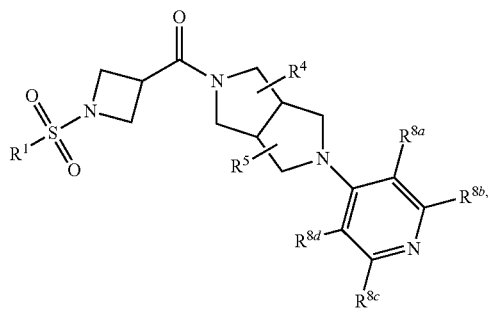

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

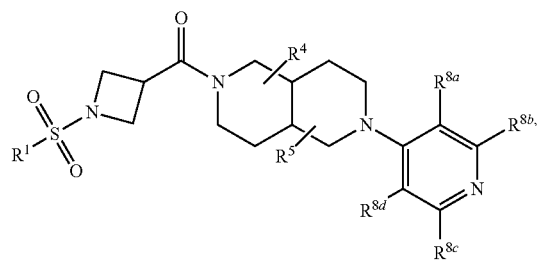

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

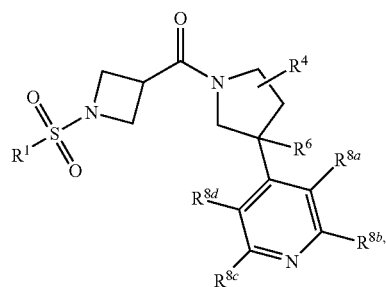

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

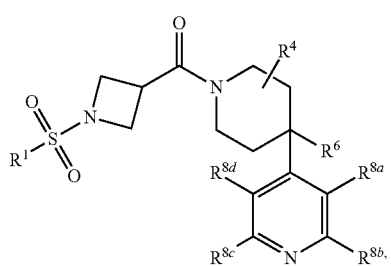

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

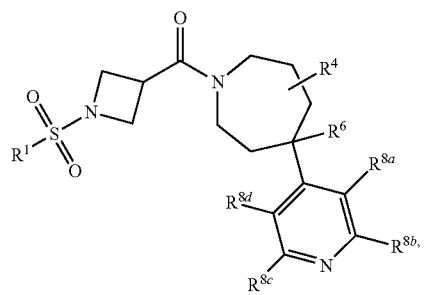

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

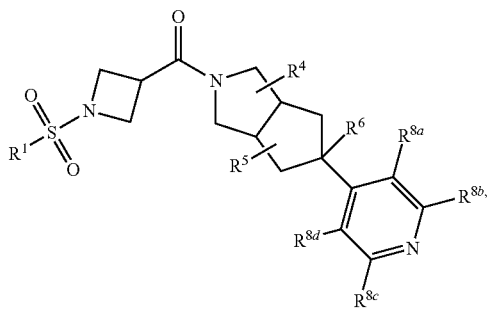

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

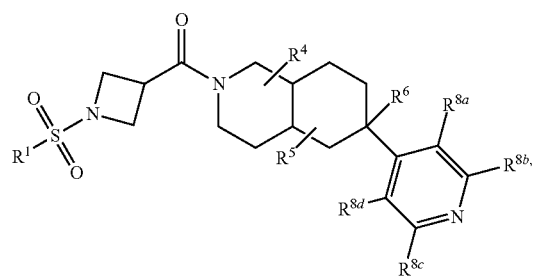

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

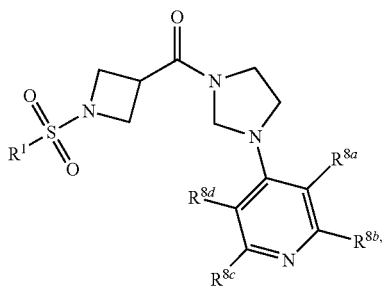

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

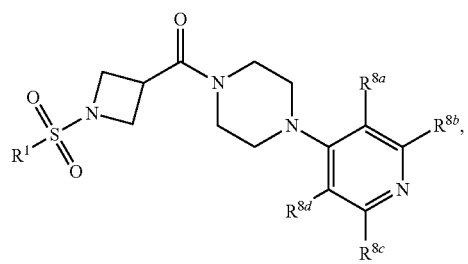

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

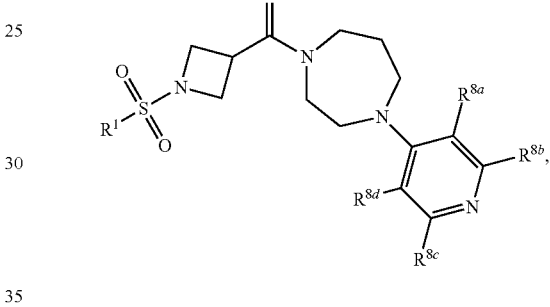

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

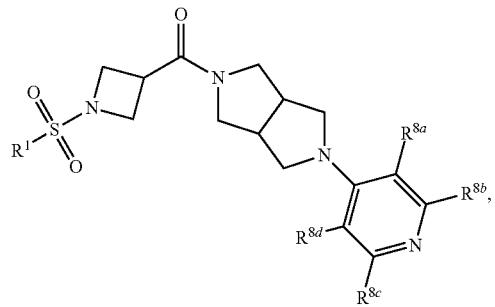

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

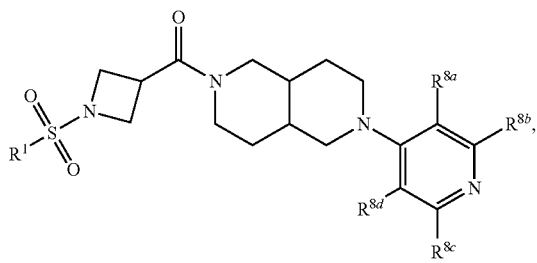

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

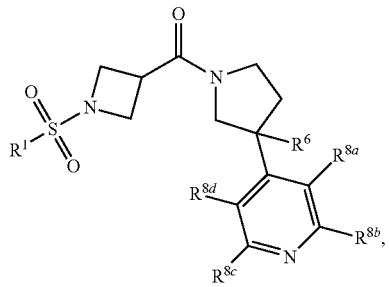

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

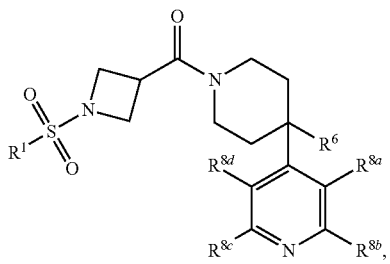

wherein each of $R^{8a}$, $R^{8b}$, $R^{8c}$ and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

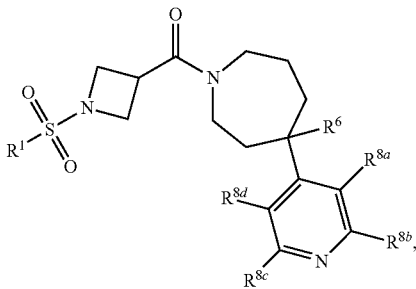

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

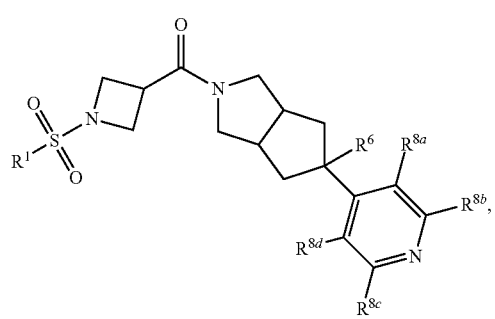

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$ and $R^{8d}$ is hydrogen.

In a further aspect, the compound has a structure represented by a formula:

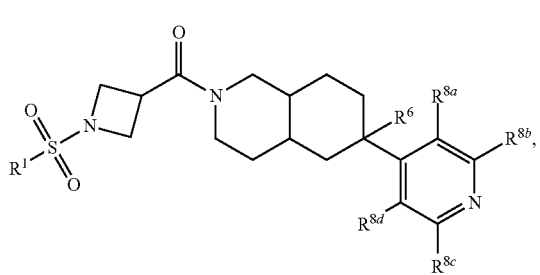

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

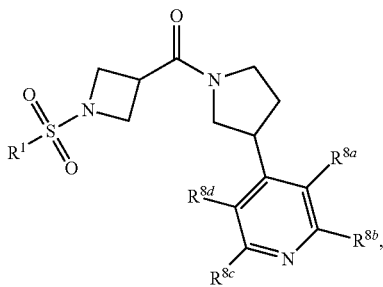

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

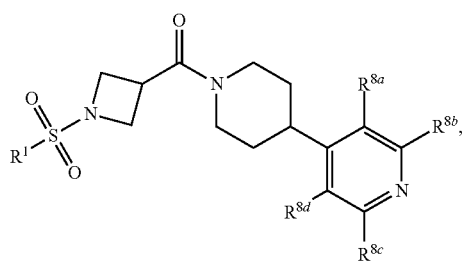

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

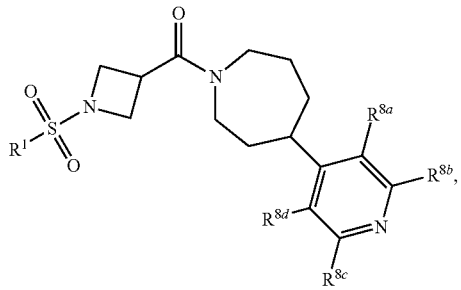

wherein each of $R^{8a}$, $R^{8b}$, $R^{8c}$ and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

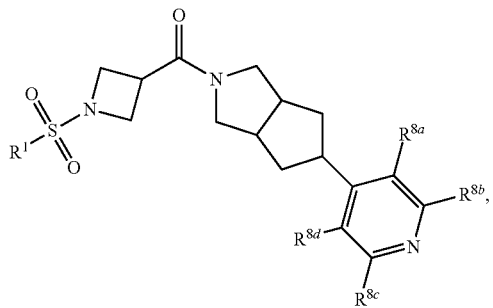

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

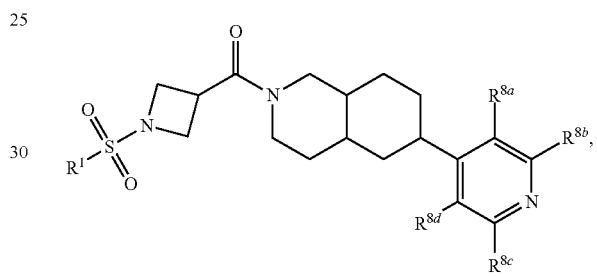

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen.

In a further aspect, the compound has a structure represented by a formula:

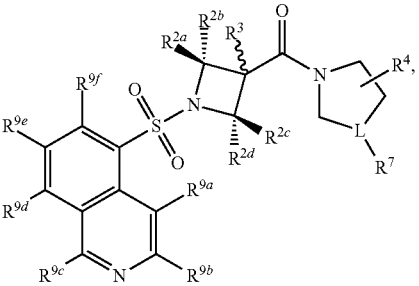

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

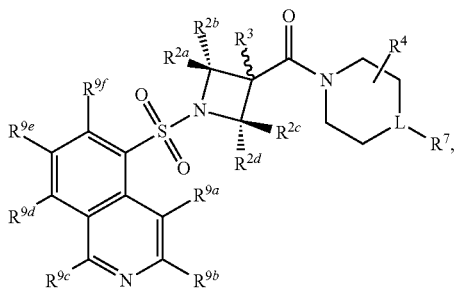

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

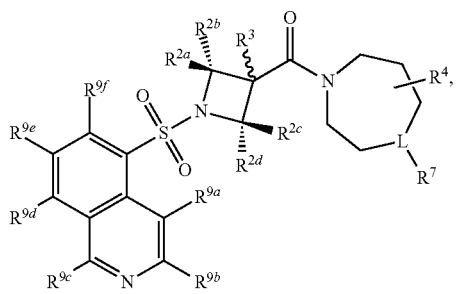

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

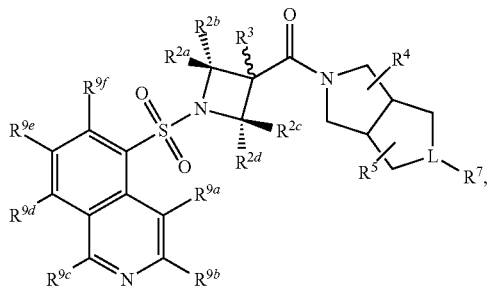

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

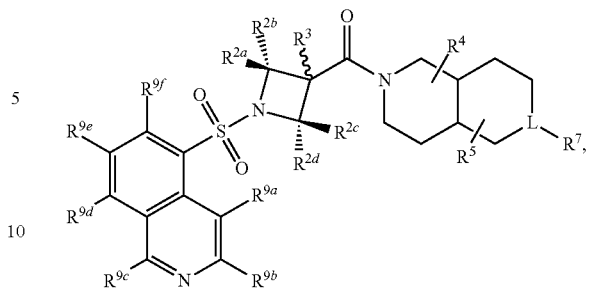

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

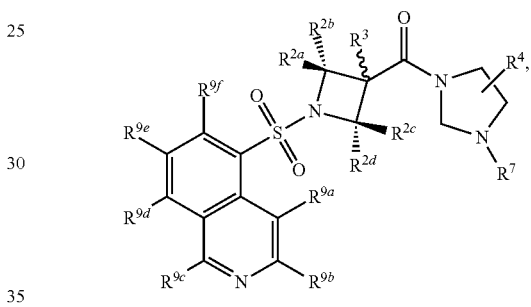

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

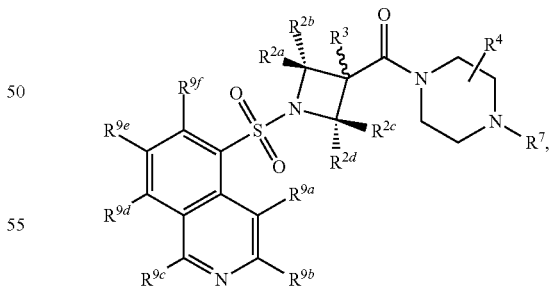

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

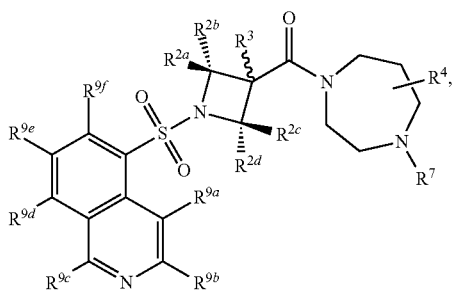

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

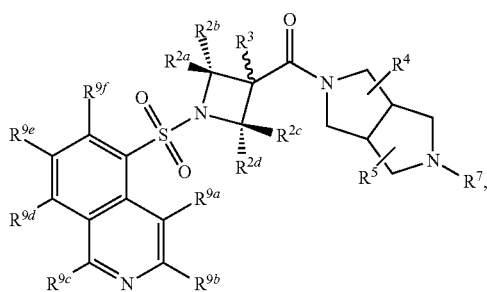

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

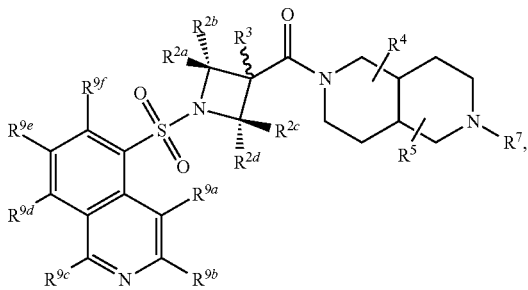

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

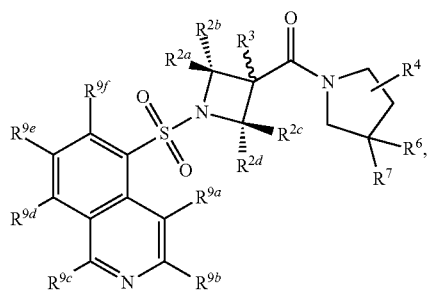

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

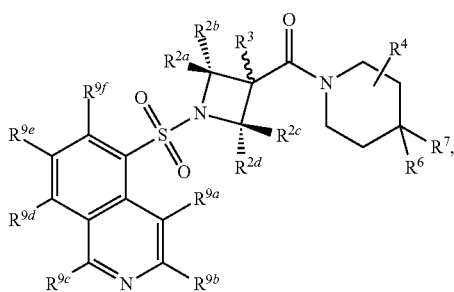

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

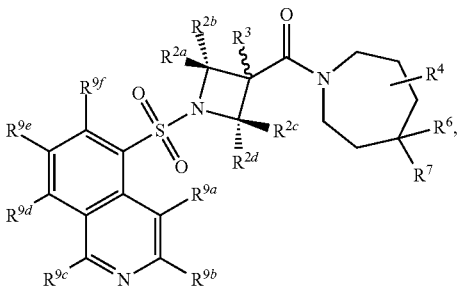

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

55

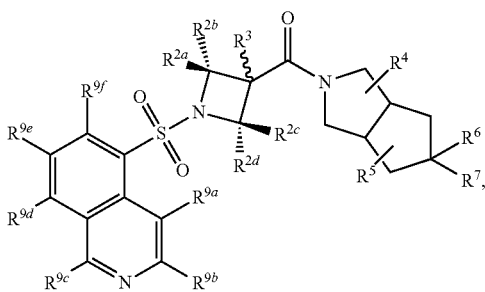

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

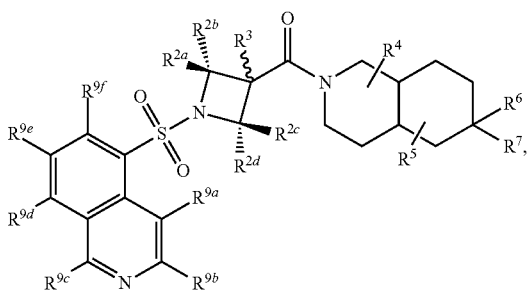

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

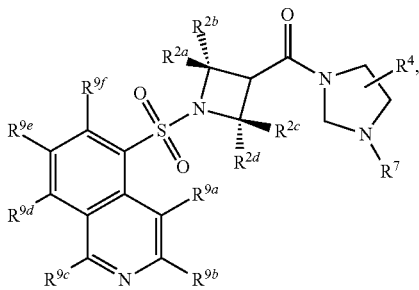

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

56

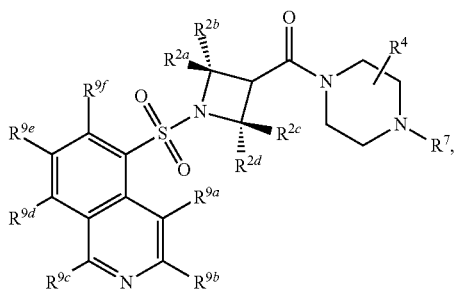

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

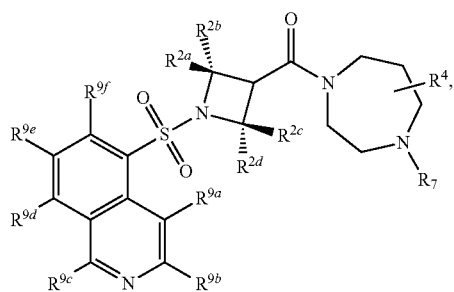

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

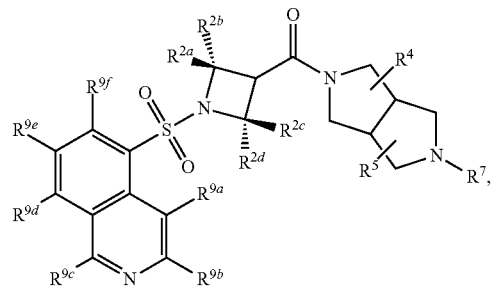

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

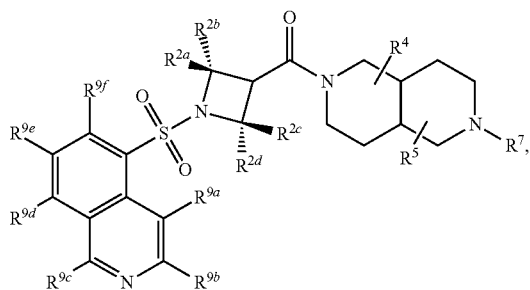

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

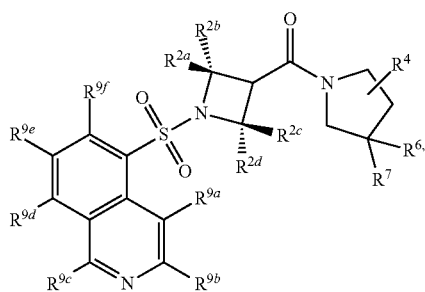

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

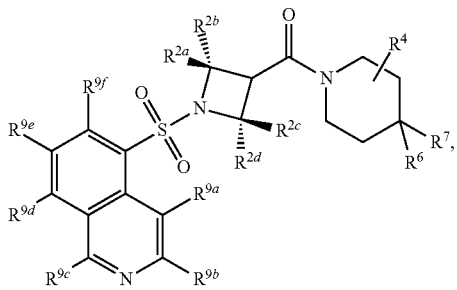

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

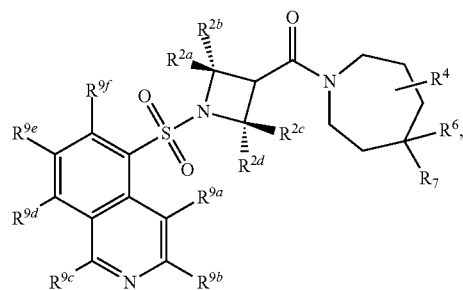

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

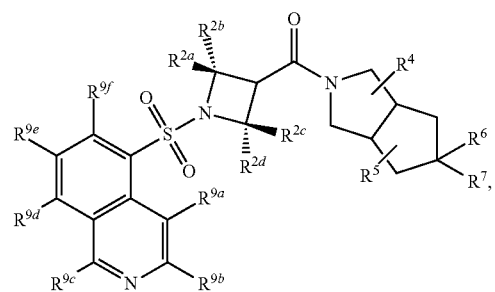

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

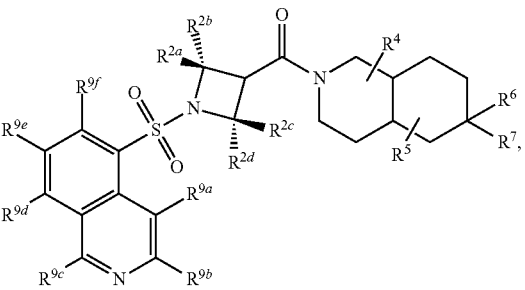

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

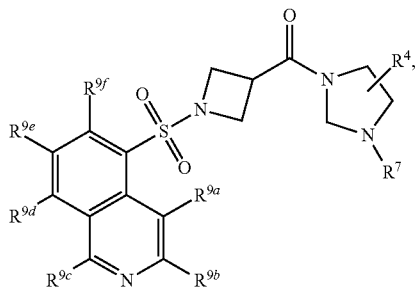

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

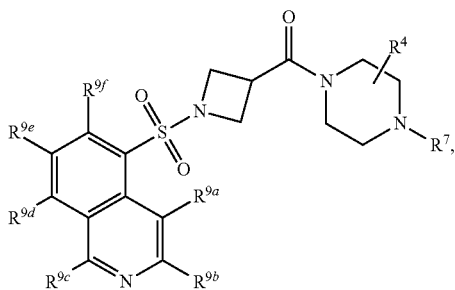

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

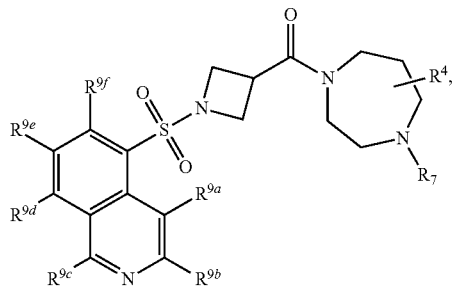

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

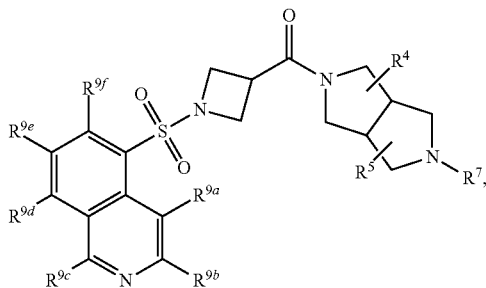

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

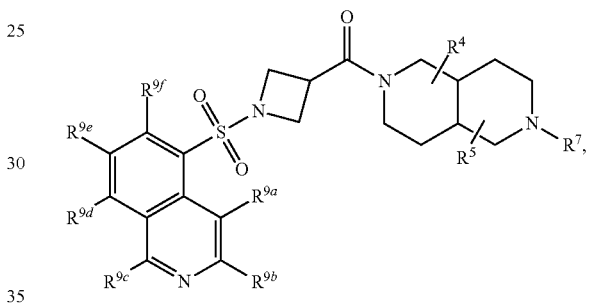

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

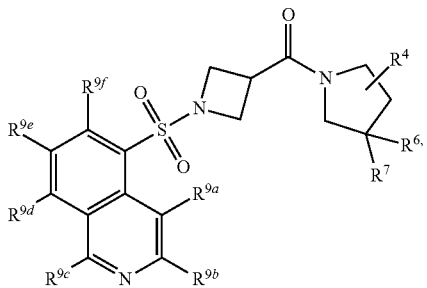

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

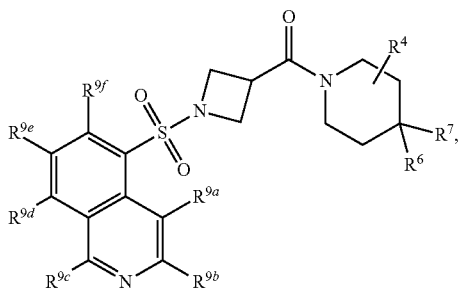

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

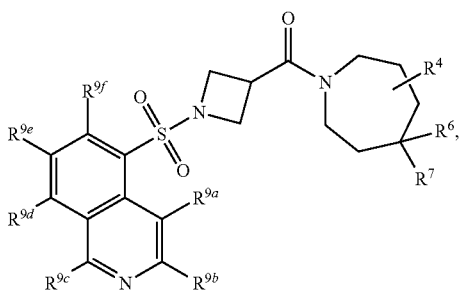

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

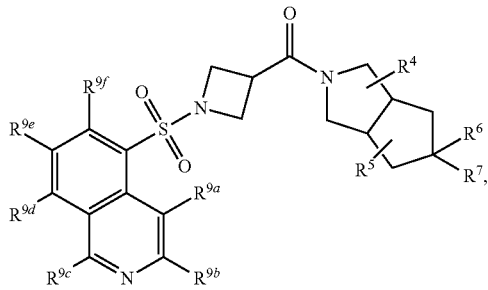

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

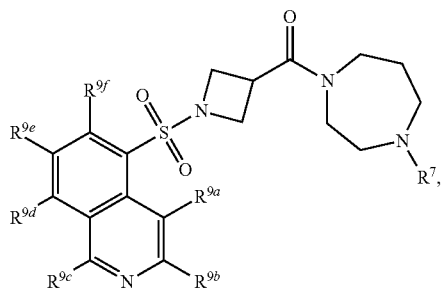

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

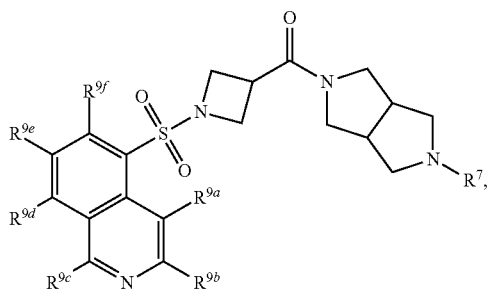

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

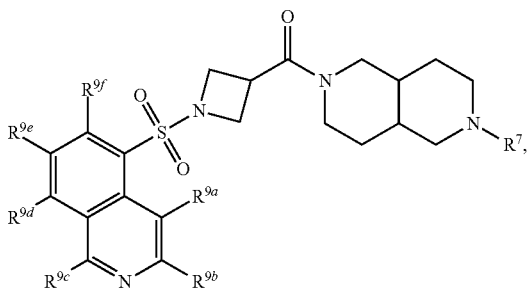

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

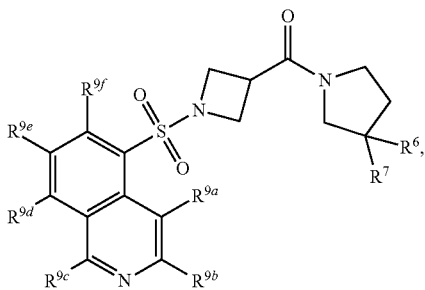

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

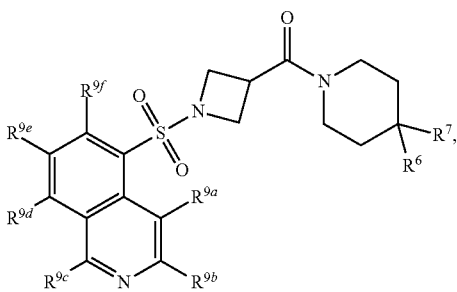

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

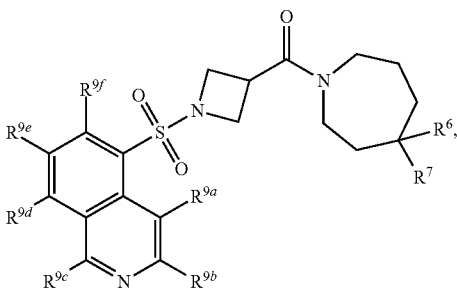

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

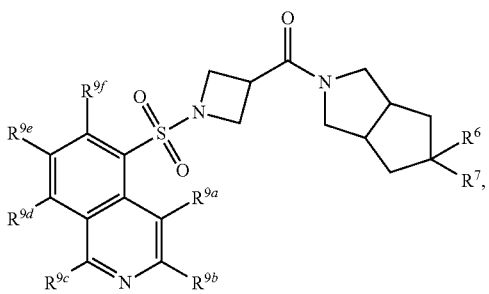

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

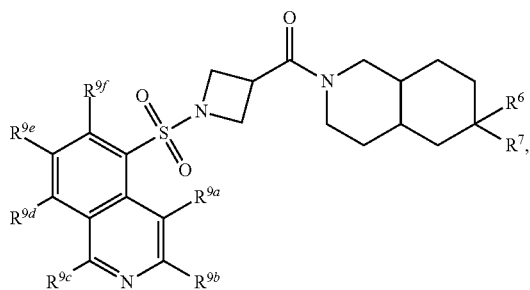

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

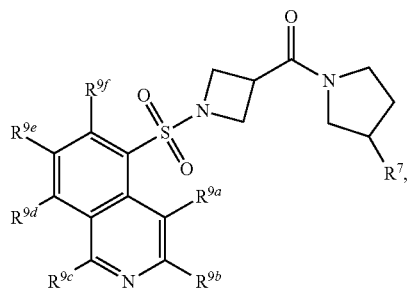

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

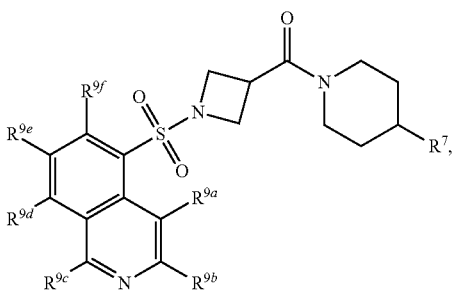

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

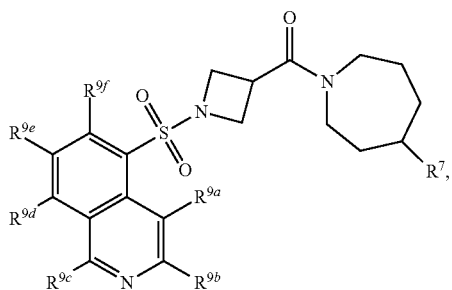

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

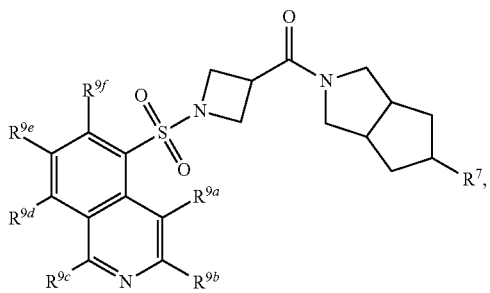

wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

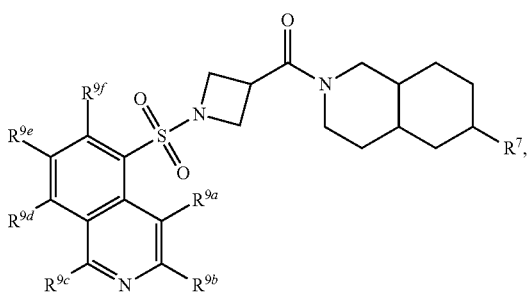

wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

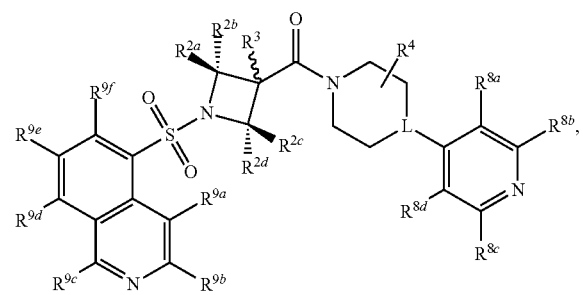

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

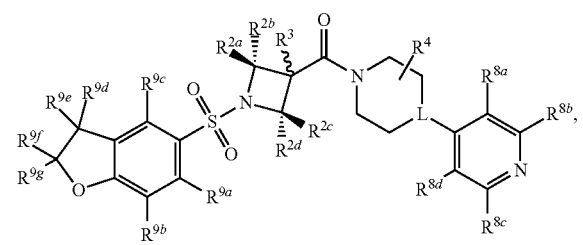

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

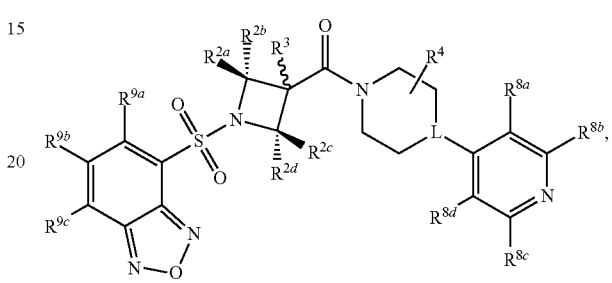

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

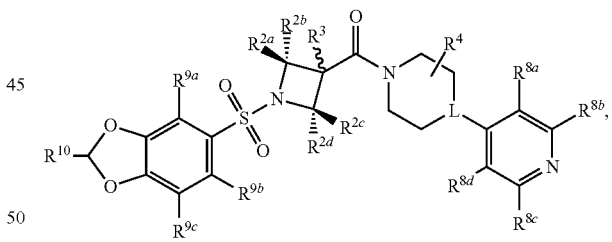

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

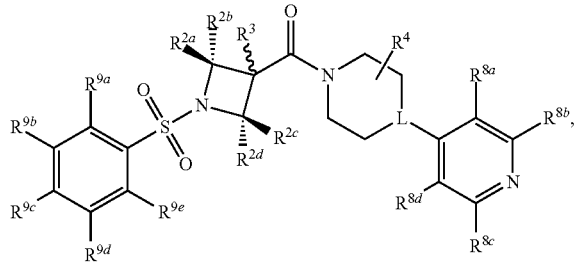

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9a}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

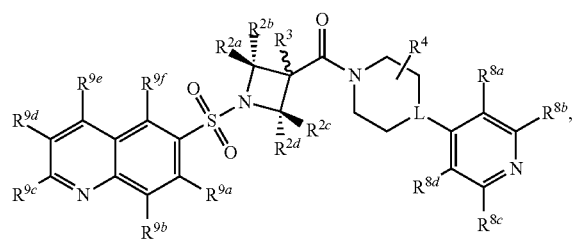

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

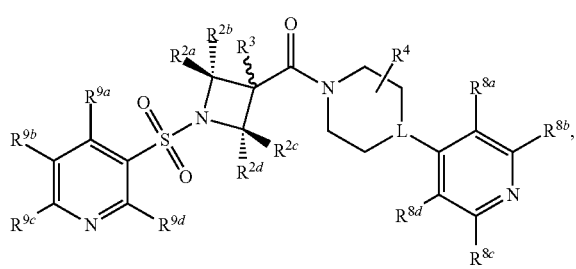

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

In a further aspect, the compound has a structure represented by a formula:

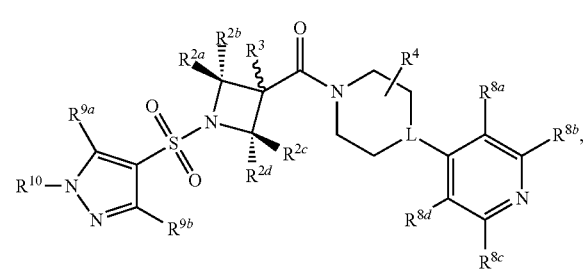

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$ and $R^{9b}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

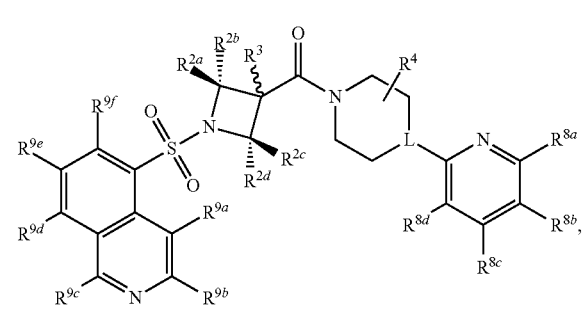

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

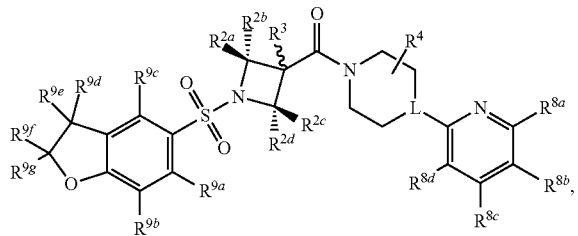

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

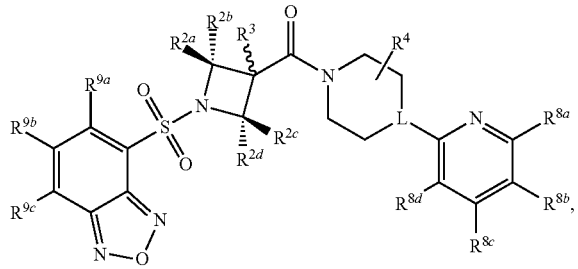

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a further aspect, the compound has a structure represented by a formula:

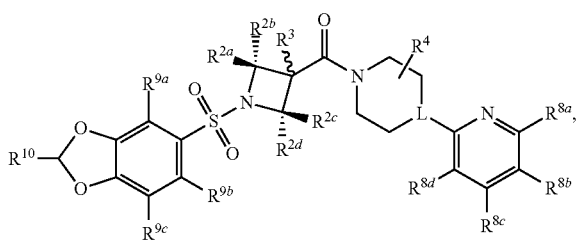

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

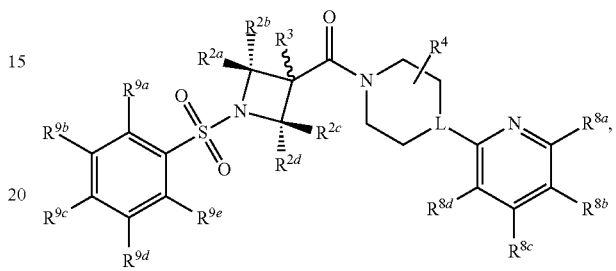

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

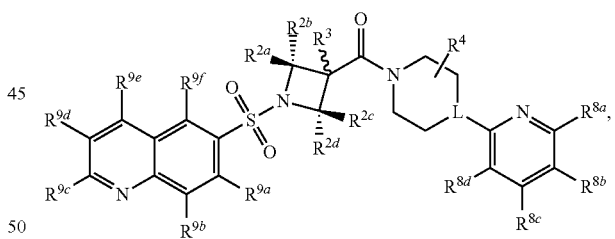

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

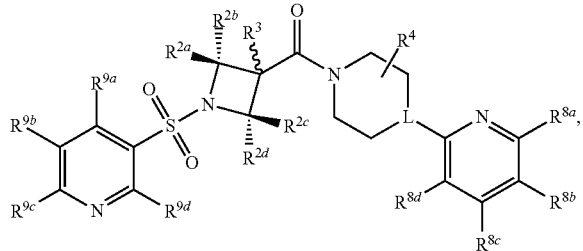

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

In a further aspect, the compound has a structure represented by a formula:

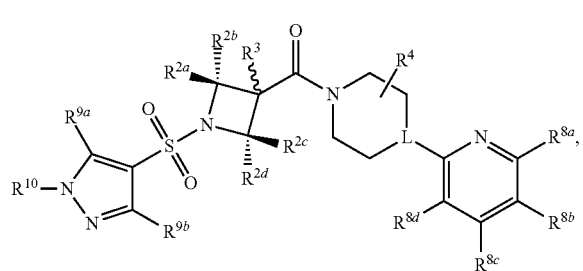

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$ and $R^{9b}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

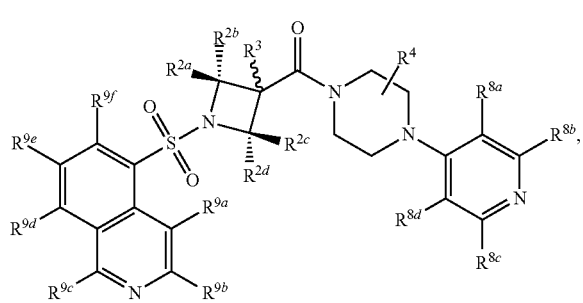

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

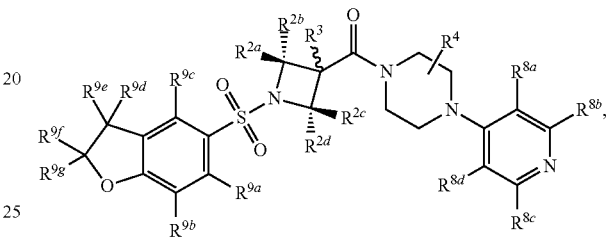

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

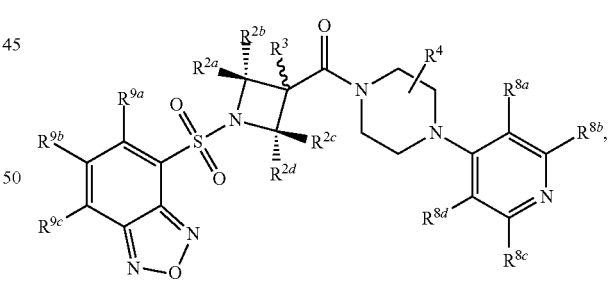

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

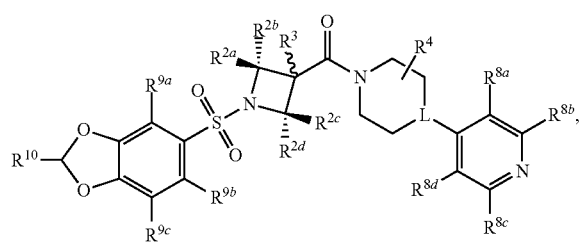

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

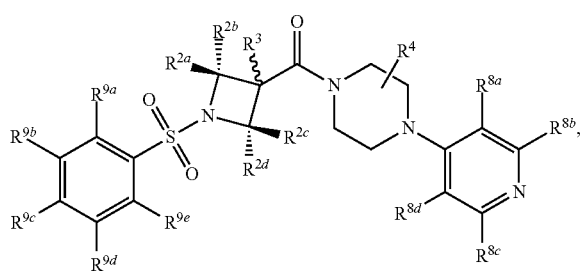

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

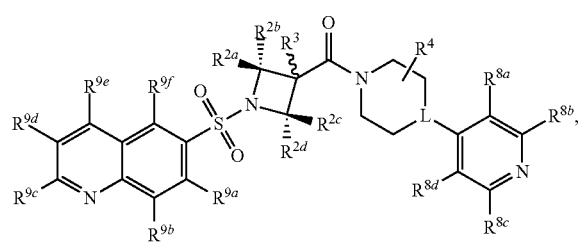

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

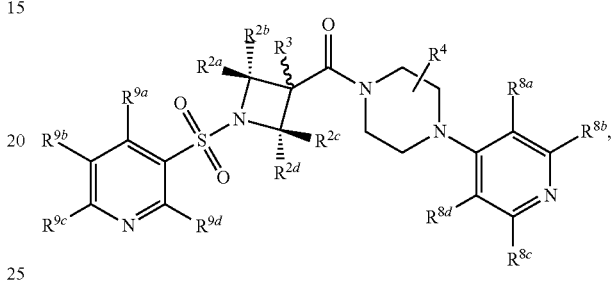

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9a}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9a}$, and $R^{9d}$ is hydrogen.

In a further aspect, the compound has a structure represented by a formula:

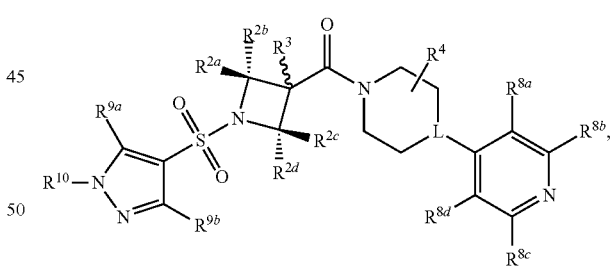

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$ and $R^{9b}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

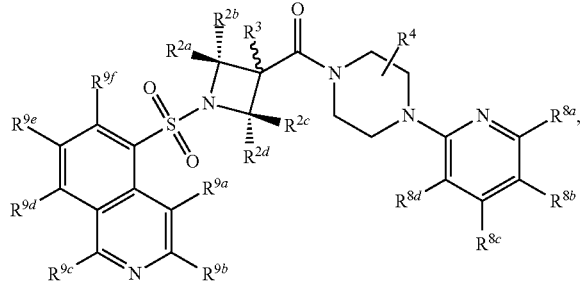

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

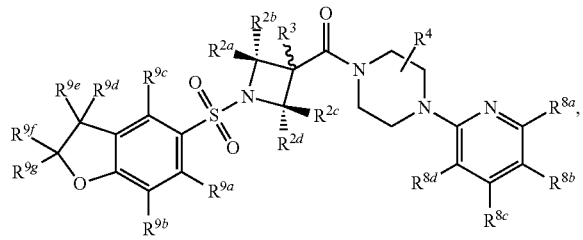

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

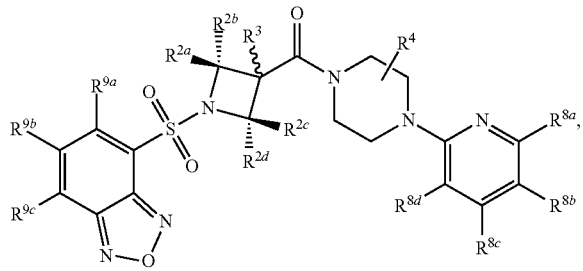

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

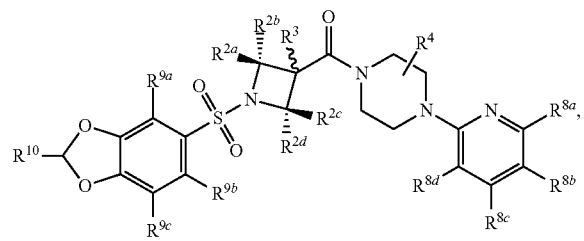

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

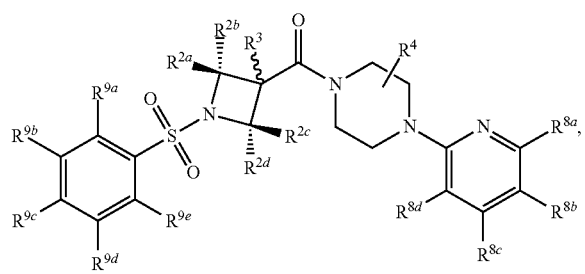

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9a}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9a}$, $R^{9d}$, and $R^{9e}$ are hydrogen.

In a further aspect, the compound has a structure represented by a formula:

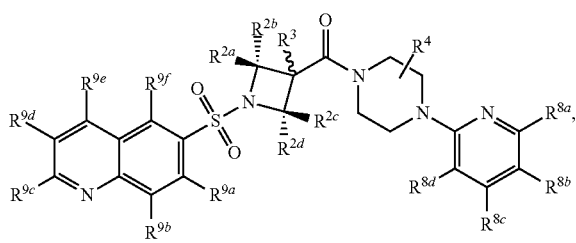

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

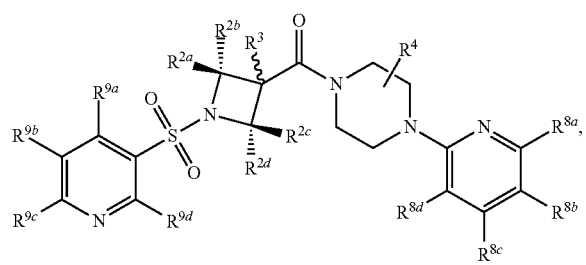

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

In a further aspect, the compound has a structure represented by a formula:

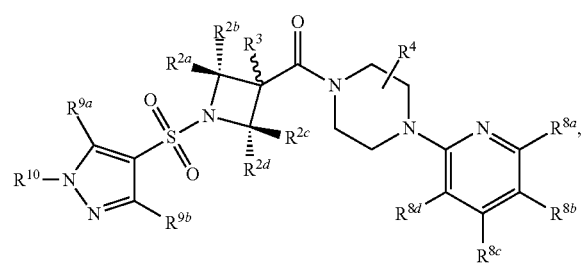

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$ and $R^{9b}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

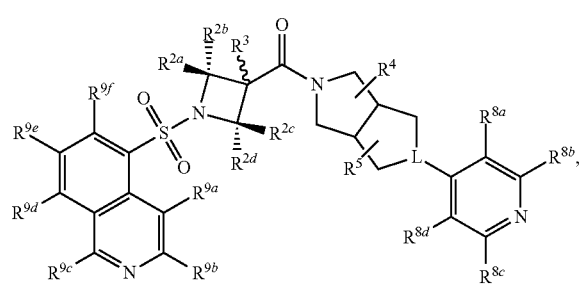

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

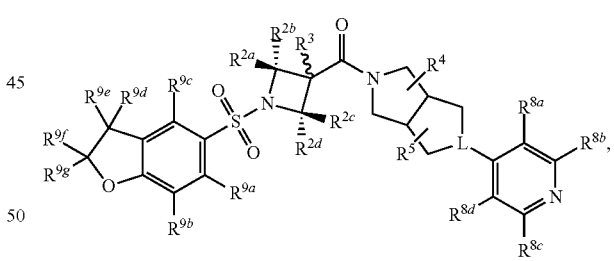

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

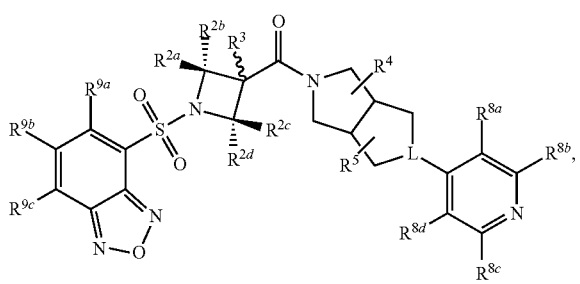

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

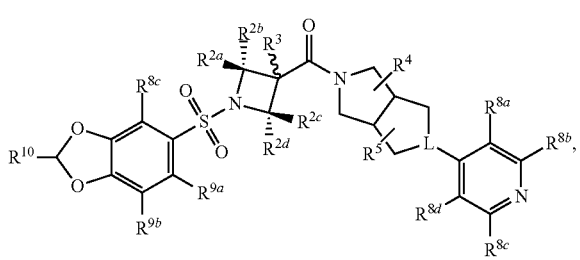

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

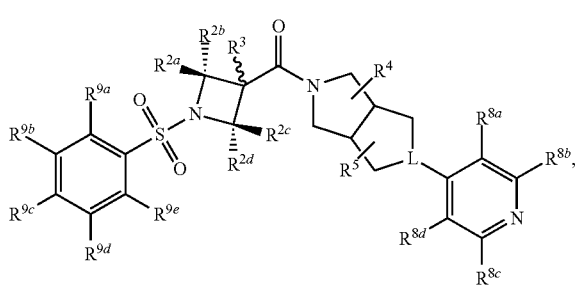

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

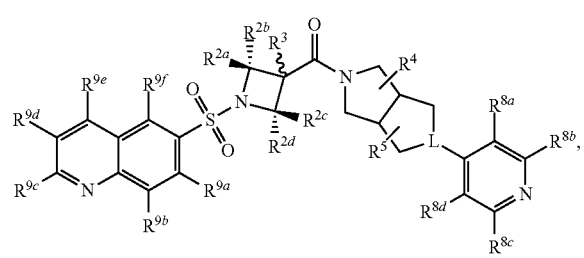

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

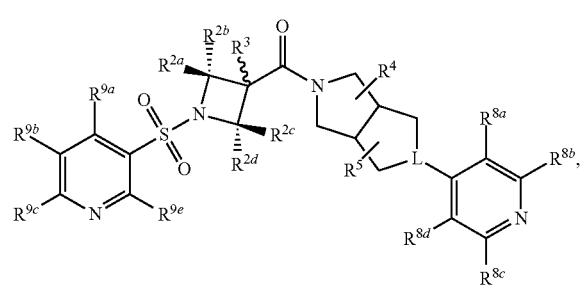

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

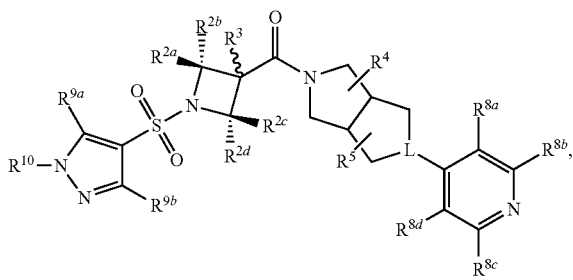

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

In a further aspect, the compound has a structure represented by a formula:

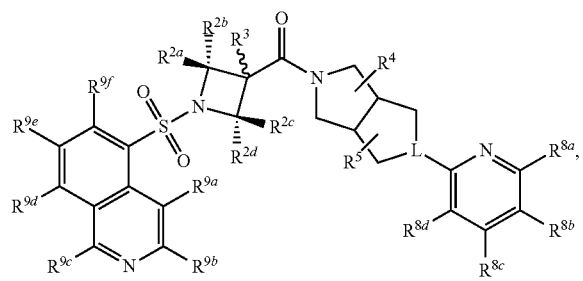

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

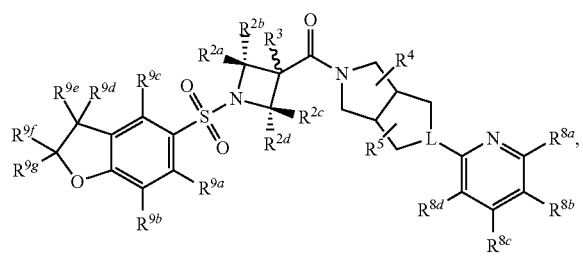

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

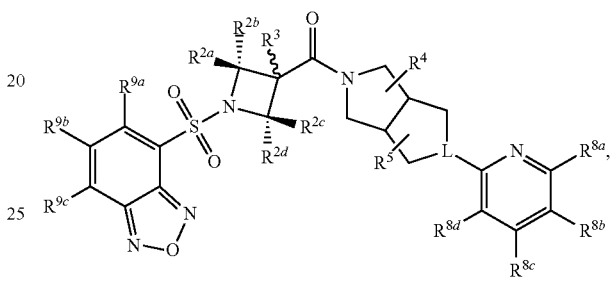

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

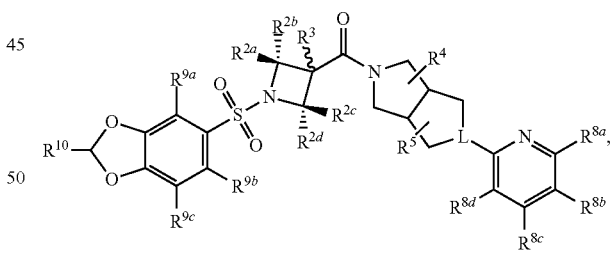

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

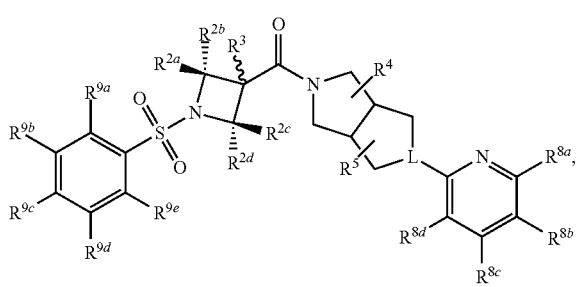

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9a}$, $R^{9d}$, and $R^{9e}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9a}$, $R^{9d}$, and $R^{9e}$ are hydrogen.

In a further aspect, the compound has a structure represented by a formula:

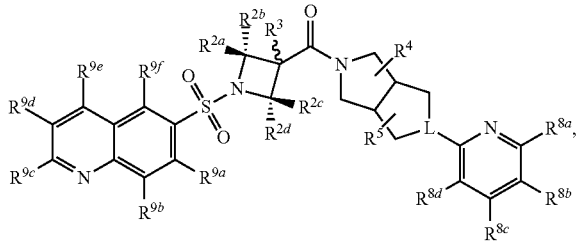

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

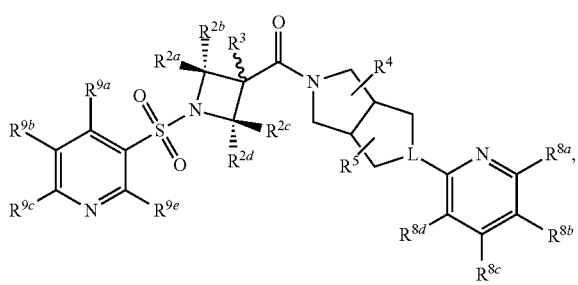

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

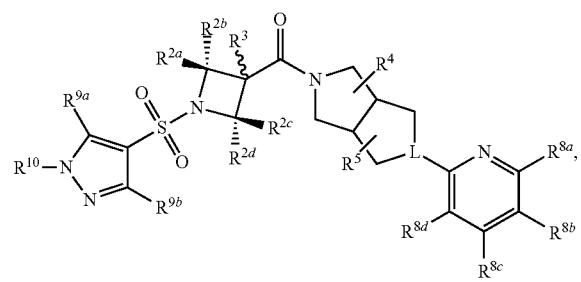

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

In a further aspect, the compound has a structure represented by a formula:

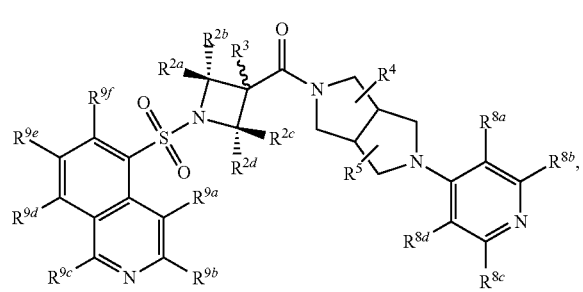

wherein each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

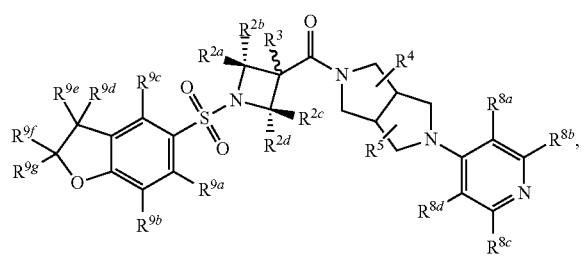

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

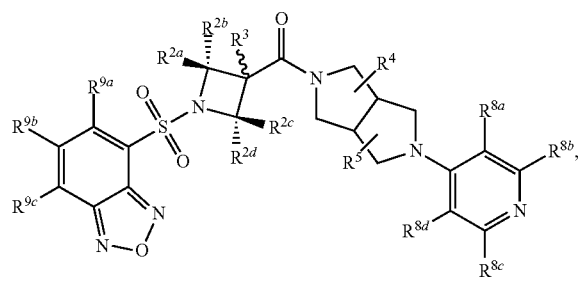

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

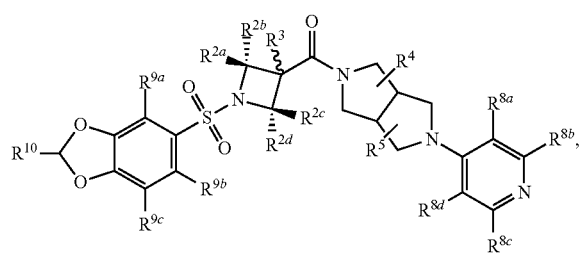

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

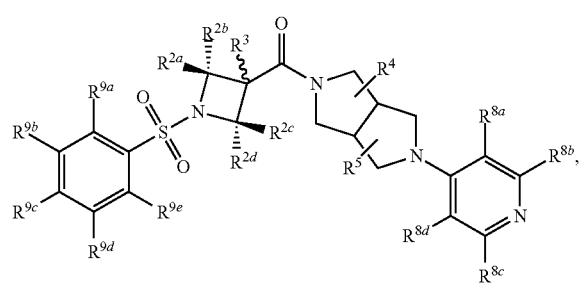

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

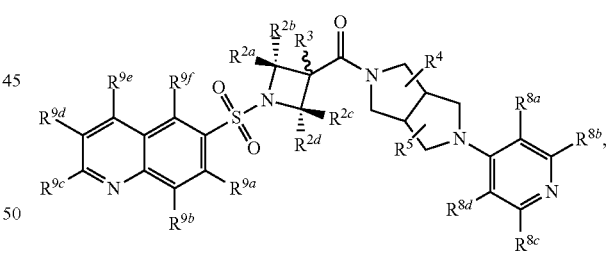

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

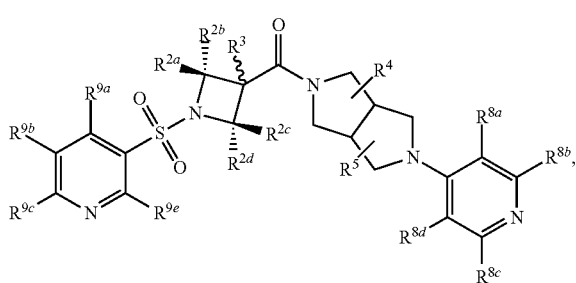

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

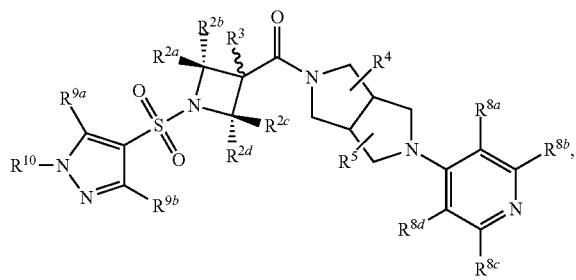

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9a}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9a}$, and $R^{9d}$ is hydrogen.

In a further aspect, the compound has a structure represented by a formula:

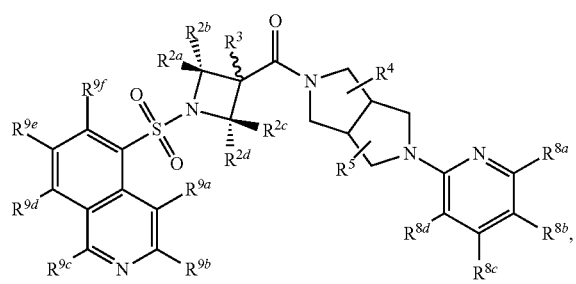

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

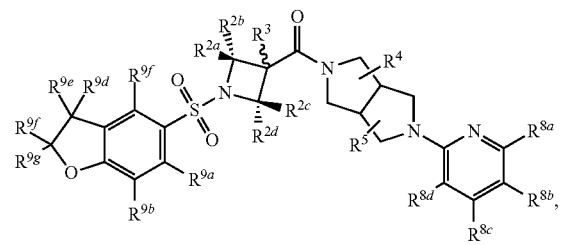

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, $R^{9f}$, and $R^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of $R^{9a}$, $R^{9b}$, $R^{9c}$, $R^{9d}$, $R^{9e}$, $R^{9f}$, and $R^{9g}$ are hydrogen.

In a further aspect, the compound has a structure represented by a formula:

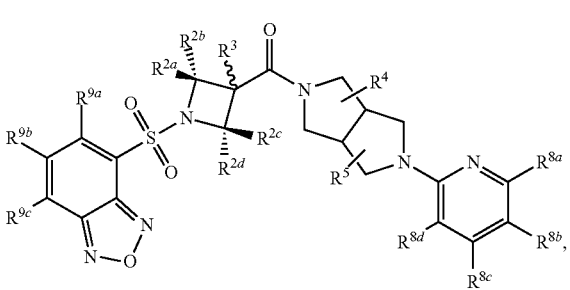

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, the compound has a structure represented by a formula:

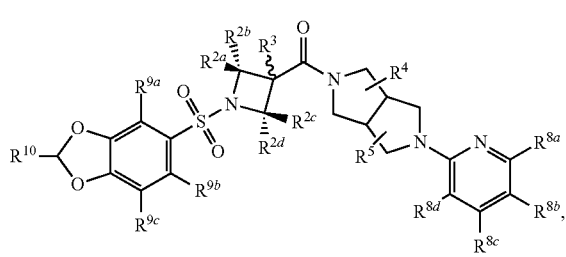

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; wherein each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino; and wherein $R^{10}$ is selected from hydrogen and C1-C6 alkyl.

In a further aspect, the compound has a structure represented by a formula:

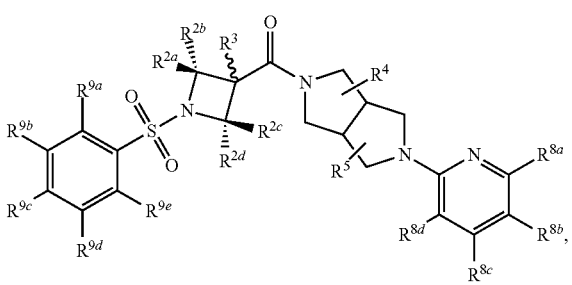

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen.

In a further aspect, the compound has a structure represented by a formula:

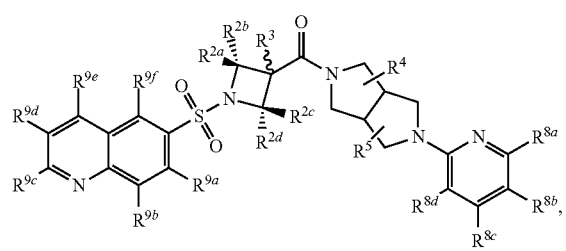

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

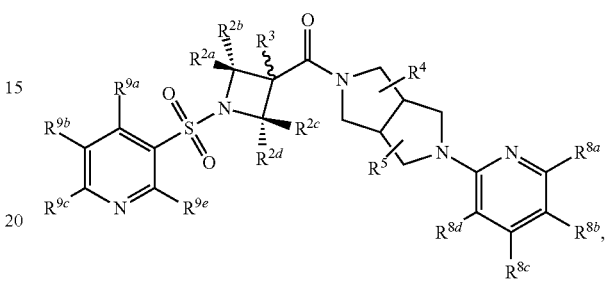

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, $R^{9d}$, $R^{9e}$, and $R^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of $R^{9a}$, $R^{9b}$, $R^{9c}$, $R^{9d}$, $R^{9e}$, and $R^{9f}$ are hydrogen.

In a further aspect, the compound has a structure represented by a formula:

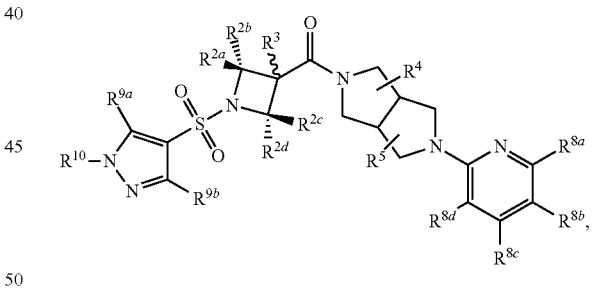

wherein each of $R^{8a}$, $R^{8b}$, $R^{8c}$, and $R^{8d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen; and wherein each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen.

a. L Groups

In one aspect, L is N or $CR^6$. In a further aspect, L is N. In a still further aspect, L is $CR^6$.

b. Q Groups

In one aspect, Q is selected from a structure represented by a formula:

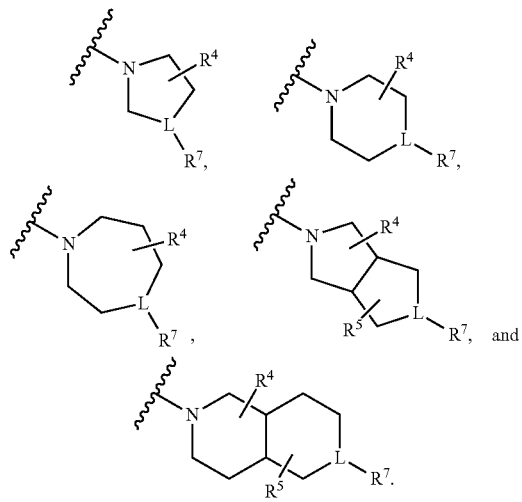

In a further aspect, Q is selected from a structure represented by a formula:

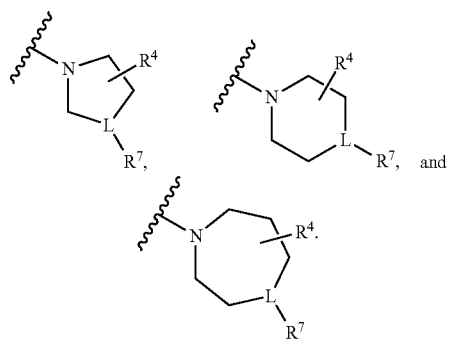

In a further aspect, Q has a structure represented by a formula:

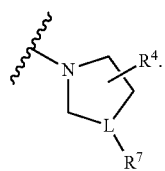

In a further aspect, Q has a structure represented by a formula:

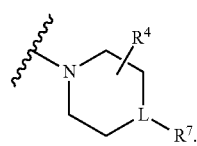

In a further aspect, Q has a structure represented by a formula:

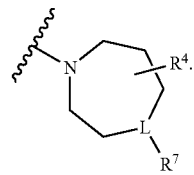

In a further aspect, Q is selected from a structure represented by a formula:

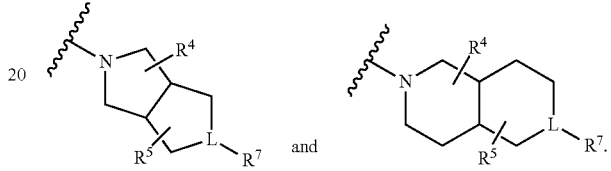

In a further aspect, Q has a structure represented by a formula:

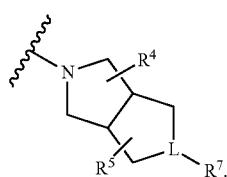

In a further aspect, Q has a structure represented by a formula:

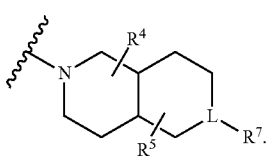

In a further aspect, Q is selected from a structure represented by a formula:

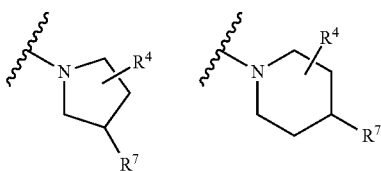

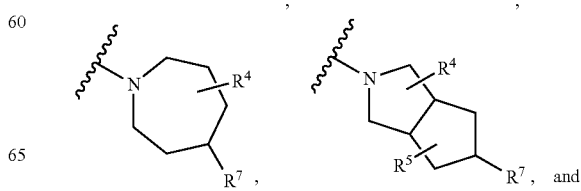

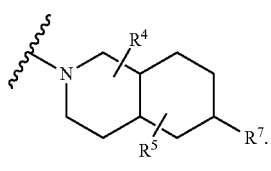

In a further aspect, Q is selected from a structure represented by a formula:

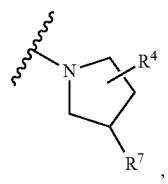 , 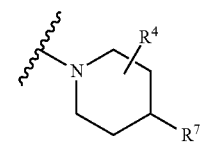 , and

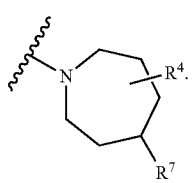

In a further aspect, Q has a structure represented by a formula:

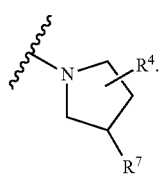

In a further aspect, Q has a structure represented by a formula:

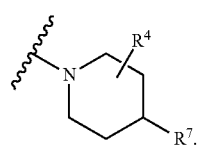

In a further aspect, Q has a structure represented by a formula:

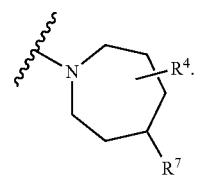

In a further aspect, Q is selected from a structure represented by a formula:

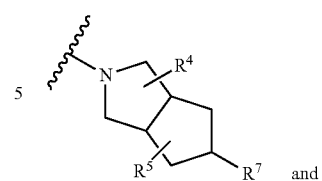 and

In a further aspect, Q has a structure represented by a formula:

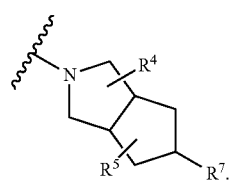

In a further aspect, Q has a structure represented by a formula:

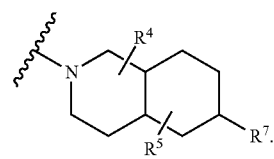

In a further aspect, Q is selected from a structure represented by a formula:

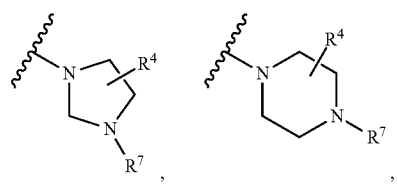 , 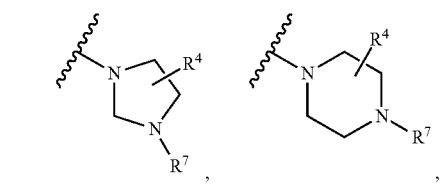 ,

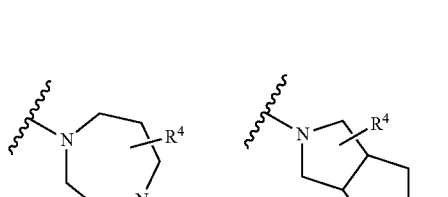 , 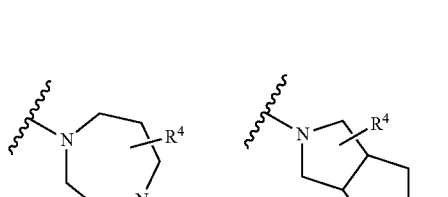 , 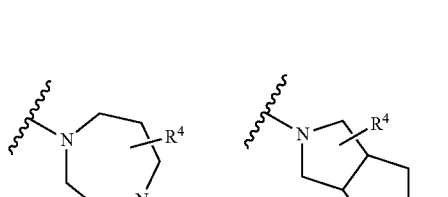 , and

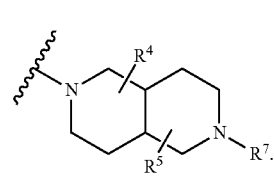

In a further aspect, Q is selected from a structure represented by a formula:

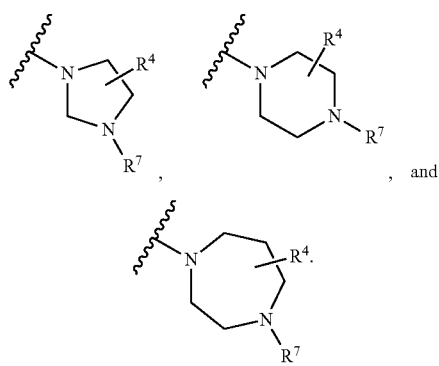

In a further aspect, Q has a structure represented by a formula:

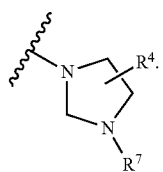

In a further aspect, Q has a structure represented by a formula:

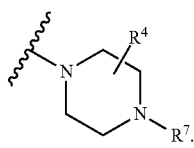

In a further aspect, Q has a structure represented by a formula:

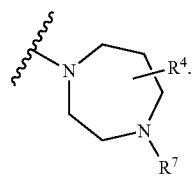

In a further aspect, Q is selected from a structure represented by a formula:

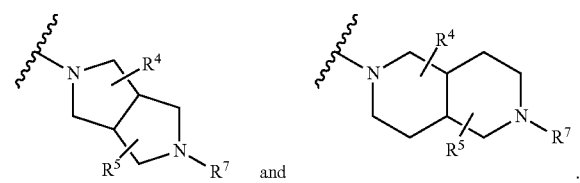

In a further aspect, Q has a structure represented by a formula:

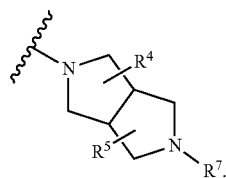

In a further aspect, Q has a structure represented by a formula:

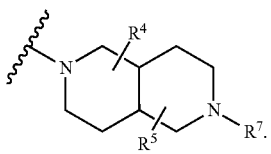

c. $R^1$ Groups

In one aspect, $R^1$ is selected from C1-C8 alkyl, C1-C8 haloalkyl, C1-C8 polyhaloalkyl, C3-C8 cycloalkyl, C3-C9 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a further aspect, $R^1$ is selected from C1-C6 alkyl, C1-C6 haloalkyl, C1-C6 polyhaloalkyl, C3-C6 cycloalkyl, C3-C6 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $R^1$ is selected from C1-C3 alkyl, C1-C3 haloalkyl, C1-C3 polyhaloalkyl, C3-C6 cycloalkyl, C3-C6 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is substituted with 1-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is substituted with 1-2 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is substituted with 2-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is substituted with 0-2 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is substituted with 0 or 1 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is selected from C1-C8 alkyl, C1-C8 haloalkyl, C1-C8 polyhaloalkyl, C3-C8 cycloalkyl, C3-C8 heterocycloalkyl, aryl and heteroaryl; and wherein $R^1$ is unsubstituted.

In a further aspect, $R^1$ is selected from C1-C8 alkyl, C1-C8 haloalkyl, and C1-C8 polyhaloalkyl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $R^1$ is selected from C1-C8 alkyl, C1-C8 haloalkyl, and C1-C8 polyhaloalkyl. In a yet further aspect, $R^1$ is selected from methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, 2,3-dimethylpentan-2-yl, —$CH_2F$, —$CH_2Cl$, —$CH_2CH_2F$, —$CH_2CH_2Cl$, —$(CH_2)_2CH_2F$, —$(CH_2)_2CH_2Cl$, —$(CH_2)_3CH_2F$, —$(CH_2)_3CH_2Cl$, —$(CH_2)_4CH_2F$, —$(CH_2)_4CH_2Cl$, —$CH(CH_2F)CH_3$, —$CH(CH_2Cl)CH_3$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$(CH_2)_3CHF_2$, —$(CH_2)_3CF_3$, —$(CH_2)_3CHCl_2$, —$(CH_2)_3CCl_3$, —$CH(CF_3)CH_3$, —$CH(CCl_3)CH_3$, —$CH(CF_3)_2$, and —$CH(CCl_3)_2$.

In a further aspect, $R^1$ is selected from C3-C8 cycloalkyl and C3-C8 heterocycloalkyl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, In a further aspect, $R^1$ is selected from aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $R^1$ is aryl and substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is a bicyclic aryl and substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is a monocyclic heteroaryl and substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, $R^1$ is phenyl and substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is phenyl and substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is phenyl monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is phenyl substituted with 0-3 groups selected from —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In a still further aspect, $R^1$ is phenyl substituted with 0-3 groups selected from —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$. In a yet further aspect, $R^1$ is phenyl substituted with 0-3 groups selected from —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^1$ is phenyl substituted with 0-3 groups selected from —F, —Cl, methyl, —$OCH_3$—$CH_2F$, —$CH_2Cl$, —$CF_3$, —$CCl_3$, —$NHCH_3$, and —$N(CH_3)_2$. In a still further aspect, $R^1$ is phenyl substituted with 0-3 groups selected from —F, —Cl, methyl, —$CH_2F$, —$CH_2Cl$, —$CF_3$, and —$CCl_3$. In a yet further aspect, $R^1$ is phenyl substituted with 0-3 halogens. In an even further aspect, $R^1$ is phenyl substituted with 0-3 —F. In a yet further aspect, $R^1$ is phenyl.

In a further aspect, $R^1$ is pyridinyl and substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is pyridinyl and substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is pyridinyl monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is pyridinyl substituted with 0-3 groups selected from —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In a still further aspect, $R^1$ is pyridinyl substituted with 0-3 groups selected from —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$. In a yet further aspect, $R^1$ is pyridinyl substituted with 0-3 groups selected from —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^1$ is pyridinyl substituted with 0-3 groups selected from —F, —Cl, methyl, —$OCH_3$—$CH_2F$, —$CH_2Cl$, —$CF_3$, —$CCl_3$, —$NHCH_3$, and —$N(CH_3)_2$. In a still further aspect, $R^1$ is pyridinyl substituted with 0-3 groups selected from —F, —Cl, methyl, —$CH_2F$, —$CH_2Cl$, —$CF_3$, and —CCl₃. In a yet further aspect, R¹ is pyridinyl substituted with 0-3 halogens. In an even further aspect, R¹ is pyridinyl substituted with 0-3 —F. In a yet further aspect, R¹ is unsubstituted pyridinyl.

In a further aspect, R¹ is pyridin-2-yl and substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, R¹ is pyridin-2-yl and substituted with 0-3 groups selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, R¹ is pyridin-2-yl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, R¹ is pyridin-2-yl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, R¹ is pyridin-2-yl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, R¹ is pyridin-2-yl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, R¹ is pyridin-2-yl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, R¹ is pyridin-2-yl substituted with 0-3 groups selected from —F, —Cl, methyl, —CH₂F, —CH₂Cl, —CF₃, and —CCl₃. In a yet further aspect, R¹ is pyridin-2-yl substituted with 0-3 halogens. In an even further aspect, R¹ is pyridin-2-yl substituted with 0-3 —F. In a yet further aspect, R¹ is unsubstituted pyridin-2-yl.

In a further aspect, R¹ is pyridin-3-yl and substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, R¹ is pyridin-3-yl and substituted with 0-3 groups selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, R¹ is pyridin-3-yl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, R¹ is pyridin-3-yl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, R¹ is pyridin-3-yl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, R¹ is pyridin-3-yl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, R¹ is pyridin-3-yl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, R¹ is pyridin-3-yl substituted with 0-3 groups selected from —F, —Cl, methyl, —CH₂F, —CH₂Cl, —CF₃, and —CCl₃. In a yet further aspect, R¹ is pyridin-3-yl substituted with 0-3 halogens. In an even further aspect, R¹ is pyridin-3-yl substituted with 0-3 —F. In a yet further aspect, R¹ is unsubstituted pyridin-3-yl.

In a further aspect, R¹ is pyridin-4-yl and substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, R¹ is pyridin-4-yl and substituted with 0-3 groups selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, R¹ is pyridin-4-yl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, R¹ is pyridin-4-yl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, R¹ is pyridin-4-yl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, R¹ is pyridin-4-yl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, R¹ is pyridin-4-yl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, R¹ is pyridin-4-yl substituted with 0-3 groups selected from —F, —Cl, methyl, —CH₂F, —CH₂Cl, —CF₃, and —CCl₃. In a yet further aspect, R¹ is pyridin-4-yl substituted with 0-3 halogens. In an even further aspect, R¹ is pyridin-4-yl substituted with 0-3 —F. In a yet further aspect, R¹ is unsubstituted pyridin-4-yl.

In a further aspect, R¹ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein R¹ is substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, R¹ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein R¹ is substituted with 0-3 groups selected from halogen, hydroxyl, cyano, —NH₂, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 groups selected from —F, —Cl, methyl, —CH$_2$F, —CH$_2$Cl, —CF$_3$, and —CCl$_3$. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 halogens. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is substituted with 0-3 —F. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, indazolyl, thiazolyl, isoxazolyl, pyrazolyl, and pyridinyl; and wherein $R^1$ is unsubstituted.

In a further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 groups selected from —F, —Cl, methyl, —CH$_2$F, —CH$_2$Cl, —CF$_3$, and —CCl$_3$. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 halogens. In an even further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is substituted with 0-3 —F. In a yet further aspect, $R^1$ is selected from isoquinolinyl, 2,3-dihydrobenzofuranyl, benzo[c][1,2,5]oxadiazolyl, benzo[d][1,3]dioxolyl, quinolinyl, benzofuranyl, and indazolyl; and wherein $R^1$ is unsubstituted.

In a further aspect, $R^1$ is isoquinolin-5-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is isoquinolin-5-yl and is substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is isoquinolin-5-yl and is monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is isoquinolin-5-yl and is substituted with 0-3 groups selected from —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In a still further aspect, $R^1$ is isoquinolin-5-yl and is substituted with 0-3 groups selected from —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$. In a yet further aspect, $R^1$ is isoquinolin-5-yl and is substituted with 0-3 groups selected from —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^1$ is isoquinolin-5-yl and is substituted with 0-3 groups selected from —F, —Cl, methyl, —$OCH_3$—$CH_2F$, —$CH_2Cl$, —$CF_3$, —$CCl_3$, —$NHCH_3$, and —$N(CH_3)_2$. In a still further aspect, $R^1$ is isoquinolin-5-yl and is substituted with 0-3 groups selected from —F, —Cl, methyl, —$CH_2F$, —$CH_2Cl$, —$CF_3$, and —$CCl_3$. In a yet further aspect, $R^1$ is isoquinolin-5-yl and is substituted with 0-3 halogens. In an even further aspect, $R^1$ is isoquinolin-5-yl and is substituted with 0-3 —F. In a yet further aspect, $R^1$ is unsubstituted isoquinolin-5-yl.

In a further aspect, $R^1$ is 2,3-dihydrobenzofuran-5-yl and is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is 2,3-dihydrobenzofuran-5-yl and is substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is 2,3-dihydrobenzofuran-5-yl and is monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is 2,3-dihydrobenzofuran-5-yl and is substituted with 0-3 groups selected from —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In a yet further aspect, $R^1$ is 2,3-dihydrobenzofuran-5-yl and is substituted with 0-3 groups selected from —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$. In a yet further aspect, $R^1$ is 2,3-dihydrobenzofuran-5-yl and is substituted with 0-3 groups selected from —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^1$ is 2,3-dihydrobenzofuran-5-yl and is substituted with 0-3 groups selected from —F, —Cl, methyl, —$OCH_3$—$CH_2F$, —$CH_2Cl$, —$CF_3$, —$CCl_3$, —$NHCH_3$, and —$N(CH_3)_2$. In a still further aspect, $R^1$ is 2,3-dihydrobenzofuran-5-yl and is substituted with 0-3 groups selected from —F, —Cl, methyl, —$CH_2F$, —$CH_2Cl$, —$CF_3$, and —$CCl_3$. In a yet further aspect, $R^1$ is 2,3-dihydrobenzofuran-5-yl and is substituted with 0-3 halogens. In an even further aspect, $R^1$ is 2,3-dihydrobenzofuran-5-yl and is substituted with 0-3 —F. In a yet further aspect, $R^1$ is unsubstituted 2,3-dihydrobenzofuran-5-yl.

In a further aspect, $R^1$ is benzo[c][1,2,5]oxadiazol-4-yl and is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is benzo[c][1,2,5]oxadiazol-4-yl and is substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is benzo[c][1,2,5]oxadiazol-4-yl and is monosubstituted with a group selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $R^1$ is benzo[c][1,2,5]oxadiazol-4-yl and is substituted with 0-3 groups selected from —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In a still further aspect, $R^1$ is benzo[c][1,2,5]oxadiazol-4-yl and is substituted with 0-3 groups selected from —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$. In a yet further aspect, $R^1$ is benzo[c][1,2,5]oxadiazol-4-yl and is substituted with 0-3 groups selected from —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$. In an even further aspect, $R^1$ is benzo[c][1,2,5]oxadiazol-4-yl and is substituted with 0-3 groups selected from —F, —Cl, methyl, —$OCH_3$—$CH_2F$, —$CH_2Cl$, —$CF_3$, —$CCl_3$, —$NHCH_3$, and —$N(CH_3)_2$. In a still further aspect, $R^1$ is benzo[c][1,2,5]oxadiazol-4-yl and is substituted with 0-3 groups selected from —F, —Cl, methyl, —$CH_2F$, —$CH_2Cl$, —$CF_3$, and —$CCl_3$. In a yet further aspect, $R^1$ is benzo[c][1,2,5]oxadiazol-4-yl and is substituted with 0-3 halogens. In an even further aspect, $R^1$ is benzo[c][1,2,5]oxadiazol-4-yl and is substituted with 0-3 —F. In a yet further aspect, $R^1$ is unsubstituted benzo[c][1,2,5]oxadiazol-4-yl.

In a further aspect, $R^1$ is benzo[d][1,3]dioxol-5-yl and is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $R^1$ is benzo[d][1,3]dioxol-5-yl and is substituted with 0-3 groups selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, $R^1$ is benzo[d][1,3]dioxol-5-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is benzo[d][1,3]dioxol-5-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is benzo[d][1,3]dioxol-5-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is benzo[d][1,3]dioxol-5-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is benzo[d][1,3]dioxol-5-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is benzo[d][1,3]dioxol-5-yl and is substituted with 0-3 groups selected from —F, —Cl, methyl, —CH$_2$F, —CH$_2$Cl, —CF$_3$, and —CCl$_3$. In a yet further aspect, R$^1$ is benzo[d][1,3]dioxol-5-yl and is substituted with 0-3 halogens. In an even further aspect, R$^1$ is benzo[d][1,3]dioxol-5-yl and is substituted with 0-3 —F. In a yet further aspect, R$^1$ is unsubstituted benzo[d][1,3]dioxol-5-yl.

In a further aspect, R$^1$ is benzofuran-5-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is benzofuran-5-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is benzofuran-5-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is benzofuran-5-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is benzofuran-5-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is benzofuran-5-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is benzofuran-5-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is benzofuran-5-yl and is substituted with 0-3 groups selected from —F, —Cl, methyl, —CH$_2$F, —CH$_2$Cl, —CF$_3$, and —CCl$_3$. In a yet further aspect, R$^1$ is benzofuran-5-yl and is substituted with 0-3 halogens. In an even further aspect, R$^1$ is benzofuran-5-yl and is substituted with 0-3 —F. In a yet further aspect, R$^1$ is unsubstituted benzofuran-5-yl.

In a further aspect, R$^1$ is 1H-indazol-6-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is 1H-indazol-6-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is 1H-indazol-6-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is 1H-indazol-6-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is 1H-indazol-6-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is 1H-indazol-6-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is 1H-indazol-6-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is 1H-indazol-6-yl and is substituted with 0-3 groups selected from —F, —Cl, methyl, —CH$_2$F, —CH$_2$Cl, —CF$_3$, and —CCl$_3$. In a yet further aspect, R$^1$ is 1H-indazol-6-yl and is substituted with 0-3 halogens. In an even further aspect, R$^1$ is 1H-indazol-6-yl and is substituted with 0-3 —F. In a yet further aspect, R$^1$ is unsubstituted 1H-indazol-6-yl.

In a further aspect, R$^1$ is quinolin-3-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is quinolin-3-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is quinolin-3-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is quinolin-3-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is quinolin-3-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is quinolin-3-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is quinolin-3-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is quinolin-3-yl and is substituted with 0-3 groups selected from —F, —Cl, methyl, —CH$_2$F, —CH$_2$Cl, —CF$_3$, and —CCl$_3$. In a yet further aspect, R$^1$ is quinolin-3-yl and is substituted with 0-3 halogens. In an even further aspect, R$^1$ is quinolin-3-yl and is substituted with 0-3 —F. In a yet further aspect, R$^1$ is unsubstituted quinolin-3-yl.

In a further aspect, R$^1$ is quinolin-6-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is quinolin-6-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is quinolin-6-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is quinolin-6-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is quinolin-6-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is quinolin-6-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is quinolin-6-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is quinolin-6-yl and is substituted with 0-3 groups selected from —F, —Cl, methyl, —CH$_2$F, —CH$_2$Cl, —CF$_3$, and —CCl$_3$. In a yet further aspect, R$^1$ is quinolin-6-yl and is substituted with 0-3 halogens. In an even further aspect, R$^1$ is quinolin-6-yl and is substituted with 0-3 —F. In a yet further aspect, R$^1$ is unsubstituted quinolin-6-yl.

In a further aspect, R$^1$ is selected from thiazolyl, isoxazolyl, and pyrazolyl; and wherein R$^1$ is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is selected from thiazolyl, isoxazolyl, and pyrazolyl; and wherein R$^1$ is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is selected from thiazolyl, isoxazolyl, and pyrazolyl; and wherein R$^1$ is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is selected from thiazolyl, isoxazolyl, and pyrazolyl; and wherein R$^1$ is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is selected from thiazolyl, isoxazolyl, and pyrazolyl; and wherein R$^1$ is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is selected from thiazolyl, isoxazolyl, and pyrazolyl; and wherein R$^1$ is substituted with 0-3 groups selected from —F, —Cl, —NH$_2$, methyl, —OCH$_3$—CH$_2$F, —CH$_2$Cl, —CHF, —CF$_3$, —CHCl$_2$, —CCl$_3$, —NHCH$_3$, and —N(CH$_3$)$_2$. In an even further aspect, R$^1$ is selected from thiazolyl, isoxazolyl, and pyrazolyl; and wherein R$^1$ is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is selected from thiazolyl, isoxazolyl, and pyrazolyl; and wherein R$^1$ is substituted with 0-3 groups selected from —F, —Cl, methyl, —CH$_2$F, —CH$_2$Cl, —CF$_3$, and —CCl$_3$. In a yet further aspect, R$^1$ is selected from thiazolyl, isoxazolyl, and pyrazolyl; and wherein R$^1$ is substituted with 0-3 halogens. In an even further aspect, R$^1$ is selected from thiazolyl, isoxazolyl, and pyrazolyl; and wherein R$^1$ is substituted with 0-3 —F. In a yet further aspect, R$^1$ is selected from thiazolyl, isoxazolyl, and pyrazolyl; and wherein R$^1$ is unsubstituted.

In a further aspect, R$^1$ is thiazol-5-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is thiazol-5-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is thiazol-5-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is thiazol-5-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is thiazol-5-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is thiazol-5-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is thiazol-5-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is thiazol-5-yl and is substituted with 0-3 groups selected from —F, —Cl, methyl, —CH$_2$F, —CH$_2$Cl, —CF$_3$, and —CCl$_3$. In a yet further aspect, R$^1$ is thiazol-5-yl and is substituted with 0-3 halogens. In an even further aspect, R$^1$ is thiazol-5-yl and is substituted with 0-3 —F. In a yet further aspect, R$^1$ is unsubstituted thiazol-5-yl.

In a further aspect, R$^1$ is isoxazol-4-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is isoxazol-4-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is isoxazol-4-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is isoxazol-4-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is isoxazol-4-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is isoxazol-4-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is isoxazol-4-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is isoxazol-4-yl and is substituted with 0-3 groups selected from —F, —Cl, methyl, —CH$_2$F, —CH$_2$Cl, —CF$_3$, and —CCl$_3$. In a yet further aspect, R$^1$ is isoxazol-4-yl and is substituted with 0-3 halogens. In an even further aspect, R$^1$ is isoxazol-4-yl and is substituted with 0-3 —F. In a yet further aspect, R$^1$ is unsubstituted isoxazol-4-yl.

In a further aspect, R$^1$ is pyrazol-4-yl and is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, R$^1$ is pyrazol-4-yl and is substituted with 0-3 groups selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, R$^1$ is pyrazol-4-yl and is monosubstituted with a group selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, R$^1$ is pyrazol-4-yl and is substituted with 0-3 groups selected from —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a still further aspect, R$^1$ is pyrazol-4-yl and is substituted with 0-3 groups selected from —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In a yet further aspect, R$^1$ is pyrazol-4-yl and is substituted with 0-3 groups selected from —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In an even further aspect, R$^1$ is pyrazol-4-yl and is substituted with 0-3 groups selected from —F, —Cl, methyl, —OCH$_3$—CH$_2$F, —CH$_2$Cl, —CF$_3$, —CCl$_3$, —NHCH$_3$, and —N(CH$_3$)$_2$. In a still further aspect, R$^1$ is pyrazol-4-yl and is substituted with 0-3 groups selected from —F, —Cl, methyl, —CH$_2$F, —CH$_2$Cl, —CF$_3$, and —CCl$_3$. In a yet further aspect, R$^1$ is pyrazol-4-yl and is substituted with 0-3 halogens. In an even further aspect, R$^1$ is pyrazol-4-yl and is substituted with 0-3 —F. In a yet further aspect, R$^1$ is unsubstituted pyrazol-4-yl.

d. R$^2$ Groups

In one aspect, each of R$^{2a}$, R$^{2b}$, R$^{2c}$, and R$^{2d}$ is independently selected from hydrogen, C1-C6 alkyl, C1-C6 haloalkyl, and C1-C6 polyhaloalkyl. In a further aspect, each of R$^{2a}$, R$^{2b}$, R$^{2c}$, and R$^{2d}$ is independently selected from hydrogen, C1-C3 alkyl, C1-C3 haloalkyl, and C1-C3 polyhaloalkyl. In a still further aspect, each of R$^{2a}$, R$^{2b}$, R$^{2c}$, and R$^{2d}$ is hydrogen.

In a further aspect, R$^{2a}$ is hydrogen; and each of R$^{2b}$, R$^{2c}$, and R$^{2d}$ is independently selected from hydrogen, C1-C6 alkyl, C1-C6 haloalkyl, and C1-C6 polyhaloalkyl. In a still further aspect, R$^{2a}$ is hydrogen; and each of R$^{2b}$, R$^{2c}$, and R$^{2d}$ is independently selected from hydrogen, C1-C3 alkyl, C1-C3 haloalkyl, and C1-C3 polyhaloalkyl. In a yet further aspect, R$^{2a}$ is hydrogen; and each of R$^{2b}$, R$^{2c}$, and R$^{2d}$ is independently selected from hydrogen, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, R$^{2a}$ is hydrogen; and each of R$^{2b}$, R$^{2c}$, and R$^{2d}$ is independently selected from hydrogen, methyl, —CH$_2$F, —CH$_2$Cl, —CHF$_2$, —CF$_3$, —CHCl$_2$, and —CCl$_3$. In a still further aspect, R$^{2a}$ is hydrogen; and each of R$^{2b}$, R$^{2c}$, and R$^{2d}$ is independently selected from hydrogen, methyl, —CH$_2$F, —CHF$_2$, and —CF$_3$.

In a further aspect, R$^{2b}$ is hydrogen; and each of R$^{2a}$, R$^{2c}$, and R$^{2d}$ is independently selected from hydrogen, C1-C6 alkyl, C1-C6 haloalkyl, and C1-C6 polyhaloalkyl. In a still further aspect, R$^{2b}$ is hydrogen; and each of R$^{2a}$, R$^{2c}$, and R$^{2d}$ is independently selected from hydrogen, C1-C3 alkyl, C1-C3 haloalkyl, and C1-C3 polyhaloalkyl. In a yet further aspect, R$^{2b}$ is hydrogen; and each of R$^{2a}$, R$^{2c}$, and R$^{2d}$ is independently selected from hydrogen, methyl, ethyl, propyl, —CH$_2$F, —CH$_2$Cl, —CH$_2$CH$_2$F, —CH$_2$CH$_2$Cl, —(CH$_2$)$_2$ $CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, $R^{2b}$ is hydrogen; and each of $R^{2a}$, $R^{2c}$, and $R^{2d}$ is independently selected from hydrogen, methyl, $-CH_2F$, $-CH_2Cl$, $-CHF_2$, $-CF_3$, $-CHCl_2$, and $-CCl_3$. In a still further aspect, $R^{2b}$ is hydrogen; and each of $R^{2a}$, $R^{2c}$, and $R^{2d}$ is independently selected from hydrogen, methyl, $-CH_2F$, $-CHF_2$, and $-CF_3$.

In a further aspect, $R^{2c}$ is hydrogen; and each of $R^{2a}$, $R^{2b}$, and $R^{2d}$ is independently selected from hydrogen, C1-C6 alkyl, C1-C6 haloalkyl, and C1-C6 polyhaloalkyl. In a still further aspect, $R^{2c}$ is hydrogen; and each of $R^{2a}$, $R^{2b}$, and $R^{2d}$ is independently selected from hydrogen, C1-C3 alkyl, C1-C3 haloalkyl, and C1-C3 polyhaloalkyl. In a yet further aspect, $R^{2c}$ is hydrogen; and each of $R^{2a}$, $R^{2b}$, and $R^{2d}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, $R^{2c}$ is hydrogen; and each of $R^{2a}$, $R^{2b}$, and $R^{2d}$ is independently selected from hydrogen, methyl, $-CH_2F$, $-CH_2Cl$, $-CHF_2$, $-CF_3$, $-CHCl_2$, and $-CCl_3$. In a still further aspect, $R^{2c}$ is hydrogen; and each of $R^{2a}$, $R^{2b}$, and $R^{2d}$ is independently selected from hydrogen, methyl, $-CH_2F$, $-CHF_2$, and $-CF_3$.

In a further aspect, $R^{2d}$ is hydrogen; and wherein each of $R^{2a}$, $R^{2b}$, and $R^{2c}$ is independently selected from hydrogen, C1-C6 alkyl, C1-C6 haloalkyl, and C1-C6 polyhaloalkyl. In a still further aspect, $R^{2d}$ is hydrogen; and each of $R^{2a}$, $R^{2b}$, and $R^{2c}$ is independently selected from hydrogen, C1-C3 alkyl, C1-C3 haloalkyl, and C1-C3 polyhaloalkyl. In a yet further aspect, $R^{2d}$ is hydrogen; and each of $R^{2a}$, $R^{2b}$, and $R^{2c}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, $R^{2d}$ is hydrogen; and each of $R^{2a}$, $R^{2b}$, and $R^{2c}$ is independently selected from hydrogen, methyl, $-CH_2F$, $-CH_2Cl$, $-CHF_2$, $-CF_3$, $-CHCl_2$, and $-CCl_3$. In a still further aspect, $R^{2d}$ is hydrogen; and each of $R^{2a}$, $R^{2b}$, and $R^{2c}$ is independently selected from hydrogen, methyl, $-CH_2F$, $-CHF_2$, and $-CF_3$.

In a further aspect, each of $R^{2a}$ and $R^{2b}$ is hydrogen; and each of $R^{2c}$ and $R^{2d}$ is independently selected from hydrogen, C1-C6 alkyl, C1-C6 haloalkyl, and C1-C6 polyhaloalkyl. In a still further aspect, each of $R^{2a}$ and $R^{2b}$ is hydrogen; and each of $R^{2c}$ and $R^{2d}$ is independently selected from hydrogen, C1-C3 alkyl, C1-C3 haloalkyl, and C1-C3 polyhaloalkyl. In a yet further aspect, each of $R^{2a}$ and $R^{2b}$ is hydrogen; and each of $R^{2c}$ and $R^{2d}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, each of $R^{2a}$ and $R^{2b}$ is hydrogen; and each of $R^{2c}$ and $R^{2d}$ is independently selected from hydrogen, methyl, $-CH_2F$, $-CH_2Cl$, $-CHF_2$, $-CF_3$, $-CHCl_2$, and $-CCl_3$. In a still further aspect, each of $R^{2a}$ and $R^{2b}$ is hydrogen; and each of $R^{2c}$ and $R^{2d}$ is independently selected from hydrogen, methyl, $-CH_2F$, $-CHF_2$, and $-CF_3$.

In a further aspect, each of $R^{2a}$ and $R^{2c}$ is hydrogen; and each of $R^{2b}$ and $R^{2d}$ is independently selected from hydrogen, C1-C6 alkyl, C1-C6 haloalkyl, and C1-C6 polyhaloalkyl. In a still further aspect, each of $R^{2a}$ and $R^{2c}$ is hydrogen; and each of $R^{2b}$ and $R^{2d}$ is independently selected from hydrogen, C1-C3 alkyl, C1-C3 haloalkyl, and C1-C3 polyhaloalkyl. In a yet further aspect, each of $R^{2a}$ and $R^{2c}$ is hydrogen; and each of $R^{2b}$ and $R^{2d}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, each of $R^{2a}$ and $R^{2c}$ is hydrogen; and each of $R^{2b}$ and $R^{2d}$ is independently selected from hydrogen, methyl, $-CH_2F$, $-CH_2Cl$, $-CHF_2$, $-CF_3$, $-CHCl_2$, and $-CCl_3$. In a still further aspect, each of $R^{2a}$ and $R^{2c}$ is hydrogen; and each of $R^{2b}$ and $R^{2d}$ is independently selected from hydrogen, methyl, $-CH_2F$, $-CHF_2$, and $-CF_3$.

In a further aspect, each of $R^{2a}$ and $R^{2d}$ is hydrogen; and each of $R^{2b}$ and $R^{2c}$ is independently selected from hydrogen, C1-C6 alkyl, C1-C6 haloalkyl, and C1-C6 polyhaloalkyl. In a still further aspect, each of $R^{2a}$ and $R^{2d}$ is hydrogen; and each of $R^{2b}$ and $R^{2c}$ is independently selected from hydrogen, C1-C3 alkyl, C1-C3 haloalkyl, and C1-C3 polyhaloalkyl. In a yet further aspect, each of $R^{2a}$ and $R^{2d}$ is hydrogen; and each of $R^{2b}$ and $R^{2c}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, each of $R^{2a}$ and $R^{2d}$ is hydrogen; and each of $R^{2b}$ and $R^{2c}$ is independently selected from hydrogen, methyl, $-CH_2F$, $-CH_2Cl$, $-CHF_2$, $-CF_3$, $-CHCl_2$, and $-CCl_3$. In a still further aspect, each of $R^{2a}$ and $R^{2d}$ is hydrogen; and each of $R^{2b}$ and $R^{2c}$ is independently selected from hydrogen, methyl, $-CH_2F$, $-CHF_2$, and $-CF_3$.

In a further aspect, each of $R^{2b}$ and $R^{2c}$ is hydrogen; and each of $R^{2a}$ and $R^{2d}$ is independently selected from hydrogen, C1-C6 alkyl, C1-C6 haloalkyl, and C1-C6 polyhaloalkyl. In a still further aspect, each of $R^{2b}$ and $R^{2c}$ is hydrogen; and each of $R^{2a}$ and $R^{2d}$ is independently selected from hydrogen, C1-C3 alkyl, C1-C3 haloalkyl, and C1-C3 polyhaloalkyl. In a yet further aspect, each of $R^{2b}$ and $R^{2c}$ is hydrogen; and each of $R^{2a}$ and $R^{2d}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, each of $R^{2b}$ and $R^{2c}$ is hydrogen; and each of $R^{2a}$ and $R^{2d}$ is independently selected from hydrogen, methyl, $-CH_2F$, $-CH_2Cl$, $-CHF_2$, $-CF_3$, $-CHCl_2$, and $-CCl_3$. In a still further aspect, each of $R^{2b}$ and $R^{2c}$ is hydrogen; and each of $R^{2a}$ and $R^{2d}$ is independently selected from hydrogen, methyl, $-CH_2F$, $-CHF_2$, and $-CF_3$.

In a further aspect, each of $R^{2b}$ and $R^{2d}$ is hydrogen; and each of $R^{2a}$ and $R^{2c}$ is independently selected from hydrogen, C1-C6 alkyl, C1-C6 haloalkyl, and C1-C6 polyhaloalkyl. In a still further aspect, each of $R^{2b}$ and $R^{2d}$ is hydrogen; and each of $R^{2a}$ and $R^{2c}$ is independently selected from hydrogen, C1-C3 alkyl, C1-C3 haloalkyl, and C1-C3 polyhaloalkyl. In a yet further aspect, each of $R^{2b}$ and $R^{2d}$ is hydrogen; and each of $R^{2a}$ and $R^{2c}$ is independently selected from hydrogen, methyl, ethyl, propyl, $-CH_2F$, $-CH_2Cl$, $-CH_2CH_2F$, $-CH_2CH_2Cl$, $-(CH_2)_2CH_2F$, $-(CH_2)_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-(CH_2)_2CHF_2$, $-(CH_2)_2CF_3$, $-(CH_2)_2CHCl_2$, and $-(CH_2)_2CCl_3$. In an even further aspect, each of $R^{2b}$ and $R^{2d}$ is hydrogen; and each of $R^{2a}$ and $R^{2c}$ is independently selected from hydrogen, methyl, —$CH_2F$, —$CH_2Cl$, —$CHF_2$, —$CF_3$, —$CHCl_2$, and —$CCl_3$. In a still further aspect, each of $R^{2b}$ and $R^{2d}$ is hydrogen; and each of $R^{2a}$ and $R^{2c}$ is independently selected from hydrogen, methyl, —$CH_2F$, —$CHF_2$, and —$CF_3$.

In a further aspect, each of $R^{2c}$ and $R^{2d}$ is hydrogen; and each of $R^{2a}$ and $R^{2b}$ is independently selected from hydrogen, C1-C6 alkyl, C1-C6 haloalkyl, and C1-C6 polyhaloalkyl. In a still further aspect, each of $R^{2c}$ and $R^{2d}$ is hydrogen; and each of $R^{2a}$ and $R^{2b}$ is independently selected from hydrogen, C1-C3 alkyl, C1-C3 haloalkyl, and C1-C3 polyhaloalkyl. In a yet further aspect, each of $R^{2c}$ and $R^{2d}$ is hydrogen; and each of $R^{2a}$ and $R^{2b}$ is independently selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^{2c}$ and $R^{2d}$ is hydrogen; and each of $R^{2a}$ and $R^{2b}$ is independently selected from hydrogen, methyl, —$CH_2F$, —$CH_2Cl$, —$CHF_2$, —$CF_3$, —$CHCl_2$, and —$CCl_3$. In a still further aspect, each of $R^{2c}$ and $R^{2d}$ is hydrogen; and each of $R^{2a}$ and $R^{2b}$ is independently selected from hydrogen, methyl, —$CH_2F$, —$CHF_2$, and —$CF_3$.

In a further aspect, each of $R^{2a}$, $R^{2b}$, and $R^{2c}$ is hydrogen; and $R^{2d}$ is selected from hydrogen, C1-C6 alkyl, C1-C6 haloalkyl, and C1-C6 polyhaloalkyl. In a still further aspect, each of $R^{2a}$, $R^{2b}$, and $R^{2c}$ is hydrogen; and $R^{2d}$ is selected from hydrogen, C1-C3 alkyl, C1-C3 haloalkyl, and C1-C3 polyhaloalkyl. In an even further aspect, each of $R^{2a}$, $R^{2b}$, and $R^{2c}$ is hydrogen; and $R^{2d}$ is selected from C1-C3 alkyl, C1-C3 haloalkyl, and C1-C3 polyhaloalkyl. In a yet further aspect, each of $R^{2a}$, $R^{2b}$, and $R^{2c}$ is hydrogen; and $R^{2d}$ is selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^{2a}$, $R^{2b}$, and $R^{2c}$ is hydrogen; and $R^{2d}$ is selected from hydrogen, methyl, —$CH_2F$, —$CH_2Cl$, —$CHF_2$, —$CF_3$, —$CHCl_2$, and —$CCl_3$. In a still further aspect, each of $R^{2a}$, $R^{2b}$, and $R^{2c}$ is hydrogen; and $R^{2d}$ is selected from hydrogen, methyl, —$CH_2F$, —$CHF_2$, and —$CF_3$.

In a further aspect, each of $R^{2a}$, $R^{2b}$, and $R^{2d}$ is hydrogen; and $R^{2c}$ is selected from hydrogen, C1-C6 alkyl, C1-C6 haloalkyl, and C1-C6 polyhaloalkyl. In a still further aspect, each of $R^{2a}$, $R^{2b}$, and $R^{2d}$ is hydrogen; and $R^{2c}$ is selected from hydrogen, C1-C3 alkyl, C1-C3 haloalkyl, and C1-C3 polyhaloalkyl. In an even further aspect, each of $R^{2a}$, $R^{2b}$, and $R^{2d}$ is hydrogen; and $R^{2c}$ is selected from C1-C3 alkyl, C1-C3 haloalkyl, and C1-C3 polyhaloalkyl. In a yet further aspect, each of $R^{2a}$, $R^{2b}$, and $R^{2d}$ is hydrogen; and $R^{2c}$ is selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^{2a}$, $R^{2b}$, and $R^{2d}$ is hydrogen; and $R^{2c}$ is selected from hydrogen, methyl, —$CH_2F$, —$CH_2Cl$, —$CHF_2$, —$CF_3$, —$CHCl_2$, and —$CCl_3$. In a still further aspect, each of $R^{2a}$, $R^{2b}$, and $R^{2d}$ is hydrogen; and $R^{2c}$ is selected from hydrogen, methyl, —$CH_2F$, —$CHF_2$, and —$CF_3$.

In a further aspect, each of $R^{2a}$, $R^{2c}$, and $R^{2d}$ is hydrogen; and $R^{2b}$ is selected from hydrogen, C1-C6 alkyl, C1-C6 haloalkyl, and C1-C6 polyhaloalkyl. In a still further aspect, each of $R^{2a}$, $R^{2c}$, and $R^{2d}$ is hydrogen; and $R^{2b}$ is selected from hydrogen, C1-C3 alkyl, C1-C3 haloalkyl, and C1-C3 polyhaloalkyl. In an even further aspect, each of $R^{2a}$, $R^{2c}$, and $R^{2d}$ is hydrogen; and $R^{2b}$ is selected from C1-C3 alkyl, C1-C3 haloalkyl, and C1-C3 polyhaloalkyl. In a yet further aspect, each of $R^{2a}$, $R^{2c}$, and $R^{2d}$ is hydrogen; and $R^{2b}$ is selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^{2a}$, $R^{2c}$, and $R^{2d}$ is hydrogen; and $R^{2b}$ is selected from hydrogen, methyl, —$CH_2F$, —$CH_2Cl$, —$CHF_2$, —$CF_3$, —$CHCl_2$, and —$CCl_3$. In a still further aspect, each of $R^{2a}$, $R^{2c}$, and $R^{2d}$ is hydrogen; and $R^{2b}$ is selected from hydrogen, methyl, —$CH_2F$, —$CHF_2$, and —$CF_3$.

In a further aspect, each of $R^{2b}$, $R^{2c}$, and $R^{2d}$ is hydrogen; and $R^{2a}$ is selected from hydrogen, C1-C6 alkyl, C1-C6 haloalkyl, and C1-C6 polyhaloalkyl. In a still further aspect, each of $R^{2b}$, $R^{2c}$, and $R^{2d}$ is hydrogen; and $R^{2a}$ is selected from hydrogen, C1-C3 alkyl, C1-C3 haloalkyl, and C1-C3 polyhaloalkyl. In an even further aspect, each of $R^{2b}$, $R^{2a}$, and $R^{2d}$ is hydrogen; and $R^{2a}$ is selected from C1-C3 alkyl, C1-C3 haloalkyl, and C1-C3 polyhaloalkyl. In a yet further aspect, each of $R^{2b}$, $R^{2c}$, and $R^{2d}$ is hydrogen; and $R^{2a}$ is selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, each of $R^{2b}$, $R^{2c}$, and $R^{2d}$ is hydrogen; and $R^{2a}$ is selected from hydrogen, methyl, —$CH_2F$, —$CH_2Cl$, —$CHF_2$, —$CF_3$, —$CHCl_2$, and —$CCl_3$. In a still further aspect, each of $R^{2b}$, $R^{2c}$, and $R^{2d}$ is hydrogen; and $R^{2a}$ is selected from hydrogen, methyl, —$CH_2F$, —$CHF_2$, and —$CF_3$.

e. $R^3$ Groups

In one aspect, $R^3$ is selected from hydrogen, C1-C6 alkyl, C1-C6 haloalkyl, and C1-C6 polyhaloalkyl. In a further aspect, $R^3$ is selected from hydrogen, C1-C3 alkyl, C1-C3 haloalkyl, and C1-C3 polyhaloalkyl. In a still further aspect, $R^3$ is selected from C1-C3 alkyl, C1-C3 haloalkyl, and C1-C3 polyhaloalkyl. In a yet further aspect, $R^3$ is selected from hydrogen, methyl, ethyl, propyl, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, and —$(CH_2)_2CCl_3$. In an even further aspect, $R^3$ is selected from hydrogen, methyl, —$CH_2F$, —$CH_2Cl$, —$CHF_2$, —$CF_3$, —$CHCl_2$, and —$CCl_3$. In a still further aspect, $R^3$ is selected from hydrogen, methyl, —$CH_2F$, —$CHF_2$, and —$CF_3$. In a yet further aspect, $R^3$ is hydrogen.

f. $R^4$ Groups

In one aspect, each occurrence of $R^4$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino. In a further aspect, each occurrence of $R^4$ is independently selected from hydrogen, halogen, cyano, hydroxyl, —NH$_2$, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, and C1-C3 dialkylamino. In a still further aspect, each occurrence of R$^4$ is hydrogen.

In a further aspect, each occurrence of R$^4$ is independently selected from hydrogen, halogen, cyano, hydroxyl, —NH$_2$, C1-C6 alkyl, C1-C6 haloalkyl, and C1-C6 polyhaloalkyl. In a still further aspect, each occurrence of R$^4$ is independently selected from hydrogen, halogen, cyano, hydroxyl, —NH$_2$, C1-C3 alkyl, C1-C3 haloalkyl, and C1-C3 polyhaloalkyl. In a yet further aspect, each occurrence of R$^4$ is independently selected from hydrogen, —F, —Cl, cyano, hydroxyl, —NH$_2$, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^4$ is independently selected from hydrogen, —F, —Cl, cyano, hydroxyl, —NH$_2$, methyl, —CH$_2$F, —CH$_2$Cl, —CHF$_2$, —CF$_3$, —CHCl$_2$, and —CCl$_3$. In a still further aspect, each occurrence of R$^4$ is independently selected from hydrogen, —F, —Cl, cyano, hydroxyl, —NH$_2$, methyl, —CH$_2$F, —CHF$_2$, and —CF$_3$.

In a further aspect, each occurrence of R$^4$ is independently selected from hydrogen, halogen, C1-C6 alkyl, C1-C6 haloalkyl, and C1-C6 polyhaloalkyl. In a still further aspect, each occurrence of R$^4$ is independently selected from hydrogen, halogen, C1-C3 alkyl, C1-C3 haloalkyl, and C1-C3 polyhaloalkyl. In a yet further aspect, each occurrence of R$^4$ is independently selected from hydrogen, —F, —Cl, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^4$ is independently selected from hydrogen, —F, —Cl, methyl, —CH$_2$F, —CH$_2$Cl, —CHF$_2$, —CF$_3$, —CHCl$_2$, and —CCl$_3$. In a still further aspect, each occurrence of R$^4$ is independently selected from hydrogen, —F, —Cl, methyl, —CH$_2$F, —CHF$_2$, and —CF$_3$.

In a further aspect, each occurrence of R$^4$ is independently selected from hydrogen, C1-C6 alkyl, C1-C6 haloalkyl, and C1-C6 polyhaloalkyl. In a still further aspect, each occurrence of R$^4$ is independently selected from hydrogen, C1-C3 alkyl, C1-C3 haloalkyl, and C1-C3 polyhaloalkyl. In a yet further aspect, each occurrence of R$^4$ is independently selected from hydrogen, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^4$ is independently selected from hydrogen, methyl, —CH$_2$F, —CH$_2$Cl, —CHF$_2$, —CF$_3$, —CHCl$_2$, and —CCl$_3$. In a still further aspect, each occurrence of R$^4$ is independently selected from hydrogen, methyl, —CH$_2$F, —CHF$_2$, and —CF$_3$.

In a further aspect, each occurrence of R$^4$ is independently selected from hydrogen, halogen, —NH$_2$, C1-C6 alkyl, C1-C6 alkylamino, and C1-C6 dialkylamino. In a still further aspect, each occurrence of R$^4$ is independently selected from hydrogen, halogen, —NH$_2$, C1-C3 alkyl, C1-C3 alkylamino, and C1-C3 dialkylamino. In a yet further aspect, each occurrence of R$^4$ is independently selected from hydrogen, —F, —Cl, —NH$_2$, methyl, ethyl, propyl, isopropyl, —NHCH$_3$, —NHCH$_2$CH$_3$, —NH(CH$_2$)$_2$CH$_3$, —NHCH(CH$_3$)$_2$, and —N(CH$_3$)$_2$. In an even further aspect, each occurrence of R$^4$ is independently selected from hydrogen, —F, —Cl, —NH$_2$, methyl, —NHCH$_3$, —NHCH$_2$CH$_3$, and —N(CH$_3$)$_2$.

In a further aspect, each occurrence of R$^4$ is independently selected from hydrogen, halogen, hydroxyl, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^4$ is independently selected from hydrogen, halogen, hydroxyl, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^4$ is independently selected from hydrogen, halogen, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^4$ is independently selected from hydrogen, halogen, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^4$ is independently selected from hydrogen, hydroxyl, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^4$ is independently selected from hydrogen, hydroxyl, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^4$ is independently selected from hydrogen, halogen, hydroxyl, and C1-C6 alkoxy. In a still further aspect, each occurrence of R$^4$ is independently selected from hydrogen, halogen, hydroxyl, and C1-C3 alkoxy.

In various further aspects, it is understood that the representation of R$^4$ by a formula:

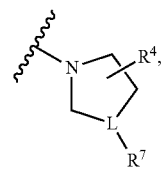

is understood to be equivalent to and discloses a formula:

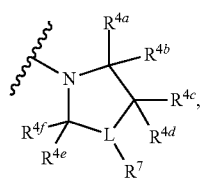

wherein R$^4$ is understood represent six independent substituents, R$^{4a}$, R$^{4b}$, R$^{4c}$, R$^{4d}$, R$^{4e}$ and R$^{4f}$, as shown above. By "independent substituents," it is meant that each R substituent can be independently defined. For example, if in one instance R$^{4a}$ is halogen, then R$^{4b}$ is not necessarily halogen in that instance.

In various further aspects, it is understood that the representation of R$^4$ by a formula:

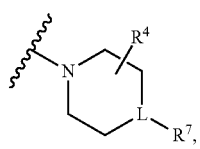

is understood to be equivalent to and discloses a formula:

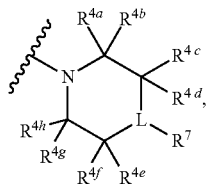

wherein $R^4$ is understood to represent eight independent substituents, $R^{4a}$, $R^{4b}$, $R^{4c}$, $R^{4d}$, $R^{4e}$, $R^{4f}$, $R^{4g}$ and $R^{4h}$, as shown above.

In various further aspects, it is understood that the representation of $R^4$ by a formula:

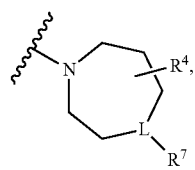

is understood to be equivalent to and discloses a formula:

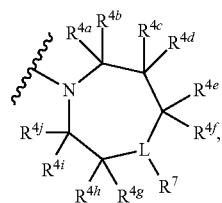

wherein $R^4$ is understood to represent ten independent substituents, $R^{4a}$, $R^{4b}$, $R^{4c}$, $R^{4d}$, $R^{4e}$, $R^{4f}$, $R^{4g}$, $R^{4h}$, $R^{4i}$, and $R^{4j}$, as shown above.

In various further aspects, it is understood that the representation of $R^4$ and $R^5$ by a formula:

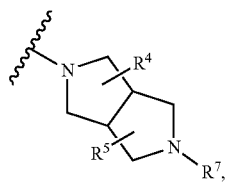

is understood to be equivalent to and discloses a formula:

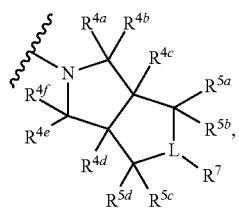

wherein $R^4$ is understood in the structure above to represent six independent substituents, $R^{4a}$, $R^{4b}$, $R^{4c}$, $R^{4d}$, $R^{4e}$ and $R^{4f}$, and wherein $R^5$ is understood in the structure above to represent four independent substituents, $R^{5a}$, $R^{5b}$, $R^{5c}$, and $R^{5d}$, as shown above.

In various further aspects, it is understood that the representation of $R^4$ and $R^5$ by a formula:

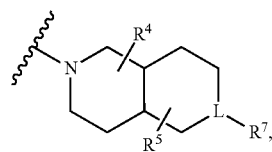

is understood to be equivalent to and discloses a formula:

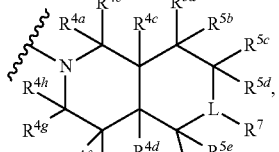

wherein $R^4$ is understood in the structure above to represent eight independent substituents, $R^{4a}$, $R^{4b}$, $R^{4c}$, $R^{4d}$, $R^{4e}$, $R^{4f}$, $R^{4g}$, and $R^{4h}$, and wherein $R^5$ is understood in the structure above to represent six independent substituents, $R^{5a}$, $R^{5b}$, $R^{5c}$, $R^{5d}$, $R^{5e}$, and $R^{5f}$, as shown above.

g. $R^5$ Groups

In one aspect, each occurrence of $R^5$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino. In a further aspect, each occurrence of $R^5$ is independently selected from hydrogen, halogen, cyano, hydroxyl, —$NH_2$, C1-C3 alkyl, C1-C3 haloalkyl, C1-C3 polyhaloalkyl, C1-C3 alkoxy, C1-C3 alkoxy-C1-C3 alkyl, C1-C3 alkylamino, C1-C3 haloalkyl-oxy-C1-C3 alkyl, C1-C3 polyhaloalkyl-oxy-C1-C3 alkyl, and C1-C3 dialkylamino. In a still further aspect, each occurrence of $R^5$ is hydrogen.

In a further aspect, each occurrence of $R^5$ is independently selected from hydrogen, halogen, cyano, hydroxyl, —$NH_2$, C1-C6 alkyl, C1-C6 haloalkyl, and C1-C6 polyhaloalkyl. In a still further aspect, each occurrence of $R^5$ is independently selected from hydrogen, halogen, cyano, hydroxyl, —$NH_2$, C1-C3 alkyl, C1-C3 haloalkyl, and C1-C3 polyhaloalkyl. In a yet further aspect, each occurrence of $R^5$ is independently selected from hydrogen, —F, —Cl, cyano, hydroxyl, —$NH_2$, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^5$ is independently selected from hydrogen, —F, —Cl, cyano, hydroxyl, —NH$_2$, methyl, —CH$_2$F, —CH$_2$Cl, —CHF$_2$, —CF$_3$, —CHCl$_2$, and —CCl$_3$. In a still further aspect, each occurrence of R$^5$ is independently selected from hydrogen, —F, —Cl, cyano, hydroxyl, —NH$_2$, methyl, —CH$_2$F, —CHF$_2$, and —CF$_3$.

In a further aspect, each occurrence of R$^5$ is independently selected from hydrogen, halogen, C1-C6 alkyl, C1-C6 haloalkyl, and C1-C6 polyhaloalkyl. In a still further aspect, each occurrence of R$^5$ is independently selected from hydrogen, halogen, C1-C3 alkyl, C1-C3 haloalkyl, and C1-C3 polyhaloalkyl. In a yet further aspect, each occurrence of R$^5$ is independently selected from hydrogen, —F, —Cl, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^5$ is independently selected from hydrogen, —F, —Cl, methyl, —CH$_2$F, —CH$_2$Cl, —CHF$_2$, —CF$_3$, —CHCl$_2$, and —CCl$_3$. In a still further aspect, each occurrence of R$^5$ is independently selected from hydrogen, —F, —Cl, methyl, —CH$_2$F, —CHF$_2$, and —CF$_3$.

In a further aspect, each occurrence of R$^5$ is independently selected from hydrogen, C1-C6 alkyl, C1-C6 haloalkyl, and C1-C6 polyhaloalkyl. In a still further aspect, each occurrence of R$^5$ is independently selected from hydrogen, C1-C3 alkyl, C1-C3 haloalkyl, and C1-C3 polyhaloalkyl. In a yet further aspect, each occurrence of R$^5$ is independently selected from hydrogen, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, each occurrence of R$^5$ is independently selected from hydrogen, methyl, —CH$_2$F, —CH$_2$Cl, —CHF$_2$, —CF$_3$, —CHCl$_2$, and —CCl$_3$. In a still further aspect, each occurrence of R$^5$ is independently selected from hydrogen, methyl, —CH$_2$F, —CHF$_2$, and —CF$_3$.

In a further aspect, each occurrence of R$^5$ is independently selected from hydrogen, halogen, —NH$_2$, C1-C6 alkyl, C1-C6 alkylamino, and C1-C6 dialkylamino. In a still further aspect, each occurrence of R$^5$ is independently selected from hydrogen, halogen, —NH$_2$, C1-C3 alkyl, C1-C3 alkylamino, and C1-C3 dialkylamino. In a yet further aspect, each occurrence of R$^5$ is independently selected from hydrogen, —F, —Cl, —NH$_2$, methyl, ethyl, propyl, isopropyl, —NHCH$_3$, —NHCH$_2$CH$_3$, —NH(CH$_2$)$_2$CH$_3$, —NHCH(CH$_3$)$_2$, and —N(CH$_3$)$_2$. In an even further aspect, each occurrence of R$^5$ is independently selected from hydrogen, —F, —Cl, —NH$_2$, methyl, —NHCH$_3$, —NHCH$_2$CH$_3$, and —N(CH$_3$)$_2$.

In a further aspect, each occurrence of R$^5$ is independently selected from hydrogen, halogen, hydroxyl, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^5$ is independently selected from hydrogen, halogen, hydroxyl, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^5$ is independently selected from hydrogen, halogen, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^5$ is independently selected from hydrogen, halogen, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^5$ is independently selected from hydrogen, hydroxyl, C1-C6 alkoxy, C1-C6 alkoxy-C1-C6 alkyl, C1-C6 haloalkyl-oxy-C1-C6 alkyl, and C1-C6 polyhaloalkyl-oxy-C1-C6 alkyl. In a still further aspect, each occurrence of R$^5$ is independently selected from hydrogen, hydroxyl, C1-C3 alkoxy, C1-C3 alkoxy-C1-C3 alkyl, C1-C3 haloalkyl-oxy-C1-C3 alkyl, and C1-C3 polyhaloalkyl-oxy-C1-C3 alkyl.

In a further aspect, each occurrence of R$^5$ is independently selected from hydrogen, halogen, hydroxyl, and C1-C6 alkoxy. In a still further aspect, each occurrence of R$^5$ is independently selected from hydrogen, halogen, hydroxyl, and C1-C3 alkoxy.

h. R$^6$ Groups

In one aspect, R$^6$, when present, is selected from hydrogen, halogen, C1-C6 alkyl, C1-C6 haloalkyl, and C1-C6 polyhaloalkyl. In a further aspect, R$^6$ is selected from hydrogen, halogen, C1-C3 alkyl, C1-C3 haloalkyl, and C1-C3 polyhaloalkyl. In a yet further aspect, R$^6$ is selected from hydrogen, —F, —Cl, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In a still further aspect, R$^6$ is selected from hydrogen, —F, —Cl, methyl, —CH$_2$F, —CH$_2$Cl, —CHF$_2$, —CF$_3$, —CHCl$_2$, and —CCl$_3$. In an even further aspect, R$^6$ is selected from hydrogen, —F, —Cl, methyl, —CH$_2$F, —CHF$_2$, and —CF$_3$.

In a further aspect, R$^6$ is selected from hydrogen, C1-C6 alkyl, C1-C6 haloalkyl, and C1-C6 polyhaloalkyl. In a still further aspect, R$^6$ is selected from hydrogen, C1-C3 alkyl, C1-C3 haloalkyl, and C1-C3 polyhaloalkyl. In a yet further aspect, R$^6$ is selected from hydrogen, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, R$^6$ is selected from hydrogen, methyl, —CH$_2$F, —CH$_2$Cl, —CHF$_2$, —CF$_3$, —CHCl$_2$, and —CCl$_3$. In a still further aspect, R$^6$ is selected from hydrogen, methyl, —CH$_2$F, —CHF$_2$, and —CF$_3$.

In a further aspect, R$^6$ is selected from halogen, C1-C6 alkyl, C1-C6 haloalkyl, and C1-C6 polyhaloalkyl. In a still further aspect, R$^6$ is selected from halogen, C1-C3 alkyl, C1-C3 haloalkyl, and C1-C3 polyhaloalkyl. In a yet further aspect, —F, —Cl, methyl, ethyl, propyl, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, and —(CH$_2$)$_2$CCl$_3$. In an even further aspect, R$^6$ is selected from —F, —Cl, methyl, —CH$_2$F, —CH$_2$Cl, —CHF$_2$, —CF$_3$, —CHCl$_2$, and —CCl$_3$. In a still further aspect, R$^6$ is selected from hydrogen, —F, —Cl, methyl, —CH$_2$F, —CHF$_2$, and —CF$_3$.

In a further aspect, R$^6$ is selected from hydrogen and halogen. In a still further aspect, R$^6$ is selected from hydrogen, —F, and —Cl. In an even further aspect, R$^6$ is selected from hydrogen and —F. In a still further aspect, R$^6$ is selected from hydrogen and —Cl. In a yet further aspect, R$^6$ is hydrogen. In an even further aspect, $R^6$ is a halogen. In a still further aspect, $R^6$ is selected from —F, —Cl and —Br. In a yet further aspect, $R^6$ is selected from —F and —Cl. In an even further aspect, $R^6$ is —F. In a still further aspect, $R^6$ is —Cl.

i. $R^7$ Groups

In one aspect, $R^7$ is selected from $Ar^1$ and $Ar^2$. In a further aspect, $R^7$ is $Ar^1$. In a further aspect, $R^7$ is $Ar^2$.

j. $R^8$ Groups

In one aspect, each of $R^{8a}$, $R^{8b}$, $R^{8c}$, and $R^{8d}$ is independently selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{8a}$, $R^{8b}$, $R^{8c}$, and $R^{8d}$ is hydrogen. In a further aspect, each of $R^{8a}$, $R^{8b}$, $R^{8c}$, and $R^{8d}$ is independently selected from hydrogen, halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino, provided that at least one of $R^{8a}$, $R^{8b}$, $R^{8c}$, and $R^{8d}$ is hydrogen. In a still further aspect, each of $R^{8a}$, $R^{8b}$, $R^{8c}$, and $R^{8d}$ is independently selected from hydrogen, —F, —Cl, —OH, —$NH_2$, methyl, ethyl, propyl, isopropyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$, provided that at least one of $R^{8a}$, $R^{8b}$, $R^{8c}$, and $R^{8d}$ is hydrogen. In a yet further aspect, each of $R^{8a}$, $R^{8b}$, $R^{8c}$, and $R^{8d}$ is independently selected from hydrogen, —F, —Cl, —$NH_2$, methyl, ethyl, —$OCH_3$, —$OCH_2CH_3$, —$CH_2F$, —$CH_2Cl$, —$CH_2CH_2F$, —$CH_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$NHCH_3$, —$NHCH_2CH_3$, —$N(CH_3)_2$, —$N(CH_3)CH_2CH_3$, and —$N(CH_2CH_3)_2$, provided that at least one of $R^{8a}$, $R^{8b}$, $R^{8c}$, and $R^{8d}$ is hydrogen. In an even further aspect, each of $R^{8a}$, $R^{8b}$, $R^{8c}$, and $R^{8d}$ is independently selected from hydrogen, —F, —Cl, —$NH_2$, methyl, —$OCH_3$—$CH_2F$, —$CH_2Cl$, —$CHF_2$, —$CF_3$, —$CHCl_2$, —$CCl_3$, —$NHCH_3$, and —$N(CH_3)_2$, provided that at least one of $R^{8a}$, $R^{8b}$, $R^{8c}$, and $R^{8d}$ is hydrogen. In a still further aspect, each of $R^{8a}$, $R^{8b}$, $R^{8c}$, and $R^{8d}$ is independently selected from hydrogen, —F, —Cl, methyl, —$OCH_3$—$CH_2F$, —$CH_2Cl$, —$CF_3$, —$CCl_3$, —$NHCH_3$, and —$N(CH_3)_2$, provided that at least one of $R^{8a}$, $R^{8b}$, $R^{8c}$, and $R^{8d}$ is hydrogen. In a yet further aspect, each of $R^{8a}$, $R^{8b}$, $R^{8c}$, and $R^{8d}$ is independently selected from hydrogen, —F, —Cl, methyl, —$CH_2F$, —$CH_2Cl$, —$CF_3$, and —$CCl_3$, provided that at least one of $R^{8a}$, $R^{8b}$, $R^{8c}$, and $R^{8d}$ is hydrogen.

In a further aspect, each of $R^{8a}$, $R^{8b}$, and $R^{8c}$ is hydrogen; and $R^{8d}$ is selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each of $R^{8a}$, $R^{8b}$, and $R^{8c}$ is hydrogen; and $R^{8d}$ is selected from hydrogen, halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In an even further aspect, each of $R^{8a}$, $R^{8b}$, and $R^{8c}$ is hydrogen; and $R^{8d}$ is selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a yet further aspect, each of $R^{8a}$, $R^{8b}$, and $R^{8c}$ is hydrogen; and $R^{8d}$ is selected from hydrogen, methyl, ethyl, propyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In an even further aspect, each of $R^{8a}$, $R^{8b}$, and $R^{8c}$ is hydrogen; and $R^{8d}$ is selected from hydrogen, methyl, —$OCH_3$, —$OCH_2CH_3$, —$CH_2F$, —$CH_2Cl$, —$CHF_2$, —$CF_3$, —$CHCl_2$, —$CCl_3$, —$NHCH_3$, and —$N(CH_3)_2$. In a still further aspect, each of $R^{8a}$, $R^{8b}$, and $R^{8c}$ is hydrogen; and $R^{8d}$ is selected from hydrogen, methyl, —$CH_2F$, —$CHF_2$, —$CF_3$, —$OCH_3$, —$NHCH_3$, and —$N(CH_3)_2$.

In a further aspect, each of $R^{8a}$, $R^{8b}$, and $R^{8d}$ is hydrogen; and $R^{8c}$ is selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each of $R^{8a}$, $R^{8b}$, and $R^{8d}$ is hydrogen; and $R^{8c}$ is selected from hydrogen, halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In an even further aspect, each of $R^{8a}$, $R^{8b}$, and $R^{8d}$ is hydrogen; and $R^{8c}$ is selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a yet further aspect, each of $R^{8a}$, $R^{8b}$, and $R^{8d}$ is hydrogen; and $R^{8c}$ is selected from hydrogen, methyl, ethyl, propyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In an even further aspect, each of $R^{8a}$, $R^{8b}$, and $R^{8d}$ is hydrogen; and $R^{8c}$ is selected from hydrogen, methyl, —$OCH_3$, —$OCH_2CH_3$, —$CH_2F$, —$CH_2Cl$, —$CHF_2$, —$CF_3$, —$CHCl_2$, —$CCl_3$, —$NHCH_3$, and —$N(CH_3)_2$. In a still further aspect, each of $R^{8a}$, $R^{8b}$, and $R^{8d}$ is hydrogen; and $R^{8c}$ is selected from hydrogen, methyl, —$CH_2F$, —$CHF_2$, —$CF_3$, —$OCH_3$, —$NHCH_3$, and —$N(CH_3)_2$.

In a further aspect, each of $R^{8a}$, $R^{8c}$, and $R^{8d}$ is hydrogen; and $R^{8b}$ is selected from hydrogen, halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each of $R^{8a}$, $R^{8c}$, and $R^{8d}$ is hydrogen; and $R^{8b}$ is selected from hydrogen, halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In an even further aspect, each of $R^{8a}$, $R^{8c}$, and $R^{8d}$ is hydrogen; and $R^{8b}$ is selected from halogen, hydroxyl, cyano, —$NH_2$, C1-C3 alkyl, C1-C3 alkoxy, C1-C3 haloalkyl, C1-C3 polyhaloalkyl, C1-C3 alkylamino, and C1-C3 dialkylamino. In a yet further aspect, each of $R^{8a}$, $R^{8c}$, and $R^{8d}$ is hydrogen; and $R^{8b}$ is selected from hydrogen, methyl, ethyl, propyl, —$OCH_3$, —$OCH_2CH_3$, —$O(CH_2)_2CH_3$, —$OCH(CH_3)_2$, —$CH_2F$, —$CH_2Cl$, —$CH_2CH_2F$, —$CH_2CH_2Cl$, —$(CH_2)_2CH_2F$, —$(CH_2)_2CH_2Cl$, —$CHF_2$, —$CF_3$, —$CHCl_2$, —$CCl_3$, —$CH_2CHF_2$, —$CH_2CF_3$, —$CH_2CHCl_2$, —$CH_2CCl_3$, —$(CH_2)_2CHF_2$, —$(CH_2)_2CF_3$, —$(CH_2)_2CHCl_2$, —$(CH_2)_2CCl_3$, —$NHCH_3$, —$NHCH_2CH_3$, —$NH(CH_2)_2CH_3$, —$NHCH(CH_3)_2$, —$N(CH_3)_2$, —$N(CH_3)CH_2CH_3$, and —$N(CH_2CH_3)_2$. In an even further aspect, each of $R^{8a}$, $R^{8c}$, and $R^{8d}$ is hydrogen; and $R^{8b}$ is selected from hydrogen, methyl, —$OCH_3$, —$OCH_2CH_3$, —$CH_2F$, —$CH_2Cl$, —CHF$_2$, —CF$_3$, —CHCl$_2$, —CCl$_3$, —NHCH$_3$, and —N(CH$_3$)$_2$. In a still further aspect, each of R$^{8a}$, R$^{8c}$, and R$^{8d}$ is hydrogen; and R$^{8b}$ is selected from hydrogen, methyl, —CH$_2$F, —CHF$_2$, —CF$_3$, —OCH$_3$, —NHCH$_3$, and —N(CH$_3$)$_2$.

In a further aspect, each of R$^{8b}$, R$^{8c}$, and R$^{8d}$ is hydrogen; and R$^{8a}$ is selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, each of R$^{8b}$, R$^{8c}$, and R$^{8d}$ is hydrogen; and R$^{8a}$ is selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In an even further aspect, each of R$^{8b}$, R$^{8c}$, and R$^{8d}$ is hydrogen; and R$^{8a}$ is selected from halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a yet further aspect, each of R$^{8b}$, R$^{8c}$, and R$^{8d}$ is hydrogen; and R$^{8a}$ is selected from hydrogen, methyl, ethyl, propyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —(CH$_2$)$_2$CH$_2$F, —(CH$_2$)$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —(CH$_2$)$_2$CHF$_2$, —(CH$_2$)$_2$CF$_3$, —(CH$_2$)$_2$CHCl$_2$, —(CH$_2$)$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In an even further aspect, each of R$^{8b}$, R$^{8c}$, and R$^{8d}$ is hydrogen; and R$^{8a}$ is selected from hydrogen, methyl, —OCH$_3$, —OCH$_2$CH$_3$, —CH$_2$F, —CH$_2$Cl, —CHF$_2$, —CF$_3$, —CHCl$_2$, —CCl$_3$, —NHCH$_3$, and —N(CH$_3$)$_2$. In a still further aspect, each of R$^{8b}$, R$^{8c}$, and R$^{8d}$ is hydrogen; and R$^{8a}$ is selected from hydrogen, methyl, —CH$_2$F, —CHF$_2$, —CF$_3$, —OCH$_3$, —NHCH$_3$, and —N(CH$_3$)$_2$.

In a further aspect, each of R$^{8a}$, R$^{8b}$, and R$^{8c}$ is hydrogen; and R$^{8d}$ is selected from hydrogen and halogen. In a still further aspect, each of R$^{8a}$, R$^{8b}$, and R$^{8c}$ is hydrogen; and R$^{8d}$ is selected from hydrogen, —F, and —Cl. In an even further aspect, each of R$^{8a}$, R$^{8b}$, and R$^{8c}$ is hydrogen; and R$^{8d}$ is —F.

In a further aspect, each of R$^{8a}$, R$^{8b}$, and R$^{8d}$ is hydrogen; and R$^{8c}$ is selected from hydrogen and halogen. In a still further aspect, each of R$^{8a}$, R$^{8b}$, and R$^{8d}$ is hydrogen; and R$^{8c}$ is selected from hydrogen, —F, and —Cl. In an even further aspect, each of R$^{8a}$, R$^{8b}$, and R$^{8d}$ is hydrogen; and R$^{8c}$ is —F.

In a further aspect, each of R$^{8a}$, R$^{8c}$, and R$^{8d}$ is hydrogen; and R$^{8b}$ is selected from hydrogen and halogen. In a still further aspect, each of R$^{8a}$, R$^{8c}$, and R$^{8d}$ is hydrogen; and R$^{8b}$ is selected from hydrogen, —F, and —Cl. In an even further aspect, each of R$^{8a}$, R$^{8c}$, and R$^{8d}$ is hydrogen; and R$^{8b}$ is —F.

In a further aspect, each of R$^{8b}$, R$^{8c}$, and R$^{8d}$ is hydrogen; and R$^{8a}$ is selected from hydrogen and halogen. In a still further aspect, each of R$^{8b}$, R$^{8c}$, and R$^{8d}$ is hydrogen; and R$^{8a}$ is selected from hydrogen, —F, and —Cl. In an even further aspect, each of R$^{8b}$, R$^{8c}$, and R$^{8d}$ is hydrogen; and R$^{8a}$ is —F.

In a further aspect, each of R$^{8a}$, R$^{8b}$, R$^{8c}$, and R$^{8d}$ is hydrogen.

k. R$^9$ Groups

In one aspect, each of R$^{9a}$, R$^{9b}$, R$^{9c}$, R$^{9d}$, R$^{9e}$, R$^{9f}$, and R$^{9g}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least four of R$^{9a}$, R$^{9b}$, R$^{9c}$, R$^{9d}$, R$^{9e}$, R$^{9f}$, and R$^{9g}$ are hydrogen. In a further aspect, each of R$^{9a}$, R$^{9b}$, R$^{9c}$, R$^{9d}$, R$^{9e}$, R$^{9f}$, and R$^{9g}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino, provided that at least four of R$^{9a}$, R$^{9b}$, R$^{9c}$, R$^{9d}$, R$^{9e}$, R$^{9f}$, and R$^{9g}$ are hydrogen. In a still further aspect, each of R$^{9a}$, R$^{9b}$, R$^{9c}$, R$^{9d}$, R$^{9e}$, R$^{9f}$, and R$^{9g}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least four of R$^{9a}$, R$^{9b}$, R$^{9c}$, R$^{9d}$, R$^{9e}$, R$^{9f}$, and R$^{9g}$ are hydrogen. In a yet further aspect, each of R$^{9a}$, R$^{9b}$, R$^{9c}$, R$^{9d}$, R$^{9e}$, R$^{9f}$, and R$^{9g}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$, provided that at least four of R$^{9a}$, R$^{9b}$, R$^{9c}$, R$^{9d}$, R$^{9e}$, R$^{9f}$, and R$^{9g}$ are hydrogen. In an even further aspect, each of R$^{9a}$, R$^{9b}$, R$^{9c}$, R$^{9d}$, R$^{9e}$, R$^{9f}$, and R$^{9g}$ is independently selected from hydrogen, —F, —Cl, —NH$_2$, methyl, —OCH$_3$, —CH$_2$F, —CH$_2$Cl, —CHF$_2$, —CF$_3$, —CHCl$_2$, —CCl$_3$, —NHCH$_3$, and —N(CH$_3$)$_2$, provided that at least four of R$^{9a}$, R$^{9b}$, R$^{9c}$, R$^{9d}$, R$^{9e}$, R$^{9f}$, and R$^{9g}$ are hydrogen. In a still further aspect, each of R$^{9a}$, R$^{9b}$, R$^{9c}$, R$^{9d}$, R$^{9e}$, R$^{9f}$, and R$^{9g}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$, provided that at least four of R$^{9a}$, R$^{9b}$, R$^{9c}$, R$^{9d}$, R$^{9e}$, R$^{9f}$, and R$^{9g}$ are hydrogen. In a yet further aspect, each of R$^{9a}$, R$^{9b}$, R$^{9c}$, R$^{9d}$, R$^{9e}$, R$^{9f}$, and R$^{9g}$ is independently selected from hydrogen, —F, —Cl, methyl, —CH$_2$F, —CH$_2$Cl, —CF$_3$, and —CCl$_3$, provided that at least four of R$^{9a}$, R$^{9b}$, R$^{9c}$, R$^{9d}$, R$^{9e}$, R$^{9f}$, and R$^{9g}$ are hydrogen. In an even further aspect, each of R$^{9a}$, R$^{9b}$, R$^{9c}$, R$^{9d}$, R$^{9e}$, R$^{9f}$, and R$^{9g}$ is independently selected from hydrogen and halogen, provided that at least four of R$^{9a}$, R$^{9b}$, R$^{9c}$, R$^{9d}$, R$^{9e}$, R$^{9f}$, and R$^{9g}$ are hydrogen. In a still further aspect, each of R$^{9a}$, R$^{9b}$, R$^{9c}$, R$^{9d}$, R$^{9e}$, R$^{9f}$, and R$^{9g}$ is independently selected from hydrogen, —F, and —Cl, provided that at least four of R$^{9a}$, R$^{9b}$, R$^{9c}$, R$^{9d}$, R$^{9e}$, R$^{9f}$, and R$^{9g}$ are hydrogen. In a yet further aspect, each of R$^{9a}$, R$^{9b}$, R$^{9c}$, R$^{9d}$, R$^{9e}$, R$^{9f}$, and R$^{9g}$ is independently selected from hydrogen and —F, provided that at least four of R$^{9a}$, R$^{9b}$, R$^{9c}$, R$^{9d}$, R$^{9e}$, R$^{9f}$, and R$^{9g}$ are hydrogen. In an even further aspect, each of R$^{9a}$, R$^{9b}$, R$^{9c}$, R$^{9d}$, R$^{9e}$, R$^{9f}$, and R$^{9g}$ is hydrogen.

In a further aspect, each of R$^{9a}$, R$^{9b}$, R$^{9c}$, R$^{9d}$, R$^{9e}$, and R$^{9f}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least three of R$^{9a}$, R$^{9b}$, R$^{9c}$, R$^{9d}$, R$^{9e}$, and R$^{9f}$ are hydrogen. In a further aspect, each of R$^{9a}$, R$^{9b}$, R$^{9c}$, R$^{9d}$, R$^{9e}$, and R$^{9f}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino, provided that at least three of R$^{9a}$, R$^{9b}$, R$^{9c}$, R$^{9d}$, R$^{9e}$, and R$^{9f}$ are hydrogen. In a still further aspect, each of R$^{9a}$, R$^{9b}$, R$^{9c}$, R$^{9d}$, R$^{9e}$, and R$^{9f}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least three of R$^{9a}$, R$^{9b}$, R$^{9c}$, $R^{9d}$, $R^{9e}$, and $R^{9f}$ are hydrogen. In a yet further aspect, each of $R^{9a}$, $R^{9b}$, $R^{9c}$, $R^{9d}$, $R^{9e}$, and $R^{9f}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$, provided that at least three of $R^{9a}$, $R^{9b}$, $R^{9c}$, $R^{9d}$, $R^{9e}$, and $R^{9f}$ are hydrogen. In an even further aspect, each of $R^{9a}$, $R^{9b}$, $R^{9c}$, $R^{9d}$, $R^{9e}$, and $R^{9f}$ is independently selected from hydrogen, —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$ provided that at least three of $R^{9a}$, $R^{9b}$, $R^{9c}$, $R^{9d}$, $R^{9e}$, and $R^{9f}$ are hydrogen. In a still further aspect, each of $R^{9a}$, $R^{9b}$, $R^{9c}$, $R^{9d}$, $R^{9e}$, and $R^{9f}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$, provided that at least three of $R^{9a}$, $R^{9b}$, $R^{9c}$, $R^{9d}$, $R^{9e}$, and $R^{9f}$ are hydrogen. In a yet further aspect, each of $R^{9a}$, $R^{9b}$, $R^{9c}$, $R^{9d}$, $R^{9e}$, and $R^{9f}$ is independently selected from hydrogen, —F, —Cl, methyl, —CH$_2$F, —CH$_2$Cl, —CF$_3$, and —CCl$_3$, provided that at least three of $R^{9a}$, $R^{9b}$, $R^{9c}$, $R^{9d}$, $R^{9e}$, and $R^{9f}$ are hydrogen. In an even further aspect, each of $R^{9a}$, $R^{9b}$, $R^{9c}$, $R^{9d}$, $R^{9e}$, and $R^{9f}$ is independently selected from hydrogen and halogen, provided that at least three of $R^{9a}$, $R^{9b}$, $R^{9c}$, $R^{9d}$, $R^{9e}$, and $R^{9f}$ are hydrogen. In a still further aspect, each of $R^{9a}$, $R^{9b}$, $R^{9c}$, $R^{9d}$, $R^{9e}$, and $R^{9f}$ is independently selected from hydrogen, —F, and —Cl, provided that at least three of $R^{9a}$, $R^{9b}$, $R^{9c}$, $R^{9d}$, $R^{9e}$, and $R^{9f}$ are hydrogen. In a yet further aspect, each of $R^{9a}$, $R^{9b}$, $R^{9c}$, $R^{9d}$, $R^{9e}$, and $R^{9f}$ is independently selected from hydrogen and —F, provided that at least three of $R^{9a}$, $R^{9b}$, $R^{9c}$, $R^{9d}$, $R^{9e}$, and $R^{9f}$ are hydrogen. In an even further aspect, each of $R^{9a}$, $R^{9b}$, $R^{9c}$, $R^{9d}$, $R^{9e}$, and $R^{9f}$ is hydrogen.

In a further aspect, each of $R^{9a}$, $R^{9b}$, $R^{9c}$, $R^{9d}$, and $R^{9e}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least two of $R^{9a}$, $R^{9b}$, $R^{9c}$, $R^{9d}$, and $R^{9e}$ are hydrogen. In a further aspect, each of $R^{9a}$, $R^{9b}$, $R^{9c}$, $R^{9d}$, and $R^{9e}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen, —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen, —F, —Cl, methyl, —CH$_2$F, —CH$_2$Cl, —CF$_3$, and —CCl$_3$, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is independently selected from hydrogen and halogen, provided that at least two of $R^{9a}$, $R^{9b}$, $R^{9c}$, $R^{9d}$, and $R^{9e}$ are hydrogen. In a still further aspect, each of $R^{9a}$, $R^{9b}$, $R^{9c}$, $R^{9d}$, and $R^{9e}$ is independently selected from hydrogen, —F, and —Cl, provided that at least two of $R^{9a}$, $R^{9b}$, $R^{9c}$, $R^{9d}$, and $R^{9e}$ are hydrogen. In a yet further aspect, each of $R^{9a}$, $R^{9b}$, $R^{9c}$, $R^{9d}$, and $R^{9e}$ is independently selected from hydrogen and —F, provided that at least two of $R^{9a}$, $R^{9b}$, $R^{9c}$, $R^{9d}$, and $R^{9e}$ are hydrogen. In an even further aspect, each of $R^{9a}$, $R^{9b}$, $R^{9c}$, $R^{9d}$, and $R^{9e}$ is hydrogen.

In a further aspect, each of $R^{9a}$, $R^{9b}$, $R^{9c}$, and $R^{9d}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino, provided that at least one of $R^{9a}$, $R^{9b}$, $R^{9c}$, and $R^{9d}$ is hydrogen. In a further aspect, each of $R^{9a}$, $R^{9b}$, $R^{9c}$, and $R^{9d}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino, provided that at least one of $R^{9a}$, $R^{9b}$, $R^{9c}$, and $R^{9d}$ is hydrogen. In a still further aspect, each of $R^{9a}$, $R^{9b}$, $R^{9c}$, and $R^{9d}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$, provided that at least one of $R^{9a}$, $R^{9b}$, $R^{9c}$, and $R^{9d}$ is hydrogen. In a yet further aspect, each of $R^{9a}$, $R^{9b}$, $R^{9c}$, and $R^{9d}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$, provided that at least one of $R^{9a}$, $R^{9b}$, $R^{9c}$, and $R^{9d}$ is hydrogen. In an even further aspect, each of $R^{9a}$, $R^{9b}$, $R^{9c}$, and $R^{9d}$ is independently selected from hydrogen, —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$, provided that at least one of $R^{9a}$, $R^{9b}$, $R^{9c}$, and $R^{9d}$ is hydrogen. In a still further aspect, each of $R^{9a}$, $R^{9b}$, $R^{9c}$, and $R^{9d}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$, provided that at least one of $R^{9a}$, $R^{9b}$, $R^{9c}$, and $R^{9d}$ is hydrogen. In a yet further aspect, each of $R^{9a}$, $R^{9b}$, $R^{9c}$, and $R^{9d}$ is independently selected from hydrogen, —F, —Cl, methyl, —CH$_2$F, —CH$_2$Cl, —CF$_3$, and —CCl$_3$, provided that at least one of $R^{9a}$, $R^{9b}$, $R^{9c}$, and $R^{9d}$ is hydrogen. In an even further aspect, each of $R^{9a}$, $R^{9b}$, $R^{9c}$, and $R^{9d}$ is independently selected from hydrogen and halogen, provided that at least one of $R^{9a}$, $R^{9b}$, $R^{9c}$, and $R^{9d}$ is hydrogen. In a still further aspect, each of $R^{9a}$, $R^{9b}$, $R^{9c}$, and $R^{9d}$ is independently selected from hydrogen, —F, and —Cl, provided that at least one of $R^{9a}$, $R^{9b}$, $R^{9c}$, and $R^{9d}$ is hydrogen. In a yet further aspect, each of $R^{9a}$, $R^{9b}$, $R^{9c}$, and $R^{9d}$ is independently selected from hydrogen and —F, provided that at least one of $R^{9a}$, $R^{9b}$, $R^{9c}$, and $R^{9d}$ is hydrogen. In an even further aspect, each of $R^{9a}$, $R^{9b}$, $R^{9c}$, and $R^{9d}$ is hydrogen.

In a further aspect, each of $R^{9a}$, $R^{9b}$, and $R^{9c}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a further aspect, each of $R^{9a}$, $R^{9b}$, and $R^{9c}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, each of $R^{9a}$, $R^{9b}$, and $R^{9c}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a yet further aspect, each of $R^{9a}$, $R^{9b}$, and $R^{9a}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of $R^{9a}$, $R^{9b}$, and $R^{9c}$ is independently selected from hydrogen, —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In a still further aspect, each of $R^{9a}$, $R^{9b}$, and $R^{9c}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$. In a yet further aspect, each of $R^{9a}$, $R^{9b}$, and $R^{9c}$ is independently selected from hydrogen, —F, —Cl, methyl, —CH$_2$F, —CH$_2$Cl, —CF$_3$, and —CCl$_3$. In an even further aspect, each of $R^{9a}$, $R^{9b}$, and $R^{9c}$ is independently selected from hydrogen and halogen. In a still further aspect, each of $R^{9a}$, $R^{9b}$, and $R^{9c}$ is independently selected from hydrogen, —F, and —Cl. In a yet further aspect, each of $R^{9a}$, $R^{9b}$, and $R^{9a}$ is independently selected from hydrogen and —F. In an even further aspect, each of $R^{9a}$, $R^{9b}$, and $R^{9c}$ is hydrogen.

In a further aspect, each of $R^{9a}$ and $R^{9b}$ is independently selected from hydrogen, halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a further aspect, each of $R^{9a}$ and $R^{9b}$ is independently selected from hydrogen, halogen, hydroxyl, cyano, —NH$_2$, C1-C3 alkyl, C1-C3 alkoxy, C1-C3 haloalkyl, C1-C3 polyhaloalkyl, C1-C3 alkylamino, and C1-C3 dialkylamino. In a still further aspect, each of $R^{9a}$ and $R^{9b}$ is independently selected from hydrogen, —F, —Cl, —OH, —NH$_2$, methyl, ethyl, propyl, isopropyl, —OCH$_3$, —OCH$_2$CH$_3$, —O(CH$_2$)$_2$CH$_3$, —OCH(CH$_3$)$_2$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —NH(CH$_2$)$_2$CH$_3$, —NHCH(CH$_3$)$_2$, —N(CH$_3$)$_2$, —N(CH$_3$)CH$_2$CH$_3$, and —N(CH$_2$CH$_3$)$_2$. In a yet further aspect, each of $R^{9a}$ and $R^{9b}$ is independently selected from hydrogen, —F, —Cl, —NH$_2$, methyl, ethyl, —OCH$_3$, —OCH$_2$CH$_3$, —CH$_2$F, —CH$_2$Cl, —CH$_2$CH$_2$F, —CH$_2$CH$_2$Cl, —CHF$_2$, —CF$_3$, —CHCl$_2$, —CCl$_3$, —CH$_2$CHF$_2$, —CH$_2$CF$_3$, —CH$_2$CHCl$_2$, —CH$_2$CCl$_3$, —NHCH$_3$, —NHCH$_2$CH$_3$, —N(CH$_3$)$_2$, —N(CH$_3$)CH$_2$CH$_3$, and —N(CH$_2$CH$_3$)$_2$. In an even further aspect, each of $R^{9a}$ and $R^{9b}$ is independently selected from hydrogen, —F, —Cl, —NH$_2$, methyl, —OCH$_3$—CH$_2$F, —CH$_2$Cl, —CHF$_2$, —CF$_3$, —CHCl$_2$, —CCl$_3$, —NHCH$_3$, and —N(CH$_3$)$_2$. In a still further aspect, each of $R^{9a}$ and $R^{9b}$ is independently selected from hydrogen, —F, —Cl, methyl, —OCH$_3$—CH$_2$F, —CH$_2$Cl, —CF$_3$, —CCl$_3$, —NHCH$_3$, and —N(CH$_3$)$_2$. In a yet further aspect, each of $R^{9a}$ and $R^{9b}$ is independently selected from hydrogen, —F, —Cl, methyl, —CH$_2$F, —CH$_2$Cl, —CF$_3$, and —CCl$_3$. In an even further aspect, each of $R^{9a}$ and $R^{9b}$ is independently selected from hydrogen and halogen. In a still further aspect, each of $R^{9a}$ and $R^{9b}$ is independently selected from hydrogen, —F, and —Cl. In a yet further aspect, each of $R^{9a}$ and $R^{9b}$ is independently selected from hydrogen and —F. In an even further aspect, each of $R^{9a}$ and $R^{9b}$ is hydrogen.

l. $R^{10}$ Groups

In one aspect, $R^{10}$ is selected from hydrogen and C1-C6 alkyl. In a further aspect, $R^{10}$ is selected from hydrogen and C1-C3 alkyl. In a still further aspect, $R^{10}$ is selected from hydrogen, methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, and 2,3-dimethylpentan-2-yl. In a yet further aspect, $R^{10}$ is selected from hydrogen, methyl, ethyl, propyl, isopropyl, tert-butyl, sec-butyl, isobutyl, and tert-butyl. In an even further aspect, $R^{10}$ is selected from hydrogen, methyl, ethyl, propyl, and isopropyl. In a still further aspect, $R^{10}$ is selected from hydrogen, methyl, and ethyl. In a yet further aspect, $R^{10}$ is selected from hydrogen and methyl. In an even further aspect, $R^{10}$ is hydrogen.

In a further aspect, $R^{10}$ is a C1-C6 alkyl. In a still further aspect, $R^{10}$ is a C1-C3 alkyl. In a yet further aspect, $R^{10}$ is selected from methyl, ethyl, propyl, isopropyl, tert-butyl, sec-butyl, isobutyl, tert-butyl, neopentyl, isopentyl, sec-pentyl, tert-pentyl, 3,3-dimethylbutan-2-yl, 3,3-dimethylpentan-2-yl, 2,3-dimethylbutan-2-yl, and 2,3-dimethylpentan-2-yl. In an even further aspect, $R^{10}$ is selected from methyl, ethyl, propyl, isopropyl, tert-butyl, sec-butyl, isobutyl, and tert-butyl. In a still further aspect, $R^{10}$ is selected from methyl, ethyl, propyl, and isopropyl. In a yet further aspect, $R^{10}$ is selected from methyl, and ethyl. In a yet further aspect, $R^{10}$ is methyl. In an even further aspect, $R^{10}$ is ethyl.

m. $Ar^1$ Groups

In one aspect, $Ar^1$ is selected from phenyl, indenyl, and napthalenyl; and wherein $Ar^1$ is substituted with 0-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, $Ar^1$ is selected from phenyl, indenyl, and napthalenyl; and wherein $Ar^1$ is substituted with 1-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is selected from phenyl, indenyl, and napthalenyl; and wherein $Ar^1$ is substituted with 1-2 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl, indenyl, and napthalenyl; and wherein $Ar^1$ is substituted with 2-3 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is selected from phenyl, indenyl, and napthalenyl; and wherein $Ar^1$ is substituted with 0-2 groups selected from halogen, hydroxyl, cyano, —NH$_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is selected from phenyl, indenyl, and napthalenyl; and wherein $Ar^1$ is substituted with 0 or 1 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In a yet further aspect, $Ar^1$ is selected from phenyl, indenyl, and napthalenyl; and wherein $Ar^1$ is monosubstituted with a group selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is selected from phenyl, indenyl, and napthalenyl; and wherein $Ar^1$ is unsubstituted.

In a further aspect, $Ar^1$ is phenyl substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is phenyl monosubstituted with a group selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is phenyl substituted with 0-3 groups selected from $-F$, $-Cl$, $-OH$, $-NH_2$, methyl, ethyl, propyl, isopropyl, $-OCH_3$, $-OCH_2CH_3$, $-O(CH_2)_2CH_3$, $-OCH(CH_3)_2$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, and $-N(CH_2CH_3)_2$. In a still further aspect, $Ar^1$ is phenyl substituted with 0-3 groups selected from $-F$, $-Cl$, $-NH_2$, methyl, ethyl, $-OCH_3$, $-OCH_2CH_3$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-N(CH_3)_2$, $-N(CH_3)CH_2CH_3$, and $-N(CH_2CH_3)_2$. In a yet further aspect, $Ar^1$ is phenyl substituted with 0-3 groups selected from $-F$, $-Cl$, $-NH_2$, methyl, $-OCH_3$$-CH_2F$, $-CH_2Cl$, $-CHF_2$, $-CF_3$, $-CHCl_2$, $-CCl_3$, $-NHCH_3$, and $-N(CH_3)_2$. In an even further aspect, $Ar^1$ is phenyl substituted with 0-3 groups selected from $-F$, $-Cl$, methyl, $-OCH_3$$-CH_2F$, $-CH_2Cl$, $-CF_3$, $-CCl_3$, $-NHCH_3$, and $-N(CH_3)_2$. In a still further aspect, $Ar^1$ is phenyl substituted with 0-3 groups selected from $-F$, $-Cl$, methyl, $-CH_2F$, $-CH_2Cl$, $-CF_3$, and $-CCl_3$. In a yet further aspect, $Ar^1$ is phenyl substituted with 0-3 halogens. In an even further aspect, $Ar^1$ is phenyl substituted with 0-3 $-F$. In a still further aspect, $Ar^1$ is phenyl monosubstituted with $-F$. In a yet further aspect, $Ar^1$ is unsubstituted phenyl.

In a further aspect, $Ar^1$ is indenyl substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is indenyl monosubstituted with a group selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is indenyl substituted with 0-3 groups selected from $-F$, $-Cl$, $-OH$, $-NH_2$, methyl, ethyl, propyl, isopropyl, $-OCH_3$, $-OCH_2CH_3$, $-O(CH_2)_2CH_3$, $-OCH(CH_3)_2$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, and $-N(CH_2CH_3)_2$. In a still further aspect, $Ar^1$ is indenyl substituted with 0-3 groups selected from $-F$, $-Cl$, $-NH_2$, methyl, ethyl, $-OCH_3$, $-OCH_2CH_3$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-N(CH_3)_2$, $-N(CH_3)CH_2CH_3$, and $-N(CH_2CH_3)_2$. In a yet further aspect, $Ar^1$ is indenyl substituted with 0-3 groups selected from $-F$, $-Cl$, $-NH_2$, methyl, $-OCH_3$$-CH_2F$, $-CH_2Cl$, $-CHF_2$, $-CF_3$, $-CHCl_2$, $-CCl_3$, $-NHCH_3$, and $-N(CH_3)_2$. In an even further aspect, $Ar^1$ is indenyl substituted with 0-3 groups selected from $-F$, $-Cl$, methyl, $-OCH_3$$-CH_2F$, $-CH_2Cl$, $-CF_3$, $-CCl_3$, $-NHCH_3$, and $-N(CH_3)_2$. In a still further aspect, $Ar^1$ is indenyl substituted with 0-3 groups selected from $-F$, $-Cl$, methyl, $-CH_2F$, $-CH_2Cl$, $-CF_3$, and $-CCl_3$. In a yet further aspect, $Ar^1$ is indenyl substituted with 0-3 halogens. In an even further aspect, $Ar^1$ is indenyl substituted with 0-3 $-F$. In a still further aspect, $Ar^1$ is indenyl monosubstituted with $-F$. In a yet further aspect, $Ar^1$ is unsubstituted indenyl.

In a further aspect, $Ar^1$ is napthalenyl substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, $Ar^1$ is napthalenyl monosubstituted with a group selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In an even further aspect, $Ar^1$ is napthalenyl substituted with 0-3 groups selected from $-F$, $-Cl$, $-OH$, $-NH_2$, methyl, ethyl, propyl, isopropyl, $-OCH_3$, $-OCH_2CH_3$, $-O(CH_2)_2CH_3$, $-OCH(CH_3)_2$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-NH(CH_2)_2CH_3$, $-NHCH(CH_3)_2$, $-N(CH_3)_2$, $-N(CH_3)CH_2CH_3$, and $-N(CH_2CH_3)_2$. In a still further aspect, $Ar^1$ is napthalenyl substituted with 0-3 groups selected from $-F$, $-Cl$, $-NH_2$, methyl, ethyl, $-OCH_3$, $-OCH_2CH_3$, $-CH_2F$, $-CH_2Cl$, $-CH_2CH_2F$, $-CH_2CH_2Cl$, $-CHF_2$, $-CF_3$, $-CHCl_2$, $-CCl_3$, $-CH_2CHF_2$, $-CH_2CF_3$, $-CH_2CHCl_2$, $-CH_2CCl_3$, $-NHCH_3$, $-NHCH_2CH_3$, $-N(CH_3)_2$, $-N(CH_3)CH_2CH_3$, and $-N(CH_2CH_3)_2$. In a yet further aspect, $Ar^1$ is napthalenyl substituted with 0-3 groups selected from $-F$, $-Cl$, $-NH_2$, methyl, $-OCH_3$$-CH_2F$, $-CH_2Cl$, $-CHF_2$, $-CF_3$, $-CHCl_2$, $-CCl_3$, $-NHCH_3$, and $-N(CH_3)_2$. In an even further aspect, $Ar^1$ is napthalenyl substituted with 0-3 groups selected from $-F$, $-Cl$, methyl, $-OCH_3$$-CH_2F$, $-CH_2Cl$, $-CF_3$, $-CCl_3$, $-NHCH_3$, and $-N(CH_3)_2$. In a still further aspect, $Ar^1$ is napthalenyl substituted with 0-3 groups selected from $-F$, $-Cl$, methyl, $-CH_2F$, $-CH_2Cl$, $-CF_3$, and $-CCl_3$. In a yet further aspect, $Ar^1$ is napthalenyl substituted with 0-3 halogens. In an even further aspect, $Ar^1$ is napthalenyl substituted with 0-3 $-F$. In a still further aspect, $Ar^1$ is napthalenyl monosubstituted with $-F$. In a yet further aspect, $Ar^1$ is unsubstituted napthalenyl.

n. $Ar^2$ Groups

In one aspect, $Ar^2$ is a heteroaryl substituted with 0-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino.

In a further aspect, $Ar^2$ is a heteroaryl substituted with 1-3 groups selected from halogen, hydroxyl, cyano, $-NH_2$, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar² is a heteroaryl substituted with 1-2 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar² is a heteroaryl substituted with 2-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, Ar² is a heteroaryl substituted with 0-2 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar² is a heteroaryl substituted with 0 or 1 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a yet further aspect, Ar² is a heteroaryl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, Ar² is an unsubstituted heteroaryl.

In a further aspect, Ar² is pyridinyl substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar² is pyridinyl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, Ar² is pyridinyl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, Ar² is pyridinyl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, Ar² is pyridinyl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, Ar² is pyridinyl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, Ar² is pyridinyl substituted with 0-3 groups selected from —F, —Cl, methyl, —CH₂F, —CH₂Cl, —CF₃, and —CCl₃. In a yet further aspect, Ar² is pyridinyl substituted with 0-3 halogens. In an even further aspect, Ar² is pyridinyl substituted with 0-3 —F. In a still further aspect, Ar² is pyridinyl monosubstituted with —F. In a yet further aspect, Ar² is unsubstituted pyridinyl.

In a further aspect, Ar² is pyridin-4-yl substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar² is pyridin-4-yl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, Ar² is pyridin-4-yl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, Ar² is pyridin-4-yl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, Ar² is pyridin-4-yl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, Ar² is pyridin-4-yl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, Ar² is pyridin-4-yl substituted with 0-3 groups selected from —F, —Cl, methyl, —CH₂F, —CH₂Cl, —CF₃, and —CCl₃. In a yet further aspect, Ar² is pyridin-4-yl substituted with 0-3 halogens. In an even further aspect, Ar² is pyridin-4-yl substituted with 0-3 —F. In a still further aspect, Ar² is pyridin-4-yl monosubstituted with —F. In a yet further aspect, Ar² is unsubstituted pyridin-4-yl.

In a further aspect, Ar² is pyridin-2-yl substituted with 0-3 groups selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In a still further aspect, Ar² is pyridin-2-yl monosubstituted with a group selected from halogen, hydroxyl, cyano, —NH₂, C1-C6 alkyl, C1-C6 alkoxy, C1-C6 haloalkyl, C1-C6 polyhaloalkyl, C1-C6 alkylamino, and C1-C6 dialkylamino. In an even further aspect, Ar² is pyridin-2-yl substituted with 0-3 groups selected from —F, —Cl, —OH, —NH₂, methyl, ethyl, propyl, isopropyl, —OCH₃, —OCH₂CH₃, —O(CH₂)₂CH₃, —OCH(CH₃)₂, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —NH(CH₂)₂CH₃, —NHCH(CH₃)₂, —N(CH₃)₂, —N(CH₃)CH₂CH₃, and —N(CH₂CH₃)₂. In a still further aspect, Ar² is pyridin-2-yl substituted with 0-3 groups selected from —F, —Cl, —NH₂, methyl, ethyl, —OCH₃, —OCH₂CH₃, —CH₂F, —CH₂Cl, —CH₂CH₂F, —CH₂CH₂Cl, —CHF₂, —CF₃, —CHCl₂, —CCl₃, —CH₂CHF₂, —CH₂CF₃, —CH₂CHCl₂, —CH₂CCl₃, —NHCH₃, —NHCH₂CH₃, —N(CH₃)₂, —N(CH₃)CH₂CH₃, and —N(CH₂CH₃)₂. In a yet further aspect, Ar² is pyridin-2-yl substituted with 0-3 groups selected from —F, —Cl, —NH₂, methyl, —OCH₃—CH₂F, —CH₂Cl, —CHF₂, —CF₃, —CHCl₂, —CCl₃, —NHCH₃, and —N(CH₃)₂. In an even further aspect, Ar² is pyridin-2-yl substituted with 0-3 groups selected from —F, —Cl, methyl, —OCH₃—CH₂F, —CH₂Cl, —CF₃, —CCl₃, —NHCH₃, and —N(CH₃)₂. In a still further aspect, Ar² is pyridin-2-yl substituted with 0-3 groups selected from —F, —Cl, methyl, —CH₂F, —CH₂Cl, —CF₃, and —CCl₃. In a yet further aspect, Ar² is pyridin-2-yl substituted with 0-3 halogens. In an even further aspect, Ar² is pyridin-2-yl substituted with 0-3 —F. In a still further aspect, Ar² is pyridin-2-yl monosubstituted with —F. In a yet further aspect, Ar² is unsubstituted pyridin-2-yl.

o. Leaving Groups

In one aspect, leaving groups can be selected from halogens. In a further aspect, a halogen is fluoro, chloro, bromo or iodo. In a still further aspect, halogen is fluoro, chloro, or bromo. In a yet further aspect, halogen is fluoro or chloro. In a further aspect, halogen is fluoro. In an even further aspect, halogen is chloro or bromo. In an even further aspect, halogen is chloro. In a yet further aspect, halogen is iodo. In a still further aspect, halogen is bromo.

2. Example Compounds

In one aspect, a compound is selected from:

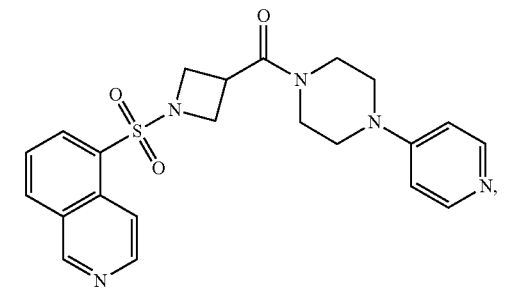

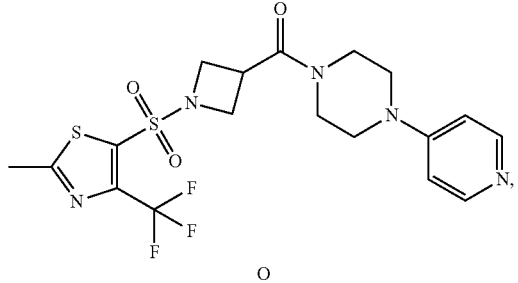

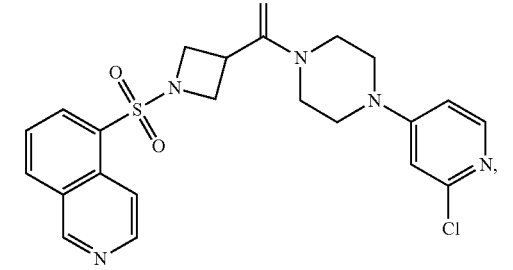

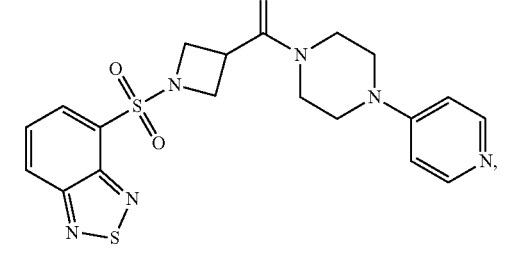

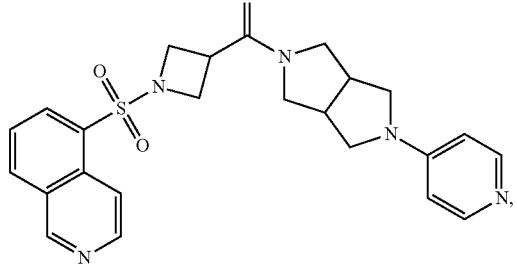

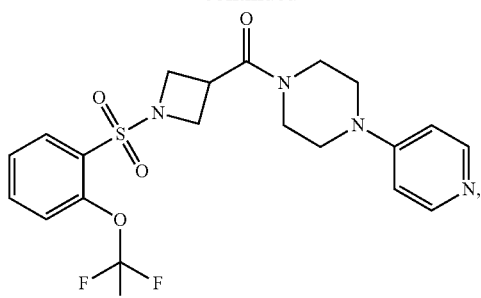

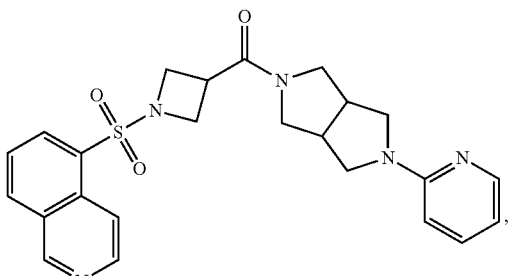

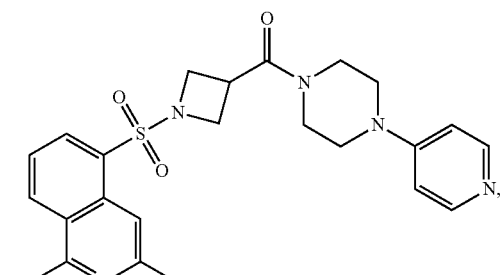

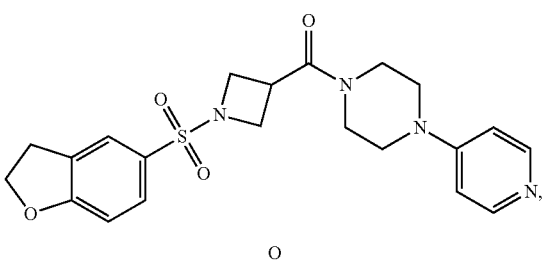

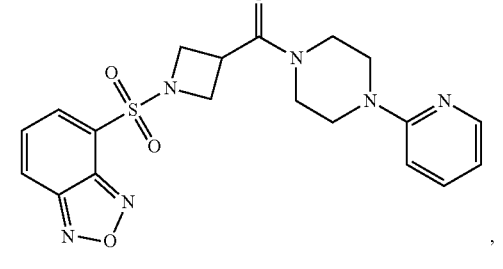

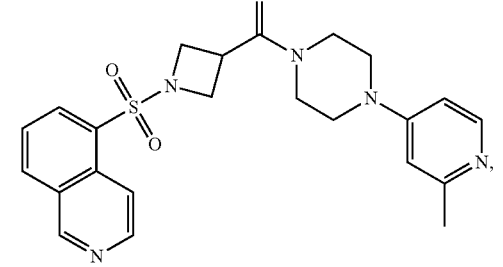

137
-continued
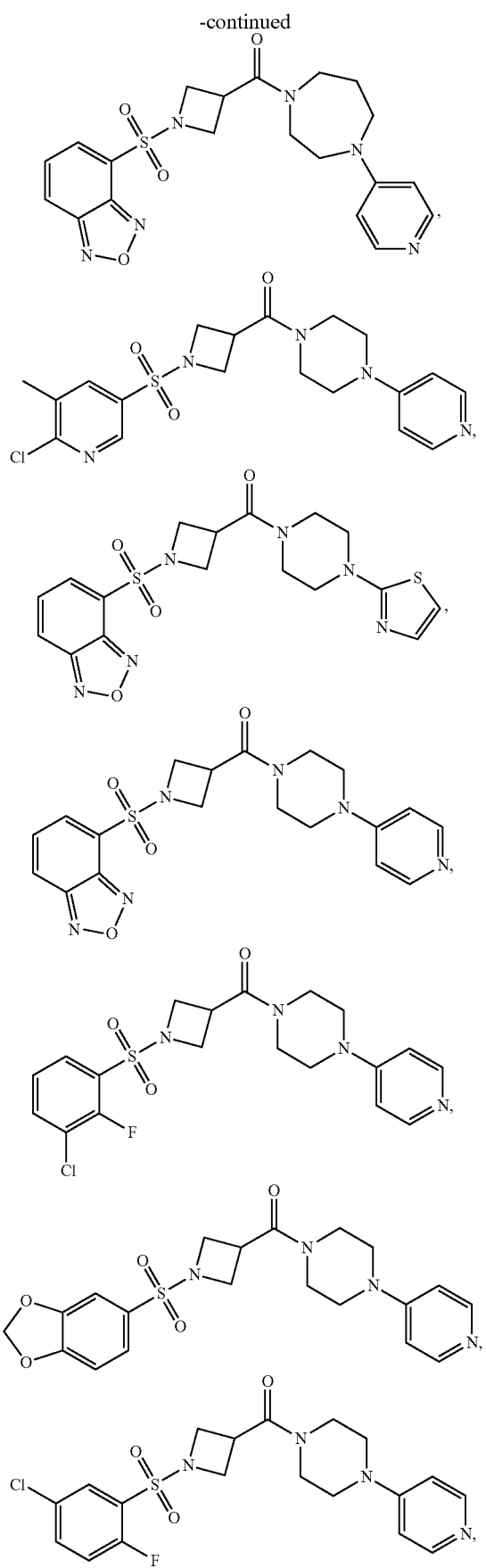
138
-continued
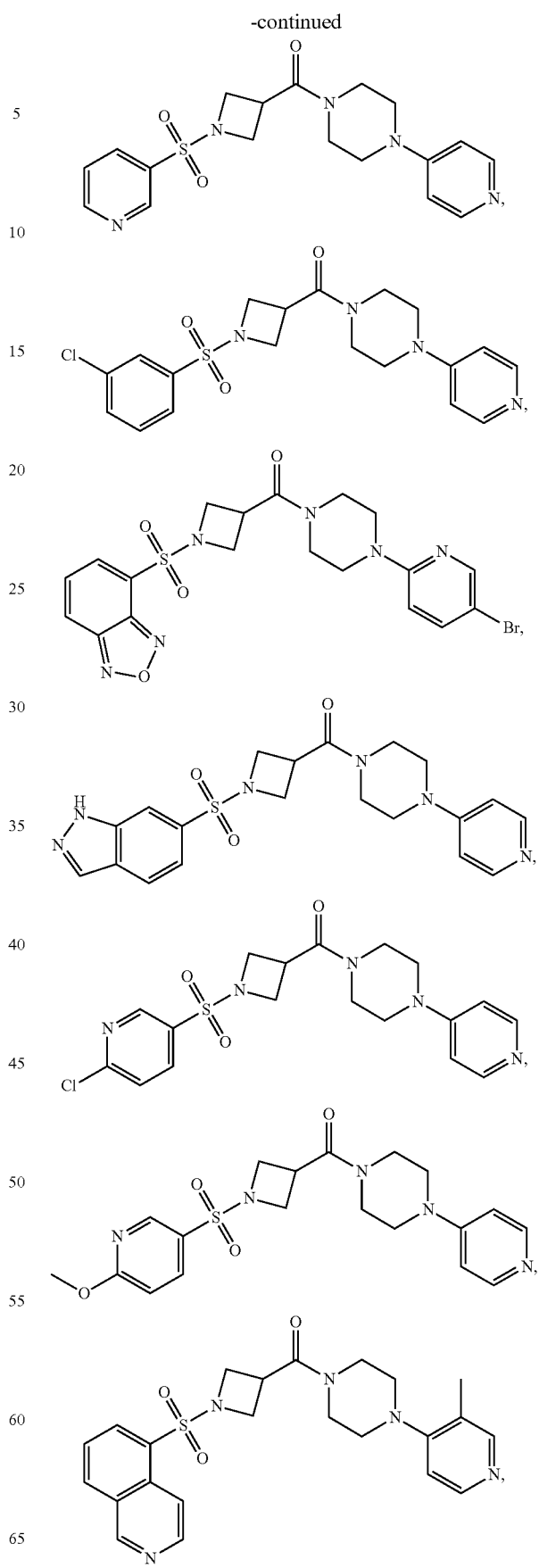

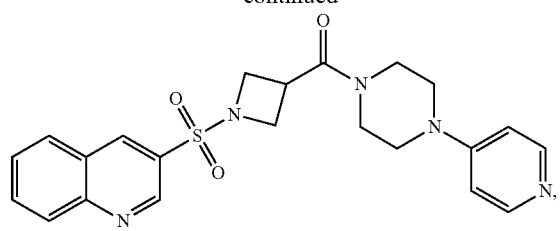
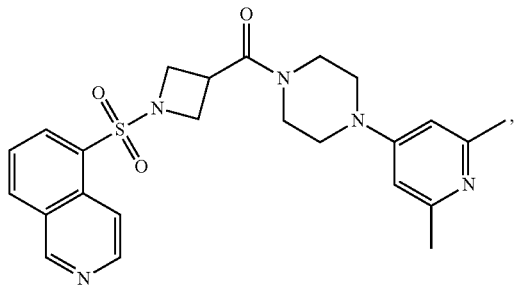
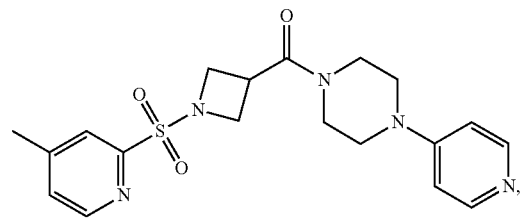
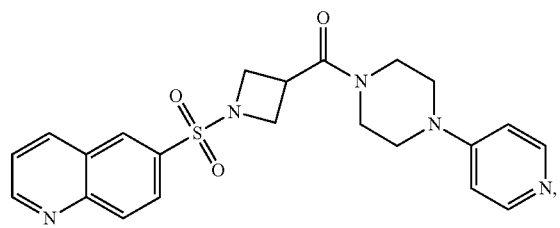
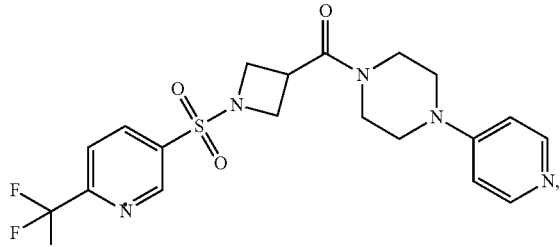
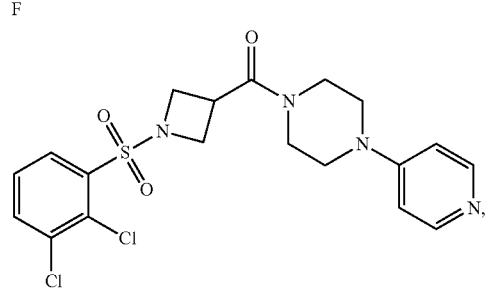
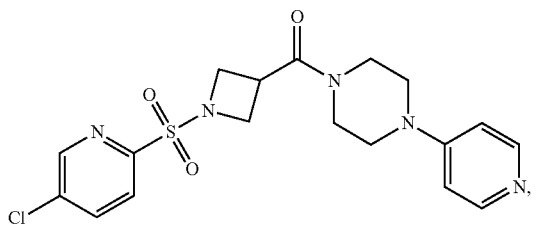
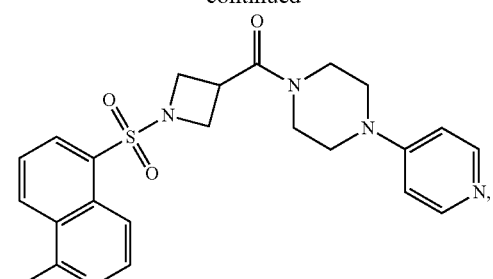
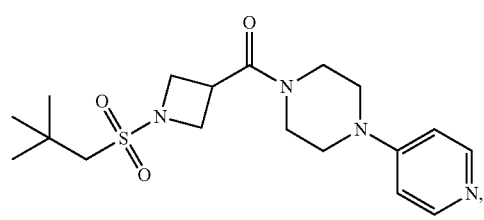
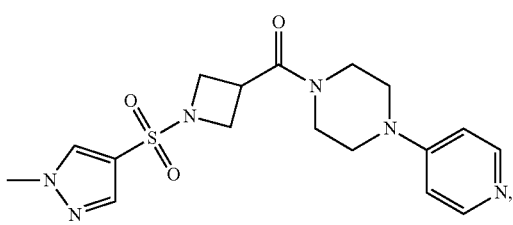
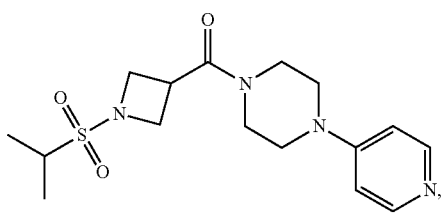
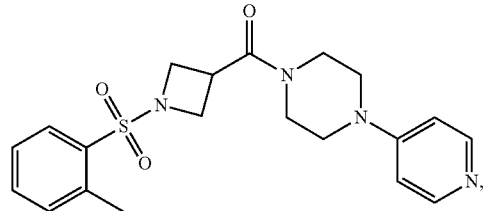
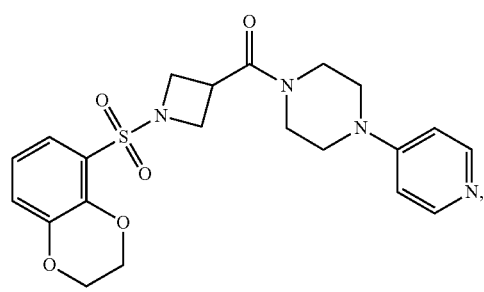

141
-continued
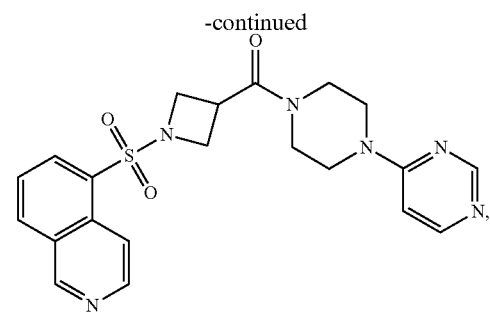
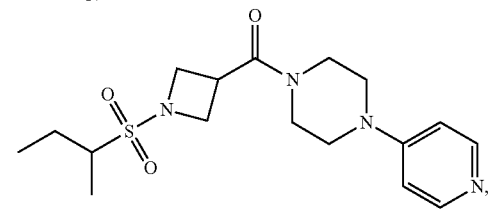
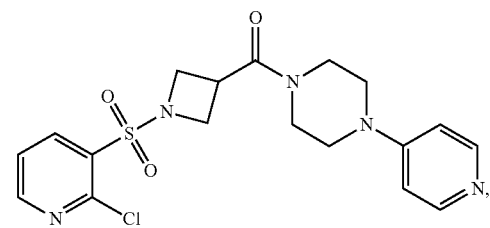
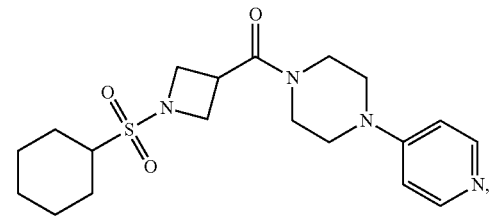
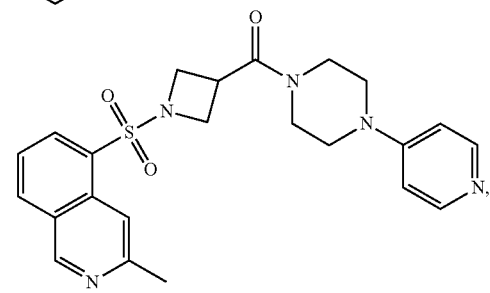
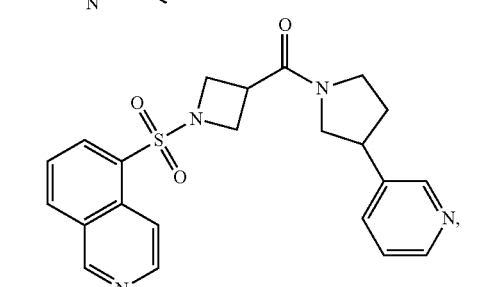
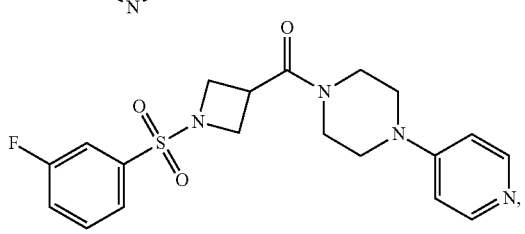
142
-continued
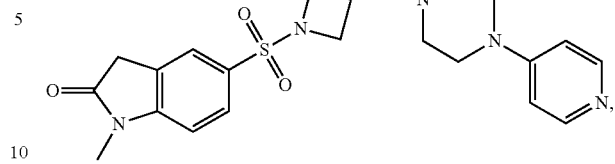
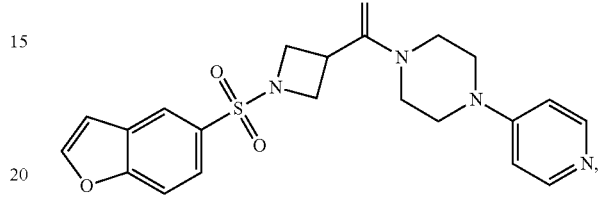
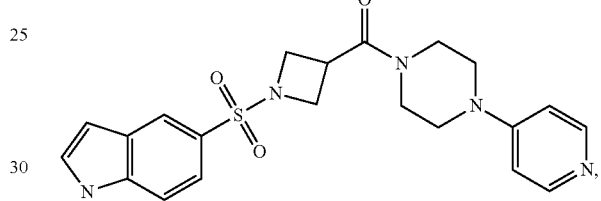
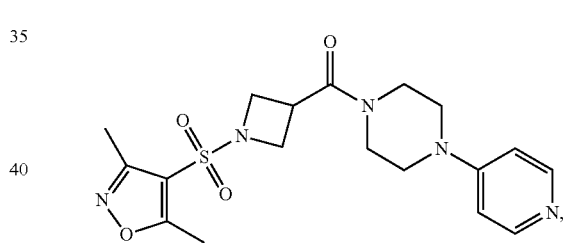
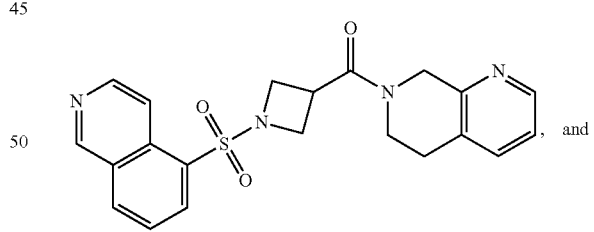
, and
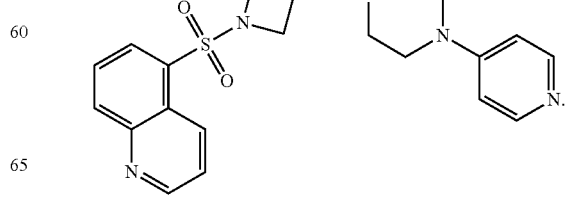

143
In one aspect, a compound is selected from:
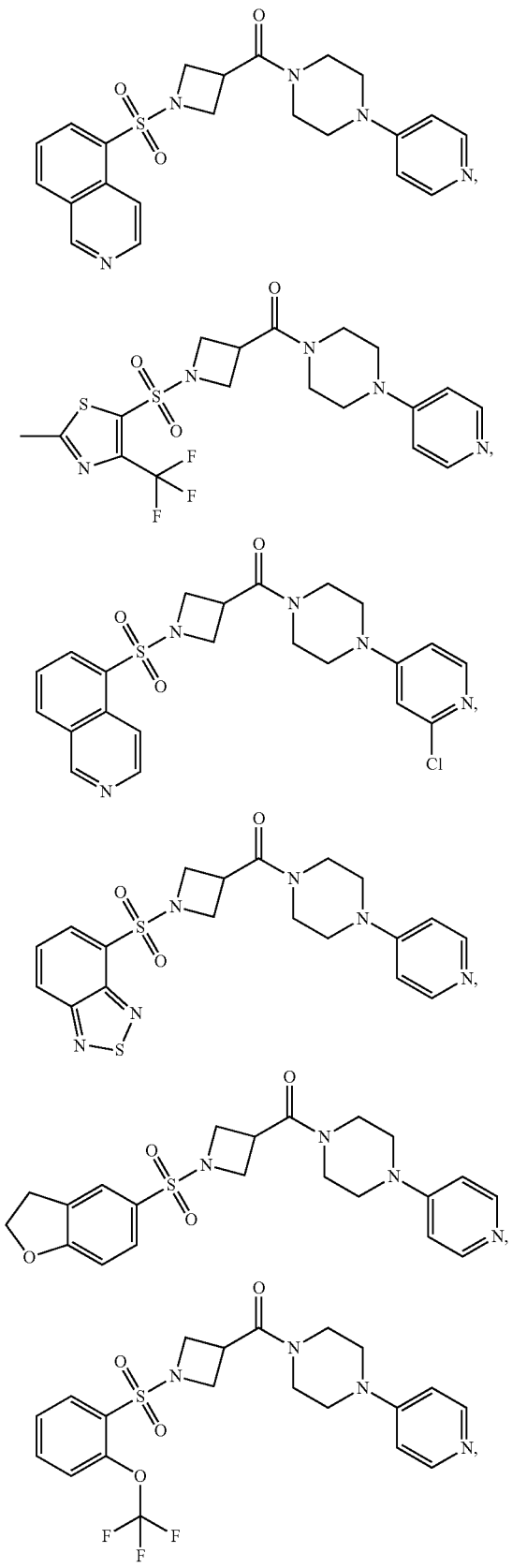
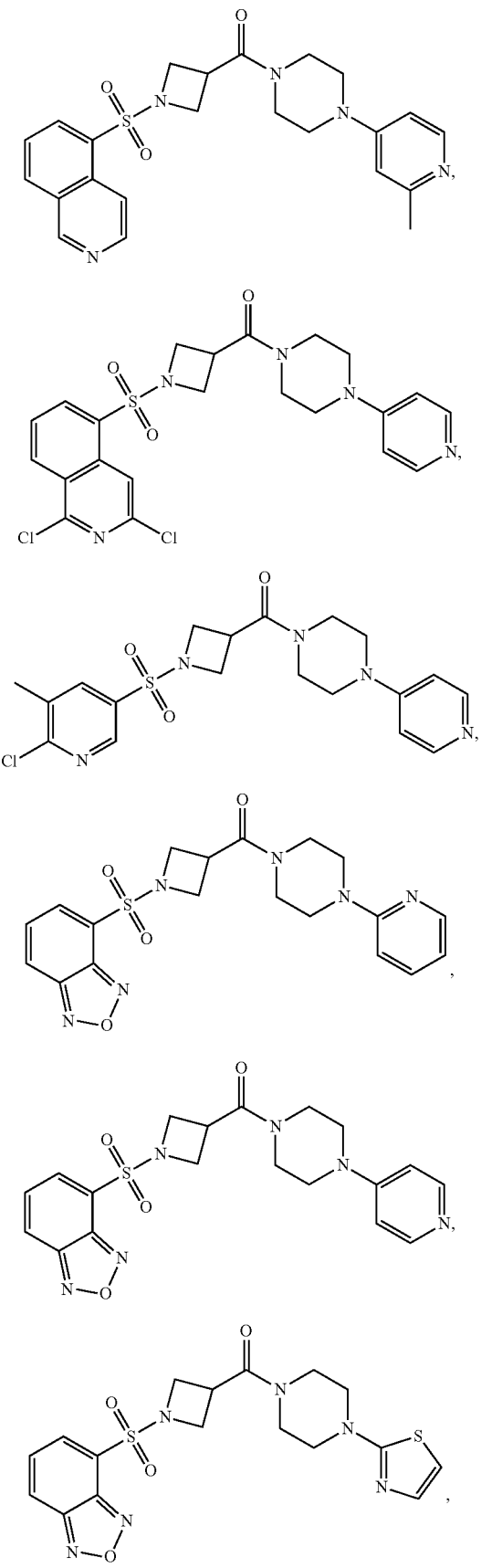

145
-continued
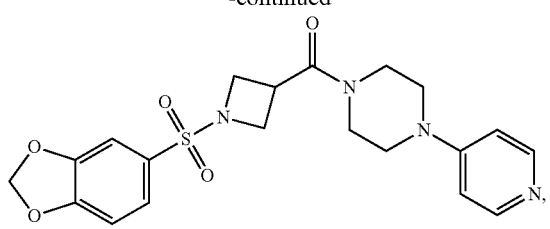
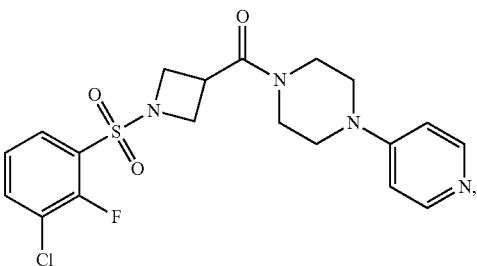
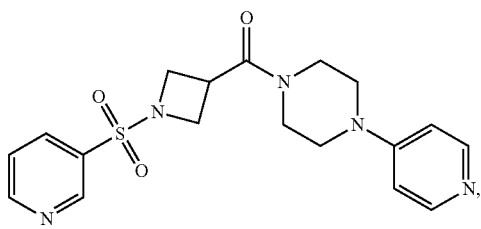
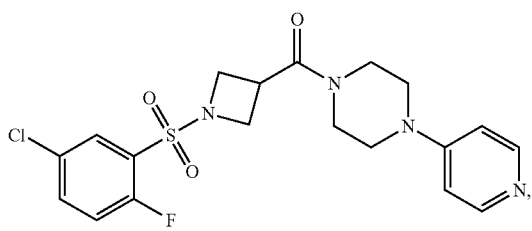
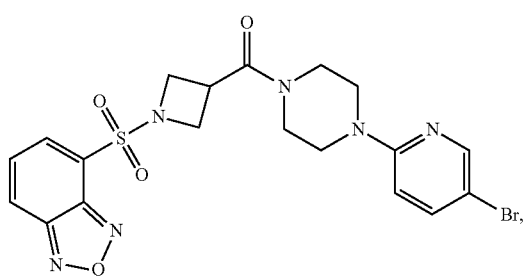
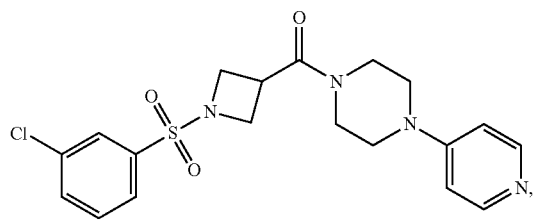
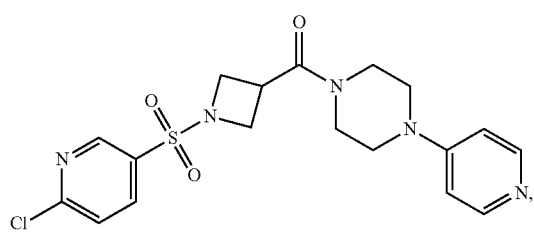
146
-continued
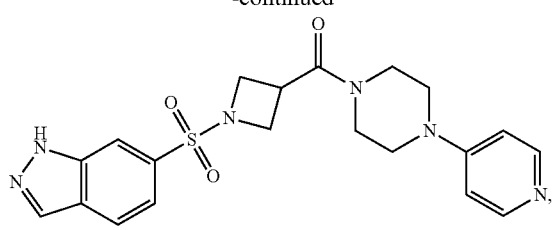
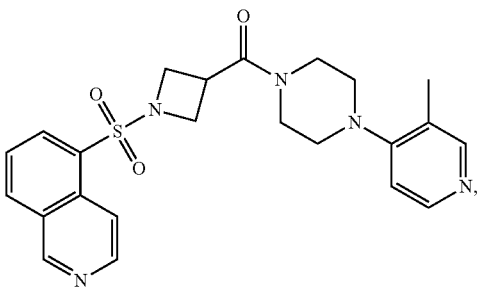
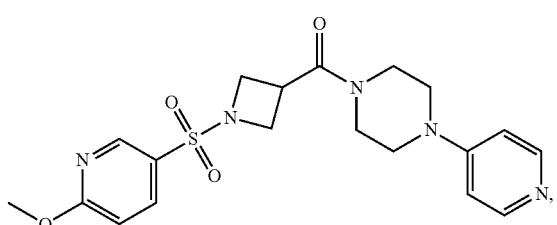
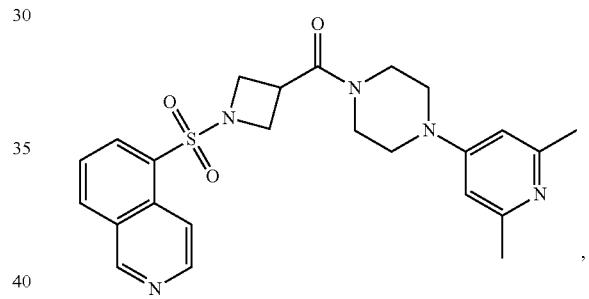
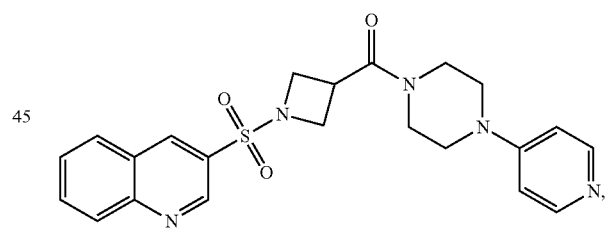
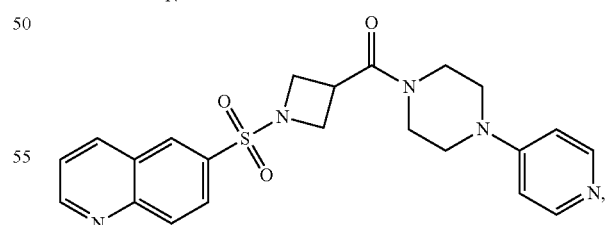
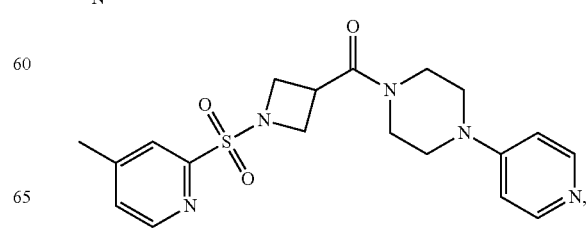

147
-continued
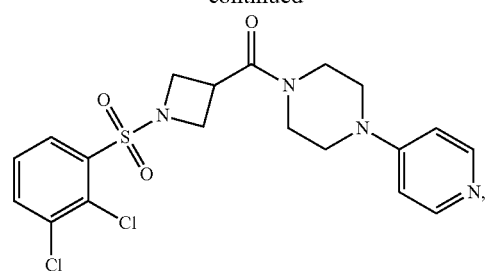
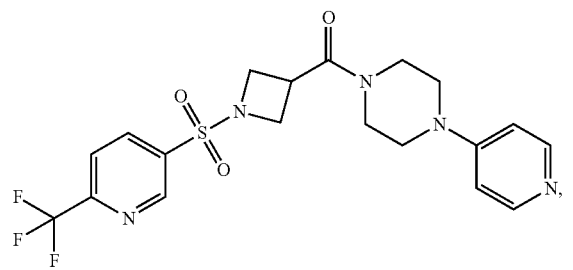
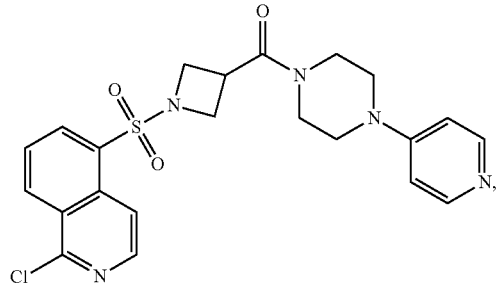
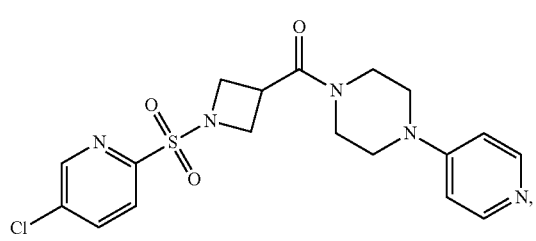
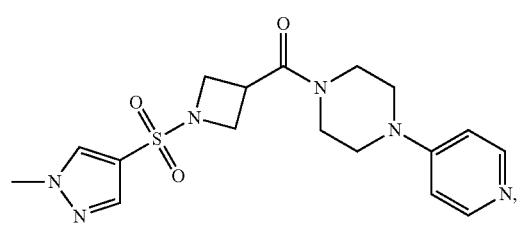
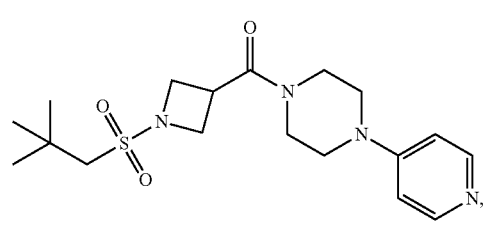
148
-continued
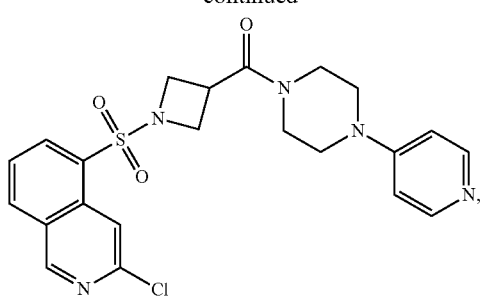
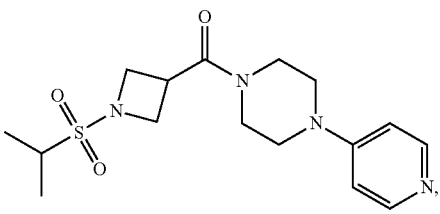
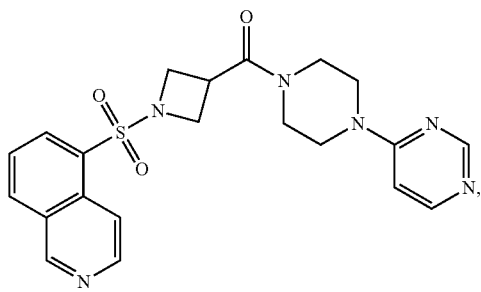 [SMILES: O=C(C1CN(S(=O)(=O)c2cccc3cnccc23)C1)N1CCN(c2ccncn2)CC1]
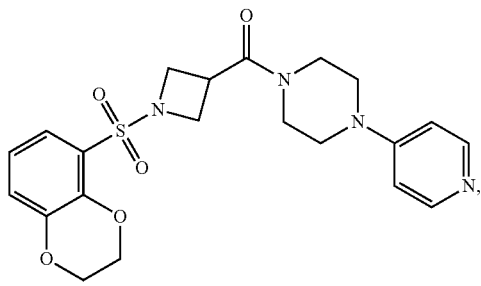
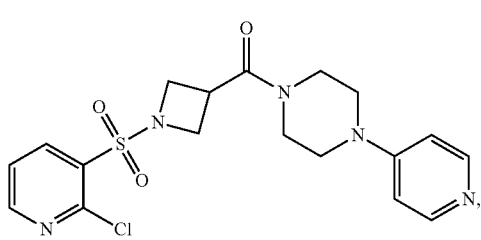
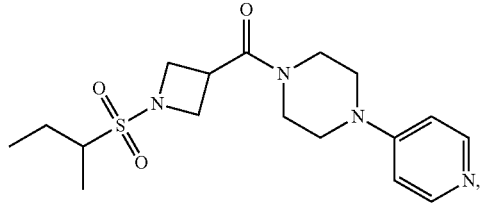

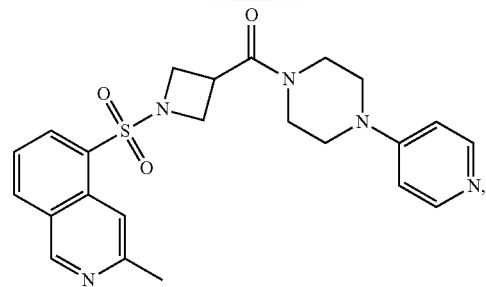
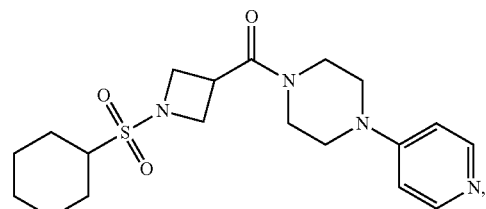
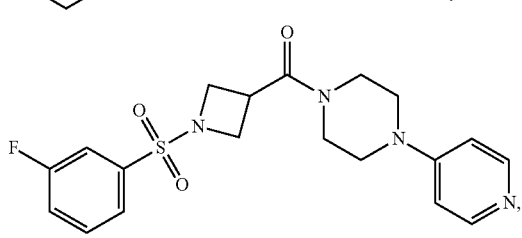
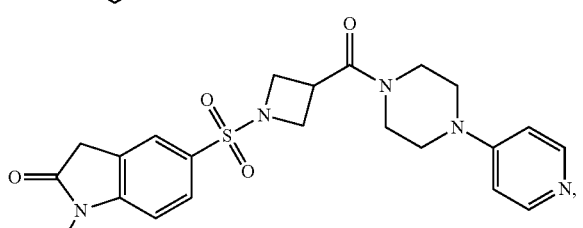
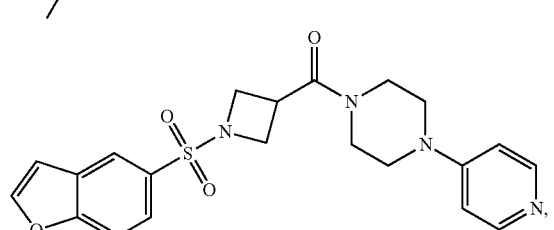
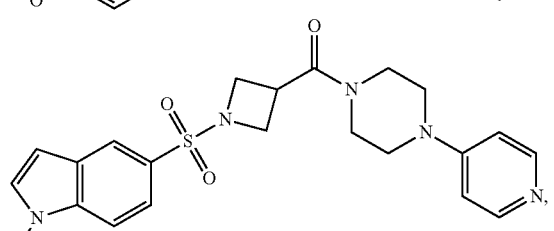
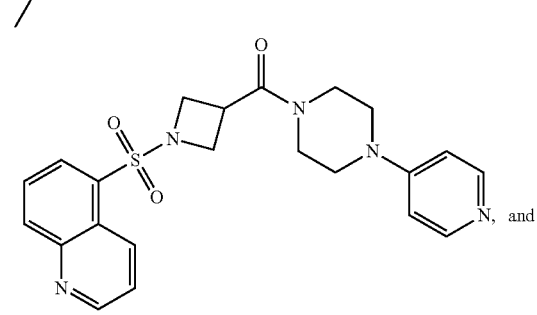
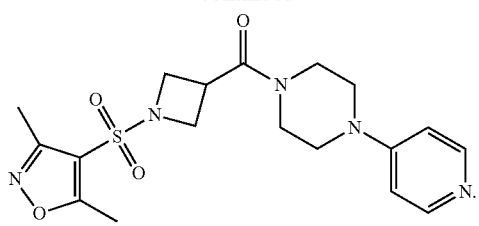
In one aspect, a compound is selected from:
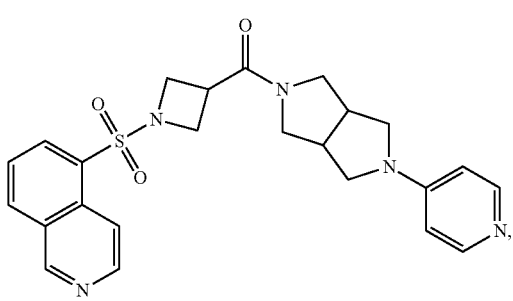
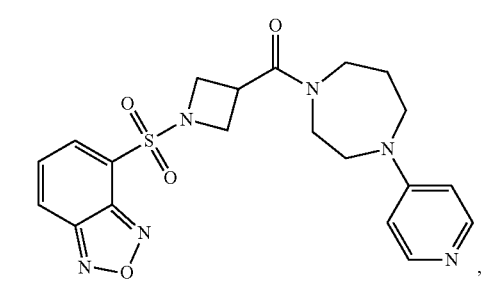
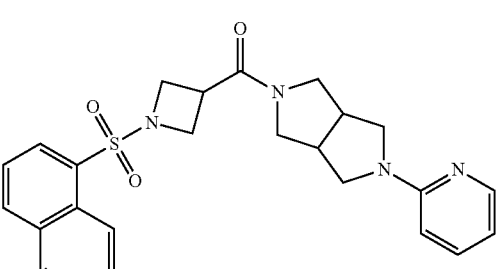
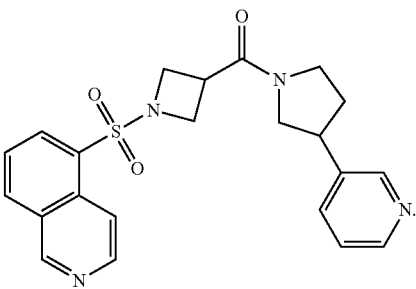

In one aspect, a compound is selected from:
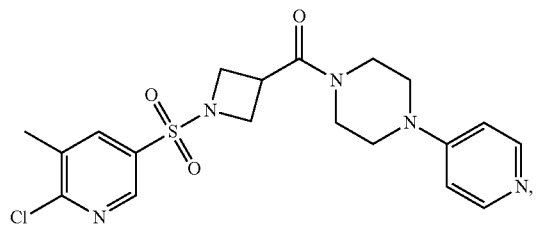
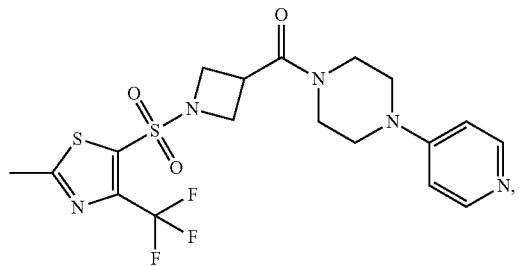
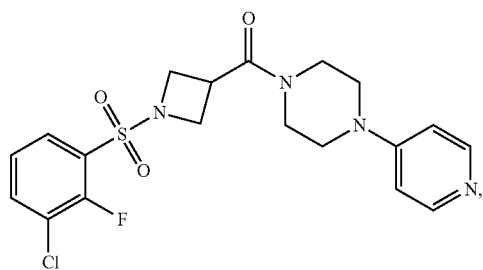
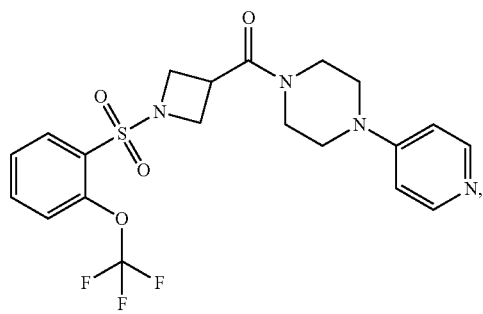
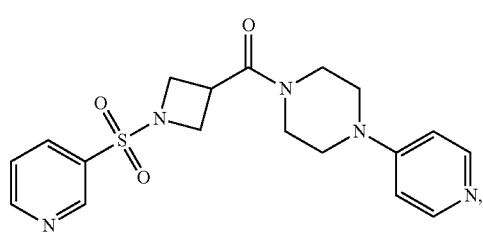
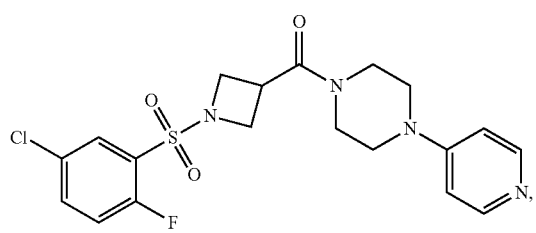
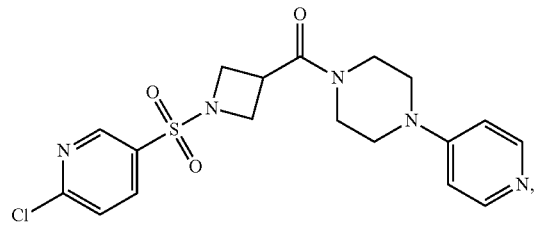
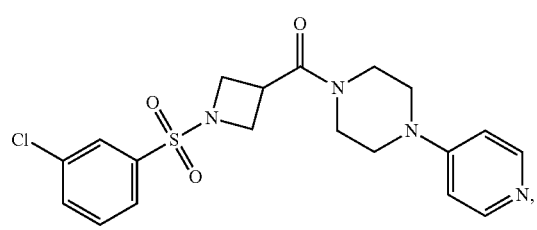
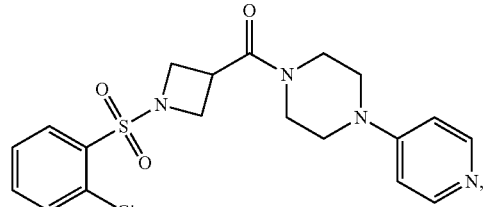
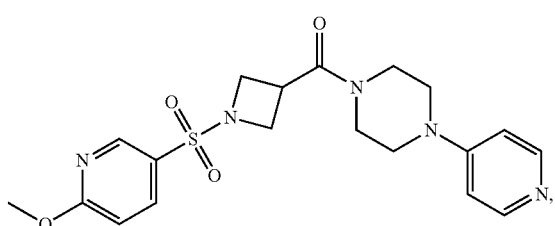
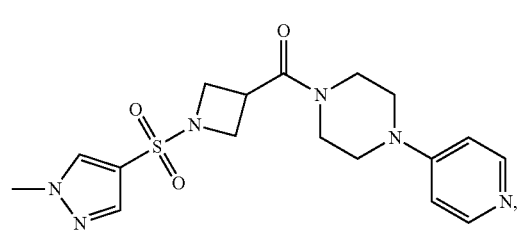
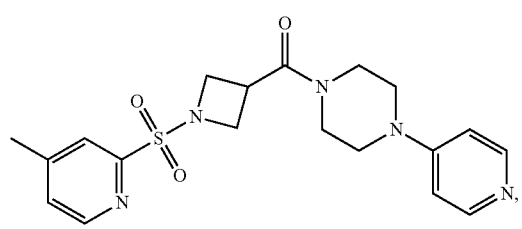
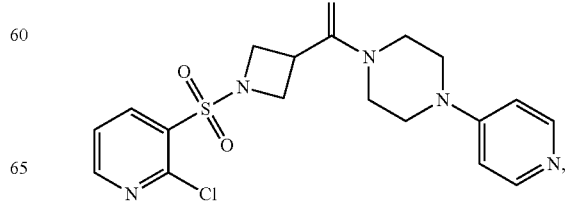

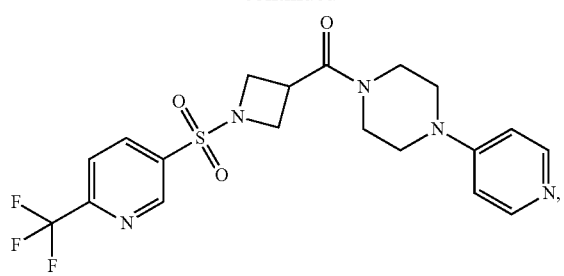
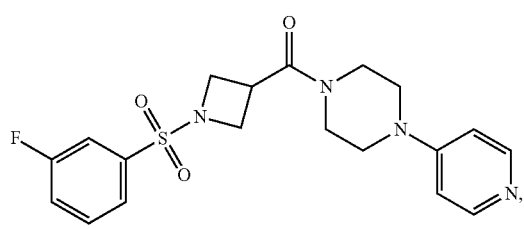
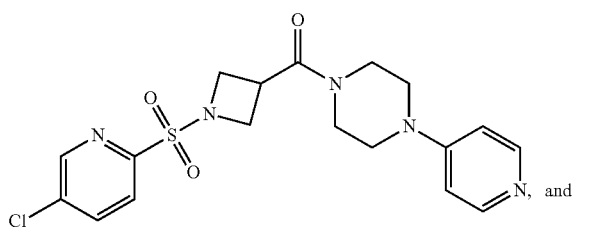
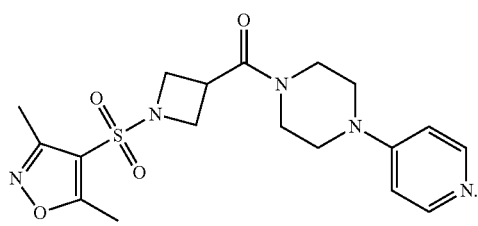
In one aspect, a compound is selected from:
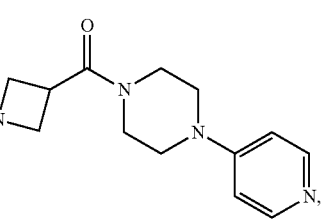
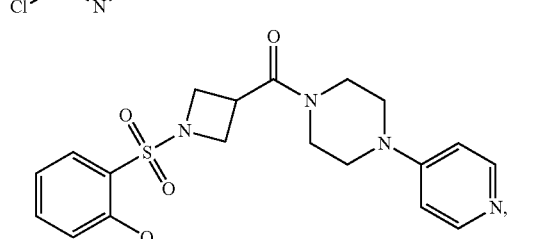
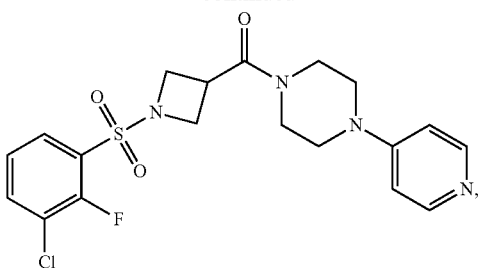
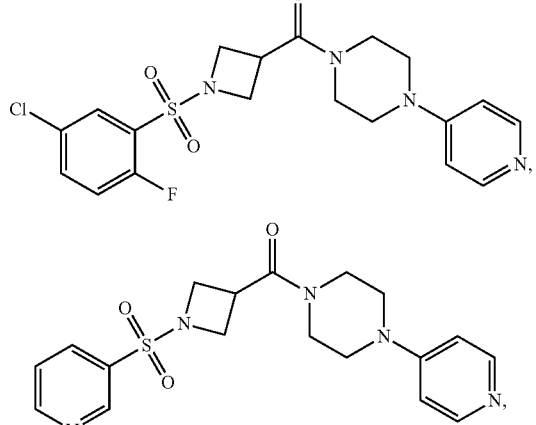
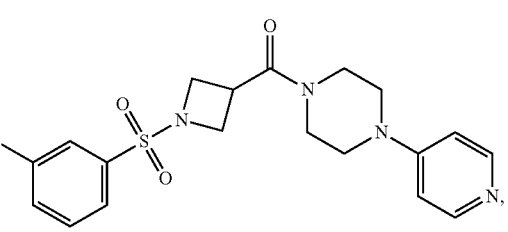
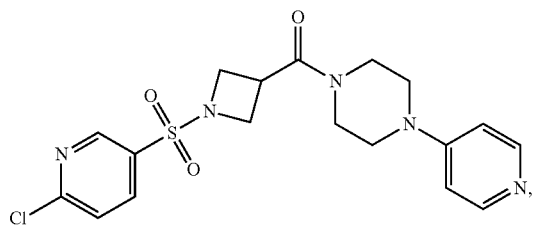
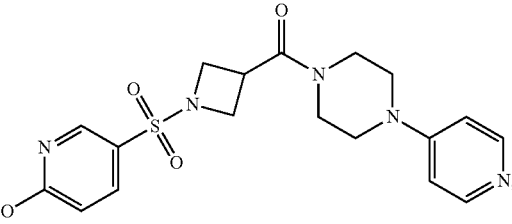
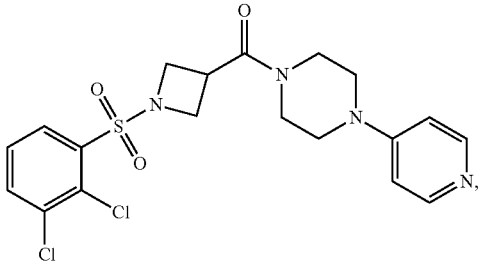

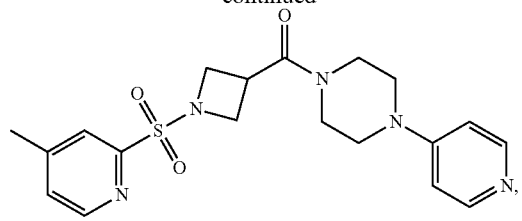
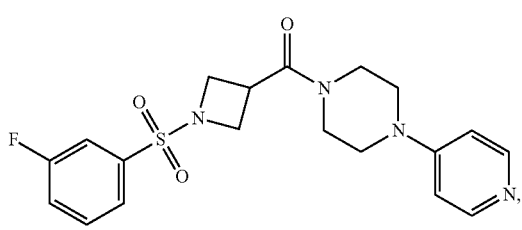
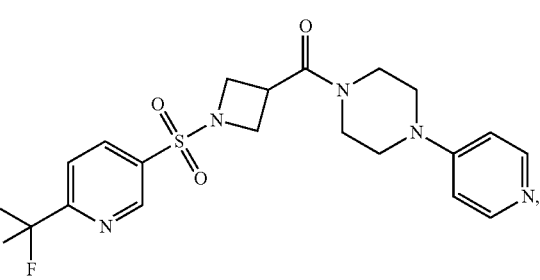
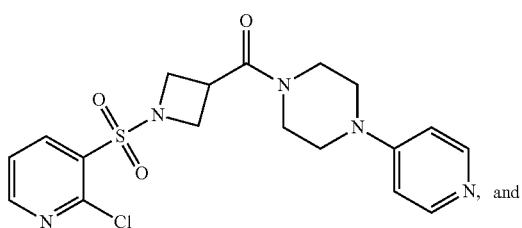
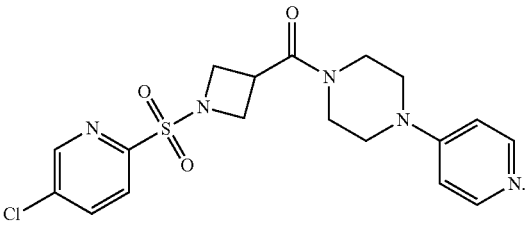
In one aspect, a compound is selected from:
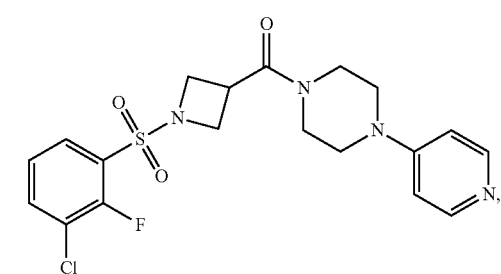
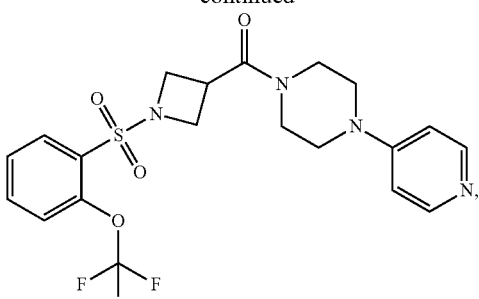
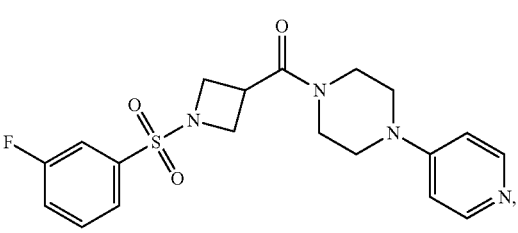
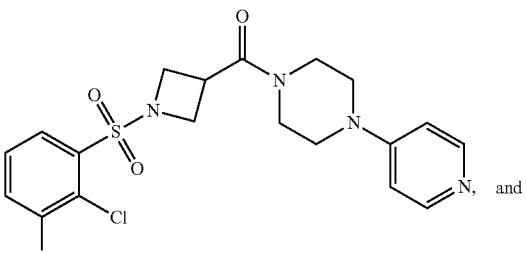
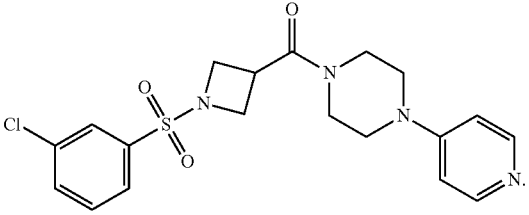
In one aspect, a compound is selected from:
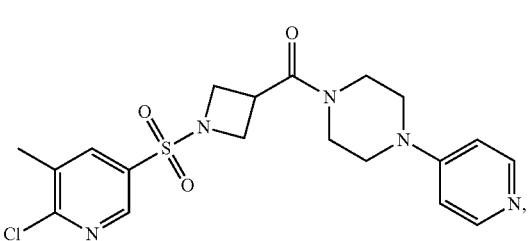

-continued
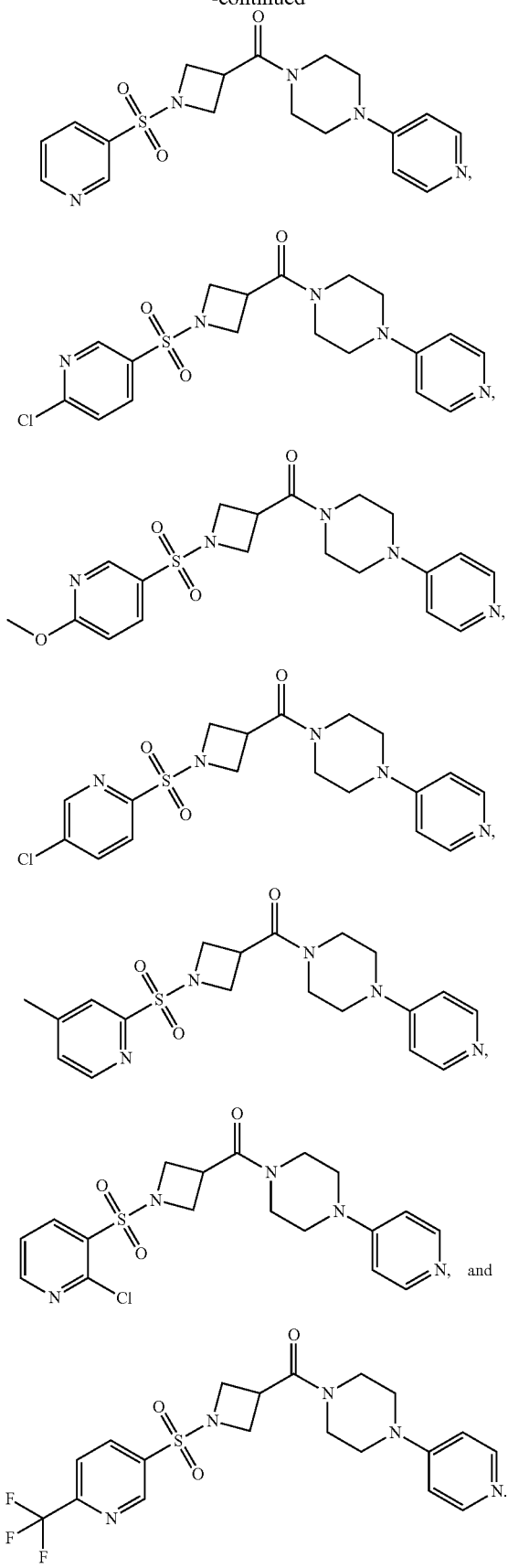
In one aspect, a compound is selected from:
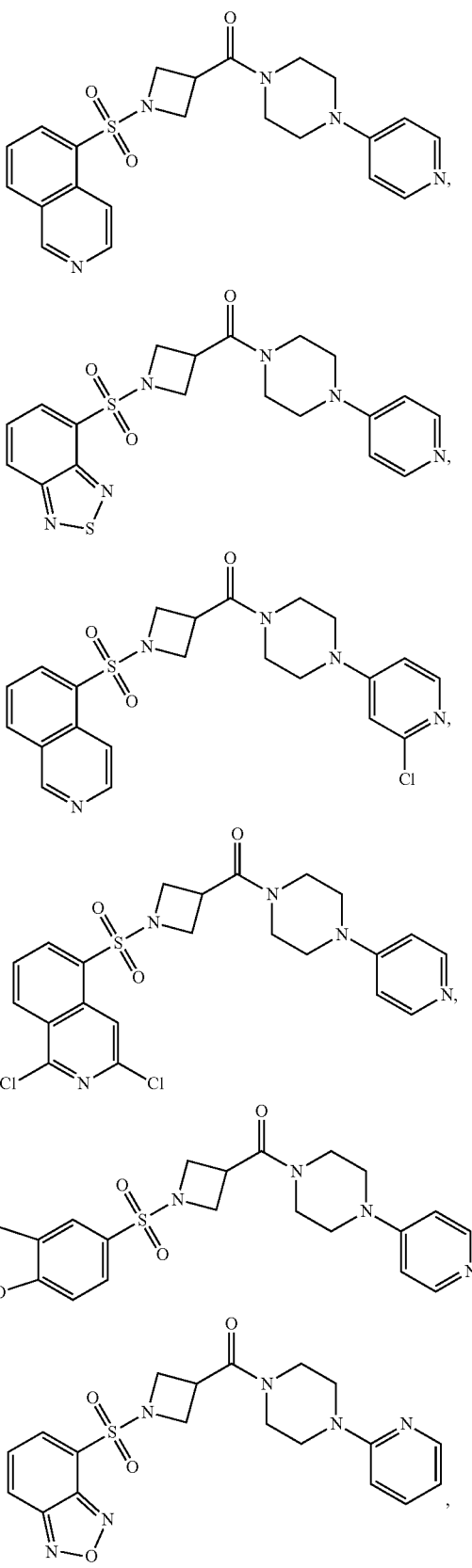

159
-continued
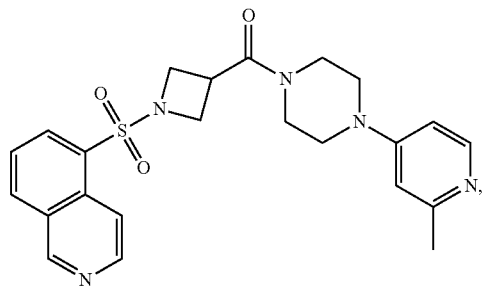
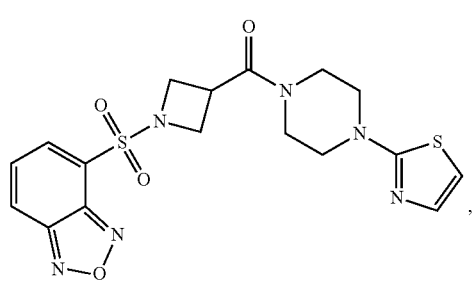
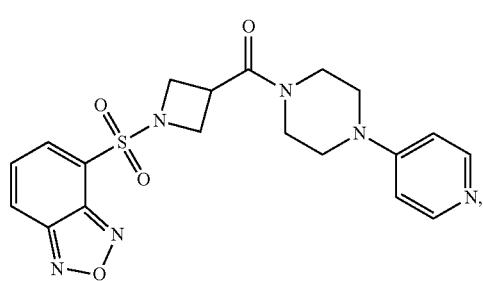
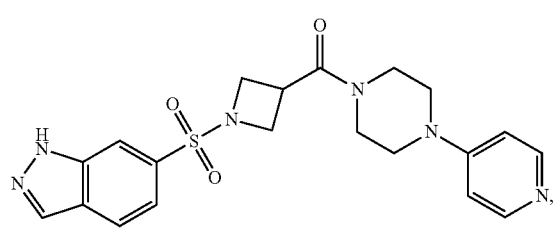
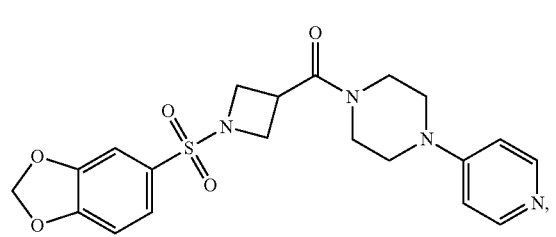
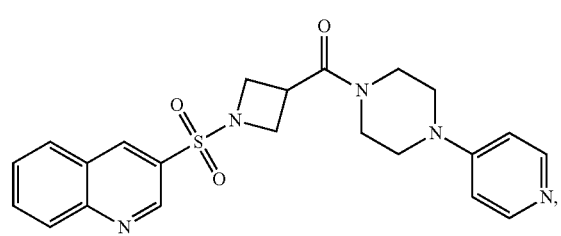
160
-continued
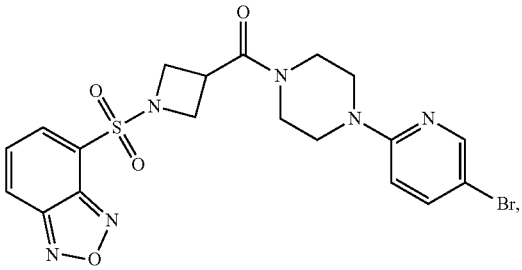
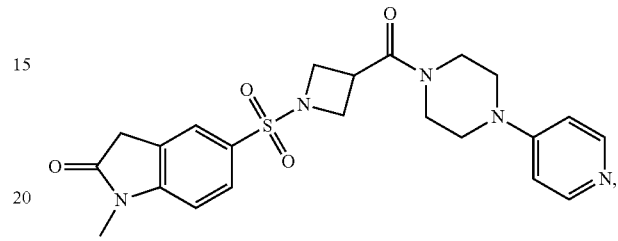
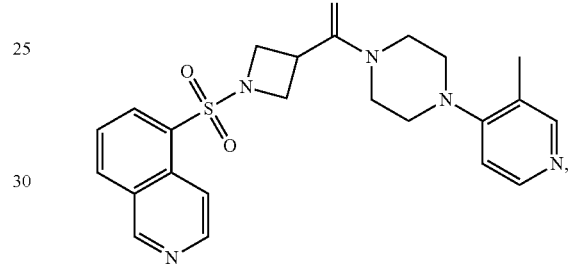
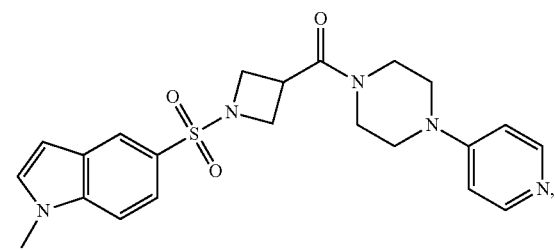
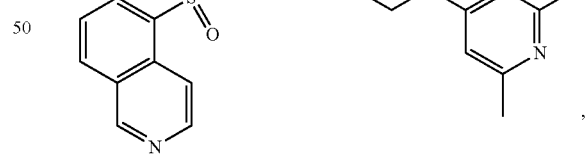
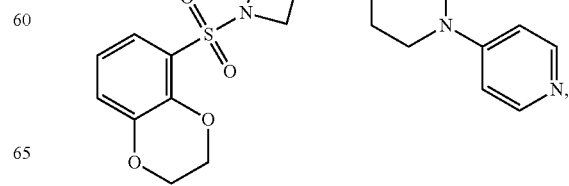

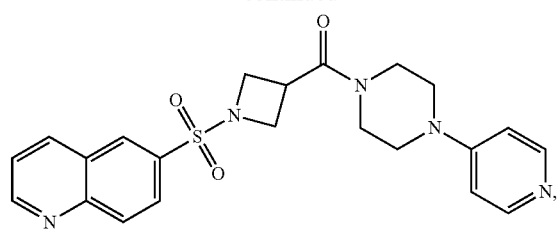
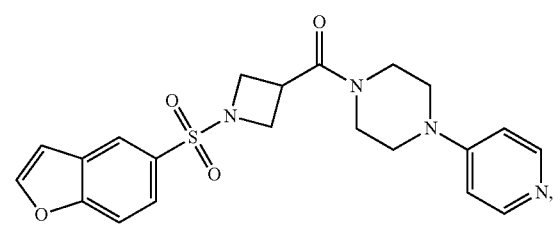
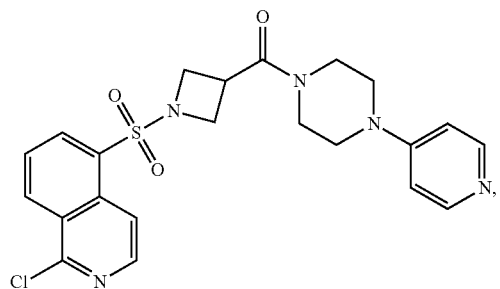 [SMILES: O=C(C1CN(S(=O)(=O)c2cccc3c(Cl)nccc23)C1)N1CCN(c2ccncc2)CC1]
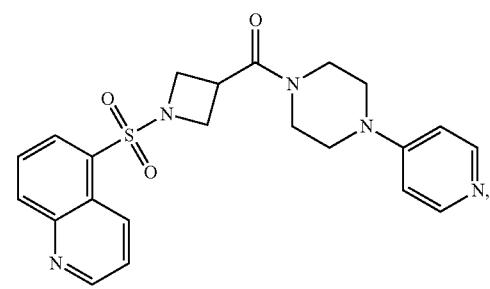
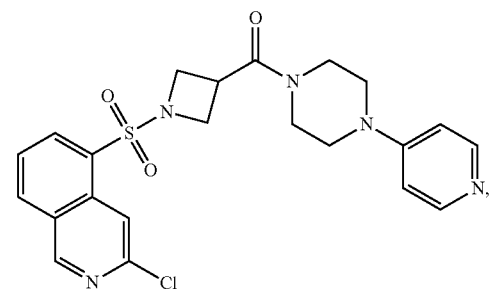
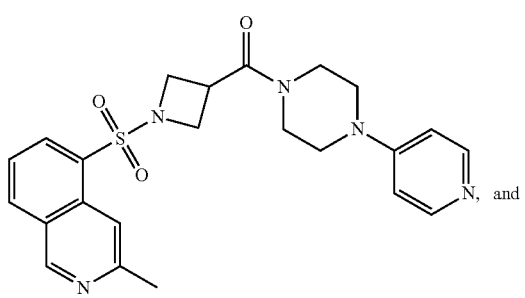
and
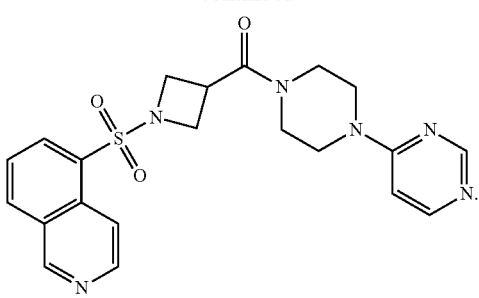
In one aspect, a compound is selected from:
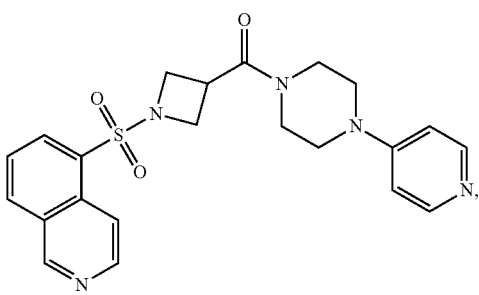
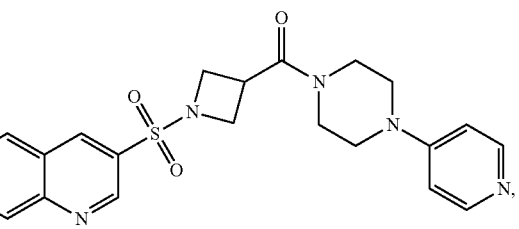
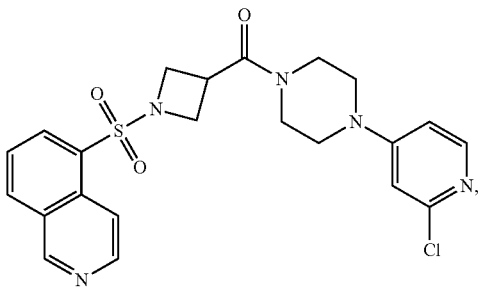
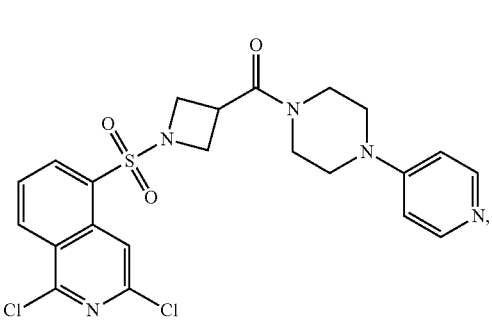

-continued
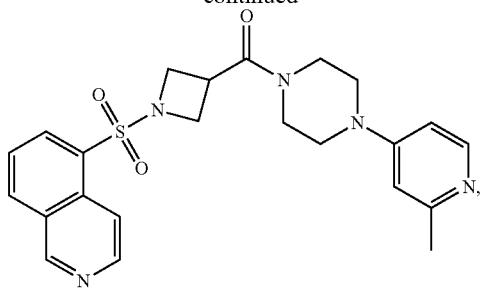
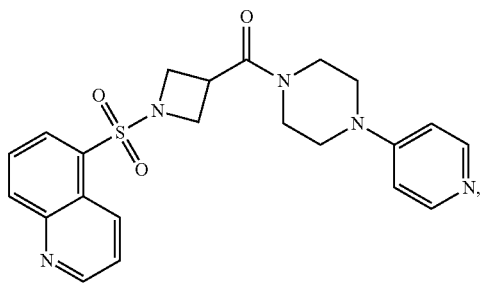
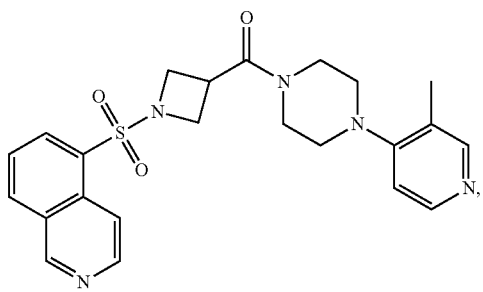
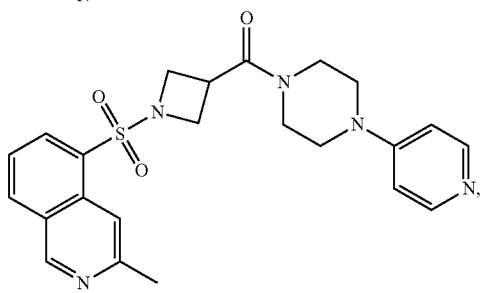
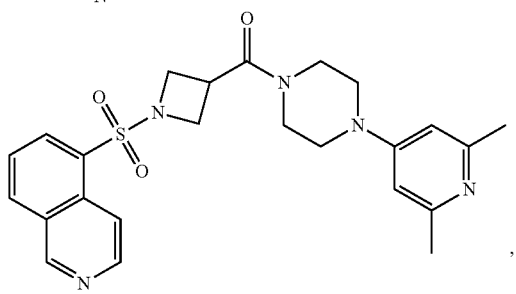
,
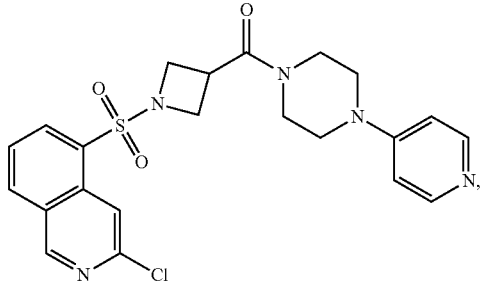
-continued
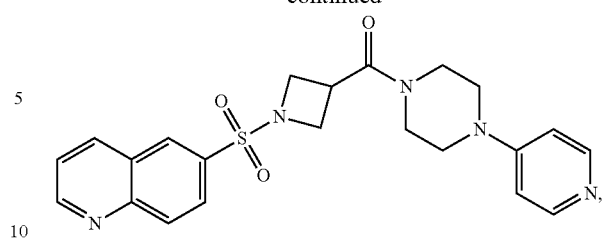
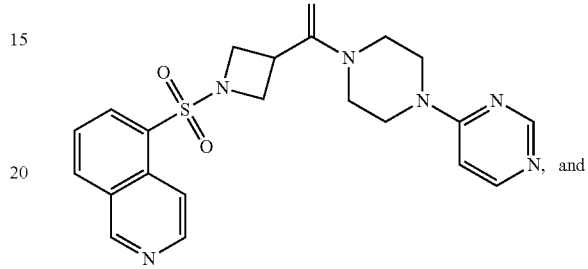
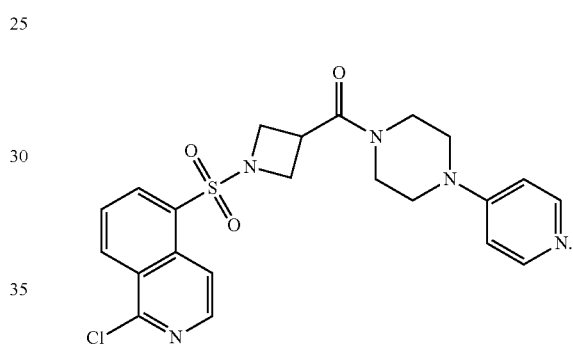
, and
In one aspect, a compound is selected from:
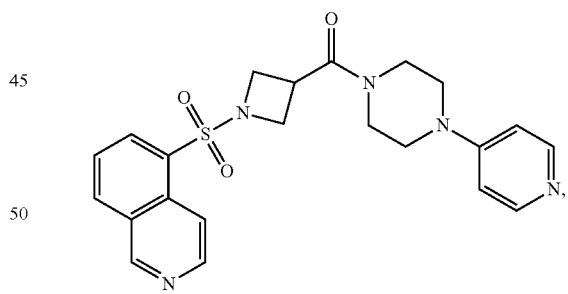
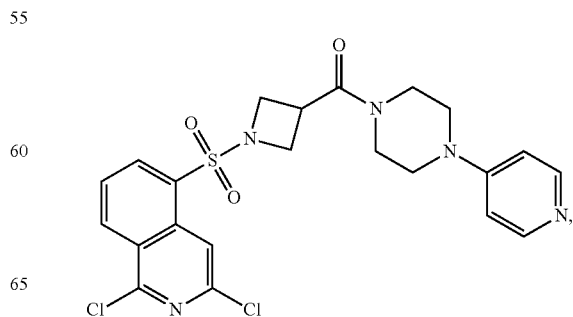

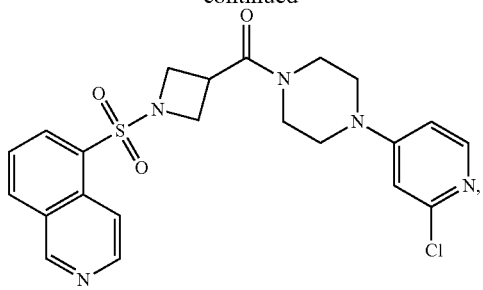
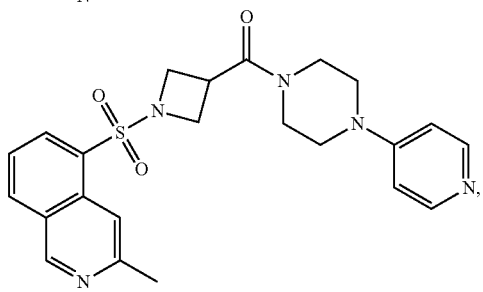
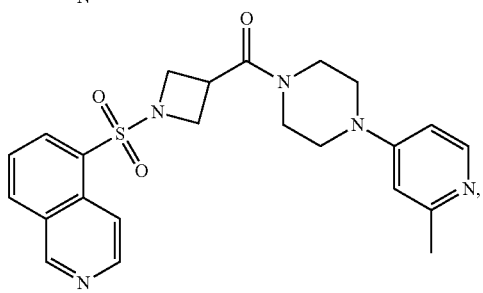
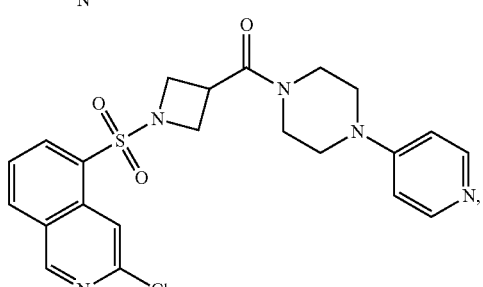
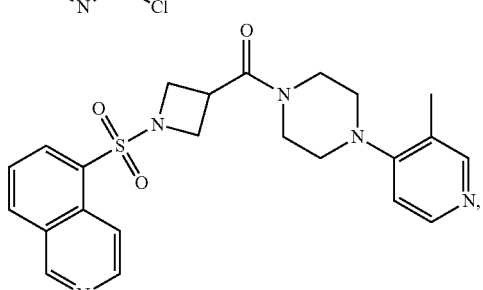
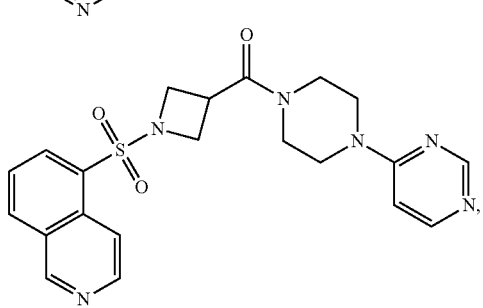
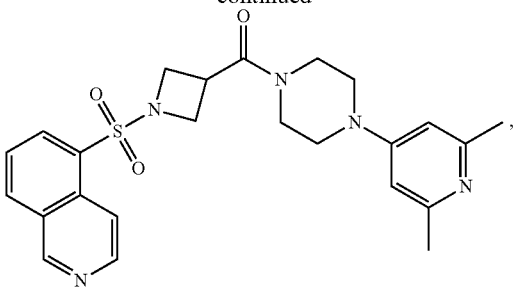
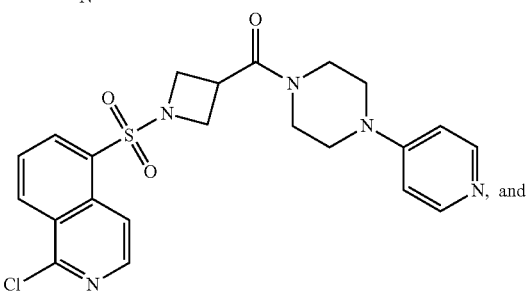
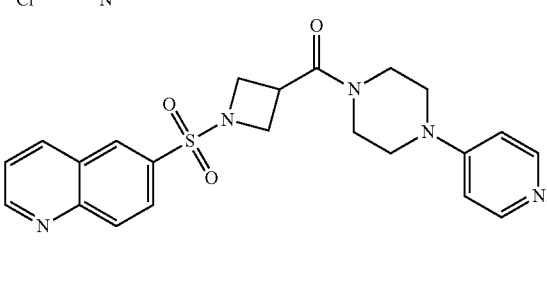
In one aspect, a compound is selected from:
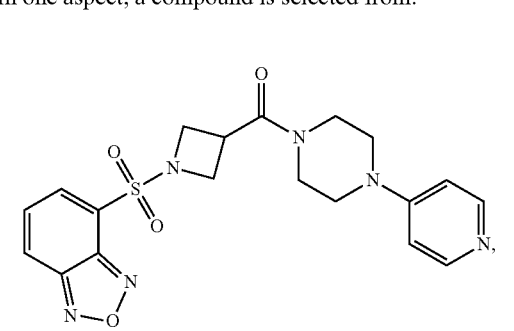
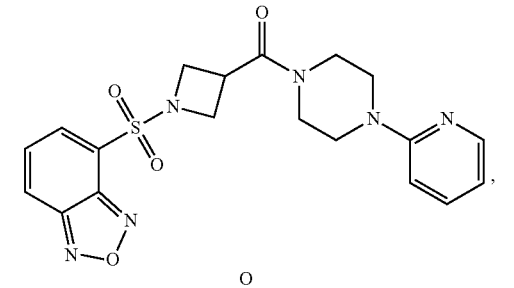
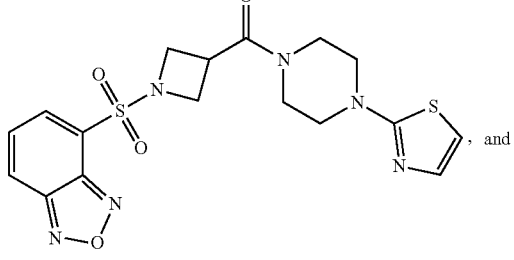

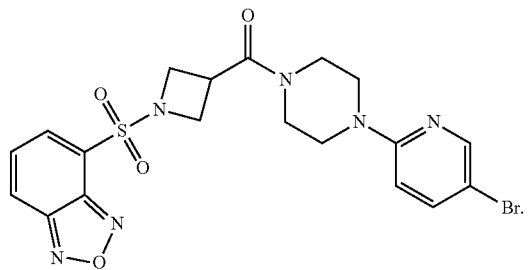
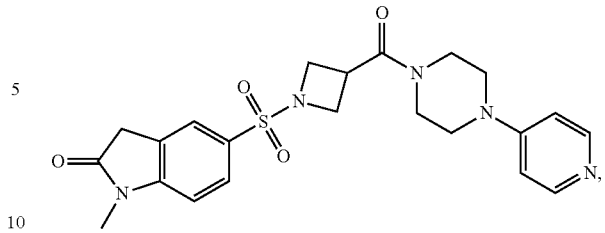
In one aspect, a compound is selected from:
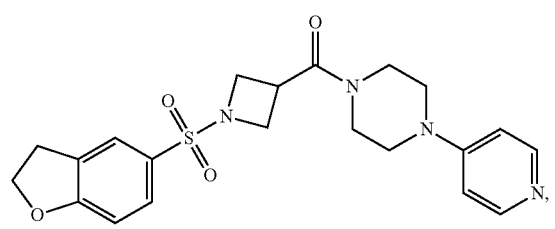
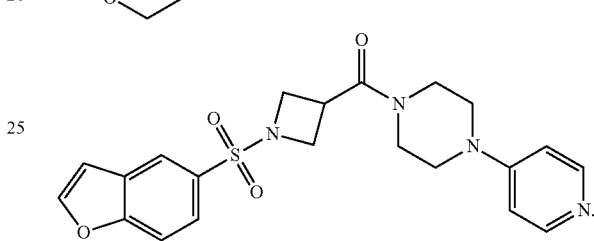
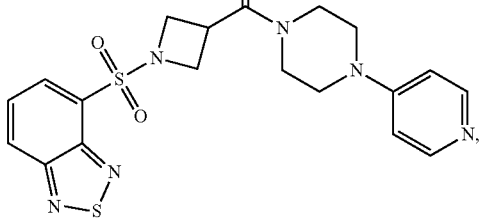
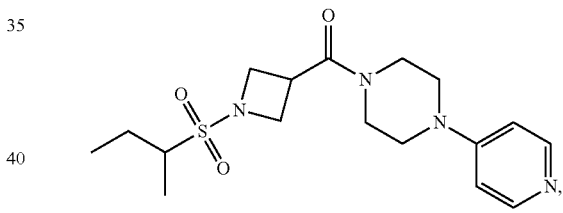
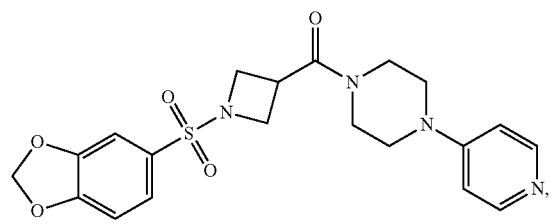
In one aspect, a compound is selected from:
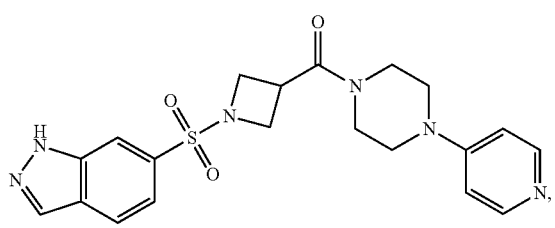
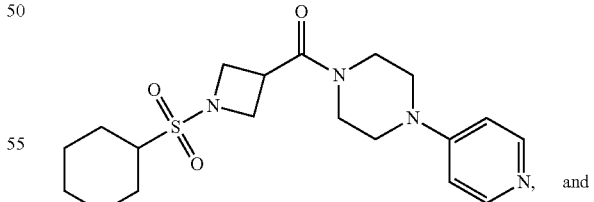
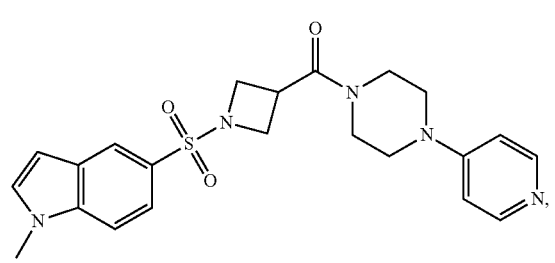
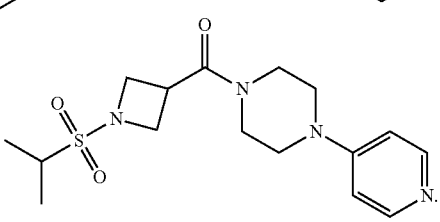

In one aspect, a compound is selected from:
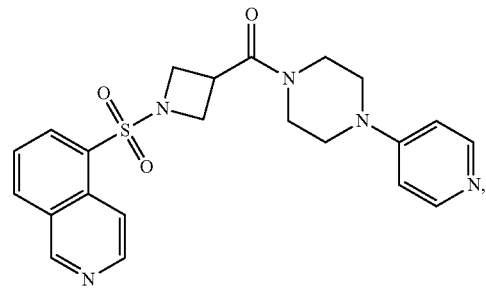
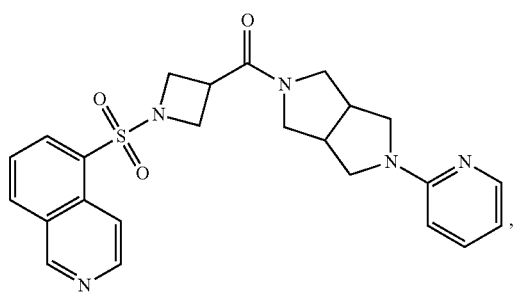
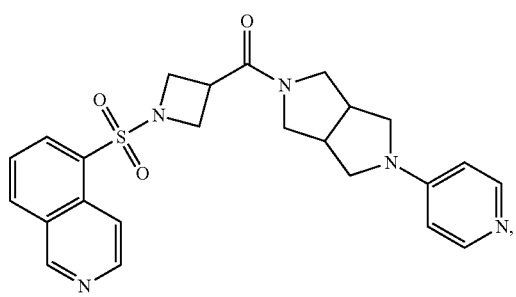
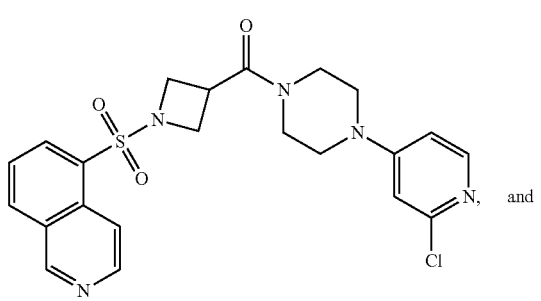
and
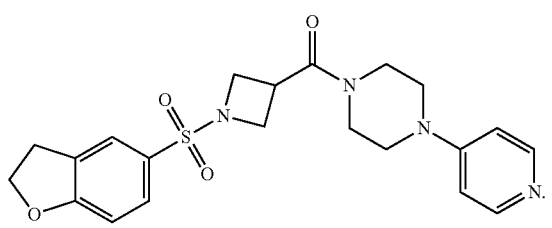
In one aspect, a compound is selected from:
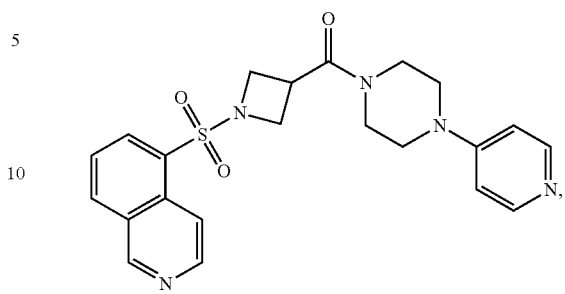
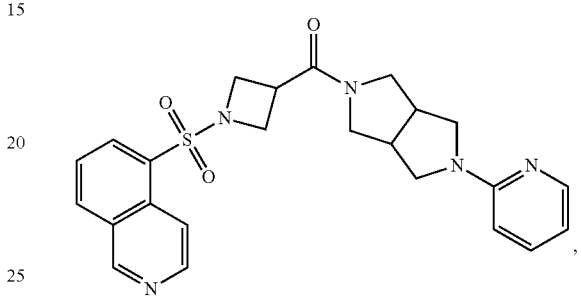
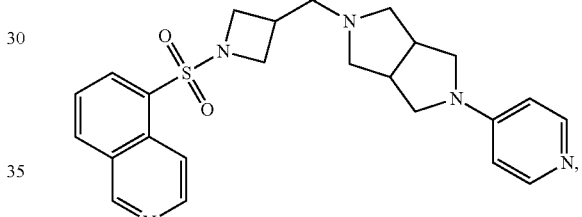
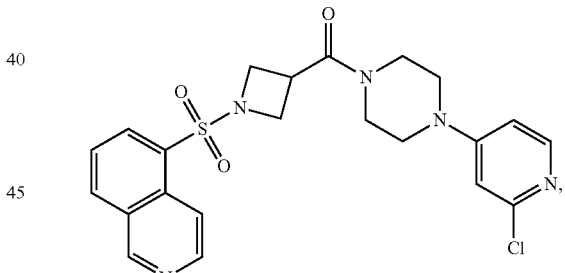
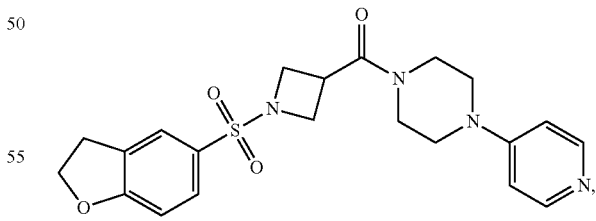
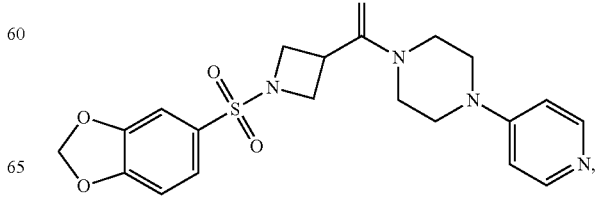

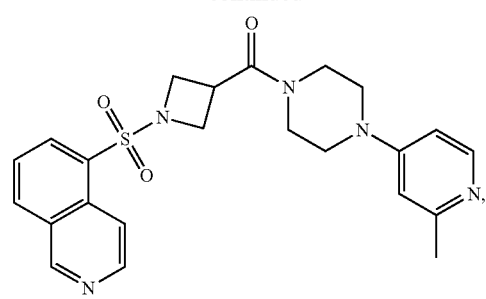
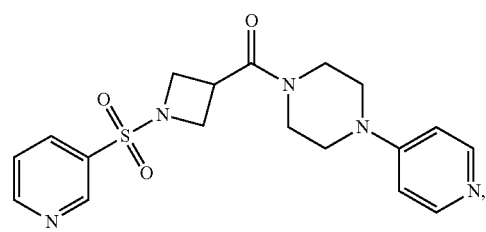
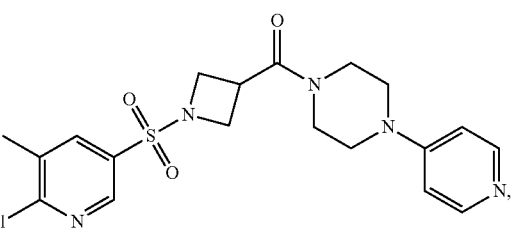
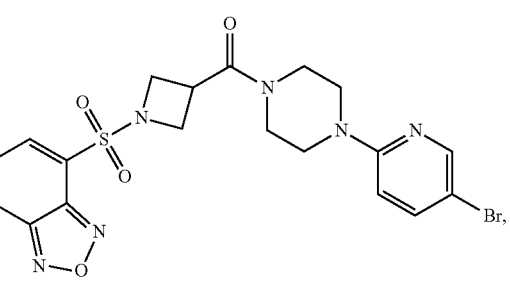
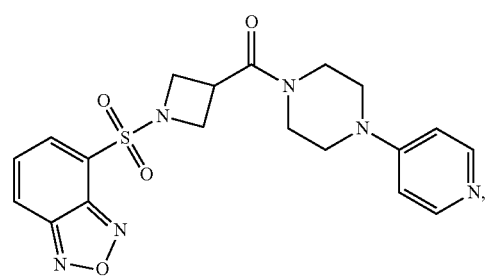
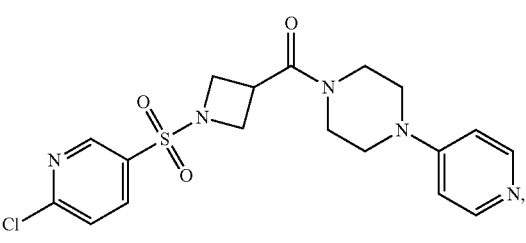
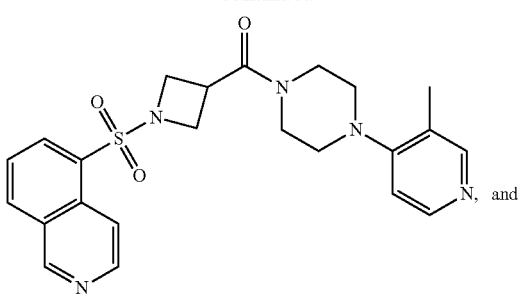
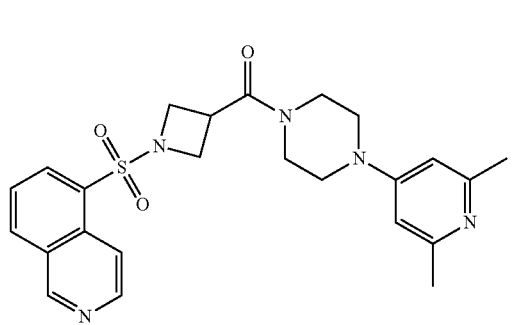
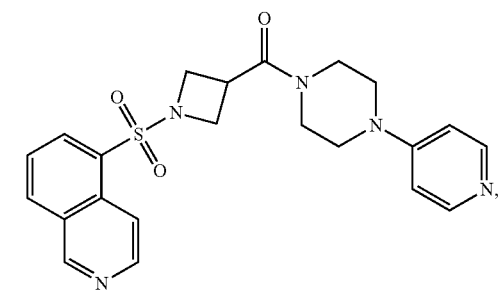
In one aspect, a compound is selected from:
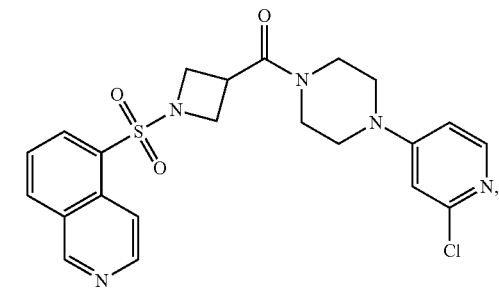

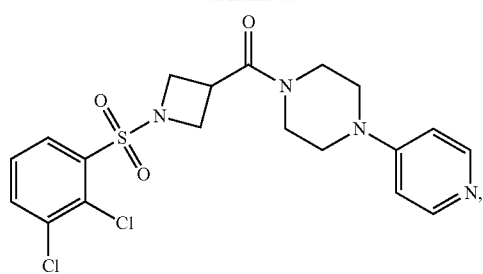
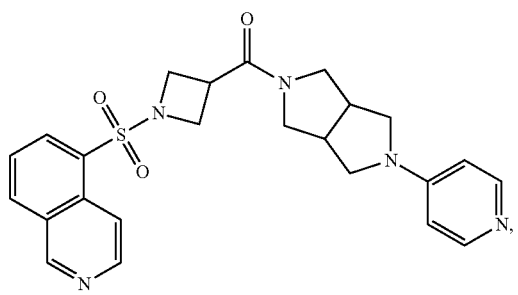
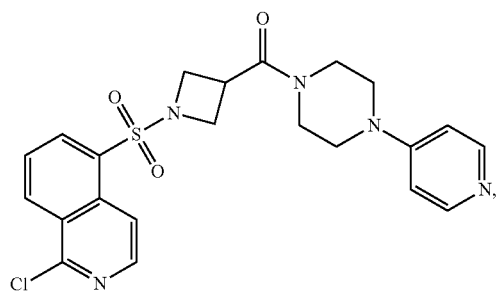
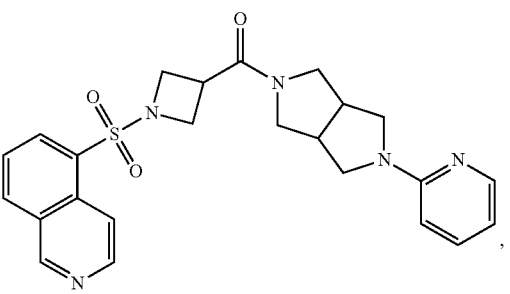 [SMILES: O=C(C1CN(S(=O)(=O)c2cccc3cnccc23)C1)N1CC2CN(c3ccncc3)CC2C1]
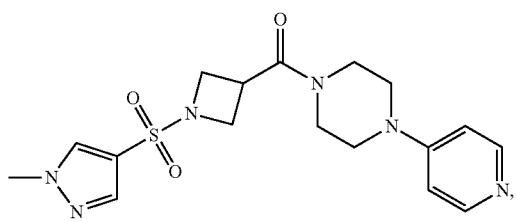
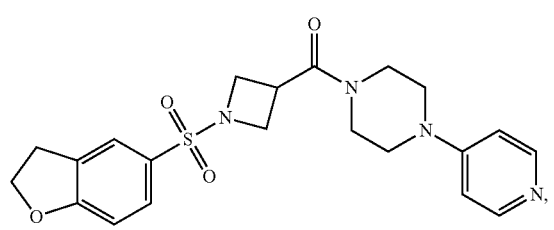 [SMILES: O=C(C1CN(S(=O)(=O)c2ccc3c(c2)CCO3)C1)N1CCN(c2ccncc2)CC1]
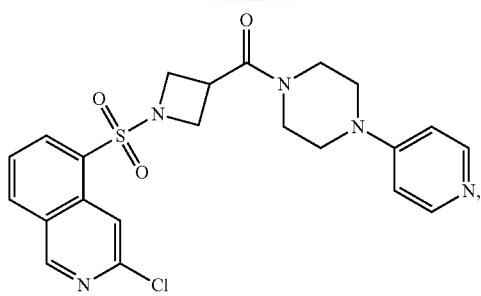
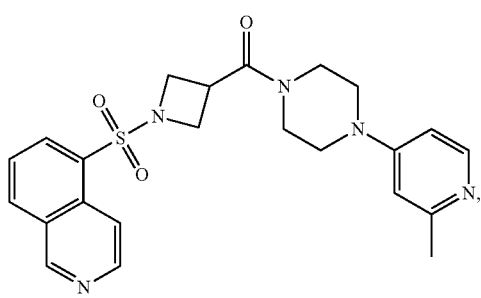
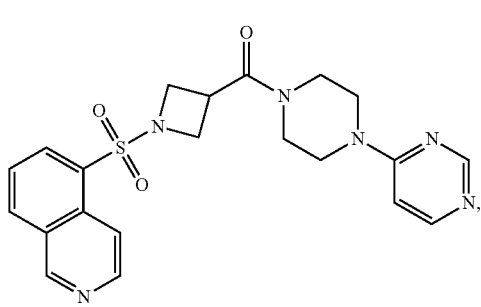
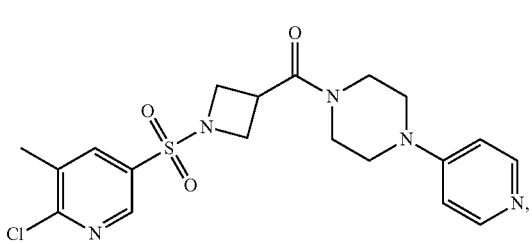
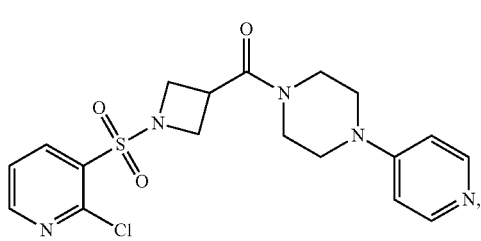
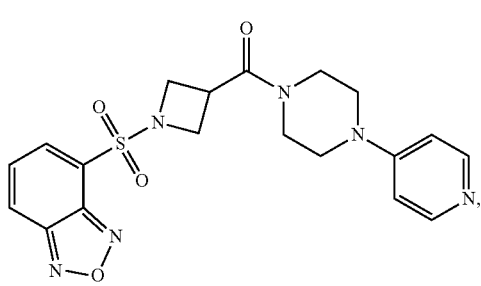

-continued
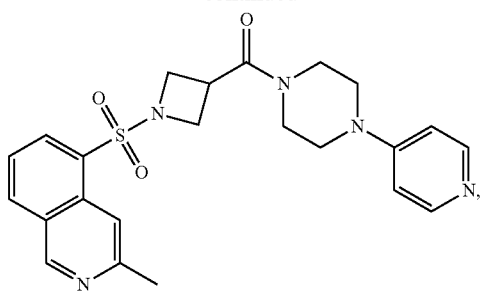
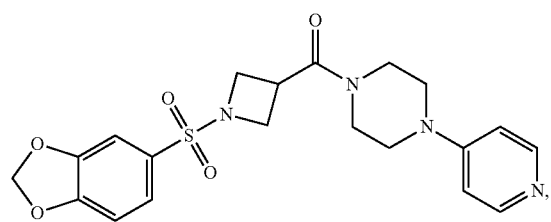 [SMILES: O=C(C1CN(S(=O)(=O)c2ccc3c(c2)OCO3)C1)N1CCN(c2ccncc2)CC1]
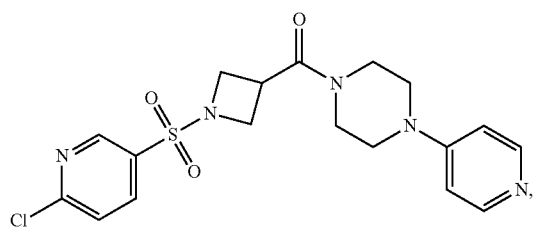
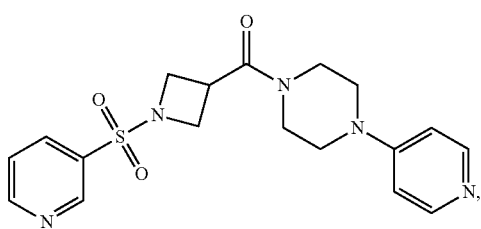
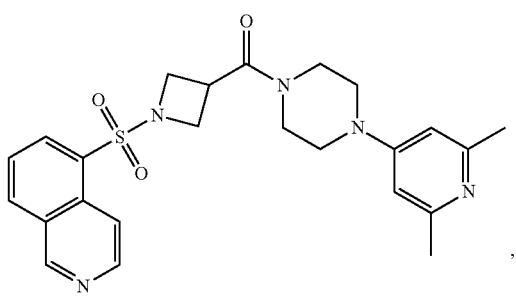
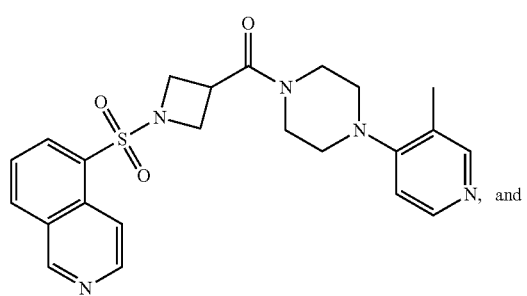
-continued
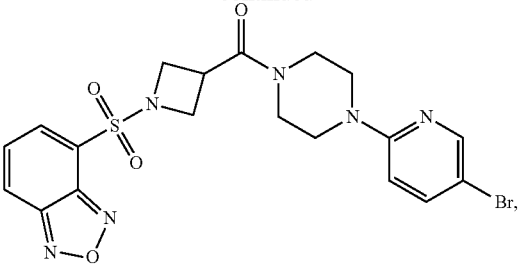
In one aspect, a compound is selected from:
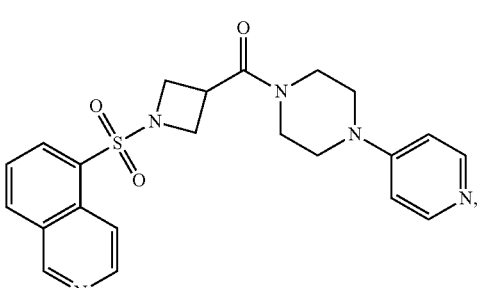
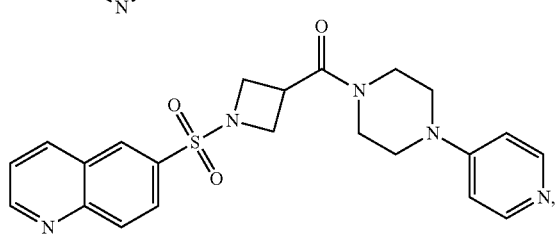
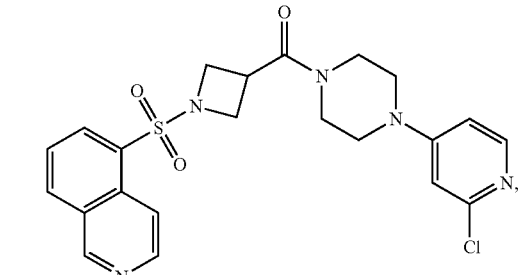
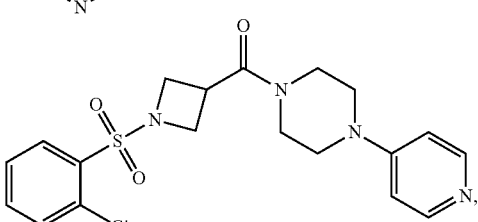
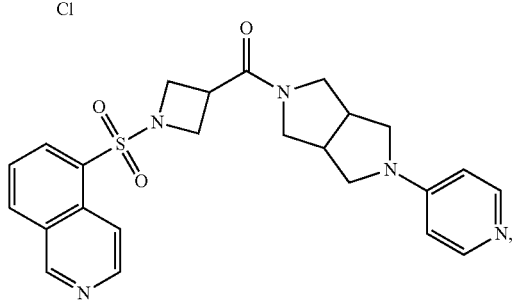

177
-continued
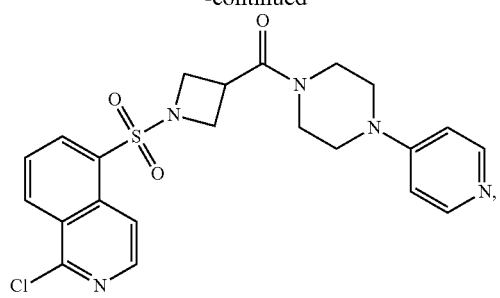
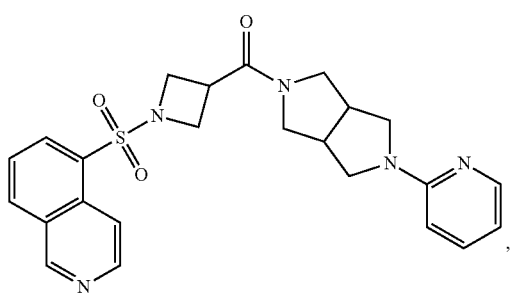
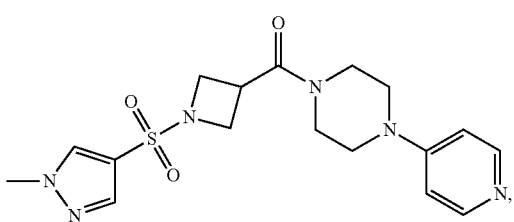 [SMILES: Cn1cc(S(=O)(=O)N2CC(C(=O)N3CCN(c4ccncc4)CC3)C2)cn1]
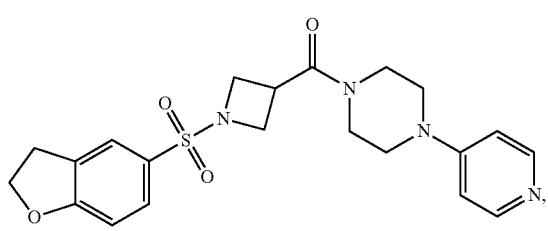
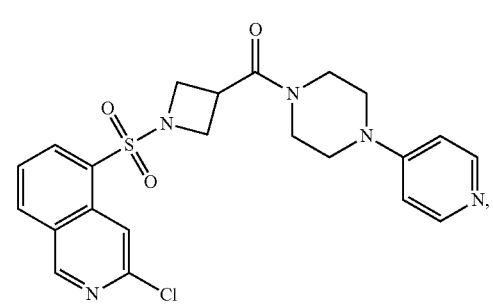
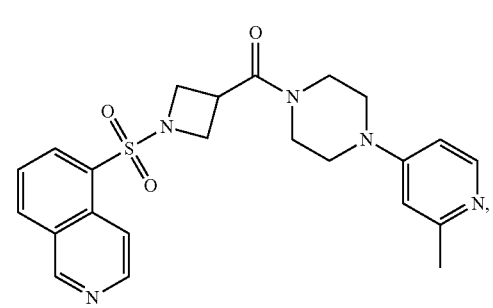
178
-continued
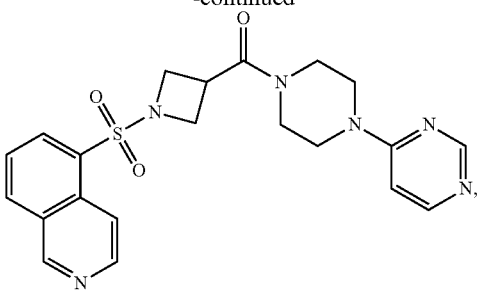
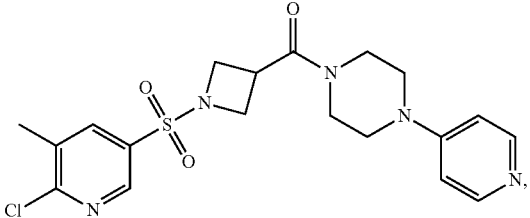
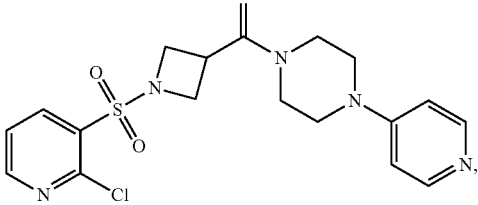
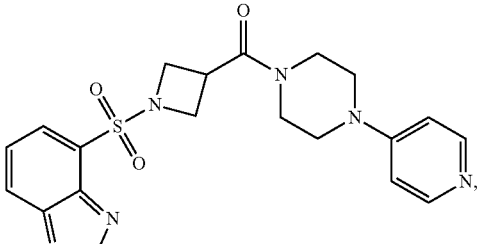
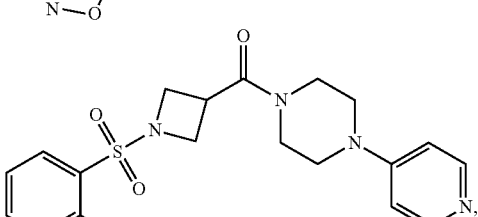
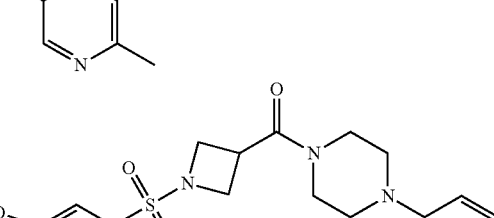
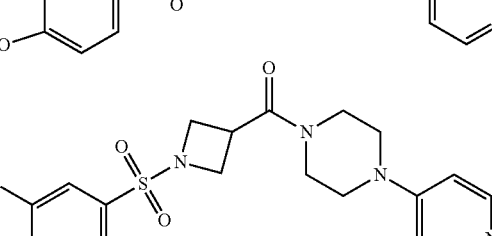

179
-continued
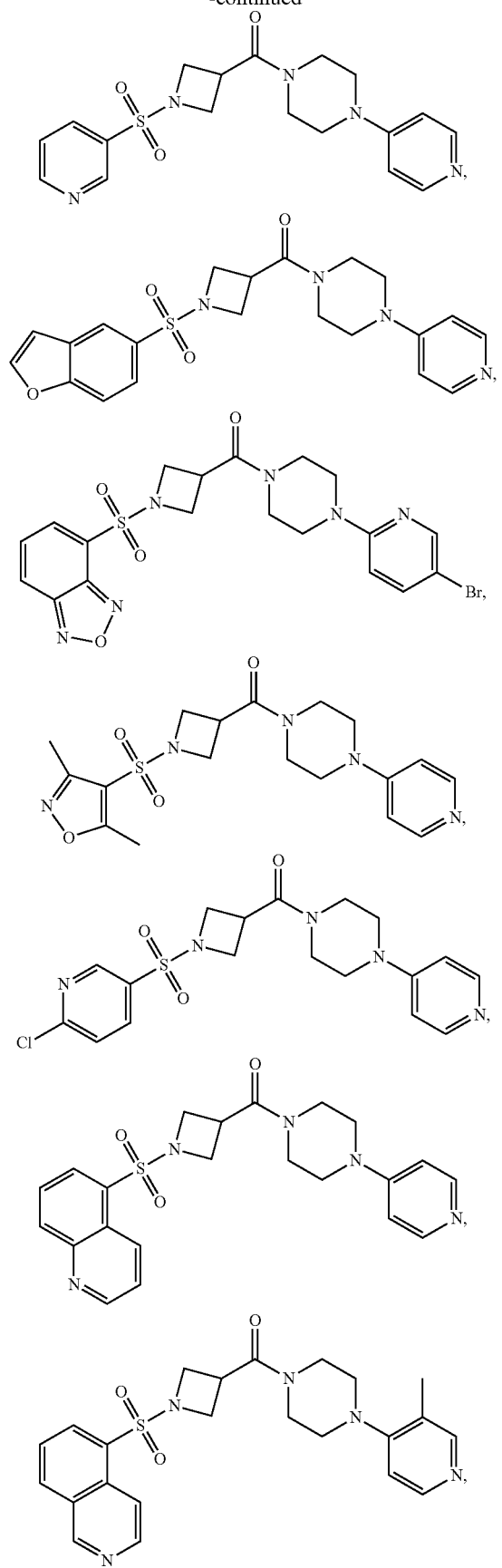
180
-continued
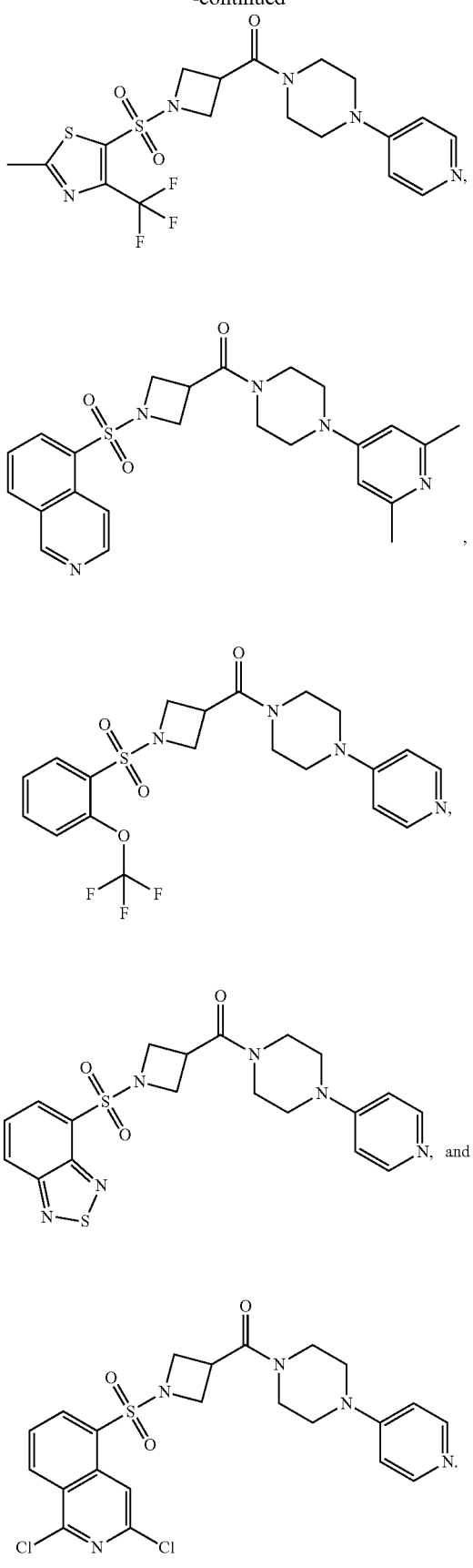

In one aspect, a compound is selected from:
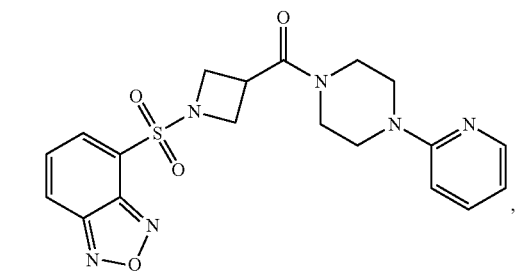
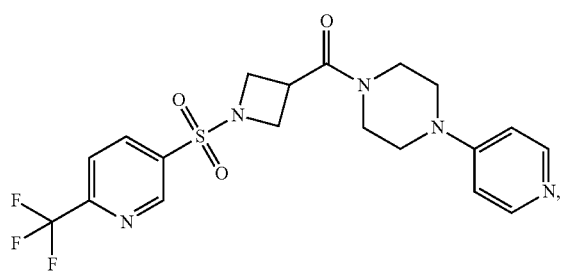
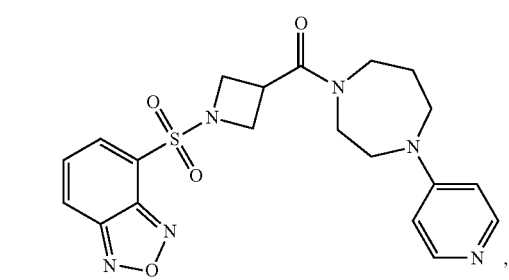
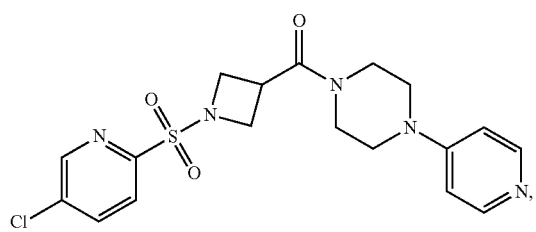
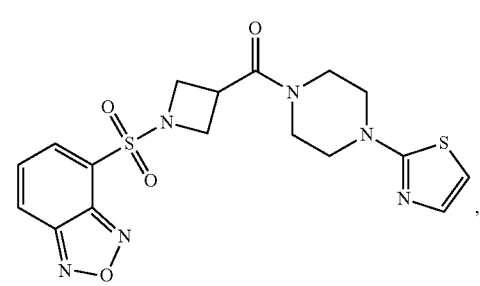
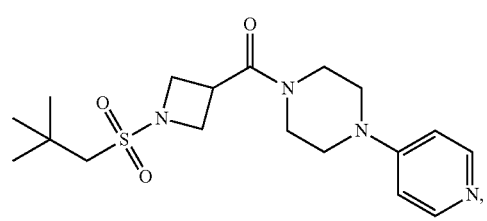
-continued
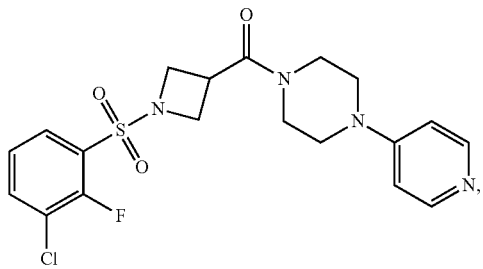
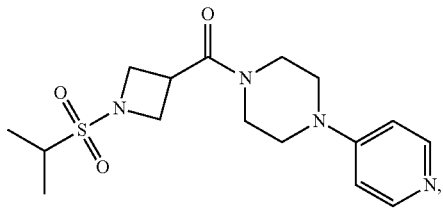
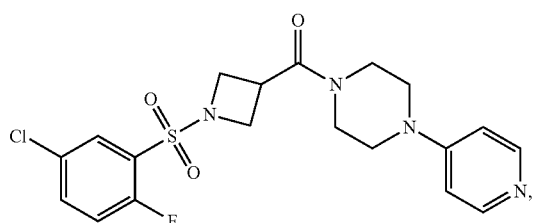
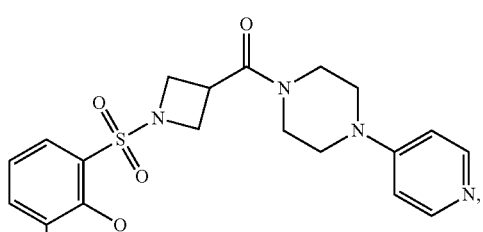
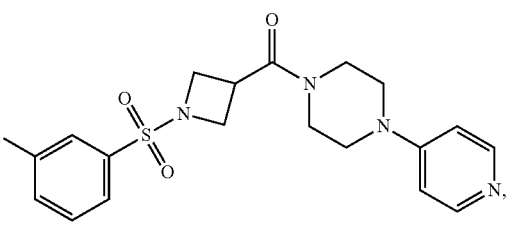
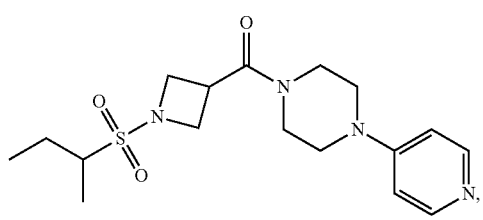
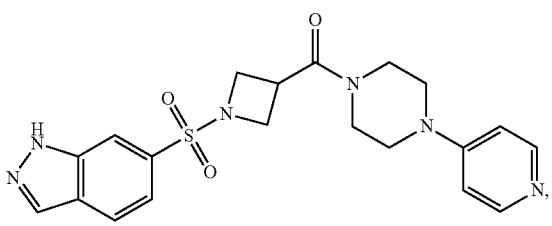

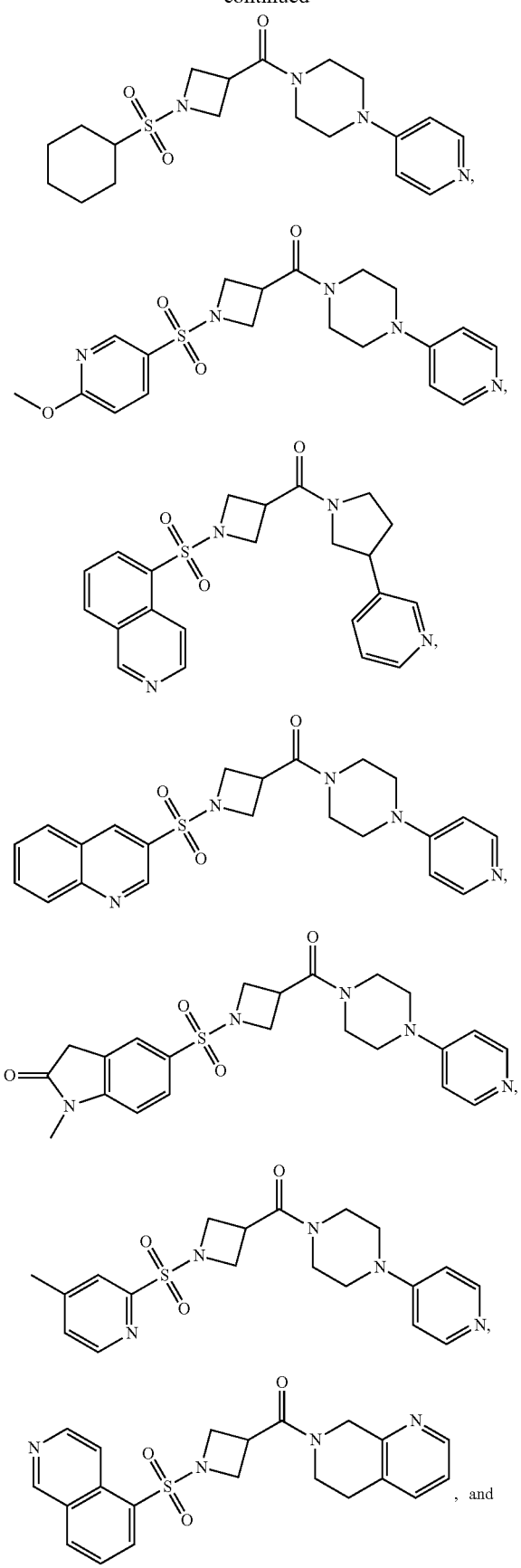

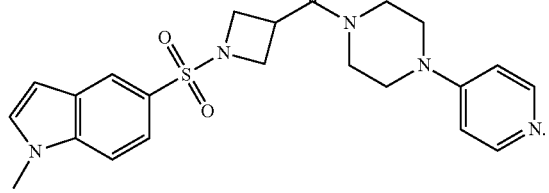

, and

It is contemplated that one or more compounds can optionally be omitted from the disclosed invention.

It is understood that the disclosed compounds can be used in connection with the disclosed methods, compositions, kits, and uses.

It is understood that pharmaceutical acceptable derivatives of the disclosed compounds can be used also in connection with the disclosed methods, compositions, kits, and uses. The pharmaceutical acceptable derivatives of the compounds can include any suitable derivative, such as pharmaceutically acceptable salts as discussed below, isomers, radiolabeled analogs, tautomers, and the like.

3. Muscarinic Acetylcholine Receptor $M_1$ Inhibition

The human muscarinic acetylcholine receptor $M_1$ (mAChR $M_1$) is a protein of 479 amino acids encoded by the CHRM1 gene. The molecular weight of the unglycosylated protein is about 51,421 kDa and it is a transmembrane GPCR. As described above, the mAChR $M_1$ is a member of the GPCR Class 1 family, or the rhodopsin-like GPCRs, which are characterized by structural features similar to rhodopsin such as seven transmembrane segments. The muscarinic acetylcholine receptors have the N-terminus oriented to the extracellular face of the membrane and the C-terminus located on the cytoplasmic face. The orthosteric binding for natural ligand, acetylcholine, for mAChRs is believed to be located within a pocket located within the transmembrane segments. The binding of ligands to the orthosteric and allosteric sites can be distinguished using methods such as those described herein and various other methods known to one skilled in the art.

In one aspect, the disclosed compounds inhibit the effect of an agonist response (e.g., acetylcholine) of mAChR $M_1$. The inhibition of mAChR $M_1$ activity can be demonstrated by methodology known in the art. For example, inhibition of mAChR $M_1$ activity can be determined by measurement of calcium flux in response to agonist, e.g. acetylcholine, in cells loaded with a $Ca^{2+}$-sensitive fluorescent dye (e.g., Fluo-4), and the response to an agonist, e.g. acetylcholine, in the presence and absence of the mAChR $M_1$ antagonist compared. In a further aspect, the calcium flux was measured as an increase in fluorescent static ratio. Without wishing to be bound by a particular theory, the compounds of the present invention can inhibit mAChR $M_1$ activity by acting as antagonists. In various aspects, the compounds can inhibit mAChR $M_1$ activity by acting as partial antagonists. In various further aspects, the compounds can inhibit mAChR $M_1$ activity by acting as negative allosteric modulators.

In one aspect, the disclosed compounds can exhibit a diminution, inhibition or abolishment of the mAChR $M_1$ response to acetylcholine and such diminution, inhibition or abolishment of the mAChR $M_1$ response can be determined from a decrease in calcium fluorescence in mAChR $M_1$-transfected CHO-K1 cells in the presence of the compound, compared to the response of equivalent CHO-K1 cells in the absence of the compound. For example, a disclosed compound can have an $IC_{50}$ of less than about 10 µM, of less than about 5 µM, of less than about 1 µM, of less than about 500 nM, of less than about 100 nM, or of less than about 50 nM. In a further aspect, the mAChR $M_1$-transfected CHO-K1 cells are transfected with human mAChR $M_1$. In a still further aspect, the mAChR $M_1$-transfected CHO-K1 cells are transfected with rat mAChR $M_1$.

In one aspect, the disclosed compounds can exhibit a decrease in the mAChR $M_1$ response to acetylcholine in CHO-K1 cells transfected with a mammalian mAChR $M_1$ in the presence of the compound, compared to the response to acetylcholine in the absence of the compound. For example, CHO-K1 cells can be transfected with human mAChR $M_1$. Alternatively, for example, CHO-K1 cells can be transfected with rat mAChR $M_1$. For example, a compound can exhibit antagonism of mAChR $M_1$ with an $IC_{50}$ of less than about 10,000 nM, of less than about 5,000 nM, of less than about 1,000 nM, of less than about 500 nM, or of less than about 100 nM when determined in CHO-K1 cells can be transfected with rat mAChR $M_1$. Alternatively, the disclosed compounds exhibit a decrease in the mAChR $M_1$ response to acetylcholine in CHO-K1 cells transfected with human mAChR $M_1$ in the presence of the compound, compared to the response to acetylcholine in the absence of the compound. For example, a compound can exhibit antagonism of mAChR $M_1$ with an $IC_{50}$ of less than about 10,000 nM, of less than about 5,000 nM, of less than about 1,000 nM, of less than about 500 nM, of less than about 100 nM, or of less than about 50 nM when determined in CHO-K1 cells can be transfected with human mAChR $M_1$.

In one aspect, a disclosed compound can exhibit antagonism of the mAChR $M_1$ response to acetylcholine. In a further aspect, a disclosed compound exhibits antagonism of the mAChR $M_1$ response to acetylcholine with an $IC_{50}$ of less than about 10,000 nM. In a still further aspect, a disclosed compound exhibits antagonism of the mAChR $M_1$ response to acetylcholine with an $IC_{50}$ of less than about 5,000 nM. In a yet further aspect, a disclosed compound exhibits antagonism of the mAChR $M_1$ response to acetylcholine with an $IC_{50}$ of less than about 1,000 nM. In an even further aspect, a disclosed compound exhibits antagonism of the mAChR $M_1$ response to acetylcholine with an $IC_{50}$ of less than about 500 nM. In a still further aspect, a disclosed compound exhibits antagonism of the mAChR $M_1$ response to acetylcholine with an $IC_{50}$ of less than about 100 nM. In a yet further aspect, a disclosed compound exhibits antagonism of the mAChR $M_1$ response to acetylcholine with an $IC_{50}$ of less than about 50 nM.

In various further aspects, a disclosed compound can exhibit a diminution, inhibition or abolishment of the mAChR $M_1$ response in mAChR $M_1$-transfected CHO-K1 cells with an $IC_{50}$ less than the $IC_{50}$ for one or more of mAChR $M_2$, mAChR $M_3$, mAChR $M_4$, or mAChR $M_5$ response in mAChR $M_2$, $M_3$, $M_4$ or $M_5$-transfected CHO-K1 cells. That is, a disclosed compound can have selectivity for the mAChR $M_1$ receptor vis-à-vis one or more of the mAChR $M_2$, $M_3$, $M_4$ or $M_5$ receptors. For example, in one aspect, a disclosed compound can diminish, abolish or inhibit the mAChR $M_1$ response with an $IC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, of about 50-fold less than that for mAChR $M_2$, of about 100-fold less than that for mAChR $M_2$, or of >100-fold less than that of that for mAChR $M_2$. In a further aspect, a disclosed compound can diminish, abolish or inhibit the mAChR $M_1$ response with an $IC_{50}$ of about 5-fold less than that for mAChR $M_3$, of about 10-fold less than that for mAChR $M_3$, of about 20-fold less than that for $M_3$, of about 30-fold less than that for mAChR $M_3$, of about 50-fold less than that for mAChR $M_3$, of about 100-fold less than that for mAChR $M_3$, or of >100-fold less than that of that for mAChR $M_3$. In a further aspect, a disclosed compound can diminish, abolish or inhibit the mAChR $M_1$ response with an $IC_{50}$ of about 5-fold less than that for mAChR $M_4$, of about 10-fold less than that for mAChR $M_4$, of about 20-fold less than that for $M_4$, of about 30-fold less than that for mAChR $M_4$, of about 50-fold less than that for mAChR $M_4$, of about 100-fold less than that for mAChR $M_4$, or of >100-fold less than that of that for mAChR $M_4$. In a further aspect, a disclosed compound can diminish, abolish or inhibit the mAChR $M_1$ response with an $IC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, of about 50-fold less than that for mAChR $M_5$, of about 100-fold less than that for mAChR $M_5$, or of >100-fold less than that of that for mAChR $M_5$. In a further aspect, a disclosed compound can diminish, abolish or inhibit the mAChR $M_1$ response with an $IC_{50}$ of about 5-fold less than that for the mAChR $M_2$, $M_3$, $M_4$ or $M_5$ receptors, of about 10-fold less than that for the mAChR $M_2$, $M_3$, $M_4$ or $M_5$ receptors, of about 20-fold less than that for the mAChR $M_2$, $M_3$, $M_4$ or $M_5$ receptors, of about 30-fold less than that for the mAChR $M_2$, $M_3$, $M_4$ or $M_5$ receptors, of about 50-fold less than that for the mAChR $M_2$, $M_3$, $M_4$ or $M_5$ receptors, of about 100-fold less than that for the mAChR $M_2$, $M_3$, $M_4$ or $M_5$ receptors, or of >100-fold than that for the mAChR $M_2$, $M_3$, $M_4$ or $M_5$ receptors. In various further aspects, a disclosed compound can diminish, abolish or inhibit the mAChR $M_1$ response in mAChR $M_1$-transfected CHO-K1 cells and is inactive for one or more of mAChR $M_2$, mAChR $M_3$, mAChR $M_4$, or mAChR $M_5$ response in mAChR $M_2$, $M_3$, $M_4$ or $M_5$-transfected CHO-K1 cells.

In various further aspects, a disclosed compound can exhibit a diminution, inhibition or abolishment of the mAChR $M_1$ response in $M_1$-transfected CHO-K1 cells with an $IC_{50}$ of less than about 10 µM and exhibits a selectivity for the $M_1$ receptor vis-à-vis one or more of the mAChR $M_2$, $M_3$, $M_4$ or $M_5$ receptors. For example, in one aspect, a disclosed compound can have an $IC_{50}$ of less than about 10 µM, of less than about 5 µM, of less than about 1 µM, of less than about 500 nM, of less than about 100 nM, or of less than about 50 nM; and the compound can also diminish, abolish or inhibit the mAChR $M_1$ response with an $IC_{50}$ of about 5-fold less than that for mAChR $M_2$, of about 10-fold less than that for mAChR $M_2$, of about 20-fold less than that for mAChR $M_2$, of about 30-fold less than that for mAChR $M_2$, or of about 50-fold less than that for mAChR $M_2$. In a further aspect, the compound can have an $IC_{50}$ of less than about 10 µM, of less than about 5 µM, of less than about 1 µM, of less than about 500 nM, of less than about 100 nM, or of less than about 50 nM; and the compound can also diminish, abolish or inhibit the mAChR $M_1$ response with an $IC_{50}$ of about 5-fold less than that for mAChR $M_3$, of about 10-fold less than that for mAChR $M_3$, of about 20-fold less than that for mAChR $M_3$, of about 30-fold less than that for mAChR $M_3$, or of about 50-fold less than that for mAChR $M_3$. In a further aspect, the compound can have an $IC_{50}$ of less than about 10 µM, of less than about 5 µM, of less than about 1 µM, of less than about 500 nM, of less than about 100 nM, or of less than about 50 nM; and the compound can also diminish, abolish or inhibit the mAChR $M_1$ response with an $IC_{50}$ of about 5-fold less than that for mAChR $M_4$, of about 10-fold less than that for mAChR $M_4$, of about 20-fold less than that for mAChR $M_4$, of about 30-fold less than that for mAChR $M_4$, or of about 50-fold less than that for mAChR $M_4$. In a further aspect, the compound can have an $IC_{50}$ of less than about 10 µM, of less than about 5 µM, of less than about 1 µM, of less than about 500 nM, of less than about 100 nM, or of less than about 50 nM; and the compound can also diminish, abolish or inhibit the mAChR $M_1$ response with an $IC_{50}$ of about 5-fold less than that for mAChR $M_5$, of about 10-fold less than that for mAChR $M_5$, of about 20-fold less than that for mAChR $M_5$, of about 30-fold less than that for mAChR $M_5$, or of about 50-fold less than that for mAChR $M_5$. In a further aspect, the compound can have an $IC_{50}$ of less than about 10 µM, of less than about 5 µM, of less than about 1 µM, of less than about 500 nM, of less than about 100 nM, or of less than about 50 nM; and the compound can also diminish, abolish or inhibit the mAChR $M_1$ response with an $IC_{50}$ of about 5-fold less than that for the mAChR $M_2$, $M_3$, $M_4$ or $M_5$ receptors, of about 10-fold less than that for the mAChR $M_2$, $M_3$, $M_4$ or $M_5$ receptors, of about 20-fold less than that for the mAChR $M_2$, $M_3$, $M_4$ or $M_5$ receptors, of about 30-fold less than that for the mAChR $M_2$, $M_3$, $M_4$ or $M_5$ receptors, or of about 50-fold less than that for the mAChR $M_2$, $M_3$, $M_4$ or $M_5$ receptors.

C. Methods of Making the Compounds

In one aspect, the invention relates to methods of making compounds useful as antagonists of the mAChR $M_1$ receptor, which can be useful in the treatment neurological and psychiatric disorders associated with muscarinic acetylcholine dysfunction and other diseases in which muscarinic acetylcholine receptors are involved. In one aspect, the invention relates to the disclosed synthesis manipulations. In a further aspect, the disclosed compounds comprise the products of the synthetic methods described herein.

In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. For clarity, examples having a fewer substituent can be shown where multiple substituents are allowed under the definitions disclosed herein. Thus, the following examples are provided so that the invention might be more fully understood, are illustrative only, and should not be construed as limiting.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Synthesis Route 1

In one aspect, substituted (1-(methylsulfonyl)azetidin-3-yl)(heterocycloalkyl) methanone analogs (1.4) of the present invention can be prepared generically by the synthesis scheme as shown below (Scheme 1A).

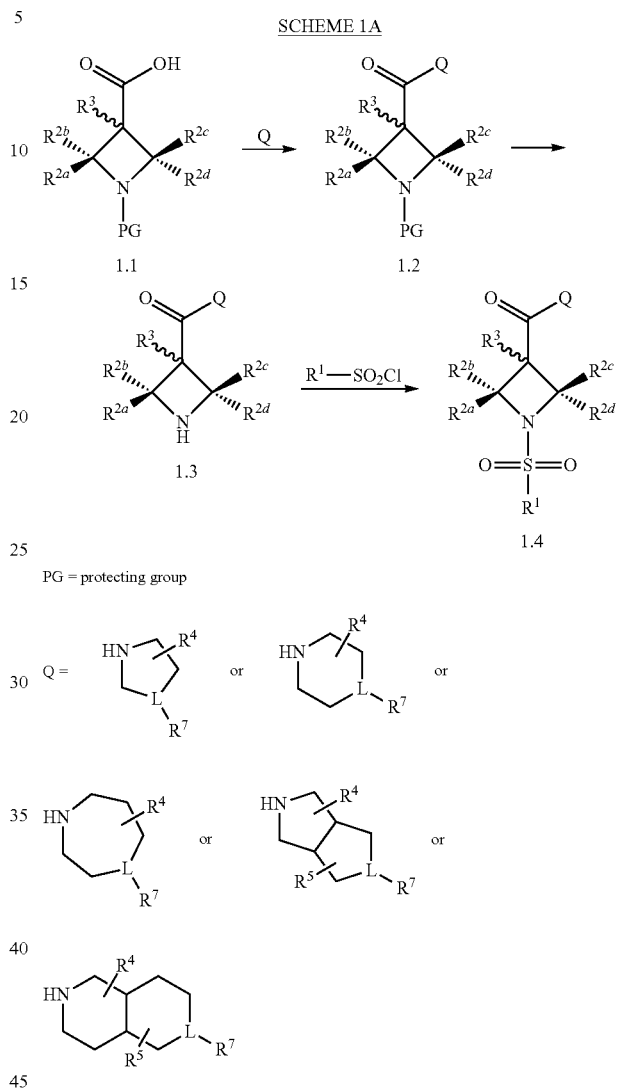

Compounds are represented in generic form, with substituents as noted in compound descriptions elsewhere herein. A more specific example is set forth below (Scheme 1B).

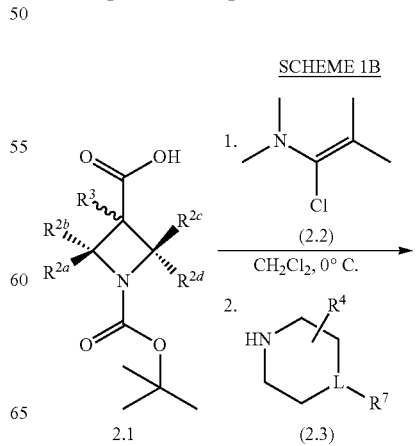

189

-continued

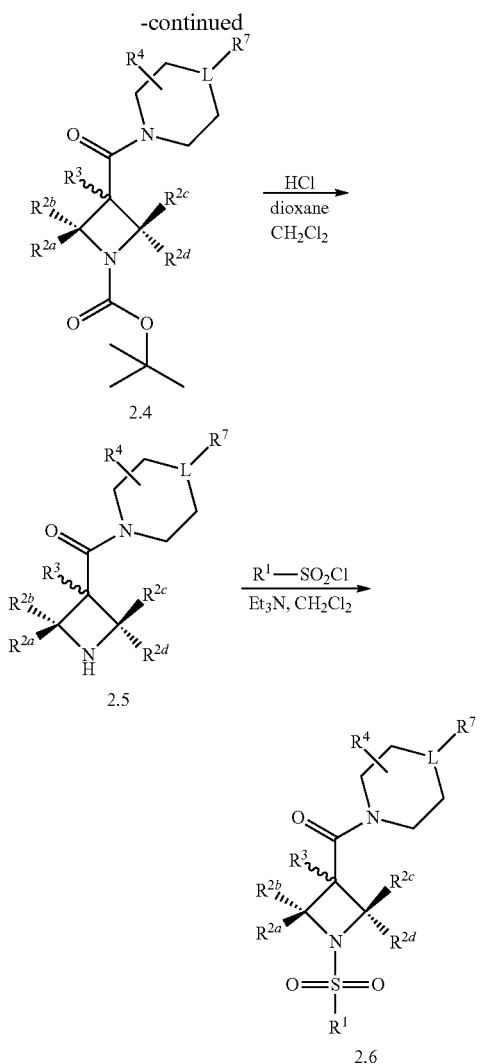

In one aspect, Scheme 1B begins with a suitable substituted azetidine-3-carboxylic acid (2.1). Suitable azetidine carboxylic acids are commercially available or can be readily prepared by one skilled in the art. The N-protected azetidine-3-carboxylic acid (2.1) is dissolved in a suitable solvent such as dichloromethane at a suitable temperature, e.g., about 0° C. The halogenating agent (e.g., Ghosez's reagent, 2.2) is typically added slowly or drop-wise to this reaction mixture, and the reaction is stirred for a sufficient amount of time and temperature to complete the reaction, (e.g., approximately 30 min at about 0° C.). Then, the amine (2.3) is added at about 0° C. and the reaction is carried out for a time sufficient to complete the reaction, e.g., about 2 h at ambient temperature (about 15-40° C.). Upon completion, the reaction mixture is diluted with solvent (e.g., dichloromethane) and an appropriate aqueous base (e.g., sodium bicarbonate). The product, a compound of type 2.4, is isolated by standard procedures used by one skilled in the art. Then, the isolated material, 2.4, is dissolved in an appropriate solvent, e.g., dichloromethane at ambient temperature (about 15-40° C.). To this mixture is added an acid in an appropriate solvent, e.g., HCl in dioxane. The reaction mixture is stirred at temperature for a time sufficient to complete the reaction, e.g., about 3 h, to provide

190 compounds of type 2.5 after adding additional solvent, e.g., methanol, and concentration under vacuum. The unpurified product of type 2.5 is suspended or dissolved in an appropriate solvent such as dichloromethane at ambient temperature (about 15-40° C.). A base (e.g., triethylamine) is added and the reaction mixture is stirred for about 30 min or a suitable amount of time. Then, an appropriate sulfonyl chloride ($(R^1SO_2Cl)$) is added and the reaction is stirred at ambient temperature (about 15-40° C., a suitable temperature) for about 2 h or a suitable time to complete the reaction. Upon completion, the reaction mixture is diluted with solvent (e.g., dichloromethane) and an appropriate aqueous base (e.g., sodium bicarbonate). The product, a compound of type 2.6, is isolated by methods known to one skilled in the art [e.g., phase separator (extraction), and concentration under a vacuum; followed by purification, e.g., chromatography].

2. Synthesis Route 2

In one aspect, substituted analogs of octahydropropylpyrrole[3,4-c]pyrroles (3.3), which is a representative example of a compound Q shown in the above schemes 1 of the present invention can be prepared generically by the synthesis scheme as shown below (Scheme 2A).

SCHEME 2A

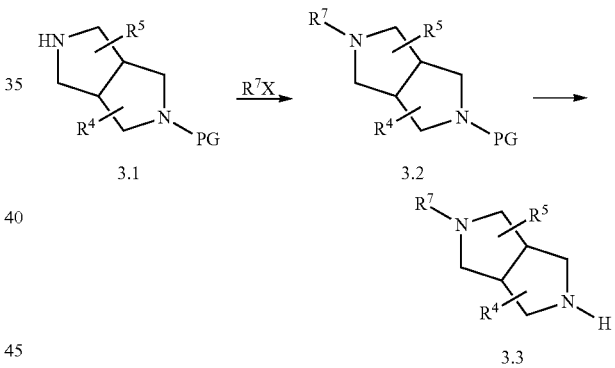

PG = protecting group

Compounds are represented in generic form, with substituents as noted in compound descriptions elsewhere herein. A more specific example is set forth below (Scheme 2B).

SCHEME 2B

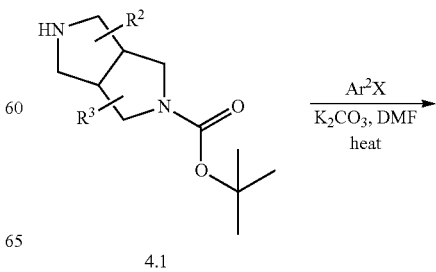

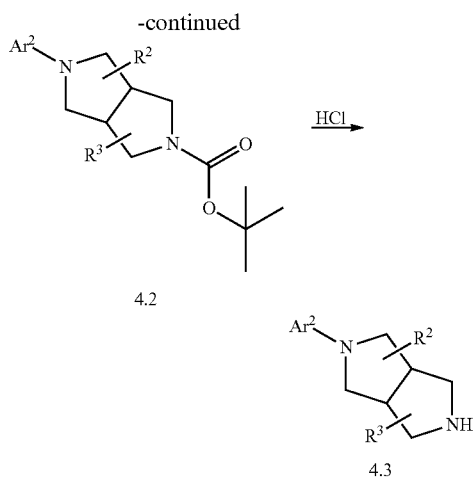

In one aspect, Scheme 2B begins with a suitable substituted tert-butyl hexahydropyrrolo[3,4-c]pyrrole-2(1H)-carboxylate (4.1). Suitable compounds of type 4.1 are commercially available or can be readily prepared by one skilled in the art. The reaction is typically carried out by dissolving 4.1 in a suitable solvent such as DMF. A base is added, e.g., $K_2CO_3$, and arene derivative ($Ar^2X$) are added to the mixture. The reaction is heated at a suitable temperature, about 140° C., using a microwave reactor for a sufficient amount of time to complete the reaction, e.g., about 30 min. Then, the reaction is cooled to ambient temperature (about 15-40° C.) and diluted with a solvent, e.g., dichloromethane and water. The product, a compound of type 4.2, is isolated by methods known to one skilled in the art (e.g., extraction, washing, drying, and concentration under a vacuum followed by purification, e.g., chromatography).

In one aspect, compounds of type 4.3 can be prepared by N-deprotecting compound type 4.2 to afford corresponding amine. For example, a reaction of this type is commonly carried out by dissolving or suspending the compound (4.2) in a suitable solvent, e.g., dichloromethane. Then, solution of an suitable acid, e.g., HCl in dioxane, is added and the mixture stirred at ambient temperature (about 15-40° C.) for a time sufficient, to complete the reaction, e.g., about 1 h. The product (4.3) is isolated by methods known to one skilled in the art (e.g., concentration under a vacuum; followed by purification if required).

D. Pharmaceutical Compositions

In one aspect, the invention relates to pharmaceutical compositions comprising the disclosed compounds. That is, a pharmaceutical composition can be provided comprising an effective amount of at least one disclosed compound, at least one product of a disclosed method, or a pharmaceutically acceptable salt, solvate, hydrate, or polymorph thereof, and a pharmaceutically acceptable carrier.

In one aspect, the invention relates to pharmaceutical compositions comprising a pharmaceutically acceptable carrier and an effective amount of at least one disclosed compound, or a pharmaceutically acceptable salt, solvate, or polymorph thereof.

In a further aspect, the effective amount is a therapeutically effective amount. In a still further aspect, the effective amount is a prophylactically effective amount.

In a further aspect, the pharmaceutical composition comprises a disclosed compound. In a yet further aspect, the pharmaceutical composition comprises a product of a disclosed method of making.

In a further aspect, the pharmaceutical composition exhibits antagonism of mAChR $M_1$ with an $IC_{50}$ of less than about 10,000 nM. In a still further aspect, the pharmaceutical composition exhibits antagonism of mAChR $M_1$ with an $IC_{50}$ of less than about 5,000 nM. In an even further aspect the pharmaceutical composition exhibits antagonism of mAChR $M_1$ with an $IC_{50}$ of less than about 1,000 nM. In a further aspect, the pharmaceutical composition exhibits antagonism of mAChR $M_1$ with an $IC_{50}$ of less than about 500 nM. In a yet further aspect, the pharmaceutical composition exhibits antagonism of mAChR $M_1$ with an $IC_{50}$ of less than about 100 nM. In a further aspect, the pharmaceutical composition exhibits antagonism of mAChR $M_1$ with an $IC_{50}$ of between from about 10,000 nM to about 1 nM. In a yet further aspect, the pharmaceutical composition exhibits antagonism of mAChR $M_1$ with an $IC_{50}$ of between from about 1,000 nM to about 1 nM. In a still further aspect, the pharmaceutical composition exhibits antagonism of mAChR $M_1$ with an $IC_{50}$ of between from about 100 nM to about 1 nM. In an even further aspect, the pharmaceutical composition exhibits antagonism of mAChR $M_1$ with an $IC_{50}$ of between from about 10 nM to about 1 nM.

In one aspect, the pharmaceutical composition is used to treat a mammal. In a yet further aspect, the mammal is a human. In a further aspect, the mammal has been diagnosed with a need for treatment of the disorder prior to administering the pharmaceutical composition. In a further aspect, the mammal has been identified to be in need of treatment of the disorder. In a further aspect, the pharmaceutical composition treats a neurological and/or psychiatric disorder. In a yet further aspect, the disorder treated by the pharmaceutical composition is associated with mAChR $M_1$ dysfunction.

In a further aspect, the pharmaceutical composition is used to treat a disorder selected from affective disorder and anxiety disorder. In a still further aspect, the pharmaceutical composition is used to treat a disorder selected from a substance abuse and dependence disorder, eating disorder, obesity, and impulse control disorder. In a yet further aspect, the pharmaceutical composition is used to treat a disorder selected from a cognitive disorder, attention deficit disorder, and hyperactivity disorder.

In a further aspect, the pharmaceutical composition is used to treat a disorder selected from psychosis, epilepsy, dystonia, fragile-X syndrome, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, Parkinson's disease, movement disorders associated with Parkinson's disease, tardive dyskinesia, drug induced and neurodegeneration based dyskinesias, attention deficit hyperactivity disorder, cognitive disorders, dementias, and memory disorders.

In a further aspect, the pharmaceutical composition is used to treat a disorder selected a movement disorder. In a still further aspect, the movement disorder is selected from Parkinson's disease, dystonia, and fragile X syndrome. In a yet further aspect, the movement disorder is fragile X syndrome.

In a further aspect, the pharmaceutical composition is used to treat a disorder selected is a pain disorder. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmenorrhea, inflammatory pain, headache, migraine headache, cluster headache, headache, primary hyperalgesia, secondary hyperalgesia, primary allodynia, and secondary allodynia.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof, of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound of the invention, and/or pharmaceutically acceptable salts thereof, can also be prepared in powder or liquid concentrate form.

In the treatment of conditions which require antagonism of mAChR $M_1$ receptor activity an appropriate dosage level will generally be about 0.01 to 500 mg per kg patient body weight per day and can be administered in single or multiple doses. Preferably, the dosage level will be about 0.1 to about 250 mg/kg per day; more preferably 0.5 to 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900 and 1000 milligrams of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

It is understood, however, that the specific dose level for any particular patient will depend upon a variety of factors. Such factors include the age, body weight, general health, sex, and diet of the patient. Other factors include the time and route of administration, rate of excretion, drug combination, and the type and severity of the particular disease undergoing therapy.

The present invention is further directed to a method for the manufacture of a medicament for inhibiting mAChR $M_1$ receptor activity (e.g., treatment of one or more neurological and/or psychiatric disorder associated with mAChR $M_1$ receptor dysfunction) in mammals (e.g., humans) comprising combining one or more disclosed compounds, products, or compositions with a pharmaceutically acceptable carrier or diluent. Thus, in one aspect, the invention relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological conditions.

It is understood that the disclosed compositions can be prepared from the disclosed compounds. It is also understood that the disclosed compositions can be employed in the disclosed methods of using.

E. Methods of Using the Compounds and Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In one aspect, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The pharmaceutical compositions and methods of the present invention can further comprise other therapeutically active compounds as noted herein which are usually applied in the treatment of the above mentioned pathological conditions.

1. Treatment Methods

The compounds disclosed herein are useful for treating, preventing, ameliorating, controlling or reducing the risk of a variety of disorders wherein the patient or subject would benefit from antagonism of the $M_1$ receptor. In one aspect, a treatment can include selective $M_1$ receptor antagonism to an extent effective to affect cholinergic activity. Thus, a disorder can be associated with cholinergic activity, for example cholinergic hyperfunction. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which muscarinic receptor inhibition is predicted to be beneficial, in a subject comprising the step of administering to the subject at least one disclosed compound; at least one disclosed pharmaceutical composition; and/or at least one disclosed product in a dosage and amount effective to treat the disorder in the subject.

The invention is directed at the use of described chemical compositions to treat diseases or disorders in patients (preferably human) wherein muscarinic receptor inhibition would be predicted to have a therapeutic effect, such as epileptic disorders, as well as certain movement disorders, including Parkinson's disease, dystonia, and fragile X syndrome, by administering one or more disclosed compounds or products.

In one aspect, provided is a method for treating or preventing anxiety, comprising: administering to a subject at least one disclosed compound; at least one disclosed pharmaceutical composition; and/or at least one disclosed product in a dosage and amount effective to treat the disorder in the subject. At present, the fourth edition of the Diagnostic and Statistical Manual of Mental Disorders (DSM-IV) (1994, American Psychiatric Association, Washington, D.C.), provides a diagnostic tool for disorders including anxiety and related disorders. These include: panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified.

Also provided is a method for the treatment of a disorder in a mammal comprising the step of administering to the mammal at least one disclosed compound, composition, or medicament.

In one aspect, the NMDA receptor is central to a wide range of CNS processes, and plays a role in a variety of disease states in humans or other species. The action of the $M_1$ receptor potentiates NMDA receptor function, which increases activation of the NMDA receptor following glutamate release from the presynaptic terminal. Changes in NMDA-mediated neurotransmission have been implicated in certain neuropsychiatric disorders such as dementia, depression and psychoses, for example schizophrenia, and learning and memory disorders, for example attention deficit disorders and autism.

In one aspect, the disclosed compounds have utility in treating a variety of neurological and psychiatric disorders associated with the muscarinic receptor, including one or more of the following conditions or diseases: epilepsy, Parkinson's Disease, fragile X syndrome, schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosis, psychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de La Tourette's syndrome, epilepsy, muscular spasms and disorders associated with muscular spasticity or weakness including tremors; dyskinesias [including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as idiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

In a specific aspect, the present invention provides a method for treating cognitive disorders, comprising: administering to a patient in need thereof an effective amount of a compound of the present invention. Particular cognitive disorders are dementia, delirium, amnestic disorders and age-related cognitive decline. At present, the text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources. In another specific embodiment, the present invention provides a method for treating anxiety disorders, comprising: administering to a patient in need thereof an effective amount of a compound of the present invention. Particular anxiety disorders are generalized anxiety disorder, obsessive-compulsive disorder and panic attack. At present, the text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, obsessive-compulsive disorder and panic attack. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

In a further specific aspect, the present invention provides a method for treating schizophrenia or psychosis comprising: administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

In a further specific aspect, the present invention provides a method for treating substance-related disorders and addictive behaviors, comprising: administering to a patient in need thereof an effective amount of a compound of the present invention. Particular substance-related disorders and addictive behaviors are persisting dementia, persisting amnestic disorder, psychotic disorder or anxiety disorder induced by substance abuse; and tolerance of, dependence on or withdrawal from substances of abuse. At present, the text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

In a still further aspect, the present invention provides a method for treating pain, comprising: administering to a patient in need thereof an effective amount of a compound of the present invention. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

In a further aspect, the present invention provides a method for treating obesity or eating disorders associated with excessive food intake and complications associated therewith, comprising: administering to a patient in need thereof an effective amount of a compound of the present invention. At present, obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-W-TR. The skilled artisan will recognize that there are alternative nomenclatures, nosologies and classification systems for general medical conditions, and that these systems evolve with medical and scientific progress. Thus, the term "obesity or eating disorders associated with excessive food intake" is intended to include like conditions and disorders that are described in other diagnostic sources.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present invention is further directed to administration of a selective $M_1$ receptor antagonist for improving treatment outcomes in the context of cognitive or behavioral therapy.

That is, in one aspect, the invention relates to a cotherapeutic method comprising the step of administering to a mammal an effective amount and dosage of at least one compound of the invention in connection with cognitive or behavioral therapy.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound.

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present invention.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present invention. When a compound of the present invention is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present invention.

The weight ratio of a disclosed compound to the second active ingredient can be varied and will depend upon the effective dose of each ingredient. Generally, an effective dose of each will be used. Thus, for example, when a compound of the present invention is combined with another agent, the weight ratio of a disclosed compound to the other agent will generally range from about 1000:1 to about 1;1000, preferably about 200:1 to about 1:200. Combinations of a compound of the present invention and other active ingredients will generally also be within the aforementioned range, but in each case, an effective dose of each active ingredient should be used.

In such combinations a disclosed compound and other active agents can be administered separately or in conjunction. In addition, the administration of one element can be prior to, concurrent to, or subsequent to the administration of other agent(s).

Accordingly, the subject compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In one aspect, the compound can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound can be administered in conjunction with the use of physical methods such as with light therapy or electrical stimulation.

In a further aspect, the compound can be employed in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In a further aspect, the compound can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexyl, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In one aspect, the compound can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In the treatment of conditions which require antagonism of the muscarinic receptor an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level can be about 0.01 to 250 mg/kg per day, about 0.05 to 100 mg/kg per day, or about 0.1 to 50 mg/kg per day. Within this range the dosage can be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10, 15, 20, 25, 50, 75, 100, 150, 200, 250, 300, 400, 500, 600, 750, 800, 900, and 1000 milligrams of the active ingredient for the symptomatic adjustment of the dosage to the patient to be treated. The compounds can be administered on a regimen of 1 to 4 times per day, preferably once or twice per day. This dosage regimen can be adjusted to provide the optimal therapeutic response. It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Thus, in one aspect, the invention relates to methods for inhibiting a muscarinic receptor in at least one cell, comprising the step of contacting the at least one cell with at least one compound of the invention, in an amount effective to reduce mAChR $M_1$ activity response in the at least one cell. In a further aspect, the cell is mammalian, for example human. In a further aspect, the cell has been isolated from a subject prior to the contacting step. In a further aspect, contacting is via administration to a subject.

a. Treating a Disorder Associated with Muscarinic Acetylcholine Receptor Activity In one aspect, the invention relates to a method for the treatment of a neurological and/or psychiatric disorder associated with muscarinic acetylcholine receptor dysfunction in a mammal comprising the step of administering to the mammal an effective amount of at least one disclosed compound; or a pharmaceutically acceptable salt, solvate, or polymorph thereof.

In a further aspect, the compound administered is a disclosed compound or a product of a disclosed method of making a compound. In a still further aspect, an effective amount is a therapeutically effective amount. In a yet further aspect, an effective amount is a prophylactically effective amount.

In a further aspect, the compound exhibits inhibition of mAChR $M_1$ activity with an $IC_{50}$ of less than about 10,000 nM. In a still further aspect, the compound exhibits inhibition of mAChR $M_1$ activity with an $IC_{50}$ of less than about 5,000 nM. In an even further aspect, the compound exhibits inhibition of mAChR $M_1$ activity with an $IC_{50}$ of less than about 1,000 nM. In a further aspect, the compound exhibits inhibition of mAChR $M_1$ activity with an $IC_{50}$ of less than about 500 nM. In a yet further aspect, the compound inhibition of mAChR $M_1$ activity with an $IC_{50}$ of less than about 100 nM.

In a further aspect, the compound exhibits inhibition of mAChR $M_1$ activity with an $IC_{50}$ of between from about 10,000 nM to about 1 nM. In a yet further aspect, the compound exhibits inhibition of mAChR $M_1$ activity with an $IC_{50}$ of between from about 1,000 nM to about 1 nM. In a still further aspect, the compound exhibits inhibition of mAChR $M_1$ activity with an $IC_{50}$ of between from about 100 nM to about 1 nM. In an even further aspect, the compound exhibits inhibition of mAChR $M_1$ activity with an $IC_{50}$ of between from about 10 nM to about 1 nM.

In a further aspect, inhibition of mAChR $M_1$ activity is antagonism of mAChR $M_1$ activity. In a still further aspect, inhibition of mAChR M$_1$ activity is partial antagonism of mAChR M$_1$ activity. In a yet further aspect, inhibition of mAChR M$_1$ activity is negative allosteric modulation of mAChR M$_1$ activity.

In one aspect, the mammal is a human. In a further aspect, the mammal has been diagnosed with a need for treatment of the disorder prior to the administering step. In a still further aspect, the mammal has been diagnosed with a need for treatment of a disorder associated with a mAChR M$_1$ dysfunction prior to the administering step. In a yet further aspect, the method further comprises the step of identifying a mammal in need of treatment of the disorder. In an even further aspect, the method further comprises the step of identifying a mammal in need of treatment of a disorder associated with a mAChR M$_1$ dysfunction.

In a further aspect, the muscarinic acetylcholine receptor is mAChR M$_1$. In a still further aspect, the compound selectively inhibits mAChR M$_1$ compared to mAChR M$_2$, mAChR M$_3$, mAChR M$_4$, and/or mAChR M$_5$.

In a further aspect, the disorder is a neurological and/or psychiatric disorder associated with a mAChR M$_1$ dysfunction. In an even further aspect, the disorder is selected from affective disorder and anxiety disorder. In a still further aspect, the disorder is selected from a substance abuse and dependence disorder, eating disorder, obesity, and impulse control disorder. In a yet further aspect, the disorder is selected from a cognitive disorder, attention deficit disorder, and hyperactivity disorder.

In a further aspect, the disorder is selected from psychosis, epilepsy, dystonia, fragile-X syndrome, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, Parkinson's disease, movement disorders associated with Parkinson's disease, tardive dyskinesia, drug induced and neurodegeneration based dyskinesias, attention deficit hyperactivity disorder, cognitive disorders, dementias, and memory disorders.

In a further aspect, the disorder is a movement disorder. In a still further aspect, the movement disorder is selected from Parkinson's disease, dystonia, and fragile X syndrome. In a yet further aspect, the movement disorder is fragile X syndrome.

In a further aspect, the disorder is a pain disorder. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesia, primary allodynia, and secondary allodynia.

b. Inhibition of Muscarinic Acetylcholine Receptor Activity

In one aspect, the invention relates to a method for inhibition of muscarinic acetylcholine receptor activity in a mammal comprising the step of administering to the mammal an effective amount of at least one disclosed compound; or a pharmaceutically acceptable salt, solvate, or polymorph thereof.

In a further aspect, the compound administered is a disclosed compound or a product of a disclosed method of making a compound. In a still further aspect, an effective amount is a therapeutically effective amount. In a yet further aspect, an effective amount is a prophylactically effective amount.

In a further aspect, the compound exhibits inhibition of mAChR M$_1$ activity with an IC$_{50}$ of less than about 10,000 nM. In a still further aspect, the compound exhibits inhibition of mAChR M$_1$ activity with an IC$_{50}$ of less than about 5,000 nM. In an even further aspect, the compound exhibits inhibition of mAChR M$_1$ activity with an IC$_{50}$ of less than about 1,000 nM. In a further aspect, the compound exhibits inhibition of mAChR M$_1$ activity with an IC$_{50}$ of less than about 500 nM. In a yet further aspect, the compound exhibits inhibition of mAChR M$_1$ activity with an IC$_{50}$ of less than about 100 nM.

In a further aspect, the compound exhibits inhibition of mAChR M$_1$ activity with an IC$_{50}$ of between from about 10,000 nM to about 1 nM. In a yet further aspect, the compound exhibits inhibition of mAChR M$_1$ activity with an IC$_{50}$ of between from about 1,000 nM to about 1 nM. In a still further aspect, the compound exhibits inhibition of mAChR M$_1$ activity with an IC$_{50}$ of between from about 100 nM to about 1 nM. In an even further aspect, the compound exhibits inhibition of mAChR M$_1$ activity with an IC$_{50}$ of between from about 10 nM to about 1 nM.

In a further aspect, inhibition of mAChR M$_1$ activity is antagonism of mAChR M$_1$ activity. In a still further aspect, inhibition of mAChR M$_1$ activity is partial antagonism of mAChR M$_1$ activity. In a yet further aspect, inhibition of mAChR M$_1$ activity is negative allosteric modulation of mAChR M$_1$ activity. In an even further aspect, the compound selectively inhibits mAChR M$_1$ compared to mAChR M$_2$, mAChR M$_3$, mAChR M$_4$, and/or mAChR M$_5$.

In one aspect, the mammal is a human. In a further aspect, the mammal has been diagnosed with a need for inhibition of muscarinic acetylcholine receptor activity prior to the administering step. In a still further aspect, the method further comprises the step of identifying a mammal in need of inhibiting muscarinic acetylcholine receptor activity. In a yet further aspect, the muscarinic acetylcholine receptor is mAChR M$_1$. In an even further aspect, inhibition of mAChR M$_1$ activity treats a disorder associated with mAChR M$_1$ activity in the mammal.

In a further aspect, inhibition of muscarinic acetylcholine receptor activity in a mammal treats a neurological and/or psychiatric disorder. In a further aspect, the disorder is a neurological and/or psychiatric disorder associated with a mAChR M$_1$ dysfunction. In an even further aspect, the disorder is selected from affective disorder and anxiety disorder. In a still further aspect, the disorder is selected from a substance abuse and dependence disorder, eating disorder, obesity, and impulse control disorder. In a yet further aspect, the disorder is selected from a cognitive disorder, attention deficit disorder, and hyperactivity disorder.

In a further aspect, the disorder is selected from psychosis, epilepsy, dystonia, fragile-X syndrome, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, Parkinson's disease, movement disorders associated with Parkinson's disease, tardive dyskinesia, drug induced and neurodegeneration based dyskinesias, attention deficit hyperactivity disorder, cognitive disorders, dementias, and memory disorders.

In a further aspect, the disorder is a movement disorder. In a still further aspect, the movement disorder is selected from Parkinson's disease, dystonia, and fragile X syndrome. In a yet further aspect, the movement disorder is fragile X syndrome.

In a further aspect, the disorder is a pain disorder. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesia, primary allodynia, and secondary allodynia.

c. Inhibiting Muscarinic Acetylcholine Receptor Activity in Cells

In one aspect, the invention relates to a method for inhibition of muscarinic acetylcholine receptor activity in at least one cell, comprising the step of contacting the cell with an effective amount of least one disclosed compound or pharmaceutically acceptable salt, solvate, or polymorph thereof.

In a further aspect, the compound contacting the cell is a disclosed compound or a product of a disclosed method of making a compound. In a still further aspect, an effective amount is a therapeutically effective amount. In a yet further aspect, an effective amount is a prophylactically effective amount.

In a further aspect, the muscarinic acetylcholine receptor is mAChR $M_1$.

In a further aspect, the compound exhibits inhibition of mAChR $M_1$ activity with an $IC_{50}$ of less than about 10,000 nM. In a still further aspect, the compound exhibits inhibition of mAChR $M_1$ activity with an $IC_{50}$ of less than about 5,000 nM. In an even further aspect, the compound exhibits inhibition of mAChR $M_1$ activity with an $IC_{50}$ of less than about 1,000 nM. In a further aspect, the compound exhibits inhibition of mAChR $M_1$ activity with an $IC_{50}$ of less than about 500 nM. In a yet further aspect, the compound inhibition of mAChR $M_1$ activity with an $IC_{50}$ of less than about 100 nM.

In a further aspect, the compound exhibits inhibition of mAChR $M_1$ activity with an $IC_{50}$ of between from about 10,000 nM to about 1 nM. In a yet further aspect, the compound exhibits inhibition of activity mAChR $M_1$ with an $IC_{50}$ of between from about 1,000 nM to about 1 nM. In a still further aspect, the compound exhibits inhibition of mAChR $M_1$ activity with an $IC_{50}$ of between from about 100 nM to about 1 nM. In an even further aspect, the compound exhibits inhibition of mAChR $M_1$ activity with an $IC_{50}$ of between from about 10 nM to about 1 nM.

In a further aspect, inhibition of mAChR $M_1$ activity is antagonism of mAChR $M_1$ activity. In a still further aspect, inhibition of mAChR $M_1$ activity is partial antagonism of mAChR $M_1$ activity. In a yet further aspect, inhibition of mAChR $M_1$ activity is negative allosteric modulation of mAChR $M_1$ activity. In an even further aspect, the compound selectively inhibits mAChR $M_1$ compared to mAChR $M_2$, mAChR $M_3$, mAChR $M_4$, and/or mAChR $M_5$.

In one aspect, the cell is mammalian. In a still further aspect, the cell is human. In a yet further aspect, the cell has been isolated from a mammal prior to the contacting step. In an even further aspect, contacting is via administration to a mammal.

In a further aspect, the mammal has been diagnosed with a need for inhibition of muscarinic acetylcholine receptor activity prior to the administering step. In a still further aspect, the method further comprises the step of identifying a mammal in need of inhibiting muscarinic acetylcholine receptor activity.

In a further aspect, the inhibition of muscarinic acetylcholine receptor activity treats a muscarinic acetylcholine receptor dysfunction. In a yet further aspect, the inhibition of muscarinic acetylcholine receptor activity treats a disorder associated with muscarinic acetylcholine receptor dysfunction in the mammal. In a still further aspect, the mammal has been diagnosed with a need for inhibition of muscarinic acetylcholine receptor activity prior to the administering step. In an even further aspect, treatment further comprises the step of identifying a mammal in need of inhibition of muscarinic acetylcholine receptor activity.

In a further aspect, inhibition of muscarinic acetylcholine receptor activity in a mammal treats a neurological and/or psychiatric disorder. In a further aspect, the disorder is a neurological and/or psychiatric disorder associated with a mAChR $M_1$ dysfunction. In an even further aspect, the disorder is selected from affective disorder and anxiety disorder. In a still further aspect, the disorder is selected from a substance abuse and dependence disorder, eating disorder, obesity, and impulse control disorder. In a yet further aspect, the disorder is selected from a cognitive disorder, attention deficit disorder, and hyperactivity disorder.

In a further aspect, the disorder is selected from psychosis, epilepsy, dystonia, fragile-X syndrome, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, Parkinson's disease, movement disorders associated with Parkinson's disease, tardive dyskinesia, drug induced and neurodegeneration based dyskinesias, attention deficit hyperactivity disorder, cognitive disorders, dementias, and memory disorders.

In a further aspect, the disorder is a movement disorder. In a still further aspect, the movement disorder is selected from Parkinson's disease, dystonia, and fragile X syndrome. In a yet further aspect, the movement disorder is fragile X syndrome.

In a further aspect, the disorder is a pain disorder. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesia, primary allodynia, and secondary allodynia.

2. Cotherapeutic Methods

The present invention is further directed to administration of a mAChR $M_1$ inhibitor for improving treatment outcomes in the context of cognitive or behavioral therapy. That is, in one aspect, the invention relates to a cotherapeutic method comprising the step of administering to a mammal an effective amount of at least one disclosed compound; or a pharmaceutically acceptable salt, solvate, or polymorph thereof.

In a further aspect, the compound administered for the cotherapeutic method is a disclosed compound or a product of a disclosed method of making a compound. In a still further aspect, an effective amount is a therapeutically effective amount. In a yet further aspect, an effective amount is a prophylactically effective amount.

In a further aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, or 7 days before or after administration of the compound. As a further example, cognitive or behavioral therapy can be provided within 1, 2, 3, or 4 weeks before or after administration of the compound. As a still further example, cognitive or behavioral therapy can be provided before or after administration within a period of time of 1, 2, 3, 4, 5, 6, 7, 8, 9, or 10 half-lives of the administered compound. It is understood that the disclosed cotherapeutic methods can be used in connection with the disclosed compounds, compositions, kits, and uses.

3. Manufacture of a Medicament

In one aspect, the invention relates to a medicament comprising one or more disclosed compounds; or a pharmaceutically acceptable salt, solvate, or polymorph thereof.

In various aspect, the invention relates methods for the manufacture of a medicament for inhibiting the activity mAChR $M_1$ (e.g., treatment of one or more neurological and/or psychiatric disorder associated with mAChR $M_1$ dysfunction) in mammals (e.g., humans) comprising combining one or more disclosed compounds, products, or compositions or a pharmaceutically acceptable salt, solvate, hydrate, or polymorph thereof, with a pharmaceutically acceptable carrier. It is understood that the disclosed methods can be performed with the disclosed compounds, products, and pharmaceutical compositions. It is also understood that the disclosed methods can be employed in connection with the disclosed methods of using.

4. Use of Compounds

Also provided are the uses of the disclosed compounds and products. In one aspect, the invention relates to use of at least one disclosed compound; or a pharmaceutically acceptable salt, solvate, or polymorph thereof.

In a further aspect, the compound used exhibits inhibition of mAChR $M_1$ activity with an $IC_{50}$ of less than about 10,000 nM. In a still further aspect, the compound used exhibits inhibition of mAChR $M_1$ activity with an $IC_{50}$ of less than about 5,000 nM. In an even further aspect, the compound used exhibits inhibition of mAChR $M_1$ with an $IC_{50}$ of less than about 1,000 nM. In a further aspect, the compound used exhibits inhibition of mAChR $M_1$ activity with an $IC_{50}$ of less than about 500 nM. In a yet further aspect, the compound used inhibition of mAChR $M_1$ activity with an $IC_{50}$ of less than about 100 nM.

In a further aspect, the compound used exhibits inhibition of mAChR $M_1$ activity with an $IC_{50}$ of between from about 10,000 nM to about 1 nM. In a yet further aspect, the compound used exhibits inhibition of mAChR $M_1$ activity with an $IC_{50}$ of between from about 1,000 nM to about 1 nM. In a still further aspect, the compound used exhibits inhibition of mAChR $M_1$ activity with an $IC_{50}$ of between from about 100 nM to about 1 nM. In an even further aspect, the compound used exhibits inhibition of mAChR $M_1$ activity with an $IC_{50}$ of between from about 10 nM to about 1 nM. In a yet further aspect, inhibition of mAChR $M_1$ activity is antagonism of mAChR $M_1$ activity.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

In various aspects, the use relates to a treatment of a disorder in a mammal. Also disclosed is the use of a compound for mAChR $M_1$ receptor inhibition. In one aspect, the use is characterized in that the mammal is a human. In one aspect, the use is characterized in that the disorder is a neurological and/or psychiatric disorder associated with a muscarinic acetylcholine receptor dysfunction. In one aspect, the neurological and/or psychiatric disorder associated with muscarinic acetylcholine receptor dysfunction is treated by inhibition of muscarinic acetylcholine receptor activity in a mammal.

In a further aspect, the use relates to the manufacture of a medicament for the treatment of a disorder associated with a muscarinic acetylcholine receptor dysfunction in a mammal. In a further aspect, the medicament is used in the treatment of a neurological and/or psychiatric disorder associated with a muscarinic acetylcholine receptor dysfunction in a mammal.

In a further aspect, the use relates to inhibition of muscarinic acetylcholine receptor activity in a mammal. In an even further aspect, the mammal is a human. In a still further aspect, the use relates to inhibiting mAChR $M_1$ activity in a cell. In a yet further aspect, the cell is a mammalian cell. In an even further aspect, the mammalian cell is a human cell.

In a further aspect, the use is treatment of a neurological and/or psychiatric disorder. In a yet further aspect, the disorder is a neurological and/or psychiatric disorder associated with muscarinic acetylcholine receptor dysfunction in the mammal. In an even further aspect, the disorder is a neurological and/or psychiatric disorder associated with a mAChR $M_1$ receptor dysfunction in a mammal. In a still further aspect, the mammal has been diagnosed with a need for inhibition of muscarinic acetylcholine receptor activity prior to the use. In an even further aspect, the use further comprises the step of identifying a mammal in need of inhibition of muscarinic acetylcholine receptor activity. In a further aspect, the neurological and/or psychiatric disorder is selected from affective disorder and anxiety disorder. In a still further aspect, the neurological and/or psychiatric disorder is selected from a substance abuse and dependence disorder, eating disorder, obesity, and impulse control disorder. In a yet further aspect, the neurological and/or psychiatric disorder is selected from a cognitive disorder, attention deficit disorder, and hyperactivity disorder.

In a further aspect, the neurological and/or psychiatric disorder is selected from psychosis, epilepsy, dystonia, fragile-X syndrome, schizophrenia, conduct disorder, disruptive behavior disorder, bipolar disorder, psychotic episodes of anxiety, anxiety associated with psychosis, psychotic mood disorders such as severe major depressive disorder; mood disorders associated with psychotic disorders, acute mania, depression associated with bipolar disorder, mood disorders associated with schizophrenia, behavioral manifestations of mental retardation, conduct disorder, autistic disorder; movement disorders, Tourette's syndrome, akinetic-rigid syndrome, Parkinson's disease, movement disorders associated with Parkinson's disease, tardive dyskinesia, drug induced and neurodegeneration based dyskinesias, attention deficit hyperactivity disorder, cognitive disorders, dementias, and memory disorders.

In a further aspect, the neurological and/or psychiatric disorder is a movement disorder. In a still further aspect, the movement disorder is selected from Parkinson's disease, dystonia, and fragile X syndrome. In a yet further aspect, the movement disorder is fragile X syndrome.

In a further aspect, the neurological and/or psychiatric disorder is a pain disorder. In a still further aspect, the pain disorder is selected from neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesia, primary allodynia, and secondary allodynia.

It is understood that the disclosed uses can be employed in connection with the disclosed compounds, methods, compositions, and kits. In a further aspect, the invention relates to the use of a disclosed compound or a disclosed product in the manufacture of a medicament for the treatment of a disorder associated with mAChR $M_1$ receptor dysfunction in a mammal. In a further aspect, the disorder is a neurological and/or psychiatric disorder.

5. Kits

In one aspect, the invention relates to kits comprising at least one disclosed compound; or a pharmaceutically acceptable salt, solvate, or polymorph thereof, and one or more of:
(a) at least one agent known to increase mAChR $M_1$ activity;
(b) at least one agent known to decrease mAChR $M_1$ activity;
(c) at least one agent known to treat a disorder associated with cholinergic activity;
(d) instructions for treating a disorder associated with cholinergic activity;
(e) instructions for treating a disorder associated with mAChR $M_1$ receptor activity; or
(f) instructions for administering the compound in connection with cognitive or behavioral therapy.

In various further aspects, the invention relates to kits comprising at least one disclosed compound or at least one product of a disclosed method and at least one agent known to have $M_1$ receptor agonist activity.

In a further aspect, the kit comprises a disclosed compound or a product of a disclosed method.

In a further aspect, the at least one compound and the at least one agent are co-formulated. In a still further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

6. Subjects

The subject of the herein disclosed methods can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. A patient refers to a subject afflicted with a disease or disorder. The term "patient" includes human and veterinary subjects.

In some aspects of the disclosed methods, the subject has been diagnosed with a need for treatment prior to the administering step. In some aspects of the disclosed method, the subject has been diagnosed with a disorder treatable by reducing activity of the muscarinic receptor and/or a need for a reduction in muscarinic receptor activity prior to the administering step. In some aspects of the disclosed method, the subject has been diagnosed with a movement related disorder, Parkinson's Disease, anxiety or a related disorder prior to the administering step. In some aspects of the disclosed methods, the subject has been identified with a need for treatment prior to the administering step. In some aspects of the disclosed method, the subject has been identified with a disorder treatable by reducing activity of the muscarinic receptor and/or or a need for antagonism of muscarinic activity prior to the administering step. In one aspect, a subject can be treated prophylactically with a compound or composition disclosed herein, as discussed herein elsewhere.

F. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General Methods $^1$H NMR spectra were recorded either on a Bruker DPX-400 or on a Bruker AV-500 spectrometer with standard pulse sequences, operating at 400 MHz and 500 MHz respectively. Chemical shifts (δ) are reported in parts per million (ppm) downfield from tetramethylsilane (TMS), which was used as internal standard. Coupling constants (J-values) are expressed in Hz units.

Microwave assisted reactions were performed in a single-mode reactor: Meris$^{tem}$ Optimizer microwave reactor (Personal Chemistry A.B., currently Biotage).

Flash column chromatography was performed using ready-to-connect cartridges from: (a) ISCO, on irregular silica gel, particle size 15-40 µm (normal layer disposable flash columns) on a Companion system from ISCO, Inc.; or, (b) Merck, on irregular silica gel, particle size 15-40 µm (normal layer disposable flash columns) on an SPOT or LAFLASH system from Armen Instrument.

Analytical HPLC was performed on an HP1100 with UV detection at 214 and 254 nm along with ELSD detection and low resolution mass spectra using an Agilent 1200 series 6130 mass spectrometer.

2. LC-MS Methods

The UPLC (Ultra Performance Liquid Chromatography) measurement was performed using an Acquity UPLC (Waters) system comprising a sampler organizer, a binary pump with degasser, a four column's oven, a diode-array detector (DAD) and a column as specified below. Column flow was used without split to the MS detector. The MS detector was configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software. [M+H], means the protonated mass of the free base of the compound and where indicated R$_T$ means retention time (in minutes).

In the LC-MS analysis, reversed phase HPLC was carried out on an Agilent 1200 with a Kinetex C18 column (2.6 µm, 2.1×30 mm) from Phenomenex, with a flow rate of 1.5 mL/min, at 45° C. The gradient conditions used are: 93% A (0.1% TFA in water), 7% B (acetonitrile), to 5% A, 95% B in 1.1 minutes. Injection volume was 3.0 µl. Low-resolution ES positive mass spectra (single quadrupole, Agilent 6130) were acquired by scanning from 100 to 700 in 0.25 seconds. The capillary needle voltage was 3 kV.

3. Intermediate 1

Preparation of
2-(pyridin-4-yl)octahydropyrrolo[3,4-c]pyrrole bishydrochloride

The overall synthesis for the preparation of Intermediate 1 is shown below.

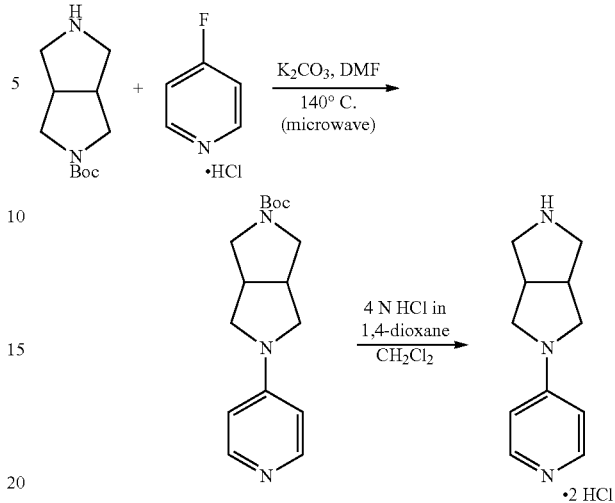

In a microwave vial fitted with a stir bar and a septa, tert-butyl hexahydropyrrolo[3,4-c]pyrrole-2(1H)-carboxylate (2.0 g, 9.42 mmol) was dissolved in DMF (10 mL). Potassium carbonate (1.9 g, 14.13 mmol) and 4-fluoropyridine hydrochloride (1.2 g, 9.42 mmol) were added. The vial was sealed and heated to 140° C. under microwave irradiation for 30 min. The vial was cooled to ambient temperature and diluted with dichloromethane (20 mL) and distilled water (50 mL). The aqueous layer was extracted with dichloromethane (3×15 mL), the organic fractions were combined and dried over Na$_2$SO$_4$, filtered and concentrated. The residue was purified on silica gel using CH$_2$Cl$_2$/MeOH/NH$_4$OH (35:7:1) as a mobile phase. In a round bottom flask fitted with a stir bar and a cap, tert-butyl 5-(pyridin-4-yl)hexahydropyrrolo[3,4-c] pyrrole-2(1H)-carboxylate (2.6 g, 8.98 mmol) was dissolved in dichloromethane (100 mL) at ambient temperature. A solution of HCl in 1,4-dioxane (10 mL, 4N) was added and the solution was stirred for 1 h at ambient temperature. The suspension was concentrated and the resulting solids were exposed to high vacuum for 24 h. The solids were used without further purification. LCMS: R$_T$=0.110 min. m/z: 189, measured (M+H): 190.

4. Example 1

Preparation of (1-(Pyridin-3-ylsulfonyl)azetidin-3-yl)(4-(pyridin-4-yl)piperazin-1-yl)methanone (5)

The overall synthesis for the preparation of Example 1 is shown below.

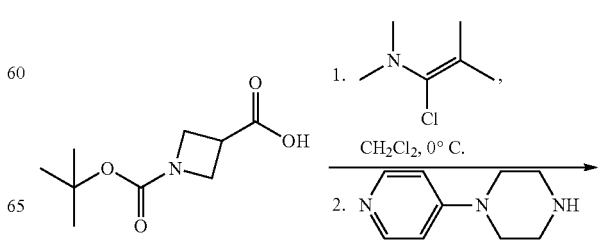

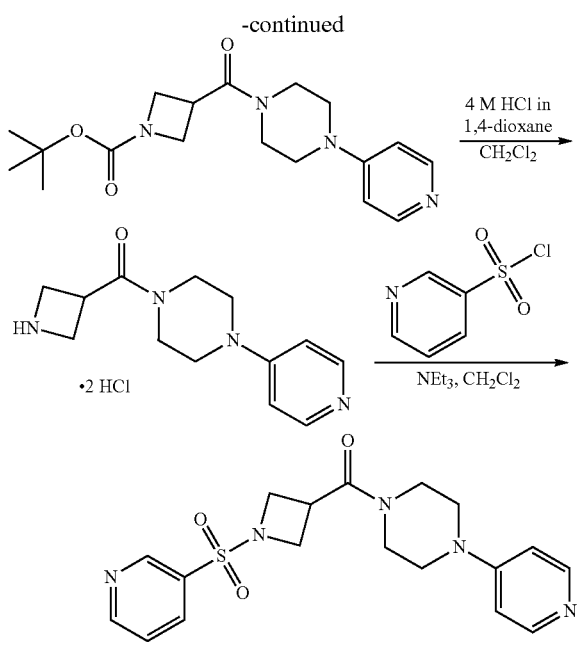

In a round bottom flask purged with argon, fitted with a stir bar and a septa, 1-(tert-butoxycarbonyl)azetidine-3-carboxylic acid (1.0 g, 5.0 mmol) was dissolved in dichloromethane (50 mL). The flask was cooled to 0° C. using in an ice bath and Ghosez's reagent (0.98 mL, 7.5 mmol) was added dropwise as a solution in dichloromethane (5 mL). The solution was stirred at 0° C. for 30 min. 1-(Pyridin-4-yl)piperazine (810 mg, 5.0 mmol) was added as a solid and the solution was stirred at ambient temperature for 2 h. The reaction mixture was diluted with dichloromethane (20 mL) and a saturated NaHCO₃ solution was added (15 mL). The biphasic mixture was vigorously shaken, passed through a phase separator, and the organic phase was concentrated in vacuo. The residue was then dissolved in dichloromethane (60 mL) at ambient temperature and 4N HCl in dioxane (12.5 mL, 49.7 mmol) was added. The solution was stirred at ambient temperature for 3 h. Methanol (10 mL) was added and the solution was concentrated in vacuo. The resulting solids were used directly in the next reaction. In a 2 dram vial fitted with a stir bar and a cap, azetidin-3-yl(4-(pyridin-4-yl)piperazin-1-yl)methanone, bis-HCl salt (135 mg, 0.42 mmol) was suspended in dichloromethane (2 mL) at ambient temperature. Triethylamine (0.24 mL, 1.7 mmol) was added and the suspension stirred for 30 min. Pyridine-3-sulfonyl chloride (98 mg, 0.47 mmol) was added as a solid and the mixture was stirred at ambient temperature for 2 h. The solution was diluted with dichloromethane (5 mL) and a saturated NaHCO₃ solution was added (2 mL). The mixture was vigorously shaken, passed through a phase separator and the organic phase was concentrated in vacuo. The residue was purified on a preparative Phenomenex Luna C18 column using 0.1% TFA in $H_2O$/acetonitrile as a mobile phase. The desired fractions were combined and concentrated to afford the target compound. LCMS: $R_f$=0.394 min, >99%@254 nm, >99%@220 nm; m/z $(M+1)^+$=388. ¹H NMR [400 MHz, CDCl₃, δ (ppm)]: 9.0 (d, J=2 Hz, 1H), 8.8 (dd, J=4.9, 1.4 Hz, 1H), 8.3 (ddd, J=8.0, 2.0, 2.0 Hz, 1H) 8.2 (d, J=7.6 Hz, 2H), 7.7 (dd, J=8.0, 4.9 Hz, 1H), 7.1 (d, J=7.6 Hz, 2H), 4.1-3.9 (m, 4H), 3.8-3.7 (m, 4H), 3.7-3.6 (m 2H), 3.6-3.5 (m, 2H), 3.3 (dd, J=5.2, 5.0 Hz, 1H), HRMS calculated for $C_{18}H_{22}N_5O_3S$ $(M+H)^+$ m/z: 388.1443, measured: 388.1443.

5. Characterization of Exemplary Compounds

The compounds in Table I were synthesized with methods identical or analogous to those described herein. The requisite starting materials were commercially available, described in the literature, or readily synthesized by one skilled in the art of organic synthesis. The mass spectrometry data were obtained using either General LC-MS Method for General LC-MS Method 1 as described above.

TABLE I

| No. | Compound | M + H |
|---|---|---|
| B1 | | 438 |
| B2 | | 472 |

TABLE I-continued

| No. | Compound | M + H |
|-----|----------|-------|
| B3 | | 464 |
| B4 | | 464 |
| B5 | | 429 |
| B6 | | 452 |
| B7 | | 436 |

TABLE I-continued

| No. | Compound | M + H |
|-----|----------|-------|
| B8  |          | 429   |
| B9  |          | 431   |
| B10 |          | 388   |
| B11 |          | 507   |
| B12 |          | 422   |
| B13 |          | 452   |

TABLE I-continued

| No. | Compound | M + H |
|---|---|---|
| B14 | | 466 |
| B15 | | 438 |
| B16 | | 455 |
| B17 | | 472 |
| B18 | | 391 |
| B19 | | 472 |

US 8,697,888 B2
TABLE I-continued
| No. | Compound | M + H |
|-----|----------|-------|
| B20 | 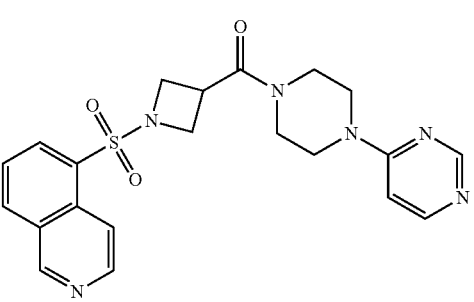 [SMILES: O=C(C1CN(S(=O)(=O)c2cccc3cnccc23)C1)N1CCN(c2ccncn2)CC1] | 439 |
| B21 | 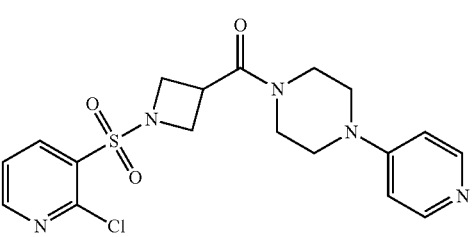 [SMILES: O=C(C1CN(S(=O)(=O)c2cccnc2Cl)C1)N1CCN(c2ccncc2)CC1] | 422 |
| B22 | 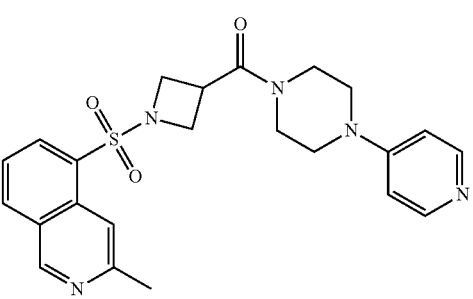 [SMILES: Cc1cc2c(S(=O)(=O)N3CC(C(=O)N4CCN(c5ccncc5)CC4)C3)cccc2cn1] | 452 |
| B23 | 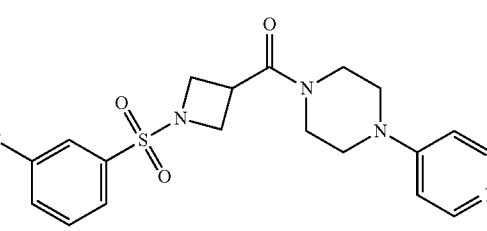 | 405 |
| B24 | 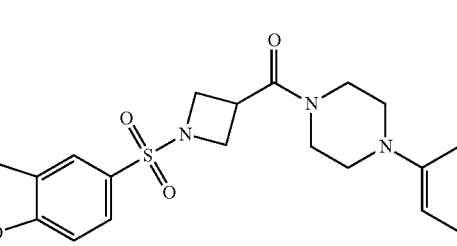 | 427 |
| B25 | 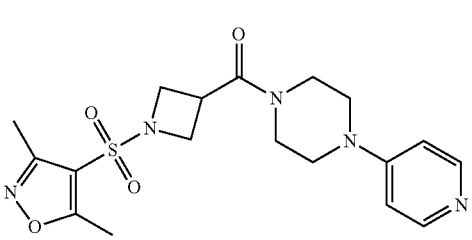 [SMILES: Cc1noc(C)c1S(=O)(=O)N1CC(C(=O)N2CCN(c3ccncc3)CC2)C1] | 406 |

TABLE I-continued

| No. | Compound | M + H |
|---|---|---|
| B26 | | 438 |
| B27 | | 476 |
| B28 | | 445 |
| B29 | | 471 |
| B30 | | 506 |

TABLE I-continued

| No. | Compound | M + H |
|---|---|---|
| B31 | | 429 |
| B32 | | 443 |
| B33 | | 435 |
| B34 | | 439 |
| B35 | | 439 |
| B36 | | 421 |

TABLE I-continued

| No. | Compound | M + H |
|---|---|---|
| B37 | 1H-indazol-6-yl-SO2-azetidine-3-C(O)-piperazine-4-pyridine | 427 |
| B38 | 6-methoxypyridin-3-yl-SO2-azetidine-3-C(O)-piperazine-4-pyridine | 418 |
| B39 | quinolin-3-yl-SO2-azetidine-3-C(O)-piperazine-4-pyridine | 438 |
| B40 | 4-methylpyridin-2-yl-SO2-azetidine-3-C(O)-piperazine-4-pyridine | 402 |
| B41 | 6-(trifluoromethyl)pyridin-3-yl-SO2-azetidine-3-C(O)-piperazine-4-pyridine | 456 |
| B42 | 5-chloropyridin-2-yl-SO2-azetidine-3-C(O)-piperazine-4-pyridine | 422 |

TABLE I-continued

| No. | Compound | M + H |
|---|---|---|
| B43 | | 381 |
| B44 | | 353 |
| B45 | | 445 |
| B46 | | 367 |
| B47 | | 393 |
| B48 | | 423 |

TABLE I-continued

| No. | Compound | M + H |
|---|---|---|
| B49 | | 456 |
| B50 | | 440 |
| B51 | | 409 |
| B52 | | 464 |
| B53 | | 471 |
| B54 | | 448 |

TABLE I-continued

| No. | Compound | M + H |
|---|---|---|
| B55 | | 407 |
| B56 | | 455 |
| B57 | | 457 |
| B58 | | 481 |
| B59 | | 431 |
| B60 | | 478 |

TABLE I-continued

| No. | Compound | M + H |
|---|---|---|
| B61 | | 444 |
| B62 | | 432 |
| B63 | | 453 |
| B64 | | 467 |
| B65 | | 467 |
| B66 | | 391 |

TABLE I-continued

| No. | Compound | M + H |
|---|---|---|
| B67 | | 388 |
| B68 | | 453 |
| B69 | | 471 |
| B70 | | 460 |
| B71 | | 469 |
| B72 | | 455 |

TABLE I-continued

| No. | Compound | M + H |
|---|---|---|
| B73 | | 459 |
| B74 | | 473 |
| B75 | | 444 |
| B76 | | 427 |
| B77 | | 437 |
| B78 | | 388 |

TABLE I-continued

| No. | Compound | M + H |
|---|---|---|
| B79 | | 456 |
| B80 | | 375 |
| B81 | | 395 |
| B82 | | 437 |
| B83 | | 417 |
| B84 | | 379 |

TABLE I-continued

| No. | Compound | M + H |
|---|---|---|
| B85 | | 393 |
| B86 | | 419 |

6. Cell Lines Expressing Muscarinic Acetylcholine Receptors

Chinese hamster ovary (CHO-K1) cells stably expressing rat (r)$M_1$ were purchased from the American Type Culture Collection and cultured according to their indicated protocol. CHO cells stably expressing human (h)$M_2$, h$M_3$, and h$M_5$ were described previously (Levey, et al., 1991); h$M_1$ and h$M_4$ cDNAs were purchased from Missouri S&T cDNA Resource; r$M_4$ cDNA was provided by T. I. Bonner (National Institutes of Health, Bethesda, Md.). r$M_2$ and r$M_3$ were cloned from a rat brain cDNA library and sequence verified. h$M_1$, r$M_2$, r$M_3$, h$M_4$, and r$M_4$ cDNAs were used to stably transfect CHO-K1 cells purchased from the American Type Culture Collection using Lipofectamine-2000. To make stable r$M_2$, h$M_2$, rM3, h$M_4$, and r$M_4$ cell lines for use in calcium mobilization assays, these cells also were stably transfected with a chimeric G-protein ($G_{qi5}$) (provided by B. R. Conklin, University of California, San Francisco) using Lipofectamine 2000. r$M_1$, h$M_1$, r$M_3$, h$M_3$, r$M_5$, and h$M_5$ cells were grown in Ham's F-12 medium containing 10% heat-inactivated fetal bovine serum (FBS), 20 mM HEPES, and 50 µg/mL G418 sulfate. rM2-$G_{qi5}$, h$M_2$-$G_{qi5}$, and h$M_4$-$G_{qi5}$ cells were grown in the same medium also containing 500 µg/mL Hygromycin B. Stable r$M_4$-$G_{qi5}$ cells were grown in DMEM containing 10% heat-inactivated FBS, 20 mM HEPES, 400 µg/mL G418 sulfate, and 500 Hygromycin B.

7. Cell-based Functional Assay of Muscarinic Acetylcholine Receptor Activity For high throughput measurement of antagonist inhibited increases in intracellular calcium, CHO-K1 cells stably expressing muscarinic receptors were plated in growth medium lacking G418 and hygromycin at 15,000 cells/20 µL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with four washes (80 µL) of assay buffer then aspirated to 20 µL. Next, 20 µL of 16 µM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 50 min at 37° C. and 5% $CO_2$. Dye was removed by washing with the ELX 405 (four 80 µL washes of assay buffer) then aspirated to 20 µL. Compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 µL) to a 2× stock using a Thermo Fisher Combi (Thermo Fisher Scientific, Waltham, Mass.).

Calcium flux was measured using the Functional Drug Screening System (FDSS) 6000 (Hamamatsu Corporation, Tokyo, Japan) as an increase in the fluorescent static ratio. Compounds were applied to cells (20 µL, 2×) using the automated system of the FDSS 6000 at 4 s into the 300 s protocol and the data were collected at 1 Hz. At 144 s into the 300 s protocol, 10 µL of an $EC_{20}$ concentration of the muscarinic receptor agonist acetylcholine was added (5×), followed by the addition of 12 µL an $EC_{80}$ concentration of acetylcholine at the 230 s time point (5×). Agonist activity was analyzed as a concentration-dependent increase in calcium mobilization upon compound addition. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLfit curve fitting software (IDBS, Bridgewater, N.J.) for Excel (Microsoft, Redmond, Wash.) or Prism (GraphPad Software, Inc., San Diego, Calif.).

The calcium mobilization assay was used to determine "potency". In the context of the assays carried out for the data in Table II, "potency" ($IC_{50}$, nM) is defined as the concentration of antagonist which was found to decrease the calcium flux by 50% as determined by the sigmoidal curve fit of the concentration response curve, or in the absence of an acceptable curve fit, the potency is stated as ">10,000" and the activity remaining at the top dose of 30 µM test compound is given as a percentage of the response elicited by a concentration of ACh that induces approximately 80% of a maximal (i.e. saturating) ACh response.

8. Activity of Compounds in Cell-based Assays

Substituted (1-(methylsulfonyl)azetidin-3-yl)(heterocycloalkyl)methanone analogs were synthesized as described above Inhibitory activity was determined in the mAChR $M_1$ cell-based functional assay as described above and the data are shown in Table II. The compound number corresponds to the compound numbers used in Table I.

TABLE II.

| No. | Potency (IC$_{50}$, nM) | Remaining Activity (%)* |
|---|---|---|
| B1 | 37 | — |
| B2 | 48 | — |
| B3 | 57 | — |
| B4 | 87 | — |
| B5 | 95 | — |
| B6 | 120 | — |
| B7 | 200 | — |
| B8 | 290 | — |
| B9 | 340 | — |
| B10 | 350 | — |
| B11 | 350 | — |
| B12 | 350 | — |
| B13 | 390 | — |
| B14 | 460 | — |
| B15 | 550 | — |
| B16 | 620 | — |
| B17 | 640 | — |
| B18 | 740 | — |
| B19 | 780 | — |
| B20 | 790 | — |
| B21 | 860 | — |
| B22 | 910 | — |
| B23 | 1500 | — |
| B24 | 1500 | — |
| B25 | 1900 | — |
| B26 | 2000 | — |
| B27 | 2000 | — |
| B28 | 2200 | — |
| B29 | 2800 | — |
| B30 | 2900 | — |
| B31 | >10,000 | 11 |
| B32 | >10,000 | 34 |
| B33 | >10,000 | 48 |
| B34 | >10,000 | 11 |
| B35 | >10,000 | 32 |
| B36 | >10,000 | 27 |
| B37 | >10,000 | 26 |
| B38 | >10,000 | 23 |
| B39 | >10,000 | 48 |
| B40 | >10,000 | 41 |
| B41 | >10,000 | 37 |
| B42 | >10,000 | 34 |
| B43 | >10,000 | 43 |
| B44 | >10,000 | 59 |
| B45 | >10,000 | 27 |
| B46 | >10,000 | 52 |
| B47 | >10,000 | 50 |
| B48 | >10,000 | 30 |
| B49 | >10,000 | 48 |
| B50 | >10,000 | 59 |
| B51 | >10,000 | 60 |
| B52 | 3500 | — |
| B53 | 2500 | — |
| B54 | 930 | — |
| B55 | >10,000 | 56 |
| B56 | 960 | — |
| B57 | 950 | — |
| B58 | 660 | — |
| B59 | 2100 | — |
| B60 | 1200 | — |
| B61 | >10,000 | ≥80% ** |
| B62 | >10,000 | ≥80% |
| B63 | >10,000 | ≥80% |
| B64 | >10,000 | ≥80% |
| B65 | >10,000 | ≥80% |
| B66 | >10,000 | ≥80% |
| B67 | >10,000 | ≥80% |
| B68 | >10,000 | ≥80% |
| B69 | >10,000 | ≥80% |
| B70 | >10,000 | ≥80% |
| B71 | >10,000 | ≥80% |
| B72 | >10,000 | ≥80% |
| B73 | >10,000 | ≥80% |
| B74 | >10,000 | ≥80% |
| B75 | >10,000 | ≥80% |
| B76 | >10,000 | ≥80% |
| B77 | >10,000 | ≥80% |
| B78 | >10,000 | ≥80% |
| B79 | >10,000 | ≥80% |
| B80 | >10,000 | ≥80% |
| B81 | >10,000 | ≥80% |
| B82 | >10,000 | ≥80% |
| B83 | >10,000 | ≥80% |
| B84 | >10,000 | ≥80% |
| B85 | >10,000 | ≥80% |
| B86 | >10,000 | ≥80% |

*Unless otherwise indicated with a numerical value, the percent remaining activity is baseline or about zero, i.e. as indicated by "—".
** Nominal value; no statistically significant decrease in the agonist response to ACh (acetylcholine) detected.

The selectivity of the disclosed compounds for mAChR $M_1$ compared to mAChR $M_2$, $M_3$, $M_4$, and $M_5$ was determined using the cell-based functional assay described below using the appropriate cell-lines (prepared as described below). The $IC_{50}$ for each of mAChR $M_2$, $M_3$, $M_4$, and $M_5$ was greater than at least 30 μM for representative compounds (i.e., there was minimal inhibition up to a concentration of about 30 μM, the upper limit of compound used in the assay).

9. Prophetic Pharmaceutical Composition Examples

"Active ingredient" as used throughout these examples relates to one or more disclosed compounds or products of disclosed methods of making as described hereinbefore, or a pharmaceutically acceptable salt, solvate, or polymorph thereof. The following examples of the formulation of the compounds of the present invention in tablets, suspension, injectables and ointments are prophetic. Typical examples of recipes for the formulation of the invention are as given below.

Typical examples of recipes for the formulation of the invention are as given below. Various other dosage forms can be applied herein such as a filled gelatin capsule, liquid emulsion/suspension, ointments, suppositories or chewable tablet form employing the disclosed compounds in desired dosage amounts in accordance with the present invention. Various conventional techniques for preparing suitable dosage forms can be used to prepare the prophetic pharmaceutical compositions, such as those disclosed herein and in standard reference texts, for example the British and US Pharmacopoeias, Remington's Pharmaceutical Sciences (Mack Publishing Co.) and Martindale The Extra Pharmacopoeia (London The Pharmaceutical Press).

The disclosure of this reference is hereby incorporated herein by reference.

a. Pharmaceutical Composition for Oral Administration

A tablet can be prepared as follows:

| Component | Amount |
|---|---|
| Active ingredient | 10 to 500 mg |
| Lactose | 100 mg |
| Crystalline cellulose | 60 mg |
| Magnesium stearate | 5 |
| Starch (e.g. potato starch) | Amount necessary to yield total weight indicated below |
| Total (per capsule) | 1000 mg |

Alternatively, about 100 mg of a disclosed compound, 50 mg of lactose (monohydrate), 50 mg of maize starch (native), 10 mg of polyvinylpyrrolidone (PVP 25) (e.g. from BASF, Ludwigshafen, Germany) and 2 mg of magnesium stearate are used per tablet. The mixture of active component, lactose and starch is granulated with a 5% solution (m/m) of the PVP in water. After drying, the granules are mixed with magnesium stearate for 5 min. This mixture is moulded using a customary tablet press (e.g. tablet format: diameter 8 mm, curvature radius 12 mm). The moulding force applied is typically about 15 kN.

Alternatively, a disclosed compound can be administered in a suspension formulated for oral use. For example, about 100-5000 mg of the desired disclosed compound, 1000 mg of ethanol (96%), 400 mg of xanthan gum, and 99 g of water are combined with stirring. A single dose of about 10-500 mg of the desired disclosed compound according can be provided by 10 ml of oral suspension.

In these Examples, active ingredient can be replaced with the same amount of any of the compounds according to the present invention, in particular by the same amount of any of the exemplified compounds. In some circumstances it may be desirable to use a capsule, e.g. a filled gelatin capsule, instead of a tablet form. The choice of tablet or capsule will depend, in part, upon physicochemical characteristics of the particular disclosed compound used.

Examples of alternative useful carriers for making oral preparations are lactose, sucrose, starch, talc, magnesium stearate, crystalline cellulose, methyl cellulose, hydroxypropyl cellulose, hydroxypropylmethyl cellulose, carboxymethyl cellulose, glycerin, sodium alginate, gum arabic, etc. These alternative carriers can be substituted for those given above as required for desired dissolution, absorption, and manufacturing characteristics.

The amount of a disclosed compound per tablet for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

b. Pharmaceutical Composition for Injectable Use

A parenteral composition can be prepared as follows:

| Component | Amount |
|---|---|
| Active ingredient | 10 to 500 mg |
| Sodium carbonate | 560 mg* |
| Sodium hydroxide | 80 mg* |
| Distilled, sterile water | Quantity sufficient to prepare total volume indicated below. |
| Total (per capsule) | 10 ml per ampule |

*Amount adjusted as required to maintain physiological pH in the context of the amount of active ingredient, and form of active ingredient, e.g. a particular salt form of the active ingredient.

Alternatively, a pharmaceutical composition for intravenous injection can be used, with composition comprising about 100-5000 mg of a disclosed compound, 15 g polyethylenglycol 400 and 250 g water in saline with optionally up to about 15% Cremophor EL, and optionally up to 15% ethyl alcohol, and optionally up to 2 equivalents of a pharmaceutically suitable acid such as citric acid or hydrochloric acid are used. The preparation of such an injectable composition can be accomplished as follows: The disclosed compound and the polyethylenglycol 400 are dissolved in the water with stirring. The solution is sterile filtered (pore size 0.22 µm) and filled into heat sterilized infusion bottles under aseptic conditions. The infusion bottles are sealed with rubber seals.

In a further example, a pharmaceutical composition for intravenous injection can be used, with composition comprising about 10-500 mg of a disclosed compound, standard saline solution, optionally with up to 15% by weight of Cremophor EL, and optionally up to 15% by weight of ethyl alcohol, and optionally up to 2 equivalents of a pharmaceutically suitable acid such as citric acid or hydrochloric acid. Preparation can be accomplished as follows: a desired disclosed compound is dissolved in the saline solution with stirring. Optionally Cremophor EL, ethyl alcohol or acid are added. The solution is sterile filtered (pore size 0.22 µm) and filled into heat sterilized infusion bottles under aseptic conditions. The infusion bottles are sealed with rubber seals.

In this example, active ingredient can be replaced with the same amount of any of the compounds according to the present invention, in particular by the same amount of any of the exemplified compounds.

The amount of a disclosed compound per ampule for use in a pharmaceutical composition for human use is determined from both toxicological and pharmacokinetic data obtained in suitable animal models, e.g. rat and at least one non-rodent species, and adjusted based upon human clinical trial data. For example, it could be appropriate that a disclosed compound is present at a level of about 10 to 1000 mg per tablet dosage unit.

Carriers suitable for parenteral preparations are, for example, water, physiological saline solution, etc. which can be used with tris(hydroxymethyl)aminomethane, sodium carbonate, sodium hydroxide or the like serving as a solubilizer or pH adjusting agent. The parenteral preparations contain preferably 50 to 1000 mg of a disclosed compound per dosage unit.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

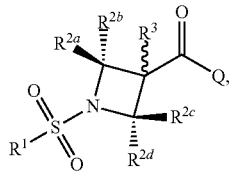

wherein Q is selected from a structure represented by a formula:

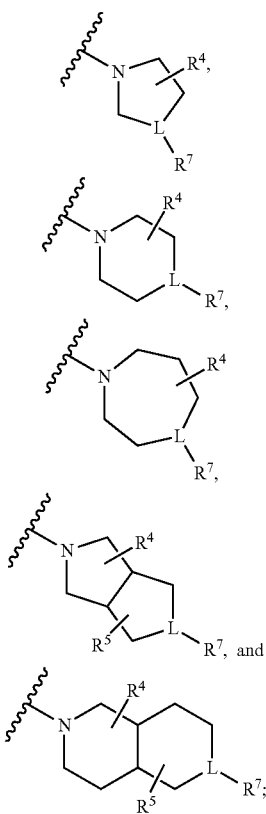

wherein L is N or $CR^6$;
wherein $R^1$ is selected from C1-C8 alkyl, C1-C8 haloalkyl, C1-C8 polyhaloalkyl, C3-C8 cycloalkyl, C3-C9 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;
wherein each of $R^{2a}$, $R^{2b}$, $R^{2c}$, and $R^{2d}$ is independently selected from hydrogen, C1-C6 alkyl, C1-C6 haloalkyl, and C1-C6 polyhaloalkyl;
wherein $R^3$ is selected from hydrogen, C1-C6 alkyl, C1-C6 haloalkyl, and C1-C6 polyhaloalkyl;
wherein each occurrence of $R^4$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;
wherein each occurrence of $R^5$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;
wherein $R^6$, when present, is selected from hydrogen, halogen, C1-C6 alkyl, C1-C6 haloalkyl, and C1-C6 polyhaloalkyl;
wherein $R^7$ is selected from $Ar^1$ and $Ar^2$;
wherein $Ar^1$ is selected from phenyl, indenyl, and napthalenyl; and wherein $Ar^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;
wherein $Ar^2$ is a heteroaryl substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;
or a pharmaceutically acceptable salt, solvate, or polymorph thereof.

2. The compound of claim 1, wherein L is N.

3. The compound of claim 1, wherein Q has a structure represented by a formula:

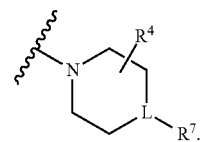

4. The compound of claim 1, wherein Q has a structure represented by a formula:

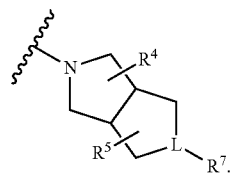

5. The compound of claim 1, wherein $R^1$ is selected from aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino 6. The compound of claim 1, having a structure represented by a formula:

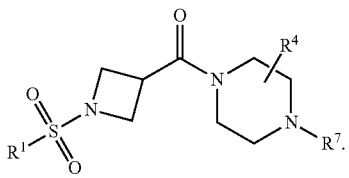

7. The compound of claim 1, having a structure represented by a formula:

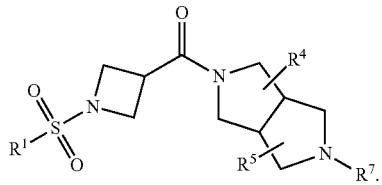

8. A pharmaceutical composition comprising an effective amount of a compound having a structure represented by a formula:

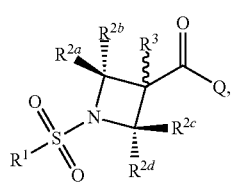

wherein Q is selected from a structure represented by a formula:

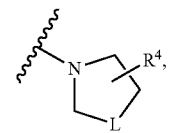

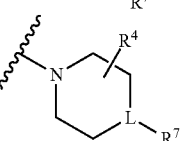

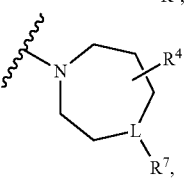

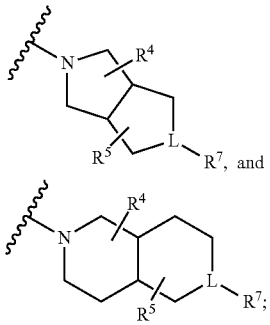

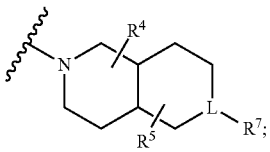

wherein L is N or $CR^6$;

wherein $R^1$ is selected from C1-C8 alkyl, C1-C8 haloalkyl, C1-C8 polyhaloalkyl, C3-C8 cycloalkyl, C3-C9 heterocycloalkyl, aryl and heteroaryl; and wherein $R^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;

wherein each of $R^{2a}$, $R^{2b}$, $R^{2c}$, and $R^{2d}$ is independently selected from hydrogen, C-C6 alkyl, C1-C6 haloalkyl, and C1-C6 polyhaloalkyl;

wherein $R^3$ is selected from hydrogen, C1-C6 alkyl, C1-C6 haloalkyl, and C1-C6 polyhaloalkyl;

wherein each occurrence of $R^4$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;

wherein each occurrence of $R^5$ is independently selected from hydrogen, halogen, cyano, hydroxyl, —$NH_2$, C1-C6 alkyl, C1-C6 haloalkyl, C1-C6 polyhaloalkyl, C1-C6 alkoxy, C1-C6 alkoxy-C1-C6 alkyl, C1-C6 alkylamino, C1-C6 haloalkyl-oxy-C1-C6 alkyl, C1-C6 polyhaloalkyl-oxy-C1-C6 alkyl, and C1-C6 dialkylamino;

wherein $R^6$, when present, is selected from hydrogen, halogen, C1-C6 alkyl, C1-C6 haloalkyl, and C1-C6 polyhaloalkyl;

wherein $R^7$ is selected from $Ar^1$ and $Ar^2$;

wherein $Ar^1$ is selected from phenyl, indenyl, and napthalenyl; and wherein $Ar^1$ is substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;

wherein $Ar^2$ is a heteroaryl substituted with 0-3 groups selected from halogen, hydroxyl, cyano, —$NH_2$, C1-C6 alkyl, C1-C6 alkoxy, C1-C6 haloalkyl, C1-C6 polyhaloalkyl, C1-C6 alkylamino, and C1-C6 dialkylamino;

or pharmaceutically acceptable salt, solvate, or polymorph thereof, and a pharmaceutically acceptable carrier.

* * * * *